United States Patent
Wells et al.

(10) Patent No.: US 12,258,584 B2
(45) Date of Patent: Mar. 25, 2025

(54) METHODS AND SYSTEMS FOR CONVERTING PRECURSOR CELLS INTO INTESTINAL TISSUES THROUGH DIRECTED DIFFERENTIATION

(71) Applicant: Children's Hospital Medical Center, Cincinnati, OH (US)

(72) Inventors: James M. Wells, Cincinnati, OH (US); Aaron M. Zorn, Cincinnati, OH (US); Jason R. Spence, Ann Arbor, MI (US); Noah F. Shroyer, Houston, TX (US)

(73) Assignee: Children's Hospital Medical Center, Cincinnati, OH (US)

( * ) Notice: Subject to any disclaimer, the term of this patent is extended or adjusted under 35 U.S.C. 154(b) by 943 days.

(21) Appl. No.: 16/599,620

(22) Filed: Oct. 11, 2019

(65) Prior Publication Data
US 2020/0190478 A1    Jun. 18, 2020

Related U.S. Application Data

(63) Continuation of application No. 15/627,588, filed on Jun. 20, 2017, now Pat. No. 10,781,425, which is a continuation of application No. 13/695,887, filed as application No. PCT/US2011/035518 on May 6, 2011, now Pat. No. 9,719,068.

(60) Provisional application No. 61/332,178, filed on May 6, 2010.

(51) Int. Cl.
C12N 5/071    (2010.01)
C12N 5/077    (2010.01)

(52) U.S. Cl.
CPC ......... *C12N 5/0679* (2013.01); *C12N 5/0661* (2013.01); *C12N 2501/119* (2013.01); *C12N 2501/155* (2013.01); *C12N 2501/16* (2013.01); *C12N 2501/385* (2013.01); *C12N 2501/415* (2013.01); *C12N 2502/02* (2013.01); *C12N 2502/45* (2013.01)

(58) Field of Classification Search
CPC .................................................. C12N 5/0679
See application file for complete search history.

(56) References Cited

U.S. PATENT DOCUMENTS

| | | | |
|---|---|---|---|
| 5,912,227 A | 6/1999 | Croom, Jr. et al. | |
| 5,942,435 A | 8/1999 | Wheeler | |
| 6,607,501 B2 | 8/2003 | Gorsuch | |
| 7,160,719 B2 | 1/2007 | Nyberg | |
| 7,291,626 B1 | 11/2007 | Beachy et al. | |
| 7,326,572 B2 | 2/2008 | Fisk et al. | |
| 7,510,876 B2 | 3/2009 | D'Amour et al. | |
| 7,514,185 B2 | 4/2009 | Fukushima et al. | |
| 7,541,185 B2 | 6/2009 | D'Amour et al. | |
| 7,625,753 B2 | 12/2009 | Kelly et al. | |
| 7,695,958 B2 | 4/2010 | Funatsu et al. | |
| 7,704,738 B2 | 4/2010 | D'Amour et al. | |
| 7,727,998 B2 | 6/2010 | Moriya et al. | |
| 7,776,592 B2 | 8/2010 | Wandinger-Ness et al. | |
| 7,927,869 B2 | 4/2011 | Rosero | |
| 7,985,585 B2 | 7/2011 | D'Amour et al. | |
| 7,993,916 B2 | 8/2011 | Agulnick et al. | |
| 8,187,878 B2 | 5/2012 | Dalton et al. | |
| 8,216,826 B2 | 7/2012 | Lee et al. | |
| 8,216,836 B2 | 7/2012 | D'Amour et al. | |
| 8,298,822 B2 | 10/2012 | Kruse et al. | |
| 8,318,492 B2 | 11/2012 | Choo et al. | |
| 8,501,476 B2 | 8/2013 | Morgan et al. | |
| 8,586,357 B2 | 11/2013 | D'Amour et al. | |
| 8,603,809 B2 | 12/2013 | Kruse | |

(Continued)

FOREIGN PATENT DOCUMENTS

| | | |
|---|---|---|
| CA | 2968065 A1 | 6/2016 |
| CN | 1299408 A | 6/2001 |

(Continued)

OTHER PUBLICATIONS

Yao et al. (2006, PNAS, vol. 103(18), pp. 6907-6912). (Year: 2006).*

(Continued)

*Primary Examiner* — Anoop K Singh
*Assistant Examiner* — David A Montanari
(74) *Attorney, Agent, or Firm* — Norton Rose Fulbright US LLP

(57) ABSTRACT

The generation of complex organ tissues from human embryonic and pluripotent stem cells (PSCs) remains a major challenge for translational studies. It is shown that PSCs can be directed to differentiate into intestinal tissue in vitro by modulating the combinatorial activities of several signaling pathways in a step-wise fashion, effectively recapitulating in vivo fetal intestinal development. The resulting intestinal "organoids" were three-dimensional structures consisting of a polarized, columnar epithelium surrounded by mesenchyme that included a smooth muscle-like layer. The epithelium was patterned into crypt-like SOX9-positive proliferative zones and villus-like structures with all of the major functional cell types of the intestine. The culture system is used to demonstrate that expression of NEUROG3, a pro-endocrine transcription factor mutated in enteric anendocrinosis is sufficient to promote differentiation towards the enteroendocrine cell lineage. In conclusion, PSC-derived human intestinal tissue should allow for unprecedented studies of human intestinal development, homeostasis and disease.

23 Claims, 26 Drawing Sheets
Specification includes a Sequence Listing.

(56) References Cited

U.S. PATENT DOCUMENTS

| | | |
|---|---|---|
| 8,609,406 B2 | 12/2013 | Subramanian et al. |
| 8,609,413 B2 | 12/2013 | Suter et al. |
| 8,623,645 B2 | 1/2014 | D'Amour et al. |
| 8,632,645 B2 | 1/2014 | Daitou et al. |
| 8,633,024 B2 | 1/2014 | D'Amour et al. |
| 8,642,339 B2 | 2/2014 | Sato et al. |
| 8,647,873 B2 | 2/2014 | D'Amour et al. |
| 8,658,151 B2 | 2/2014 | Kelly et al. |
| 8,685,386 B2 | 4/2014 | West et al. |
| 8,685,730 B2 | 4/2014 | Odorico et al. |
| 8,758,323 B2 | 6/2014 | Michaud et al. |
| 9,127,254 B2 | 9/2015 | Cohen et al. |
| 9,133,439 B2 | 9/2015 | Davis et al. |
| 9,181,301 B2 | 11/2015 | Carlson et al. |
| 9,200,258 B2 | 12/2015 | Mezghani et al. |
| 9,206,393 B2 | 12/2015 | Kruse |
| 9,234,170 B2 | 1/2016 | Snoeck et al. |
| 9,334,479 B2 | 5/2016 | Herrera Sanchez et al. |
| 9,375,514 B2 | 6/2016 | Kruse et al. |
| 9,381,181 B2 | 7/2016 | Roberts et al. |
| 9,394,522 B2 | 7/2016 | Brolen et al. |
| 9,446,076 B2 | 9/2016 | Gaussin et al. |
| 9,447,380 B2 | 9/2016 | Subramanian et al. |
| 9,476,030 B2 | 10/2016 | Gadue et al. |
| 9,499,795 B2 | 11/2016 | D'Amour et al. |
| 9,605,243 B2 | 3/2017 | D'Amour et al. |
| 9,616,039 B2 | 4/2017 | Roberts et al. |
| 9,618,500 B2 | 4/2017 | Giselbrecht et al. |
| 9,650,609 B2 | 5/2017 | Nyberg |
| 9,675,646 B2 | 6/2017 | Bitar |
| 9,677,085 B2 | 6/2017 | Guye et al. |
| 9,719,067 B2 | 8/2017 | Snoeck et al. |
| 9,719,068 B2 | 8/2017 | Wells et al. |
| 9,732,116 B2 | 8/2017 | Steiner et al. |
| 9,752,124 B2 | 9/2017 | Sato et al. |
| 9,763,964 B2 | 9/2017 | Pellicciari et al. |
| 9,765,301 B2 | 9/2017 | Ortega et al. |
| 9,771,562 B2 | 9/2017 | Shen et al. |
| 9,790,470 B2 | 10/2017 | Vallier et al. |
| 9,828,583 B2 | 11/2017 | Rauagopal et al. |
| 9,849,104 B2 | 12/2017 | Bisgaier et al. |
| 9,850,461 B2 | 12/2017 | Rizzi et al. |
| 9,856,458 B2 | 1/2018 | Rosowski et al. |
| 9,878,005 B2 | 1/2018 | Johns et al. |
| 9,914,920 B2 | 3/2018 | Goodwin et al. |
| 9,926,532 B2 | 3/2018 | Esteban et al. |
| 9,938,499 B2 | 4/2018 | Slukvin et al. |
| 10,023,922 B2 | 7/2018 | Stelzer et al. |
| 10,045,977 B2 | 8/2018 | Wu et al. |
| 10,047,341 B2 | 8/2018 | Yu et al. |
| 10,052,337 B2 | 8/2018 | Lancaster et al. |
| 10,000,740 B2 | 9/2018 | Vallier et al. |
| 10,087,416 B2 | 10/2018 | Chan et al. |
| 10,087,417 B2 | 10/2018 | Freed et al. |
| 10,100,279 B2 | 10/2018 | Nicholas et al. |
| 10,130,748 B2 | 11/2018 | Nyberg et al. |
| 10,172,889 B2 | 1/2019 | Sokal et al. |
| 10,174,289 B2 | 1/2019 | Wells et al. |
| 10,179,176 B2 | 1/2019 | Kay et al. |
| 10,220,386 B2 | 3/2019 | Williamson et al. |
| 10,222,370 B2 | 3/2019 | Keshavarzian et al. |
| 10,260,039 B2 | 4/2019 | Bhatia et al. |
| 10,265,153 B2 | 4/2019 | La Francesca et al. |
| 10,265,453 B2 | 4/2019 | Flieg et al. |
| 10,301,303 B2 | 5/2019 | Liu |
| 10,350,147 B2 | 7/2019 | Kyrkanides et al. |
| 10,369,254 B2 | 8/2019 | Yanagawa et al. |
| 10,407,664 B2 | 9/2019 | Knoblich et al. |
| 10,426,757 B2 | 10/2019 | Sabatini et al. |
| 10,449,221 B2 | 10/2019 | Kotton et al. |
| 10,472,612 B2 | 11/2019 | Ingber et al. |
| 10,479,977 B2 | 11/2019 | Wang et al. |
| 10,487,314 B2 | 11/2019 | Accili et al. |
| 10,532,111 B2 | 1/2020 | Kay et al. |
| 10,538,741 B2 | 1/2020 | Sokal et al. |
| 10,545,133 B2 | 1/2020 | Ewald et al. |
| 10,555,929 B2 | 2/2020 | Mantzoros |
| 10,668,108 B2 | 6/2020 | Takebe et al. |
| 10,781,425 B2 | 9/2020 | Wells et al. |
| 11,053,477 B2 | 7/2021 | Wells et al. |
| 11,066,650 B2 | 7/2021 | Wells et al. |
| 2003/0129751 A1 | 7/2003 | Grikscheit et al. |
| 2003/0228685 A1 | 12/2003 | Nyberg |
| 2005/0266554 A1 | 12/2005 | D'Amour et al. |
| 2006/0110369 A1 | 5/2006 | Funatsu et al. |
| 2006/0236415 A1 | 10/2006 | Silversides et al. |
| 2007/0238169 A1 | 10/2007 | Abilez et al. |
| 2007/0239083 A1 | 10/2007 | Voss |
| 2008/0193421 A1 | 8/2008 | Kruse et al. |
| 2008/0286366 A1 | 11/2008 | Fischer et al. |
| 2009/0011502 A1 | 1/2009 | D'Amour et al. |
| 2009/0042287 A1 | 2/2009 | D'Amour et al. |
| 2009/0220959 A1 | 9/2009 | D'Amour et al. |
| 2009/0253202 A1 | 10/2009 | D'Amour et al. |
| 2009/0263357 A1 | 10/2009 | Sayre et al. |
| 2009/0311765 A1 | 12/2009 | Maguire et al. |
| 2010/0016410 A1 | 1/2010 | Wagner et al. |
| 2010/0041150 A1 | 2/2010 | Kelly et al. |
| 2010/0048871 A1 | 2/2010 | Cho et al. |
| 2010/0075295 A1 | 3/2010 | Dryden et al. |
| 2010/0151568 A1 | 6/2010 | D'Amour et al. |
| 2011/0125286 A1 | 5/2011 | Selden et al. |
| 2011/0151564 A1 | 6/2011 | Menu et al. |
| 2011/0218512 A1 | 9/2011 | Tullis et al. |
| 2011/0231942 A1 | 9/2011 | He et al. |
| 2011/0294735 A1 | 12/2011 | Marsh et al. |
| 2011/0300543 A1 | 12/2011 | Wang |
| 2012/0009086 A1 | 1/2012 | Nyberg et al. |
| 2012/0009618 A1 | 1/2012 | Yu et al. |
| 2012/0070419 A1 | 3/2012 | Christiansen-Weber |
| 2012/0071451 A1 | 3/2012 | Spenard et al. |
| 2012/0135519 A1 | 5/2012 | Ameri et al. |
| 2012/0149630 A1 | 6/2012 | Zugates et al. |
| 2012/0196275 A1 | 8/2012 | Mezghanni et al. |
| 2012/0196312 A1 | 8/2012 | Sato et al. |
| 2012/0201890 A1 | 8/2012 | Williams et al. |
| 2012/0264209 A1 | 10/2012 | Odorico et al. |
| 2012/0270295 A1 | 10/2012 | Choo et al. |
| 2012/0291096 A1 | 11/2012 | Boldyrev et al. |
| 2013/0031645 A1 | 1/2013 | Touboul et al. |
| 2013/0095567 A1 | 4/2013 | Brolen et al. |
| 2013/0115673 A1 | 5/2013 | West et al. |
| 2013/0137130 A1 | 5/2013 | Wells et al. |
| 2013/0189327 A1 | 7/2013 | Ortega et al. |
| 2013/0217005 A1 | 8/2013 | Snoeck et al. |
| 2013/0281374 A1 | 10/2013 | Levy et al. |
| 2013/0316442 A1 | 11/2013 | Meurville et al. |
| 2013/0330823 A1 | 12/2013 | Rezania |
| 2014/0038279 A1 | 2/2014 | Ingber et al. |
| 2014/0044713 A1 | 2/2014 | De Lau et al. |
| 2014/0141509 A1 | 5/2014 | Gadue et al. |
| 2014/0193905 A1 | 7/2014 | Kelly et al. |
| 2014/0212910 A1 | 7/2014 | Bhatia et al. |
| 2014/0234953 A1 | 8/2014 | Vacanti et al. |
| 2014/0243227 A1 | 8/2014 | Clevers et al. |
| 2014/0273210 A1 | 9/2014 | Baker et al. |
| 2014/0302491 A1 | 10/2014 | Nadauld et al. |
| 2014/0308695 A1 | 10/2014 | Bruce et al. |
| 2014/0328808 A1 | 11/2014 | Watanabe et al. |
| 2014/0336282 A1 | 11/2014 | Ewald et al. |
| 2014/0369973 A1 | 12/2014 | Bernstein et al. |
| 2015/0017140 A1 | 1/2015 | Bhatia et al. |
| 2015/0151297 A1 | 6/2015 | Williamson et al. |
| 2015/0153326 A1 | 6/2015 | Kogel et al. |
| 2015/0185714 A1 | 7/2015 | Geveci |
| 2015/0197802 A1 | 7/2015 | Zink et al. |
| 2015/0201588 A1 | 7/2015 | Kamb et al. |
| 2015/0238656 A1 | 8/2015 | Orlando et al. |
| 2015/0247124 A1 | 9/2015 | Snoeck et al. |
| 2015/0273071 A1 | 10/2015 | Green et al. |
| 2015/0273127 A1 | 10/2015 | Flieg et al. |
| 2015/0290154 A1 | 10/2015 | Roberts et al. |
| 2015/0330970 A1 | 11/2015 | Knoblich et al. |
| 2015/0343018 A1 | 12/2015 | Sansonetti et al. |

(56) References Cited

U.S. PATENT DOCUMENTS

| | | |
|---|---|---|
| 2015/0359849 A1 | 12/2015 | Greenberg et al. |
| 2015/0361393 A1 | 12/2015 | Nicholas et al. |
| 2016/0002602 A1 | 1/2016 | Almeida-Porada et al. |
| 2016/0022873 A1 | 1/2016 | Besner et al. |
| 2016/0046905 A1 | 2/2016 | Inoue et al. |
| 2016/0060707 A1 | 3/2016 | Goldenberg et al. |
| 2016/0068805 A1 | 3/2016 | Martin et al. |
| 2016/0101133 A1 | 4/2016 | Basu et al. |
| 2016/0102289 A1 | 4/2016 | Yu et al. |
| 2016/0121023 A1 | 5/2016 | Edelman et al. |
| 2016/0122722 A1 | 5/2016 | Ejiri et al. |
| 2016/0143949 A1 | 5/2016 | Ingber et al. |
| 2016/0177270 A1 | 6/2016 | Takebe et al. |
| 2016/0184387 A1 | 6/2016 | Charmot et al. |
| 2016/0186140 A1 | 6/2016 | Dalton et al. |
| 2016/0206664 A1 | 7/2016 | Sokal et al. |
| 2016/0237400 A1 | 8/2016 | Xian |
| 2016/0237401 A1 | 8/2016 | Vallier et al. |
| 2016/0237409 A1 | 8/2016 | Little et al. |
| 2016/0244724 A1 | 8/2016 | Ferro |
| 2016/0245653 A1 | 8/2016 | Park et al. |
| 2016/0256672 A1 | 9/2016 | Arumugaswami et al. |
| 2016/0257937 A1 | 9/2016 | Wauthier et al. |
| 2016/0263098 A1 | 9/2016 | Mantzoros |
| 2016/0289635 A1 | 10/2016 | Sasai et al. |
| 2016/0296599 A1 | 10/2016 | Dinh et al. |
| 2016/0298087 A1 | 10/2016 | Qu et al. |
| 2016/0312181 A1 | 10/2016 | Freed et al. |
| 2016/0312190 A1 | 10/2016 | Ghaedi et al. |
| 2016/0312191 A1 | 10/2016 | Spence et al. |
| 2016/0319240 A1 | 11/2016 | Chan et al. |
| 2016/0340645 A1 | 11/2016 | D'Amour et al. |
| 2016/0340749 A1 | 11/2016 | Stelzer et al. |
| 2016/0354408 A1 | 12/2016 | Hariri et al. |
| 2016/0361466 A1 | 12/2016 | Yanagawa et al. |
| 2016/0376557 A1 | 12/2016 | Dubart Kupperschmitt et al. |
| 2017/0002330 A1 | 1/2017 | Vunjak-Novakovic et al. |
| 2017/0027994 A1 | 2/2017 | Kotton et al. |
| 2017/0035661 A1 | 2/2017 | Kyrkanides et al. |
| 2017/0035784 A1 | 2/2017 | Lancaster et al. |
| 2017/0037043 A1 | 2/2017 | Liu |
| 2017/0067014 A1 | 3/2017 | Takebe et al. |
| 2017/0292116 A1 | 3/2017 | Wells et al. |
| 2017/0101628 A1 | 4/2017 | Ingber et al. |
| 2017/0107469 A1 | 4/2017 | Costa et al. |
| 2017/0107483 A1 | 4/2017 | Pendergraft et al. |
| 2017/0107498 A1 | 4/2017 | Sareen et al. |
| 2017/0128625 A1 | 5/2017 | Bhatia et al. |
| 2017/0151049 A1 | 6/2017 | La Francesca et al. |
| 2017/0152486 A1 | 6/2017 | Shen et al. |
| 2017/0152528 A1 | 6/2017 | Zhang |
| 2017/0184569 A1 | 6/2017 | Keshavarzian et al. |
| 2017/0191030 A1 | 7/2017 | Huch Ortega et al. |
| 2017/0198261 A1 | 7/2017 | Sabaawy et al. |
| 2017/0202885 A1 | 7/2017 | Agulnick |
| 2017/0204375 A1 | 7/2017 | Accili et al. |
| 2017/0205396 A1 | 7/2017 | Izpisua Belmonte et al. |
| 2017/0205398 A1 | 7/2017 | Bruce et al. |
| 2017/0239262 A1 | 8/2017 | Lefebvre |
| 2017/0240863 A1 | 8/2017 | Sokal et al. |
| 2017/0240866 A1 | 8/2017 | Wells et al. |
| 2017/0240964 A1 | 8/2017 | Leung et al. |
| 2017/0258772 A1 | 9/2017 | Sabatini et al. |
| 2017/0260501 A1 | 9/2017 | Semechkin et al. |
| 2017/0260509 A1 | 9/2017 | Hung et al. |
| 2017/0266145 A1 | 9/2017 | Nahmias et al. |
| 2017/0267970 A1 | 9/2017 | Gupta et al. |
| 2017/0266977 A1 | 9/2017 | Huang et al. |
| 2017/0275592 A1 | 9/2017 | Sachs et al. |
| 2017/0285002 A1 | 10/2017 | Taniguchi et al. |
| 2017/0296621 A1 | 10/2017 | Sansonetti et al. |
| 2017/0304294 A1 | 10/2017 | Wu et al. |
| 2017/0304369 A1 | 10/2017 | Ang et al. |
| 2017/0319548 A1 | 11/2017 | Lefebvre |
| 2017/0321188 A1 | 11/2017 | Viczian et al. |
| 2017/0321191 A1 | 11/2017 | Kojima |
| 2017/0335283 A1 | 11/2017 | Wang et al. |
| 2017/0342385 A1 | 11/2017 | Sachs et al. |
| 2017/0348433 A1 | 12/2017 | Kay et al. |
| 2017/0349659 A1 | 12/2017 | Garcia et al. |
| 2017/0349884 A1 | 12/2017 | Karp et al. |
| 2017/0360962 A1 | 12/2017 | Kay et al. |
| 2017/0362573 A1 | 12/2017 | Wells et al. |
| 2017/0362574 A1 | 12/2017 | Sareen et al. |
| 2018/0021341 A1 | 1/2018 | Harriman et al. |
| 2018/0030409 A1 | 2/2018 | Lewis et al. |
| 2018/0042970 A1 | 2/2018 | Rossen et al. |
| 2018/0043357 A1 | 2/2018 | Bocchi et al. |
| 2018/0059119 A1 | 3/2018 | Takats et al. |
| 2018/0112187 A1 | 4/2018 | Smith et al. |
| 2018/0171302 A1 | 6/2018 | Accili |
| 2018/0179496 A1 | 6/2018 | Rajesh et al. |
| 2018/0193421 A1 | 7/2018 | Soula |
| 2018/0250410 A1 | 9/2018 | Borros Gomez et al. |
| 2018/0258400 A1 | 9/2018 | Ng et al. |
| 2018/0344901 A1 | 12/2018 | Spence et al. |
| 2019/0031992 A1 | 1/2019 | Kerns et al. |
| 2019/0078055 A1 | 3/2019 | Wells et al. |
| 2019/0093076 A1 | 3/2019 | Schulz |
| 2019/0153395 A1 | 5/2019 | Barrett et al. |
| 2019/0153397 A1 | 5/2019 | Wells et al. |
| 2019/0298775 A1 | 10/2019 | Takebe et al. |
| 2019/0314387 A1 | 10/2019 | Takebe et al. |
| 2019/0367882 A1 | 12/2019 | Wells et al. |
| 2020/0040309 A1 | 2/2020 | Takebe et al. |
| 2020/0056157 A1 | 2/2020 | Takebe et al. |
| 2020/0102543 A1 | 4/2020 | Okazaki et al. |
| 2020/0149004 A1 | 5/2020 | Spence et al. |
| 2020/0190478 A1 | 6/2020 | Wells et al. |
| 2020/0199537 A1 | 6/2020 | Takebe et al. |
| 2020/0199538 A1 | 6/2020 | Ng et al. |
| 2021/0008123 A1 | 1/2021 | Takebe et al. |
| 2021/0030811 A1 | 2/2021 | Kim et al. |
| 2021/0096126 A1 | 4/2021 | Takebe et al. |
| 2021/0115366 A1 | 4/2021 | Mahe et al. |
| 2021/0180026 A1 | 6/2021 | Takebe et al. |
| 2021/0189349 A1 | 6/2021 | Wells et al. |
| 2021/0292714 A1 | 9/2021 | Takebe et al. |
| 2021/0324334 A1 | 10/2021 | Takebe et al. |
| 2021/0363490 A1 | 11/2021 | Yoshihara et al. |
| 2021/0371815 A1 | 12/2021 | Holloway et al. |
| 2021/0395695 A1 | 12/2021 | Kim et al. |
| 2022/0041684 A1 | 2/2022 | Patterson |
| 2022/0056420 A1 | 2/2022 | Wells et al. |
| 2022/0090011 A1 | 3/2022 | Ngan et al. |
| 2022/0275345 A1 | 9/2022 | Mayhew et al. |

FOREIGN PATENT DOCUMENTS

| | | |
|---|---|---|
| CN | 101600461 A | 12/2009 |
| CN | 101855554 A | 10/2010 |
| CN | 102307990 A | 1/2012 |
| CN | 103068970 | 1/2012 |
| CN | 102439135 | 5/2012 |
| CN | 102459574 A | 5/2012 |
| CN | 102740888 A | 10/2012 |
| CN | 103154237 A | 6/2013 |
| CN | 103237888 | 8/2013 |
| CN | 103561751 A | 2/2014 |
| CN | 104387451 A | 3/2015 |
| CN | 104995294 | 10/2015 |
| CN | 105209605 | 12/2015 |
| CN | 105985395 A | 10/2016 |
| CN | 109415685 A | 3/2019 |
| CN | 110371967 | 10/2019 |
| CN | 110381967 | 10/2019 |
| CN | 110582564 | 12/2019 |
| EP | 1063289 | 12/2000 |
| EP | 2393917 A2 | 12/2011 |
| EP | 2412800 | 2/2012 |
| EP | 2393917 B1 | 4/2016 |
| EP | 3 228 306 A1 | 10/2017 |
| JP | 2003-521673 A | 7/2003 |
| JP | 2004-166717 | 6/2004 |

(56) References Cited

FOREIGN PATENT DOCUMENTS

| | | |
|---|---|---|
| JP | 2008-503203 A | 2/2008 |
| JP | 2008-505638 A | 2/2008 |
| JP | 2008-539697 | 11/2008 |
| JP | 2012516685 A | 7/2012 |
| JP | 2012254081 A | 12/2012 |
| JP | 2013-066414 A | 4/2013 |
| JP | 2013-511969 | 4/2013 |
| JP | 2013-521810 | 6/2013 |
| JP | 2013528397 A | 7/2013 |
| JP | 2013-535201 | 9/2013 |
| JP | 2014516562 A | 7/2014 |
| JP | 2014233281 A | 12/2014 |
| JP | 2016-514968 | 5/2016 |
| JP | 2019000014 A | 1/2019 |
| JP | 2020516247 A | 6/2020 |
| JP | 2020-523000 | 8/2020 |
| JP | 7068305 B2 | 5/2022 |
| JP | 7148552 B2 | 10/2022 |
| KR | 2006-0114355 A | 11/2006 |
| WO | WO 92/07615 | 5/1992 |
| WO | WO 1999/049807 | 12/1997 |
| WO | WO 98/21312 | 5/1998 |
| WO | 9945100 A1 | 9/1999 |
| WO | WO-9949807 A2 | 10/1999 |
| WO | 03046141 A2 | 6/2003 |
| WO | WO 2003/082201 A2 | 10/2003 |
| WO | WO 2004/020614 | 3/2004 |
| WO | WO 2005/001072 A1 | 1/2005 |
| WO | 2005063971 A2 | 7/2005 |
| WO | WO 2005/081970 A2 | 9/2005 |
| WO | WO 2005/097974 A2 | 10/2005 |
| WO | WO 2005/113747 A2 | 12/2005 |
| WO | WO 2006/126236 A1 | 11/2006 |
| WO | 2008073352 A1 | 6/2008 |
| WO | WO 2008/075339 A2 | 6/2008 |
| WO | WO 2009/022907 A2 | 2/2009 |
| WO | WO-2009086596 A1 | 7/2009 |
| WO | WO 2009/146911 A2 | 12/2009 |
| WO | WO 2010/008905 A2 | 1/2010 |
| WO | WO 2010/090513 A2 | 8/2010 |
| WO | WO 2010/094694 A1 | 8/2010 |
| WO | WO 2010/127399 A1 | 11/2010 |
| WO | 2010136583 A2 | 12/2010 |
| WO | WO 2010/143747 A1 | 12/2010 |
| WO | WO-2011050672 A1 | 5/2011 |
| WO | WO 2011/064309 | 6/2011 |
| WO | WO-2011116930 A1 | 9/2011 |
| WO | WO 2011/139628 A1 | 11/2011 |
| WO | WO 2011/140441 A2 | 11/2011 |
| WO | WO 2012/014076 A2 | 2/2012 |
| WO | WO 2012/027474 A1 | 3/2012 |
| WO | WO 2012/089669 A1 | 7/2012 |
| WO | WO 2012/118799 A2 | 9/2012 |
| WO | WO 2012/154834 A1 | 11/2012 |
| WO | WO 2012/155110 A1 | 11/2012 |
| WO | WO 2012/166903 A1 | 12/2012 |
| WO | WO 2012/168930 A2 | 12/2012 |
| WO | WO 2012/178215 A1 | 12/2012 |
| WO | WO 2013/040087 A2 | 3/2013 |
| WO | WO 2013/067498 A1 | 5/2013 |
| WO | WO 2013/086486 A1 | 6/2013 |
| WO | WO 2013/086502 A1 | 6/2013 |
| WO | WO 2013/093812 A2 | 6/2013 |
| WO | WO 2013/096741 A2 | 6/2013 |
| WO | WO 2013/127921 A1 | 9/2013 |
| WO | WO 2013/155060 A1 | 10/2013 |
| WO | WO 2013/174794 A1 | 11/2013 |
| WO | WO-2013176772 A1 | 11/2013 |
| WO | WO 2013/192290 A1 | 12/2013 |
| WO | WO 2014/013334 A2 | 1/2014 |
| WO | WO-2014018691 A1 | 1/2014 |
| WO | WO 2014/048637 A1 | 4/2014 |
| WO | WO 2014/053596 A1 | 4/2014 |
| WO | WO-2014062138 A1 | 4/2014 |
| WO | WO 2014/082096 A1 | 5/2014 |
| WO | WO 2014/090993 A1 | 6/2014 |
| WO | WO-2014083132 A1 | 6/2014 |
| WO | WO-2014093595 A1 | 6/2014 |
| WO | WO-2014093622 A2 | 6/2014 |
| WO | WO-2014093655 A2 | 6/2014 |
| WO | WO-2014093661 A2 | 6/2014 |
| WO | WO-2014093712 A1 | 6/2014 |
| WO | WO 2014/127170 A1 | 8/2014 |
| WO | 2014148646 A1 | 9/2014 |
| WO | WO 2014/151921 A1 | 9/2014 |
| WO | WO 2014/153230 A1 | 9/2014 |
| WO | WO 2014/153294 A1 | 9/2014 |
| WO | WO 2014/159356 A1 | 10/2014 |
| WO | WO 2014/173907 A1 | 10/2014 |
| WO | WO 2014/182885 A2 | 11/2014 |
| WO | WO 2014/197934 A1 | 12/2014 |
| WO | WO 2014/199622 A1 | 12/2014 |
| WO | WO-2014204728 A1 | 12/2014 |
| WO | WO-2014204729 A1 | 12/2014 |
| WO | WO 2015/021358 A2 | 2/2015 |
| WO | WO 2015/060790 A1 | 4/2015 |
| WO | WO 2015/075175 A1 | 5/2015 |
| WO | WO 2015/076388 A1 | 5/2015 |
| WO | WO-2015071474 A2 | 5/2015 |
| WO | WO 2015/108893 A1 | 7/2015 |
| WO | WO 2015/123183 A1 | 8/2015 |
| WO | WO 2015/129822 A1 | 9/2015 |
| WO | WO 2015/130919 A1 | 9/2015 |
| WO | WO 2015/135893 A1 | 9/2015 |
| WO | WO 2015/138032 A2 | 9/2015 |
| WO | WO 2015/152954 A1 | 10/2015 |
| WO | WO 2015/156929 A1 | 10/2015 |
| WO | WO 2015/157163 A1 | 10/2015 |
| WO | WO 2015/168022 A1 | 11/2015 |
| WO | WO 2015/173425 A1 | 11/2015 |
| WO | 2015189320 A1 | 12/2015 |
| WO | WO 2015/183920 A2 | 12/2015 |
| WO | WO 2015/184273 A1 | 12/2015 |
| WO | WO 2015/184375 A2 | 12/2015 |
| WO | WO 2015/185714 A1 | 12/2015 |
| WO | WO 2015/196012 A1 | 12/2015 |
| WO | WO 2015/200901 A1 | 12/2015 |
| WO | WO 2016/011377 A1 | 1/2016 |
| WO | WO 2016/015158 A1 | 2/2016 |
| WO | WO 2016/030525 A1 | 3/2016 |
| WO | WO 2016/033163 A1 | 3/2016 |
| WO | WO 2016/057571 A1 | 4/2016 |
| WO | WO 2016/061464 A1 | 4/2016 |
| WO | WO-2016056999 A1 | 4/2016 |
| WO | WO 2016/073989 A2 | 5/2016 |
| WO | WO 2016/083612 A1 | 6/2016 |
| WO | WO 2016/083613 A2 | 6/2016 |
| WO | WO 2016/085765 A1 | 6/2016 |
| WO | WO 2016/094948 A1 | 6/2016 |
| WO | WO 2016/103002 A1 | 6/2016 |
| WO | WO 2016/103269 A1 | 6/2016 |
| WO | WO 2016/115326 | 7/2016 |
| WO | WO 2016/121512 A1 | 8/2016 |
| WO | 2016141131 A1 | 9/2016 |
| WO | WO 2016/140716 A1 | 9/2016 |
| WO | WO 2016/141084 | 9/2016 |
| WO | WO 2016/141137 A1 | 9/2016 |
| WO | WO 2016/141224 | 9/2016 |
| WO | WO 2016/144769 A1 | 9/2016 |
| WO | WO 2016/164413 A1 | 10/2016 |
| WO | WO 2016/168950 A1 | 10/2016 |
| WO | WO 2016/174604 A1 | 11/2016 |
| WO | WO 2016/176208 A1 | 11/2016 |
| WO | WO 2016/183143 A1 | 11/2016 |
| WO | 2016204809 A1 | 12/2016 |
| WO | WO 2016/193441 A2 | 12/2016 |
| WO | WO 2016/207621 A1 | 12/2016 |
| WO | WO 2016/210313 A1 | 12/2016 |
| WO | WO 2016/210416 A2 | 12/2016 |
| WO | WO 2017/009263 A1 | 1/2017 |
| WO | WO-2017023803 A1 | 2/2017 |
| WO | WO 2017/036533 A1 | 3/2017 |
| WO | WO 2017/037295 A1 | 3/2017 |
| WO | WO 2017/041041 A1 | 3/2017 |

(56) References Cited

FOREIGN PATENT DOCUMENTS

| | | |
|---|---|---|
| WO | WO 2017/048193 A1 | 3/2017 |
| WO | WO 2017/048322 A1 | 3/2017 |
| WO | WO 2017/049243 A1 | 3/2017 |
| WO | WO 2017/059171 A1 | 4/2017 |
| WO | WO 2017/060884 A1 | 4/2017 |
| WO | WO 2017/066507 A1 | 4/2017 |
| WO | WO 2017/066659 A1 | 4/2017 |
| WO | WO 2017/070007 A2 | 4/2017 |
| WO | WO 2017/070224 A1 | 4/2017 |
| WO | WO 2017/070471 A1 | 4/2017 |
| WO | WO 2017/070506 A1 | 4/2017 |
| WO | WO 2017/070633 | 4/2017 |
| WO | WO-2017070337 A1 | 4/2017 |
| WO | 2017083696 A1 | 5/2017 |
| WO | WO 2017/075389 A1 | 5/2017 |
| WO | WO 2017/077535 A1 | 5/2017 |
| WO | WO 2017/079632 A1 | 5/2017 |
| WO | WO 2017/083705 A1 | 5/2017 |
| WO | WO 2017/083838 | 5/2017 |
| WO | WO 2017/096192 A1 | 6/2017 |
| WO | WO 2017/096282 A1 | 6/2017 |
| WO | WO 2017/112901 A1 | 6/2017 |
| WO | WO 2017/115982 A1 | 7/2017 |
| WO | WO 2017/117333 A1 | 7/2017 |
| WO | WO 2017/117547 A1 | 7/2017 |
| WO | WO 2017/117571 A1 | 7/2017 |
| WO | WO 2017/120543 A1 | 7/2017 |
| WO | WO 2017/121754 A1 | 7/2017 |
| WO | WO 2017/123791 A1 | 7/2017 |
| WO | WO 2017/136462 A2 | 8/2017 |
| WO | WO 2017/136479 A1 | 8/2017 |
| WO | WO 2017/139455 A1 | 8/2017 |
| WO | WO 2017/139638 A1 | 8/2017 |
| WO | WO 2017/142069 A1 | 8/2017 |
| WO | WO 2017/143100 A1 | 8/2017 |
| WO | WO 2017/149025 A1 | 9/2017 |
| WO | WO 2017/153992 A1 | 9/2017 |
| WO | WO 2017/160234 A1 | 9/2017 |
| WO | WO 2017/160671 A1 | 9/2017 |
| WO | WO 2017/172638 A1 | 10/2017 |
| WO | WO 2017/174609 A1 | 10/2017 |
| WO | WO 2017/176810 A1 | 10/2017 |
| WO | WO 2017/184586 A1 | 10/2017 |
| WO | WO-2017175876 A1 | 10/2017 |
| WO | WO 2017/192997 A1 | 11/2017 |
| WO | WO 2017/205511 A1 | 11/2017 |
| WO | WO 2017/218287 A1 | 12/2017 |
| WO | WO 2017/220586 A1 | 12/2017 |
| WO | WO 2018/011558 A1 | 1/2018 |
| WO | WO 2018/019704 A1 | 2/2018 |
| WO | WO 2018/026947 A1 | 2/2018 |
| WO | WO 2018/027023 A1 | 2/2018 |
| WO | WO 2018/027112 A1 | 2/2018 |
| WO | WO 2018/035574 A1 | 3/2018 |
| WO | WO 2018/038042 A1 | 3/2018 |
| WO | WO 2018/044685 A1 | 3/2018 |
| WO | WO 2018/044885 A1 | 3/2018 |
| WO | WO 2018/044937 A2 | 3/2018 |
| WO | WO 2018/044940 A1 | 3/2018 |
| WO | WO 2018/085615 A1 | 5/2018 |
| WO | WO 2018/091677 | 5/2018 |
| WO | WO 2018/094522 A1 | 5/2018 |
| WO | WO-2018085622 A1 | 5/2018 |
| WO | WO-2018085623 A1 | 5/2018 |
| WO | WO 2018/106628 A1 | 6/2018 |
| WO | WO-2018115852 A1 | 6/2018 |
| WO | 2018170280 A1 | 9/2018 |
| WO | WO-2018191673 A1 | 10/2018 |
| WO | WO 2018/197544 A1 | 11/2018 |
| WO | WO-2018200481 A1 | 11/2018 |
| WO | WO 2018/229251 | 12/2018 |
| WO | WO-2018226267 A1 | 12/2018 |
| WO | WO 2019/060336 | 3/2019 |
| WO | WO 2019/074793 A1 | 4/2019 |
| WO | WO-2019126626 A1 | 6/2019 |
| WO | 2019140151 A1 | 7/2019 |
| WO | WO-2020023245 A1 | 1/2020 |
| WO | WO-2020056158 A1 | 3/2020 |
| WO | WO-2020069285 A1 | 4/2020 |
| WO | WO 2020/100481 | 5/2020 |
| WO | WO 2020/154374 | 7/2020 |
| WO | WO 2020/160371 | 8/2020 |
| WO | WO 2020/227711 | 11/2020 |
| WO | WO 2020/247528 | 12/2020 |
| WO | WO-2020243633 A1 | 12/2020 |
| WO | WO-2021030373 A1 | 2/2021 |
| WO | WO-2021041443 A2 | 3/2021 |
| WO | WO 2021/262676 | 12/2021 |
| WO | 2022261471 A2 | 12/2022 |
| WO | WO 2023/030158 | 3/2023 |

OTHER PUBLICATIONS

Zorn et al. (ePUB Aug. 12, 2009, Annu. Rev. Cell Dev., vol. 25, pp. 221-251) (Year: 2009).*
Coghlan et al. (2000, Chemistry & Biology, vol. 7, pp. 793-803). (Year: 2000).*
Duh et al. (2000, Pediatric Res., vol. 48(6), pp. 794-802). (Year: 2000).*
Bain G., "Embryonic Stem Cells Express Neuronal Properties in Vitro," Developmental Biology, 1995, vol. 168, pp. 842-357.
Burns A.J., et al., "Enteric Nervous System Development: Analysis of the Selective Developmental Potentialities of Vagal and Sacral Neural Crest Cells using Quail-Chick Chimeras," The Anatomical Record, 2001, vol. 262, pp. 16-28.
Burrin D., et al., "Enteral Obeticholic Acid Prevents Hepatic Cholestasis in Total Parenteral Nutrition-Fed Neonatal Pigs", Hepatology, vol. 62, Oct. 2015, p. 307A.
Chauhan R.K., et al., "Genetic and Functional Studies of Hirschsprung Disease", Doctoral Thesis: Department of Clinical Genetics, Erasmus University Rotterdam, the Netherlands, 2016; 202 pages.
Cunningham T.J., et al., "Mechanisms of Retinoic Acid Signalling and its Roles in Organ and Limb Development", Nature Reviews Molecular Cell Biology, vol. 16, No. 2, Jan. 5, 2015, pp. 110-123.
Dunn, "Cationic Nanoparticles for the Targeting and Delivery of Nucleic Acids to the Pulmonary Endothelium," University of Cincinnati, Sep. 19, 2018, Doctoral Thesis; downloaded from https://etd.ohiolink.edu/apexprod/rws_olink/r/1501/10?clear=10&p10_accession_num=ucin1544098242321181; 160 pages.
Goldstein A.M., et al., "BMP Signaling is Necessary for Neural Crest Cell Migration and Ganglion Formation in the Enteric Nervous System", Mechanisms of Development, 2005, vol. 122, pp. 821-833.
Guan Y., et al., "Human Hepatic Organoids for the Analysis of Human Genetic Diseases", JCI Insight, Sep. 7, 2017, vol. 2, Issue 17, e94954; 17 pages.
Huang H., "Differentiation of Human Embryonic Stem Cells into Smooth Muscle Cells in Adherent Monolayer Culture", Biochemical and Biophysical Research Communications, 2006, vol. 351 pp. 321-327.
Jones P., et al., "Stromal Expression of Jagged 1 Promotes Colony Formation by Fetal Hematopoietic Progenitor Cells", Blood, Sep. 1, 1998, vol. 92, No. 5, pp. 1505-1511.
Kruitwagen H.S., et al., "SCH-O-5 Long-Term Adult Feline Liver Organoid Cultures For Disease Modelling of Hepatic Lipidosis," Research Communications of the 26th ECVIM-CA Congress, Sep. 2016, ECVIM Abstracts pp. 203-204.
Kruitwagen H.S., et al., "Long-Term Adult Feline Liver Organoid Cultures for Disease Modeling of Hepatic Steatosis", Stem Cell Reports, Apr. 2017, vol. 8(4), pp. 822-830.
Lachmann N., et al., "Large-Scale Hematopoietic Differentiation of Human Induced Pluripotent Stem Cells Provides Granulocytes or Macrophages for Cell Replacement Therapies," Stem Cell Report, Feb. 10, 2015, vol. 4, pp. 282-296.
Lai F.P-L., et al., "Correction of Hirschsprung-Associated Mutations in Human Induced Pluripotent Stem Cells Via Clustered

(56) References Cited

OTHER PUBLICATIONS

Regularly Interspaced Short Palindromic Repeats/Cas9, Restores Neural Crest Cell Function," Gastroenterology, 2017, vol. 153, No. 1, pp. 139-153.
Liu J.A-J., et al., "Identification of GLI Mutations in Patients with Hirschsprung Disease that Disrupt Enteric Nervous System Development in Mice," Gastroenterology, 2015, vol. 149, No. 7, pp. 1837-1848.
McCracken K.W., et al., "Generating Human Intestinal Tissue from Pluripotent Stem Cells in Vitro," Nature Protocols, vol. 6, No. 12, Nov. 10, 2011, pp. 1920-1928.
McCracken K.W., et al., "Modelling Human Development and Disease in Pluripotent Stem- Cell-Derived Gastric Organoids," Nature, Oct. 29, 2014, vol. 516, No. 7531, pp. 400-404.
Mori R., et al., "Micropatterned Organoid Culture of Rat Hepatocytes and HepG2 Cells," Journal of Bioscience and Bioengineering, Sep. 2008, vol. 106(3), pp. 237-242.
Nantasanti S., et al., "Concise Review: Organoids are a Powerful Tool for the Study of Liver Disease and Personalized Treatment Design in Humans and Animals: Organoids for Disease Modeling and Therapy", Stem Cells Translational Medicine, Jan. 21, 2016, vol. 5(3), pp. 325-330.
Okada Y., et al., "Retinoic-Acid-Concentration-Dependent Acquisition of Neural Cell Identity during in Vitro Differentiation of Mouse Embryonic Stem Cells," Developmental Biology, 2004, vol. 275, Issue 1, pp. 124-142.
Paddison P.J., et al., "Short Hairpin Activated Gene Silencing in Mammalian Cells", Methods in Molecular Biology, 2004, vol. 265, pp. 85-100.
Ricchi M., et al., "Differential Effect of Oleic and Palmitic Acid on Lipid Accumulation and Apoptosis in Cultured Hepatocytes", Journal of Gastroenterology and Hepatology, May 2009, vol. 24, Issue 5, pp. 830-840.
Sherwood, et al., "Transcriptional Dynamics of Endodermal Organ Formation", Developmental Dynamics, Jan. 2009, vol. 238, Issue 1, pp. 29-42.
Siller R., et al., "Small-Molecule-Driven Hepatocyte Differentiation of Human Pluripotent Stem Cells", Stem Cell Reports, May 2015, vol. 4, No. 5, pp. 939-952.
Simkin J.E., et al., "Retinoic Acid Upregulates Ret and Induces Chain Migration and Population Expansion in Vagal Neural Crest Cells to Colonise the Embryonic Gut", PLoS ONE, May 2013, vol. 8(5), e64077, pp. 1-12.
Vu J., et al., "Regulation of Appetite, Body Composition and Metabolic Hormones by Vasoactive Intestinal Polypeptide (VIP)", Journal of Molecular Neuroscience, Apr. 23, 2015, vol. 56, No. 2, pp. 377-387.
Yamaguchi Y., et al., "Purified Interleukin 5 Supports the Terminal Differentiation and Proliferation of Murine Eosinophilic Precursors," Journal of Experimental Medicine, Jan. 1988, vol. 167, No. 1, pp. 43-56.
Zhang H., et al., "The Existence of Epithelial-to-Mesenchymal Cells with the Ability to Support Hematopoiesis in Human Fetal Liver," Cell Biology International, Mar. 2005, vol. 29, No. 3, pp. 213-219.
Cincinnati Children's Hospital Medical Center, "Scientists grow human esophagus in lab: Tiny organoids enable personalized disease diagnosis, regenerative therapies," CCHMC Public Press Release, Sep. 20, 2018, 2 pgs.
Mullin, E., "Tiny Human Esophagus Grown in the Lab—Here's Why: Miniature versions of the organ that guides food to the stomach could help scientists treat a variety of medical ailments," National Geographic, Sep. 20, 2018, downloaded from https://www.nationalgeographic.com/science/2018/09/news-human-esophagus-grown-lab-stem-cells-cancer-health.html, 5 pgs.
Sandoiu, A., "Scientists create human esophagus in stem cell first," Medical News Today, Sep. 21, 2018, downloaded from https://www.medicalnewstoday.com/articles/323118.php, 4 pgs.
Alkhatatbeh M.J., et al., "Low Simvastatin Concentrations Reduce Oleic Acid-Induced Steatosis in HepG2 Cells: An In Vitro Model of Non-Alcoholic Fatty Liver Disease," Experimental and Therapeutic Medicine, 2016, vol. 11 (4), pp. 1487-1492.
Bain C.C., et al., "Constant Replenishment from Circulating Monocytes Maintains the Macrophage Pool in Adult Intestine," Nat Immunol, Oct. 2014, vol. 15 (10), pp. 929-937.
Bain C.C., et al., "Resident and Pro-Inflammatory Macrophages in the Colon Represent Alternative Context-Dependent Fates of the Same Ly6Chi Monocyte Precursors, " Mucosal Immunology, May 2013, vol. 6 (3), pp. 498-510.
Bayha E., et al., "Retinoic Acid Signaling Organizes Endodermal Organ Specification Along the Entire Antero-Posterior Axis," PLoS one, Jun. 10, 2009, vol. 4 (6), e5845, 15 pages.
Bort R., et al., "Hex Homeobox Gene-Dependent Tissue Positioning is Required for Organogenesis of the Ventral Pancreas," Development, Jan. 2004, vol. 131 (4), pp. 797-806.
Bujko A., et al., "Transcriptional and Functional Profiling Defines Human Small Intestinal Macrophage Subsets," Journal of Experimental Medicine, 2018, vol. 215 (2), pp. 441-458.
Bulmer J.N., et al., "Macrophage Populations in the Human Placenta and Amniochorion," Clinical Experimental Immunology, 1984, vol. 57 (2), pp. 393-403.
Camp J.G., et al., "Multilineage Communication Regulates Human Liver Bud Development from Pluripotency," Nature, 2017, vol. 546 (7659), pp. 533-538.
Campbell E.L., et al., "Transmigrating Neutrophils Shape the Mucosal Microenvironment Through Localized Oxygen Depletion to Influence Resolution of Inflammation," Immunity, 2014, vol. 40 (1), pp. 66-77.
Choi K.D., et al., "Identification of the Hemogenic Endothelial Progenitor and Its Direct Precursor in Human Pluripotent Stem Cell Differentiation Cultures," Cell Reports, Sep. 27, 2012, vol. 2(3), pp. 553-567.
Cumano A., et al., "Lymphoid Potential, Probed before Circulation in Mouse, Is Restricted to Caudal Intraembryonic Splanchnopleura," Cell, Sep. 20, 1996, vol. 86 (6), pp. 907-916.
Davies L.C., et al., "Tissue-Resident Macrophages," Nat Immunol, Oct. 2013, vol. 14 (10), pp. 986-995.
Dekkers R., et al., "A Bioassay Using Intestinal Organoids to Measure CFTR Modulators in Human Plasma," Journal of Cystic Fibrosis, 2015, vol. 14 (2), pp. 178-181.
DeSchepper S., et al., "Self-Maintaining Gut Macrophages Are Essential for Intestinal Homeostasis," Cell, Oct. 4, 2018, vol. 175 (2), pp. 400-415.
Feldstein A.E., et al., "Free Fatty Acids Promote Hepatic Lipotoxicity By Stimulating TNF-α0 Expression Via a Lysosomal Pathway," Hepatology, Jul. 2004, vol. 40 (1), pp. 185-194.
Fukuda A., et al., "Ectopic Pancreas Formation in Hes1-Knockout Mice Reveals Plasticity of Endodermal Progenitors of the Gut, Bile Duct, and Pancreas," The Journal of Clinical Investigation, Jun. 2006, vol. 116 (6), pp. 1484-1493.
Glocker E.O., et al., "Inflammatory Bowel Disease and Mutations Affecting the Interleukin-10 Receptor," N Engl J Med, Nov. 19, 2009, vol. 361 (21), pp. 2033-2045.
Hentsch B., et al., "HIx Homeo Box Gene is Essential for an Inductive Tissue Interaction that Drives Expansion of Embryonic Liver and Gut," Genes & Development, 1996, vol. 10 (1), pp. 70-79.
Higashiyama H., et al., "Embryonic Cholecystitis and Defective Gallbladder Contraction in the Sox17-Haploinsufficient Model of Biliary Atresia," Development, 2017, vol. 144 (10), pp. 1906-1917.
Hoeffel G., et al., "C-Myb+ Erythro-Myeloid Progenitor-Derived Fetal Monocytes Give Rise to Adult Tissue-Resident Macrophages," Immunity, Apr. 21, 2015, vol. 42 (4), pp. 665-678.
Iacovino M., et al., "HoxA3 is an Apical Regulator of Hemogenic Endothelium," Nat Cell Biol, Jan. 2011, vol. 13 (1), pp. 72-78.
Jørgensen M.C., et al., "Neurog3-Dependent Pancreas Dysgenesis Causes Ectopic Pancreas in Hes1 Mutant Mice," Development, 2018, vol. 145 (17), 11 pages.
Kennedy M., et al., "T Lymphocyte Potential Marks the Emergence of Definitive Hematopoietic Progenitors in Human Pluripotent Stem Cell Differentiation Cultures," Cell Reports, Dec. 27, 2012, vol. 2 (6), pp. 1722-1735.
Kuci Z., et al., "Mesenchymal Stromal Cells from Pooled Mononuclear Cells of Multiple Bone Marrow Donors as Rescue Therapy in

(56) References Cited

OTHER PUBLICATIONS

Pediatric Severe Steroid-Refractory Graft-Versus-Host Disease: A Multicenter Survey," Haematologica, 2016, vol. 101 (8), pp. 985-994.
Lanctot P.M., et al., "The Glycans of Stem Cells," Curr Opin Chem Biol, Aug. 2007, vol. 11(4), pp. 373-380.
Maeno M., et al., "The Role of BMP-4 and GATA-2 in the Induction and Differentiation of Hematopoietic Mesoderm in Xenopus Laevis," Blood, Sep. 15, 1996, vol. 88 (6), pp. 1965-1972.
Maheshwari A., et al., "TGF-B2 Suppresses Macrophage Cytokine Production and Mucosal Inflammatory Responses In the Developing Intestine," Gastroenterology, 2011, vol. 140 (1), pp. 242-253.
Man A.L., et al., "CX3CR1+ Cell-Mediated Salmonella Exclusion Protects the Intestinal Mucosa during the Initial Stage of Infection," The Journal Immunology, 2017, vol. 198 (1), pp. 335-343.
Martin M.J., et al., "Human Embryonic Stem Cells Express An Immunogenic Nonhuman Sialic Acid," Nature Medicine, Feb. 2005, vol. 11(2), pp. 228-232.
Miller., A.J., et al. "Generation of Lung Organoids from Human Pluripotent Stem Cells in Vitro," Nature, Feb. 28, 2019, vol. 14, No. 2, pp. 518-540.
Montalbano G., et al., "Synthesis of Bioinspired Collagen/Alginate/Fibrin Based Hydrogels for Soft Tissue Engineering," Material Science & Engineering, C 91, 2018, pp. 236-246.
Nissim S., et al., "Iterative Use of Nuclear Receptor Nr5a2 Regulates Multiple Stages of Liver and Pancreas Development," Development Biology, Jul. 26, 2016, vol. 418 (1), pp. 108-123.
Palaria A., et al., "Patterning of the Hepato-Pancreatobiliary Boundary by BMP Reveals Heterogeneity Within the Murine Liver Bud," Hepatology, Jul. 2018, vol. 68 (1), pp. 274-288.
Perdiguero E.G., et al., "Development and Maintenance of Resident Macrophages," Nature Immunology, Jan. 2016, vol. 17 (1), pp. 2-8.
Perdiguero E.G., et al., "Tissue-Resident Macrophages Originate from Yolk-Sac-Derived Erythro-Myeloid Progenitors," Nature, Feb. 26, 2015, vol. 518 (7540), pp. 547-551.
Rankin S.A., et al., "A Retinoic Acid-Hedgehog Cascade Coordinates Mesoderm-Inducing Signals and Endoderm Competence During Lung Specification," Cell Reports, Jun. 28, 2016, vol. 16 (1), pp. 66-78.
San Roman A.K., et al., "Boundaries, Junctions and Transitions in the Gastrointestinal Tract," Exp Cell Res, Nov. 15, 2011, vol. 317 (19), pp. 2711-2718.
Shaw T.N., et al., "Tissue-Resident Macrophages in the Intestine are Long Lived and Defined by Tim-4 and CD4 Expression," Journal of Experimental Medicine, 2018, vol. 215 (6), pp. 1507-1518.
Sheng J., et al., "Most Tissue-Resident Macrophages Except Microglia Are Derived from Fetal Hematopoietic Stem Cells," Immunity, Aug. 18, 2015, vol. 43 (2), pp. 382-393.
Shibata Y., et al., "Prediction of Hepatic Clearance and Availability by Cryopreserved Human Hepatocytes: An Application of Serum Incubation Method," Drug Metabolism and Disposition, 2002, vol. 30(8), pp. 892-896.
Shih H.P., et al., "A Gene Regulatory Network Cooperatively Controlled by Pdx1 and Sox9 Governs Lineage Allocation of Foregut Progenitor Cells," Cell Reports, Oct. 13, 2015, vol. 13 (2), 326-336.
Smith D.M., et al., "Roles of BMP Signaling and Nkx2.5 in Patterning at the Chick Midgut-Foregut Boundary," Development, 2000, vol. 127 (17), pp. 3671-3681.
Smith P.D., et al., "Intestinal Macrophages Lack CD14 and CD89 and Consequently are Down-Regulated for LPS- and IgA-Mediated Activities," The Journal of Immunology, 2001, vol. 167 (5), pp. 2651-2656.
Spence J.R., et al., "Sox17 Regulates Organ Lineage Segregation of Ventral Foregut Progenitor Cells," Dev Cell, Jul. 2009, vol. 17 (1), pp. 62-74.
Stresser D.M., et al., "Validation of Pooled Cryopreserved Human Hepatocytes as a Model for Metabolism Studies," BD Biosciences, Jan. 1, 2004, Retrieved from https://www.researchgate.net/profile/David-Stresser/publication/268359224_Validation_of_Pooled_Cryopreserved_Human_Hepatocytes_as_a_Model_for_Metabolism_Studies/links/54ed49710cf2465f5330eddc/Validation-of-Pooled-Cryopreserved-Human-Hepatocytes-as-a-Model-for-Metabolism-Studies.pdf on Jan. 15, 2021, 2 pages.
Sturgeon C.M., et al., "Wnt Signaling Controls the Specification of Definitive and Primitive Hematopoiesis from Human Pluripotent Stem Cells," Natural Biotechnology, Jun. 2014, vol. 32 (6), pp. 554-561.
Sumazaki R., et al., "Conversion of Biliary System to Pancreatic Tissue in Hes1-Deficient Mice," Nature Genetics, Jan. 2004, vol. 36 (1), pp. 83-87.
Takata K., et al., "Induced-Pluripotent-Stem-Cell-Derived Primitive Macrophages Provide a Platform for Modeling Tissue-Resident Macrophage Differentiation and Function," Immunity, Jul. 18, 2017, vol. 47 (1), pp. 183-198.
Tepass U., et al., "Epithelium Formation in the *Drosophila* Midgut Depends on the Interaction of Endoderm and Mesoderm," Development, 1994, vol. 120 (3), pp. 579-590.
Thamm K., et al., "Notch Signaling During Larval and Juvenile Development in the Polychaete Annelid *Capitella* sp. I," Developmental Biology, 2008, vol. 320 (1), pp. 304-318.
Tugizov S.M., et al., "Differential Transmission of HIV Traversing Fetal Oral/Intestinal Epithelia and Adult Oral Epithelia," Journal of Virology, 2012, vol. 86 (5), pp. 2556-2570.
Udager A., et al., "Dividing the Tubular Gut: Generation of Organ Boundaries at the Pylorus," Progress in Molecular Biology and Translational Science, 2010, vol. 96, pp. 35-62.
Uhlén M., et al., "A Human Protein Atlas for Normal and Cancer Tissues Based on Antibody Proteomics," Molecular & and Cellular Proteomics, Aug. 27, 2005, vol. 4 (12), pp. 1920-1932.
Yeung E.N.W., et al., "Fibrinogen Production is Enhanced in an In-Vitro Model of Non-Alcoholic Fatty Liver Disease: An Isolated Risk Factor for Cardiovascular Events?," Lipids in Health and Disease, 2015, vol. 14 (86), 8 pages.
Zhang Y., et al., "Palmitic and Linoleic Acids Induce ER Stress and Apoptosis in Hepatoma Cells," Lipids in Health and Disease, 2012, vol. 11 (1), 8 pages.
Zhang Z., et al., "Syndecan4 Coordinates Wnt/JNK and BMP Signaling to Regulate Foregut Progenitor Development," Developmental Biology, 2016, vol. 416 (1), pp. 187-199.
Zhang Y., et al., "Development and Stem Cells of the Esophagus," Seminars in Cell & Developmental Biology, Dec. 19, 2016, vol. 66, pp. 25-35.
Ader. M., et al., "Modeling human development in 3D culture," Current Opinion in Cell Biology, 2014, 31:23-28, 6 pgs.
Adorini, L., et al., "Farnesoid X receptor targeting to treat nonalcoholic steatohepatitis," Drug Discovery Today, Sep. 2012, 17(17/18):988-997, 10 pgs.
Agopian, V.G., et al., "Intestinal Stem Cell Organoid Transplantation Generates Neomucosa in Dogs," Journal of Gastrointestinal Surgery, Jan. 23, 2009, 13(5):971-982, XP055241418, 12 pgs.
Ahnfelt-Ronne, J., et al., "An improved method for three-dimensional reconstruction of protein expression patterns in intact mouse and chicken embryos and organs," J. Histochem. Cytochem., 2007, 55:925-930, 6 pgs.
Ajmera, V., et al., "Novel Plasma Biomarkers Associated with Liver Disease Severity in Adults with Nonalcoholic Fatty Liver Disease," Hepatology, 2017, 65(1):65-77, 21 pgs.
Aleo, M.D., et al., "Human Drug-Induced Liver Injury Severity is Highly Associated with Dual Inhibition of Liver Mitochondrial Function and Bile Salt Export Pump," Hepatology, 2014, 60:1015-1022, 8 pgs.
Alessi, D.R., et al., "LKB1-Dependent Signaling Pathways," Annu. Rev. Biochem., 2006, 75:137-63, 30 pgs.
Allard, J., et al., "Immunohistochemical toolkit for tracking and quantifying xenotransplanted human stem cells," Regenerative Medicine, 2014, 9(4):437-452, 11 pgs.
Altman, G.H., et al., "Cell differentiation by mechanical stress," The FASEB Journal, 2001, 16(2):270-272, 13 pgs.
Ameri, J., et al., "FGF2 Specifies hESC-Derived Definitive Endoderm into Foregut/Midgut Cell Lineages in a Concentration-Dependent Manner," Stem Cells, ePUB Nov. 3, 2009, 28(1):45-56, 12 pgs.

(56) References Cited

OTHER PUBLICATIONS

Amieva, M.R., et al. "*Helicobacter pylori* enter and survive within multivesicular vacuoles of epithelial cells," Cell. Microbiol., 2002, 4(10):677-690, 15 pgs.

An, W.F., et al., "Discovery of Potent and Highly Selective Inhibitors of GSK3b," Molecular Libraries, Probe Report, May 2014, 115 pgs.

Anderson, G., et al., "Loss of enteric dopaminergic neurons and associated changes in colon motility in an MPTP mouse model of Parkinson's disease," Exp Neurol, Sep. 2007, 207:4-12, 16 pgs.

Andrews, et al., "Embryonic stem (ES) cells and embryonal carcinoma (EC) cells: opposite sides of the same coin," Biochem Soc Trans, 2005, 339(part 6):1526-1530, 5 pgs.

Andrews, P.W., et al., "Embryonic stem (ES) cells and embryonal carcinoma (EC) cells: opposite sides of the same coin," Biochem Soc Trans, 2005, 33(part 6): 1526-1530, 5 pgs.

Ang, S-L, et al., "The formation and maintenance of the definitive endoderm lineage in the mouse: involvement of HNF3/forkhead proteins," Development, 1993, 119:1301-1315, 15 pgs.

Anlauf, M., et al., "Chemical coding of the human gastrointestinal nervous system: cholinergic, VIPergic, and catecholaminergic phenotypes," The Journal of Comparative Neurology, 2003, 459:90-111, 22 pgs.

Aronson, B.E., et al., "GATA4 represses an ileal program of gene expression in the proximal small intestine by inhibiting the acetylation of histone H3, lysine 27," Biochim, Biophys. Acta, 2014, 1839(11):1273-1282, 31 pgs.

Arora, N., et al., "A process engineering approach to increase organoid yield," Development, 2017, 144:1128-1136, 9 pgs.

Arroyo, J.D., et al., "Argonaute2 complexes carry a population of circulating microRNAs independent of vesicles in human plasma," PNAS, 2011, 108(12):5003-5008, 6 pgs.

Asai, A., et al. "Paracrine signals regulate human liver organoid maturation from induced pluripotent stem cells," Development, 2017, 144:1056-1064, 30 pgs.

Aurora, M., et al., "hPSC-derived lung and intestinal organoids as models of human fetal tissue," Developmental Biology, 2016, 420:230-238, 9 pgs.

Avansino, J.R., et al., "Orthotopic transplantation of intestinal mucosal organoids in rodents," Surgery, Sep. 2006, 140(3):423-434, XP005610494, 12 pgs.

Baetge, G., et al., "Transient catecholaminergic (TC) cells in the vagus nerves and bowel of fetal mice: relationship to the development of enteric neurons," Developmental Biology, 1989, 132:189-211, 23 pgs.

Bahar Halpern, K., et al. "Single-cell spatial reconstruction reveals global division of labour in the mammalian liver," Nature, 2017, 542:352-356, 18 pgs.

Bajpai, R., et al., "CHD7 cooperates with PBAF to control multipotent neural crest formation," Nature, Feb. 18, 2010, 463:958-962, 7 pgs.

Bansal, D., et al., "An ex-vivo human intestinal model to study *Entamoeba histolytica* Pathogenesis," PLoS Neglected Tropical Diseases, Nov. 2009, 3(11):e551.

Baptista, P.M., et al., "The Use of Whole Organ Decellularization for the Generation of a Vascularized Liver Organoid," Hepatology, 2011, 53(2):604-617, 14 pgs.

Bar-Ephraim, Y.E., et al., "Modelling cancer immunomodulation using epithelial organoid cultures," bioRxiv, 2018, accessed from Http://dx.doi.org/10.1101/377655v1.full, 13 pgs.

Barker, N., et al., "Lgr5$^{+ve}$ Stem Cells Drive Self-Renewal in the Stomach and Build Long-Lived Gastric Units In Vitro," Cell Stem Cell, 2010, 6:25-36, 12 pgs.

Barker, N., et al., "Tissue-Resident Adult Stem Cell Populations of Rapidly Self-Renewing Organs," Cell Stem Cell, Dec. 2010, 7:656-670, 15 pgs.

Barlow, A.J., et al., "Critical numbers of neural crest cells are required in the pathways from the neural tube to the foregut to ensure complete enteric nervous system formation," Development, 2008, 135:1681-1691, 11 pgs.

Bartfeld, S., et al., "In Vitro Expansion of Human Gastric Epithelial Stem Cells and Their Responses to Bacterial Infection," Gastroenterology, Jan. 2015, 148(1):126-136, 22 pgs.

Bartfeld, S., et al., "Stem cell-derived organoids and their application for medical research and patient treatment," J Mol Med, 2017, 95:729-738, 10 pgs.

Barth, C.A., et al., "Transcellular transport of fluorescein in hepatocyte monolayers: Evidence for functional polarity of cells in culture," Proc Natl Acad Sci USA, 1982, 79:4985-4987, 3 pgs.

Bastide, P., et al. "Sox9 regulates cell proliferation and is required for Paneth cell differentiation in the intestinal epithelium," JCB, 2007, 178(4), pp. 635-648, 14 pgs.

Battle, M.A., et al., "GATA4 is essential for jejunal function in mice," Gastroenterology, 2008, 135:1676-1686, 17 pgs.

Baumann, K., "Colonic organoids for drug testing and colorectal disease modelling," Nature Reviews Molecular Cell Biology, Jul. 2017, 1 pg.

Beck, F., et al., "Expression of Cdx-2 in the mouse embryo and placenta: possible tole in patterning of the extra-embryonic membranes," Dev Dyn, 1995, 204:219-227.

Begriche, K., et al., "Drug-induced toxicity on mitochondria and lipid metabolism: Mechanistic diversity and deleterious consequences for the liver," J Hepatol, 2011, 54:773-794, 22 pgs.

Bell, L.N., et al., "Epidemiology of Idiosyncratic Drug-Induced Liver Injury," Semin Liver Dis, 2009, 29(4):337-347, 11 pgs.

Bergeles, C., et al., "From Passive Tool Holders to Microsurgeons: Safer, Smaller, Smarter Surgical Robots," IEEE Trans Biomed Eng, 2014, 61(5):1565-1576, 12 pgs.

Bergner, A.J., et al., "Birthdating of myenteric neuron subtypes in the small intestine of the mouse," The Journal of Comparative Neurology, 2014, 522:514-527, 14 pgs.

Bernardi, P., "The permeability transition pore. Control points of a cyclosporin A-sensitive mitochondrial channel involved in cell death," Biochim Biophys Acta, 1996, 1275:5-9, 5 pgs.

Bernstein, B.E., et al., "The NIH Roadmap Epigenomics Mapping Consortium," Nat Biotechnol. 2010; 28(10):1045-1048, 9 pgs.

Beuling, E., et al., "Co-Localization of Gata4 and Hnfla in the Gastrointestinal Tract is Restricted to the Distal Stomach and Proximal Small Intestine," Gastroenterology, AGA Abstracts, Abstract T1933, 2007a, 132:A586, 1 pg.

Beuling, E., et al., "Conditional Gata4 deletion in mice induces bile acid absorption in the proximal small intestine," Gut, 2010, 59(7):888-895, 19 pgs.

Beuling, E., et al., "Fog Cofactors Partially Mediate Gata4 Function in the Adult Mouse Small Intestine," Gastroenterology, AGA Abstracts, Abstract W1467, 2007b, 132:A692-A693, 2 pgs.

Beuling, E., et al., "GATA4 mediates gene repression in the mature mouse small intestine through interactions with Friend of GATA (FOG) cofactors," Dev Biol, 2008a, 322(1):179-189, 23 pgs.

Beuling, E., et al., "The Absence of GATA4 in the Distal Small Intestine Defines the Ileal Phenotype," Gastroenterology, ABA Abstract, Abstract 602, 2008b, 134:A83-A84, 2 pgs.

Bharadwaj, S., et al., "Current status of intestinal and multivisceral transplantation," Gastroentrerol Rep (Oxf)., 2017, 5(1):20-28, 9 pgs.

Bhutani, N., et al., Reprogramming towards pluripotency requires AID-dependent DNA demethylation, Nature, 2010, 463(7284):1042-1047, 17 pgs.

Bitar, K.N., et al., "Intestinal Tissue Engineering: Current Concepts and Future Vision of Regenerative Medicine in the Gut," Neurogastroenterol Motil., Jan. 2012, 24(1):7-19, 20 pgs.

Blaugrund, E., et al., "Distinct subpopulations of enteric neuronal progenitors defined by time of development, sympathoadrenal lineage markers and Mash-1-dependence," Development 122, 1996, 309-320, 12 pgs.

Bohan, T.P., et al., "Effect of L-carnitine treatment for valproate-induced hepatotoxicity," Neurology, 2001, 56:1405-1409, 5 pgs.

Bohorquez, D.V., et al., "An Enteroendocrine Cell—Enteric Glia Connection Revealed by 3D Electron Microscopy," PLoS One, Feb. 2014, 9(2):e89881, 13 pgs.

Bonilla-Claudio, M., et al., "Bmp signaling regulates a dose-dependent transcriptional program to control facial skeletal development," Development, 2012, 139:709-719, 11 pgs.

(56) References Cited

OTHER PUBLICATIONS

Boroviak, T., et al., "Single cell transcriptome analysis of human, marmoset and mouse embryos reveals common and divergent features of preimplantation development," Development, 2018, 145(21):dev167833, 35 pgs.
Bort, R., et al., "Diclofenac Toxicity to Hepatocytes: A Role for Drug Metabolism in Cell Toxicity," J Pharmacol Exp Ther, 1998, 288(1):65-72, 8 pgs.
Bosse, T., et al., "Gata4 and Hnf1α are partially required for the expression of specific intestinal genes during development," Am J Physiol Gastrointest Liver Physiol, 2007, 292:G1302-G1314, 13 pgs.
Bouchi, R., et al., "FOXO1 Inhibition Yields Functional Insulin-Producing Cells In Human Gut Organoid Cultures," Nat Commun, 2014, 5:4242, 24 pgs.
Boullata, J.I., et al. "A.S.P.E.N. Clinical Guidelines: Parenteral Nutrition Ordering, Order Review, Compounding, Labeling, and Dispensing," J Parenter Enteral Nutr, 2014, 38(3):334-377, 44 pgs.
Bragdon, B., et al., "Bone Morphogenetic Proteins: A critical review," Cellular Signalling, 2011, 23:609-620, 12 pgs.
Bravo, P., et al., "Efficient In Vitro Vectorial Transport of a Fluorescent Conjugated Bile Acid Analogue by Polarized Hepatic Hybrid WIF-B and WIF-B9 Cells," Hepatology, 1998, 27:576-583, 8 pgs.
Brevini, T.A.L., et al., "No. shortcuts to pig embryonic stem cells," Theriogenology, 2010, 74:544-550, 7 pgs.
Broda, T.R., et al., "Generation of human antral and fundic gastric organoids from pluripotent stem cells," Nature Protocols, Nov. 2018, 14(1):28-50, 23 pgs., XP036660403.
Browning, J.D., et al., "Molecular mediators of hepatic steatosis and liver injury," J Clin Invest, 2004, 114(2):147-152, 6 pgs.
Bruens, L., et al., "Expanding the Tissue Toolbox: Deriving Colon Tissue from Human Pluripotent Stem Cells," Cell Stem Cell, Jul. 2017, 21(1):3-5, 3 pgs.
Brugmann, S.A., et al., "Building additional complexity to in vitro-derived intestinal tissues," Stem Cell Research & Therapy, 2013, 4(Suppl 1):S1, 5 pgs.
Burke, P., et al., "Towards a single-chip, implantable RFID system: is a single-cell radio possible?" Biomed Microdevices, 2010, 12:589-596, 8 pgs.
Burn, S.F., et al., "Left-right asymmetry in gut development: what happens next?" BioEssays, 2009, 31:1026-1037, 12 pgs.
Burnicka-Turek, O., et al., "INSL5-Deficient Mice Display an Alteration in Glucose Homeostasis and an Impaired Fertility," Endocrinology, Oct. 2012, 153(10):4655-4665, 11 pgs.
Burns, A.J., et al., "In ovo transplantation of enteric nervous system precursors from vagal to sacral neural crest results in extensive hindgut colonisation," Development, 2002, 129:2785-2796, 12 pgs.
Burns, A.J., et al., "Neural stem cell therapies for enteric nervous system disorders," Nature Reviews/Gastroenterology & Hepatology, May 2014, 11:317-328, 12 pgs.
Buta, C., et al., "Reconsidering pluripotency tests: Do we still need teratoma assays?" Stem Cell Research, 2013, 11:552-562, 11 pgs.
Cabezas, J., et al., "Nonalcoholic Fatty Liver Disease: A Pathological View," Chapter 8, in *Liver Biopsy—Indications, Procedures, Results*, N. Tagaya (Ed.), InTechOpen, Nov. 21, 2012, pp. 161-188, 29 pgs., ISBN 978-953-51-0853-5.
Campbell, F.C., et al., "Transplantation of cultured small bowel enterocytes," Gut, 1993, 34:1153-1155, 4 pgs.
Caneparo, L., et al., "Intercellular Bridges in Vertebrate Gastrulation," PloS ONE, 2011, 6(5):e20230, 6 pgs.
Cao, L., et al., "Development of Intestinal Organoids as Tissue Surrogates: Cell Composition and the Epigenetic Control of Differentiation," Molecular Carcinogenesis, 2015, 54:189-202, 14 pgs.
Capeling, M.M., et al., "Nonadhesive Alginate Hydrogels Support Growth of Pluripotent Stem Cell-Derived Intestinal Organoids," Stem Cell Reports, Feb. 2019, 12(2):381-394, 14 pgs.
Chai, P.R., et al., "Utilizing an Ingestible Biosensor to Assess Real-Time Medication Adherence," J Med Toxicol, 2015, 11:439-444, 6 pgs.

Chai, P.R., et al., "Ingestible Biosensors for Real-Time Medical Adherence Monitoring: MyTMed," Proc Annu Hawaii Int Conf Syst Sci, Jan. 2016, 2016:3416-3423, 12 pgs.
Chang, H-M., et al., "BMP15 Suppresses Progesterone production by Down-Regulating StAR via ALK3 in Human Granulosa Cells," Molecular Endocrinology, 2013, 27:2093-2104, 12 pgs.
Chang, J.H., et al., "Evaluating the In Vitro Inhibition of UGT1A1, OATP1B1, OATP1B3, MRP2, and BSEP in Predicting Drug-Induced Hyperbilirubinemia," Mol Pharm, 2013, 10:3067-3075, 9 pgs.
Chatterjee, S., et al., "Hepatocyte-based in vitro model for assessment of drug-induced cholestasis," Toxicol Appl Pharmacol, 2014, 274:124-136, 13 pgs.
Chen, B., et al., "Dynamic Imaging of Genomic Loci in Living Human Cells by an Optimized CRISPR/Cas System," Cell, 2013, 155(7):1479-1491, 23 pgs.
Chen, C., et al., "Pdx1 inactivation restricted to the intestinal epithelium in mice alters duodenal gene expression in enterocytes and enteroendocrine cells," Am. J. Physiol. Gastrointest. Liver Pyshiol., 2009, 297:G1126-G1137, 12 pgs.
Chen, L.Y., et al., "Mass fabrication and delivery of 3D multilayer µTags into living cells," Sci Rep, 2013, 3:2295, 6 pgs.
Chen, T-W., et al., "Ultrasensitive fluorescent proteins for imaging neuronal activity," Nature, Jul. 18, 2013, 499:295-300, 8 pgs.
Chen, Y., et al., "Retinoic acid signaling is essential for pancreas development and promotes endocrine at the expense of exocrine cell differentiation in *Xenopus*," Dev Biol, 2004, 271:144-160, 17 pgs.
Cheng, X., et al., "Self-renewing endodermal progenitor lines generated from human pluripotent stem cells," Cell Stem Cell, Apr. 6, 2012, 10:371-384, 14 pgs.
Choi, E., et al., "Cell lineage distribution atlas of the human stomach reveals heterogeneous gland populations in the gastric antrum," *Gut*, 2014, 63(11):1711-1720, 20 pgs.
Choi, E., et al., "Expression of Activated Ras in Gastric Chief Cells of Mice Leads to the Full Spectrum of Metaplastic Lineage Transitions," Gastroenterology, Apr. 2016, 150(4):918-930, 23 pgs.
Christoffersson, J., et al., "Developing organ-on-a-chip concepts using bio-mechatronic design methodology," Biofabrication, 2017, 9:025023, 14 pgs.
Chughlay, M.F., et al., "N-acetylcysteine for non-paracetamol drug-induced liver injury: a systematic review," Br J Clin Pharmacol, 2016, 81:1021-1029, 9 pgs.
Churin, Y., et al., "*Helicobacter pylori* CagA protein targets the c-Met receptor and enhances the motogenic response," J. Cell Biol., 2003, 161:249-255, 7 pgs.
Cieslar-Pobuda, A., et al., The expression pattern of PFKFB3 enzyme distinguishes between induced-pluripotent stem cells and cancer stem cells, Oncotarget, 6(30):29753-29770, 18 pgs.
Clarke, L.L., "A guide to Ussing chamber studies of mouse intestine," Am J Physiol Gastrointest Liver Physiol, 2009, 296:G1151-G1166, 16 pgs.
Clevers, H., "Modeling Development and Disease with Organoids," Cell, Jun. 2016, 165:1586-1597, 12 pgs.
Coghlan, M.P., et al., "Selective small molecule inhibitors of glycogen synthase kinase-3 modulate glycogen metabolism and gene transcription," Chem. Biol., 2000, 7(10):793-803, 11 pgs.
Collier, A.J., et al., "Comprehensive Cell Surface Protein Profiling Identifies Specific Markers of Human Naïve and Primed Pluripotent States," Cell Stem Cell, 2017, 20:874-890, 25 pgs.
Correia, C., et al., "Combining Hypoxia and Bioreactor Hydrodynamics Boosts Induced Pluripotent Stem Cell Differentiation Towards Cardiomyocytes," Stem Cell Rev and Rep, 2014, 10:786-801, 16 pgs.
Cortez, et al., "Transplantation of human intestinal organoids into the mouse mesentery: A more physiological and anatomic engraftment site," Surgery, 2018, 164:643-650, 8 pgs.
Costa, M., et al., "A method for genetic modification of human embryonic stem cells using electroporation," Nature Protocols, Apr. 5, 2007, 2:792-796, 5 pgs.
Couzin, J., "Small RNAs Make Big Splash," Science, 2002, 298:2296-2297, 2 pgs.

(56) References Cited

OTHER PUBLICATIONS

Covacci, A., et al., "Molecular characterization of the 128-kDa immunodominant antigen of *Helicobacter pylori* associated with cytotoxicity and duodenal ulcer," Proc Natl Acad Sci USA, Jun. 1993, 90:5791-5795, 5 pgs.
Crespo, M., et al., "Colonic organoids derived from human induced pluripotent stem cells for modeling colorectal cancer and drug testing," Nature Medicine, 2017, 23(7):878-884, 11 pgs.
Crocenzi, F.A., et al., "$Ca^{2+}$-Dependent Protein Kinase C Isoforms Are Critical to Estradiol 17β-D-Glucuronide-Induced Cholestasis in the Rat," Hepatology, 2008, 48:1885-1895, 12 pgs.
Curchoe, C.L., et al., "Early acquisition of neural crest competence during hESCs neuralization," PloS One, Nov. 2010, 5:1-17, 17 pgs.
Cutrin, J.C., et al., "Reperfusion Damage to the Bile Canaliculi in Transplanted Human Liver," Hepatology, 1996, 24:1053-1057, 5 pgs.
D'Amour, K.A., et al., "Efficient differentiation of human embryonic stem cells to definitive endoderm," Nature Biotechnology, 2005, 23(12):1534-1541, 8 pgs.
Dahl, A., et al., "Translational Regenerative Medicine—Hepatic Systems," Chapter 34, Clinical Aspects of Regenerative Medicine, eds. A. Atala, M.D. and J. Allickson, PhD, Elsevier, Inc., 2015, pp. 469-484, 16 pgs.
D'Amour, K.A., et al., "Efficient differentiation of human embryonic stem cells to definitive endoderm," Nature Biotechnology, 2005, 23:1534-1541, 8 pgs.
D'Amour, K.A., et al., "Production of pancreatic hormone-expressing endocrine cells from human embryonic stem cells," Nat Biotechnol, 206, 24:1392-1401, 10 pgs.
Das, R., "RFID Forecasts, Players and Opportunities 2017-2027," IDTechEx, 2017, downloaded from https://www.idtechex.com/en/research-report/rfid-forecasts-players-and-opportunities-2017-2027/546, 8 pgs. Summary only.
Dash, A., et al., "Pharmacotoxicology of clinically-relevant concentrations of obeticholic acid in an organotypic human hepatocyte system," Toxicology In Vitro, 2017, 39:93-103, 11 pgs.
Date, S., et al., "Mini-Gut Organoids: Reconstitution of the Stem Cell Niche," Annual Review of Cell and Developmental Biology, Nov. 2015, 31:269-289.
Davenport, C., et al., "Anterior-Posterior Patterning of Definitive Endoderm Generated from Human Embryonic Stem Cells Depends on the Differential Signaling of Retinoic Acid, Wnt-, and BMP-Signaling," Stem Cells, 2016, 34:2635-2647, 13 pgs.
Davidson, M.D., et al., "Long-term exposure to abnormal glucose levels alters drug metabolism pathways and insulin sensitivity in primary human hepatocytes," Sci Rep, 2016, 6:28178, 11 pgs.
De Santa Barbara, P., et al., "Bone Morphogenetic Protein Signaling Pathway Plays Multiple Roles During Gastrointestinal Tract Development," Developmental Dynamics, 2005, 234:312-322, 11 pgs.
De Santa Barbara, P., et al., "Development and differentiation of the intestinal epithelium," Cell Mol Life Sci, 2003, 60(7):1322-1332, 11 pgs.
Dedhia, P.H., et al., "Organoid Models of Human Gastrointestinal Development and Disease," Gastroenterology, 2016, 150:1098-1112, 15 pgs.
Dekaney, C.M., et al., "Expansion of intestinal stem cells associated with long-term adaptation following ileocecal resection in mice," Am J Physiol Gastrointest Liver Physiol, Sep. 13, 2007, 293:G1013-G1022, 10 pgs.
Dekkers, J.F., et al., "A functional CFTR assay using primary cystic fibrosis intestinal organoids," Nat Med, 2013, 19(7):939-945, 9 pgs.
Demehri, F.R., et al., "Development of an endoluminal intestinal attachment for clinically applicable distraction enterogenesis device," Journal of Pediatric Surgery, 2016, 51:101-106, 6 pgs.
Demehri, F.R., et al., "Development of an endoluminal intestinal lengthening device using a geometric intestinal attachment approach," Surgery, 2015, 158(3):802-811, 10 pgs.
Deng, H., "Mechanisms of retinoic acid on the induction of differentiation of neural stem cells for newborn rat striatum," Chinese Doctoral and Master Dissertations Full-Text Database (Doctoral) Basic Science, Issue 4, Apr. 15, 2006, pp. 1-89. [Reference unavailable, citing referencing Search Report, 3 pgs.].
Deng, H., et al., "Effects of all-trans retinoic acid on the differentiation of neural stem cells and the expression of c-myc gene," Chinese Journal of Tissue Engineering Research, Mar. 18, 2007, 11(11):2039-2042. [Reference unavailable, citing referencing Search Report, 3 pgs.].
Denham, M., et al., "Multipotent caudal neural progenitors derived from human pluripotent stem cells that give rise to lineages of the central and peripheral nervous system," Stem Cells, Mar. 5, 2015, 33:1759-1770, 12 pgs.
Dessimoz, J., et al., "FGF signaling is necessary for establishing gut tube domains along the anterior-posterior axis in vivo," Mech Dev, 2006, 123:42-55, 14 pgs.
Deward, A.D., et al., "Cellular Heterogeneity in the Mouse Esophagus Implicates the Presence of a Nonquiescent Epithelial Stem Cell Population," Cell Reports, 2014, 9:701-711, 12 pgs.
Discher, D.E., et al., "Growth Factors, Matrices, and Forces Combine and Control Stem Cells," Science, Jun. 2009, 324:1673-1677, 5 pgs.
Dobreva, G., et al., "SATB2 Is a Multifunctional Determinant of Craniofacial Patterning and Osteoblast Differentiation," Cell, 2006, 125:971-986, 16 pgs.
Driver, I., et al., "Specification of regional intestinal stem cell identity during Drosophila metamorphosis," Development, 2014, 141:1848-1856, 9 pgs.
Duluc, I., et al., "Fetal Endoderm Primarily Holds the Temporal and Positional Information Required for Mammalian Intestinal Development," The Journal of Cell Biology, 1994, 126(1):211-221, 11 pgs.
Dumortier, G., et al., "Tolérance hépatique des antipsychotiques atypiques, [Hepatic tolerance of atypical antipsychotic drugs]," L'Encéphale, 2002, 28(1):542-551, 10 pgs.
Dvir-Ginzberg, M., et al., "Liver Tissue Engineering Within Alginate Scaffolds: Effects of Cell-Seeding Density on Hepatocyte Viability, Morphology, and Function," Tissue Eng, 2003, 9(4):757-766, 10 pgs.
Eberhard, J., et al., "A cohort study of the prognostic and treatment predictive value of SATB2 expression in colorectal cancer," British Journal of Cancer, 2012, 106:931-938, 8 pgs.
Edling, Y., et al., "Increased sensitivity for troglitazone-induced cytotoxicity using a human in vitro co-culture model," Toxicol In Vitro, 2009, 23:1387-1395, 9 pgs.
Eicher, A.K., et al., "Translating Developmental Principles to Generate Human Gastric Organoids," Cellular and Molecular Gastroenterology and Hepatology, 2018, 5(3):353-363, 11 pgs.
Ekser, B., et al., "Comparable outcomes in intestinal retransplantation: Single-center cohort study," The Journal of Clinical and Translational Research, 2018, 32(7):e13290, 10 pgs.
Elbashir, S.M., et al., "Functional anatomy of siRNAs for mediating efficient RNAi in *Drosophila melanogaster* embryo lysate," EMBO J., 2001, 20(23):6877-6888, 12 pgs.
El Kasmi, K.C., et al., "Phytosterols Promote Liver Injury and Kupffer Cell Activation in Parenteral Nutrition-Associated Liver Disease," Sci Transl Med, 2013, 5(206):206ra137, 10 pgs.
El Taghdouini, A., et al., "In vitro reversion of activated primary human hepatic stellate cells," Fibrogenesis & Tissue Repair, 2015, 8:14, 15 pgs.
The Encode Project Consortium, "An integrated encyclopedia of DNA elements in the human genome," Nature, 2012, 489:57-74, 18 pgs.
Engmann, J., et al., "Fluid mechanics of eating, swallowing and digestion—overview and perspectives," Food & Function, 2013, 4:443-447, 5 pgs.
Evans, M.J et al., "Establishment in culture of pluripotent cells from mouse embryos," Nature, 1981, 292(5819): 154-156, 3 pgs.
Ezashi, T., et al., "Low $O_2$ tensions and the prevention of differentiation of hES cells," PNAS, Mar. 2005, 102(13):4783-4788, 6 pgs.
Fagerberg, L., et al., "Analysis of the Human Tissue-specific Expression by Genome-wide Integration of Transcriptomics and Antibody-based Proteomics," Mol Cell Proteomics, 2014, 13:397-406, 10 pgs.

(56) References Cited

OTHER PUBLICATIONS

Fahrmayr, C., et al., "Phase I and II metabolism and MRP2-mediated export of bosentan in a MDCKII-OATP1B1-CYP3A4-UGT1A1-MRP2 quadruple-transfected cell line," Br J Pharmacol, 2013, 169:21-33, 13 pgs.
Falasca, L., et al., "The effect of retinoic acid on the re-establishment of differentiated hepatocyte phenotype in primary culture," Cell Tissue Res, 1998, 293:337-347, 11 pgs.
Fatehullah, A., et al., "Organoids as an in vitro model of human development and disease," Nature Cell Biology, Mar. 2106, 18(3):246-254, 9 pgs.
Finkbeiner, S.R., et al., "A Gutsy Task: Generating Intestinal Tissue from Human Pluripotent Stem Cells," Dig Dis Sci, 2013, 58:1176-1184, 9 pgs.
Finkbeiner, S.R., et al., "Stem Cell-Derived Human Intestinal Organoids as an Infection Model for Rotaviruses," mBio, Jul./Aug. 2012, 3(4):e00159-12, 6 pgs.
Finkbeiner, S.R., et al., "Transcriptome-wide Analysis Reveals Hallmarks of Human Intestine Development and Maturation In Vitro and In Vivo," Stem Cell Reports, 2015, 4:1140-1155, 16 pgs.
Finkenzeller, K., *RFID Handbook: Fundamentals and Applications in Contactless Smart Cards, Radio Frequency Identification and Near-Field Communication, Third Edition*. John Wiley & Sons, Ltd., Chichester, West Sussex, 2010, 8 pgs. (Table of Contents Only).
Fisher, A., et al., "Entacapone-Induced Hepatotoxicity and Hepatic Dysfunction," Mov Disord, 2002, 17:1362-1365, 4 pgs.
Fitzpatrick, D.R., et al., "Identification of SATB2 as the cleft palate gene on 2q32-q33," Human Molecular Genetics, 2003, 12(19):2491-2501, 11 pgs.
Fon Tacer, K., et al., "Research Resource: Comprehensive Expression Atlas of the Fibroblast Growth Factor System in Adult Mouse," Mol Endocrinol, Oct. 2010, 24(10):2050-2064, 15 pgs.
Fordham, R.P., et al., "Transplantation of expanded fetal intestinal progenitors contributes to colon regeneration after injury," Cell Stem Cell, Dec. 5, 2013, 13:734-744, 11 pgs.
Fromenty, B., "Drug-induced liver injury in obesity," J Hepatol, 2013, 58:824-826, 3 pgs.
Fu, M., et al., "Embryonic development of the ganglion plexuses and the concentric layer structure of human gut: a topographical study," Anatomy and Embryology, Feb. 27, 2004, 208:33-41, 10 pgs.
Fu, M., et al., "HOXB5 Expression is Spatially and Temporarily Regulated in Human Embryonic Gut During Neural Crest Cell Colonization and Differentiation of Enteric Neuroblasts," Developmental Dynamics, 2003, 228:1-10, 10 pgs.
Furness, J.B., "The enteric nervous system and neurogastroenterology," Nature Reviews/Gastroenterology & Hepatology, May 2012, 9:286-294, 9 pgs.
Gafni, O., et al., "Derivation of novel human ground state naïve pluripotent stem cells," Nature, 2013, 504:282-286, 20 pgs.
Geerts, A., et al., "Formation of Normal Desmin Intermediate Filaments in Mouse Hepatic Stellate Cells Requires Vimentin," Hepatology, 2001, 33:177-188, 12 pgs.
Genthe, J.R., et al., "Ventromorphins: A new class of small molecule activators of the canonical BMP signaling pathway," ACS Chem Biol, 2017, 12(9):2436-2447, 21 pgs.
Georgas, K.M., et al., "An illustrated anatomical ontology of the developing mouse lower urogenital tract," Development, 2015, 142:1893-1908, 16 pgs.
Gerdes, H-H., et al., "Tunneling nanotubes, an emerging intercellular communication route in development," 2013, 130:381-387, 7 pgs.
Gessner, R.C., et al., "Functional ultrasound imaging for assessment of extracellular matrix scaffolds used for liver organoid formation," Biomaterials, 2013, 34:9341-9351, 11 pgs.
Giles, D.A., et al., "Thermoneutral housing exacerbates nonalcoholic fatty liver disease in mice and allows for sex-independent disease modeling," Nature Medicine, 2017, 23(7):829-838, 13 pgs.
Ginestet, C., Book Review in the Journal of the Royal Statistical Society. Series A (Statistics in Society) (2011), of *ggplot2: Elegant Graphics for Data Analysis*, by H. Wickham, 2009; 174(1):245, 2 pgs.
Glorioso, J.M., et al., "Pivotal Preclinical Trial of the Spheroid Reservoir Bioartificial Liver," J Hepatol, 2015, 63(2):388-398, 27 pgs.
Goldenring, J.R., et al., "Differentiation of the Gastric Mucosa: III. Animal models of oxyntic atrophy and metaplasia," Am J Physiol Gastrointestinal and Liver Physiol, 2006, 291:G999-G1004, 6 pgs.
Goldenring, J.R., et al., "Overexpression of Transforming Growth Factor-α Alters Differentiation of Gastric Cell Lineages," Dig. Dis. Sci., 1996, 41(4):773-784, 12 pgs.
Gomez, M.C., et al., "Derivation of cat embryonic stem-like cells from in vitro- produced blastocysts on homologous and heterologous feeder cells," Theriogenology, 2010, 74:498-515, 18 pgs.
Gomez-Pinilla, P.J., et al., "Ano1 is a selective marker of interstitial cells of Cajal in the human and mouse gastrointestinal tract," Am J Physiol Gastrointest Liver Physiol, 2009, 296:G1370-G1381, 12 pgs.
Gori, M., et al., "Investigating Nonalcoholic Fatty Liver Disease in a Liver-on-a-Chip Microfluidic Device," PLoS One, Jul. 2016, 11(7):e0159729, 15 pgs.
Gouon-Evans, V., et al., "BMP-4 is required for hepatic specification of mouse embryonic stem cell-derived definitive endoderm," Nature Biotechnology, Nov. 2006, 24(11):1402-1411, 10 pgs.
Gracz, A.D., et al., "Brief report: CD24 and CD44 mark human intestinal epithelial cell populations with characteristics of active and facultative stem cells," Stem Cells, Apr. 4, 2013, 31:2024-2030, 7 pgs.
Gracz, A.D., et al., "Sox9 Expression Marks a Subset of CD24-expressing Small Intestinve Epithelial Stem Cells the Form Organoids in vitro," Am J Physiol Gastrointest Liver Physiol, 2010, 298:G590-600.
Gradwohl, G., et al., "neurogenin3 is required for the development of the four endocrine cell lineages of the pancreas," Proc Natl Acad Sci USA, 2000, 97:1607-1611, 5 pgs.
Grapin-Botton, A., "Three-dimensional pancreas organogenesis models," Diabetes Obes Metab, 2016, 18(Suppl 1):33-40, 8 pgs.
Green, M.D., et al., "Generation of anterior foregut endoderm from human embryonic and induced pluripotent stem cells," Nature Biotechnology, Mar. 2011, 29(3):267-272, 7 pgs.
Gregersen, H., et al., "The Zero-Stress State of the Gastrointestinal Tract: Biomechanical and Functional Implications," Digestive Diseases and Sciences, 2000, 45(12):2271-2281, 11 pgs.
Gregorieff, A., et al., "Wnt signaling in the intestinal epithelium: from endoderm to cancer," Genes & Dev., 2005, 19:877-890, 15 pgs.
Groneberg, D.A., et al., "Intestinal peptide transport: ex vivo uptake studies and localization of peptide carrier PEPT1," Am J Physiol Gastrointest Liver Physiol, Sep. 2001, 281:G697-G704, 8 pgs.
Grosse, A.S., et al., "Cell dynamics in fetal intestinal epithelium: implications for intestinal growth and morphogenesis," Development, 2011, 138:4423-4432, 10 pgs.
Guilak, F., et al., "Control of Stem Cell Fate by Physical Interactions with the Extracellular Matrix," Cell Stem Cell, Jul. 2009, 5:17-26, 10 pgs.
Guo, G., et al., "Epigenetic resetting of human pluripotency," Development, 2017, 144:2748-2763, 17 pgs.
Guo, Z., et al., "Injury-induced BMP signaling negatively regulates Drosophila midgut homeostasis," J Cell Biol., 2013, 201(6):945-961, 17 pgs.
Gurdon, J.B., "Adult Frogs Derived from the Nuclei of Single Somatic Cells," Dev Biol, 1962, 4:256-273, 18 pgs.
Gurken, A., "Advances in small bowel transplantation," Turk J Surg., 2017, 33(3):135-141, 7 pgs.
Gyorgy, A.B., et al., "SATB2 interacts with chromatin-remodeling molecules in differentiating cortical neurons" European Journal of Neuroscience, 2008, 27:865-873, 9 pgs.
Haimovich, G., et al., "Intercellular mRNA trafficking via membrane nanotube-like extensions in mammalian cells," 2017, PNAS, pp. E9873-E9882, 10 pgs.

(56) References Cited

OTHER PUBLICATIONS

Han, B., et al., "Microbiological safety of a novel bio-artificial liver support system based on porcine hepatocytes: a experimental study," European Journal of Medical Research, 2012, 17:13, 8 pgs.
Han, M-E., et al., "Gastric stem cells and gastric cancer stem cells," Anatomy & Cell Biology, 2013, 46:8-18, 11 pgs.
Hannan, N.R.F., et al., "Generation of Multipotent Foregut Stem Cells from Human Pluripotent Stem Cells," Stem Cell Reports, Oct. 2013, 1:293-306, 14 pgs.
Hannon, G.J., "RNA interference," Nature, 2002, 418:244-251, 8 pgs.
Hao, M.M., et al., "Development of enteric neuron diversity," J. Cell. Mol. Med., 2009 13:1193-1210, 18 pgs.
Haramis, A-P.G., et al., "De Novo Crypt Formation and Juvenile Polyposis on BMP Inhibition in Mouse Intestine," Science, 2004, 303:1684-1686, 4 pgs.
Hardwick, J.C.H., et al., "Bone Morphogenetic Protein 2 Is Expressed by, and Acts Upon, Mature Epithelial Cells in the Colon," Gastroenterology, 2004, 126:111-121, 11 pgs.
Hardy, T., et al., "Nonalcoholic fatty liver disease: new treatments," Curr Opin Gastroenterol, May 2015, 31(3):175-183, 9 pgs.
Hassan, W., et al., "Reduced Oxidative Stress Contributes to the Lipid Lowering Effects of Isoquercitrin in Free Fatty Acids Induced Hepatocytes," Oxid Med Cell Longev, 2014, 313602, 18 pgs.
Haveri, H., et al., "Transcription factors GATA-4 and GATA-6 in normal and neoplastic human gastrointestinal mucosa," BMC Gastroenterology, 2008, 8:9, 13 pgs.
He, X.C., et al., "BMP signaling inhibits intestinal stem cell self-renewal through suppression of Wnt-β-catenin signaling," Nature Genetics, 2004, 36(10):1117-1121, 5 pgs.
Heidari, R., et al., "Factors affecting drug-induced liver injury: antithyroid drugs as instances," Clin Mol Hepatol, 2014, 20:237-248, 12 pgs.
Hernandez, F., et al., "Refining Indications for Intestinal Retransplantation," International Small Bowel Symposium 2013; Abstract 12.241 (online: https://www.tts.org/component/%20tts/?view=presentation&id=13241) Accessed Jun. 12, 2017, 3 pgs.
Higuchi, Y., et al., "Gastrointestinal Fibroblasts Have Specialized, Diverse Transcriptional Phenotypes: A Comprehensive Gene Expression Analysis of Human Fibroblasts," PloS One, Jun. 2015, 10(6):e0129241, 19 pgs.
Hockemeyer, D., et al., "Genetic engineering of human ES and iPS cells using TALE nucleases," Nat Biotechnol., 2012, 29:731-734, 8 pgs.
Hoffmann, W., "Current Status on Stem Cells and Cancers of the Gastric Epithelium," Int. J. Mol. Sci., 2015, 16:19153-19169, 17 pgs.
Holland, P.W.H., et al., "Classification and nomenclature of all human homeobox genes," BMC Biology, 2007, 5:47, 29 pgs.
Hooton, D., et al., "The Secretion and Action of Brush Border Enzymes in the Mammalian Small Intestine," Rev Physiol Biochem Pharmacol, 2015, 168:59-118, 60 pgs.
Hou, P., et al., "Pluripotent Stem Cells Induced from Mouse Somatic Cells by Small-Molecule Compounds," Science, 2013, 341:651-654, 4 pgs.
Howell, J.C., et al., "Generating intestinal tissue from stem cells: potential for research and therapy," Regen Med., 6(6):743-755, 22 pgs.
Hsu, F., et al., "The UCSC Known Genes," Bioinformatics, 2006, 22(9):1036-1046, 11 pgs.
Hu, H., et al., "Long-Term Expansion of Functional Mouse and Human Hepatocytes as 3D Organoids," Cell, 2018, 175:1591-1606, 36 pgs.
Hu, X., et al., "Micrometer-Scale Magnetic-Resonance-Coupled Radio-Frequency Identification and Transceivers for Wireless Sensors in Cells," Physical Review Applied, 2017, 8:014031, 13 pgs.
Huch, M., et al., "Lgr5+ liver stem cells, hepatic organoids and regenerative medicine," Regen. Med., 2013, 8(4):385-387, 3 pgs.
Huch, M., et al., "Long-Term Culture of Genome-Stable Bipotent Stem Cells from Adult Human Liver," Cell, 2015, 160:299-312, 14 pgs.
Huch, M., et al., "Modeling mouse and human development using organoid cultures," Development, 2015, 142:3113-3125, 13 pgs.
Huebsch, N., et al., "Automated video-based analysis of contractility and calcium flux in human-induced pluripotent stem cell-derived cardiomyocytes cultured over different spatial scales," Tissue Engineering: Part C, 2015, 21:467-479, 15 pgs.
Huh, W.J., et al., "Ménétrier's Disease: Its Mimickers and Pathogenesis," Journal of Pathology and Translational Medicine, 2016; 50:10-16, 7 pgs.
Hutvagner, G., et al., "A microRNA in a Multiple-Turnover RNAi Enzyme Complex," Science, Sep. 20, 2002, 297:2056-2060, 6 pgs.
Hynds, R.E., et al., "The relevance of human stem cell-derived organoid models for epithelial translational medicine," Stem Cells, 2013, 31(3):417-422, 11 pgs.
Ijpenberg, A., et al., "Wt1 and retinoic acid signaling are essential for stellate cell development and liver morphogenesis," Dev Biol, 2007, 312:157-170, 14 pgs.
Inoue, H., et al., "iPS cells: a game changer for future medicine," EMBO J, 2014, 33(5):409-417, 9 pgs.
Ito, K., et al., "Temporal Transition of Mechanical Characteristics of HUVEC/MSC Spheroids Using a Microfluidic Chip with Force Sensor Probes," Micromachines, 2016, 7:221, 14 pgs.
Jalan-Sakrikar, N., et al., "Hedgehog Signaling Overcomes an EZH2-Dependent Epigenetic Barrier to Promote Cholangiocyte Expansion," PLoS One, 2016, 11(12):e0168266, 19 pgs.
Jean, C., et al., "Pluripotent genes in avian stem cells," Develop Growth Differ, 2013, 55:41-51, 11 pgs.
Jeejeebhoy, K.N., "Short bowel syndrome: a nutritional and medical approach," CMAJ, 2002, 166(10):1297-1302, 6 pgs.
Jenny, M., et al., "Neurogenin3 is differentially required for endocrine cell fate specification in the intestinal and gastric epithelium," EMBO J, 2002, 21(23):6338-6347, 10 pgs.
Johannesson, M., et al., "FGF4 and Retinoic Acid Direct Differentiation of hESCs into PDX1-Expressing Foregut Endoderm in a Time- and Concentration-Dependent Manner," PL0S One, Mar. 2009, 4(3):1-13, 13 pgs.
Johansson, K.A., et al., "Temporal Control of Neurogenin3 Activity in Pancreas Progenitors Reveals Competence Windows for the Generation of Different Endocrine Cell Types," Dev Cell, 2007, 12:457-465, 9 pgs.
Johnson, L.R., et al., "Stimulation of rat oxyntic gland mucosal growth by epidermal growth factor," Am. J. Physiol., 1980, 238:G45-49, 5 pgs.
Johnston, T.B., et al., "Extroversion of the Bladder, Complicated by the Presence of Intestinal Openings on the Surface of the Extroverted Area," J Anat Physiol, 1913, 48(Pt 1):89-106, 18 pgs.
Jung, P., et al., "Isolation and in vitro expansion of human colonic stem cells," Nature Medicine, Oct. 2011, 17:1225-1227, 3 pgs.
Juno, R.J., et al., "A serum factor after intestinal resection stimulates epidermal growth factor receptor signaling and proliferation in intestinal epithelial cells," Surgery, Aug. 2002, 132:377-383, 7 pgs.
Juno, R.J., et al., "A serum factor(s) after small bowel resection induces intestinal epithelial cell proliferation: effects of timing, site, and extent of resection," Journal of Pediatric Surgery, Jun. 2003, 38:868-874, 7 pgs.
Kabouridis, P.S., et al., "Microbiota controls the homeostasis of glial cells in the gut lamina propria," Neuron, Jan. 21, 2015, 85:289-295, 8 pgs.
Kaji, K., et al., "Virus free induction of pluripotency and subsequent excision of reprogramming factors," Nature, 2009, 458(7239):771-775, 10 pgs.
Kanuri, G., et al., "In Vitro and in Vivo Models of Non-Alcoholic Fatty Liver Disease (NAFLD)," Int J Mol Sci, 2013, 14:11963-11980, 18 pgs.
Karlikow, M., et al., "*Drosophila* cells use nanotube-like structures to transfer dsRNA and RNAi machinery between cells," Scientific Reports, 2016, 6:27085, 9 pgs.
Katoh, M., "WNT Signaling in Stem Cell Biology and Regenerative Medicine," Current Drug Targets, 2008, 9(7):565-570, 6 pgs.

(56) References Cited

OTHER PUBLICATIONS

Kawaguchi, J., et al., "Isolation and propagation of enteric neural crest progenitor cells from mouse embryonic stem cells and embryos," Development, 2010, 137:693-704, 12 pgs.

Kawaguchi, Y., et al., "The role of the transcriptional regulator Ptf1a in converting intestinal to pancreatic progenitors," Nat Genet, 2002, 32:128-134, 7 pgs.

Keeley, T.M., et al., "Cytodifferentiation of the postnatal mouse stomach in normal and Huntingtin-interacting protein 1-related-deficient mice," Am. J. Physiol. Gastrointest. Liver Physiol., 2010, 299:G1241-G1251, 11 pgs.

Keitel, V., et al., "De Novo Bile Salt Transporter Antibodies as a Possible Cause of Recurrent Graft Failure After Liver Transplantation: A Novel Mechanism of Cholestasis," Hepatology, 2009, 50:510-517, 8 pgs.

Kelly, G.M., et al., "Retinoic Acid and the Development of the Endoderm," J Dev Biol, 2015, 3:25-56, 32 pgs.

Keung, A.J., et al., "Presentation Counts: Microenvironmental Regulation of Stem Cells by Biophysical and Material Cues," Annu. Rev. Cell Dev. Biol., 2010, 26:533-556, 26 pgs.

Khan, F.A., et al., "Overview of intestinal and multivisceral transplantation," UpToDate, Sep. 2018 [online: https://www.uptodate.com/contents/overview-of-intestinal-and-multivisceral-transplantation/print], 32 pgs.

Kilens, S., et al., "Parallel derivation of isogenic human primed and naïve induced pluripotent stem cells," Nat Commun, 2018, 9:360, 13 pgs.

Kilpinen, H., et al., "Common genetic variation drives molecular heterogeneity in human iPSCs," Nature, 2017, 546(7658):370-375, 51 pgs.

Kim, B-M., et al., "Regulation of mouse stomach development and Barx1 expression by specific microRNAs," Development, 2011, 138:1081-1086, 6 pgs.

Kim, B-M., et al., "The Stomach Mesenchymal Transcription Factor Barx1 Specifies Gastric Epithelial Identity through Inhibition of Transient Wnt Signaling," Developmental Cell, 2005, 8:611-622, 12 pgs.

Kim, D., et al., "HISAT: a fast spliced aligner with low memory requirements," Nature Methods, 2015, 12(4):357-360, 6 pgs.

Kim, T-H., et al., "Stomach development, stem cells and disease," Development, 2016, 143:554-565, 12 pgs.

Klimanskaya, I., et al., "Human embryonic stem cells derived without feeder cells," Lancet, 2005, 365(9471): 1636-1641, 6 pgs.

Kock, K., et al., "A Perspective on Efflux Transport Proteins in the Liver," Clin Pharmacol Ther, 2012, 92(5):599-612, 29 pgs.

Koehler, E.M., et al., "Presence of Diabetes Mellitus and Steatosis Is Associated With Liver Stiffness In A General Population: The Rotterdam Study," Hepatology, 2016, 63:138-147, 10 pgs.

Kohlnhofer, B.M., et al., "GATA4 Regulates Epithelial Cell Proliferation to Control Intestinal Growth and Development in Mice," Cellular and Molecular Gastroenterology and Hepatology, 2016, 2(2):189-209, 21 pgs.

Koike, M., et al., "Effects of mechanical strain on proliferation and differentiation of bone marrow stromal cell line ST2," J Bone Miner Metab, 2005, 23:219-225, 7 pgs.

Kolahchi, A.R., et al., "Microfluidic-Bases Multi-Organ Platforms for Drug Discovery," Micromachines, 2016, 7(162):1-33, 33 pgs.

Kolodny, G.M., "Evidence for Transfer of Macromolecular RNA Between Mammalian Cells in Culture," Exp Cell Res, 1971, 65:313-324, 12 pgs.

Koo, B-K, et al., "Controlled gene expression in primary *Lgr5* organoid cultures," Nature Methods, Jan. 1, 2012, 9(1):81-83, XP055225249, 5 pgs.

Kordes, C., et al., "Hepatic stellate cells contribute to progenitor cells and liver regeneration," J Clin Invest, 2014, 124(12):5503-5515, 13 pgs.

Kosinski, C., et al., "Indian hedgehog regulates intestinal stem cell fate through epithelial-mesenchymal interactions during development," Gastroenterology, Sep. 2010, 139:893-903, 17 pgs.

Kostrzewski, T., et al., "Three-dimensional perfused human in vitro model of non- alcoholic fatty liver disease," World J Gastroenterol, 2017, 23(2):204-215, 13 pgs.

Kovalenko, P.L., et al., "The Correlation Between the Expression of Differentiation Markers in Rat Small Intestinal Mucosa and the Transcript Levels of Schlafen 3," JAMA Surg., Sep. 4, 2013, 148:1013-1019, 7 pgs.

Krähenbühl, S., et al., "Toxicity of Bile Acids on the Electron Transport Chain of Isolated Rat Liver Mitochondria," Hepatology, 1994, 19:471-479, 9 pgs.

Kraus, M.R.C., et al., "Patterning and shaping the endoderm in vivo and in culture," Current Opinion Genetics & Development., 2012, 22:347-353, 7 pgs.

Krausova, M., et al., "Wnt signaling in adult intestinal stem cells and cancer," Cellular Signalling, 2014, 26:570-579, 10 pgs.

Kretzschmar, K., et al., "Organoids: Modeling Development and the Stem Cell Niche in a Dish," Developmental Cell, Sep. 2016, 38:590-600, 11 pgs.

Kroon, E., et al., "Pancreatic endoderm derived from human embryonic stem cells generates glucose-responsive insulin secreting cells in vivo," Nat Biotechnol, 2008, 26(4):443-52.

Kubal, C.A., et al., "Challenges with Intestine and Multivisceral Re-Transplantation: Importance of Timing of Re-Transplantation and Optimal Immunosuppression," Ann Transplant, 2018, 23:98-104, 7 pgs.

Kubo, A., et al., "Development of definitive endoderm from embryonic stem cells in culture," Development, 2004, 131(7):1651-1662, 12 pgs.

Kudoh, T., et al., "Distinct roles for Fgf, Wnt and retinoic acid in posteriorizing the neural ectoderm," Development, 2002, 129:4335-4346, 12 pgs.

Kullak-Ublick, G.A., et al., "Drug induced liver injury: recent advantages in diagnosis and risk assessment," Gut, 2017, 66:1154-1164, 11 pgs.

Kumar, J.A., et al., "Controversies in the Mechanism of Total Parenteral Nutrition Induced Pathology," Children, 2015, 2:358-370, 13 pgs.

Kumar, M., et al., "Signals from lateral plate mesoderm instruct endoderm toward a pancreatic fate," Dev Biol, 2003, 259:109-122, 14 pgs.

Kuratnik, A., et al., "Intestinal organoids as tissue surrogates for toxicological and pharmacological studies," Biochemical Pharmacology, 2013, 85:1721-1726, 6 pgs.

Kurpios, N.A., et al., "The direction of gut looping is established by changes in the extracellular matrix and in cell:cell adhesion," PNAS, 2008, 105(25):8499-8506, 8 pgs.

Lahar, N., et al., "Intestinal subepithelial myofibroblasts support in vitro and in vivo growth of human small intestinal epithelium," PLoS One, Nov. 2011, 6:e26898, 9 pgs.

Lambert, P.F., et al., "Using an immortalized cell line to study the HPV life cycle in organotypic 'raft' cultures," Methods in Molecular Medicine, 2005, 119:141-155, 15 pgs.

Lambrecht, N.W.G., et al., "Identification of the K efflux channel coupled to the gastric H-K-ATPase during acid secretion," Physiological Genomics, 2005, 21:81-91, 11 pgs.

Lameris, A.L., et al., "Expression profiling of claudins in the human gastrointestinal tract in health and during inflammatory bowel disease," Scandinavian Journal of Gastroenterology, 2013, 48:58-69, 12 pgs.

Lancaster, M.A., et al., "Organogenesis in a dish: Modeling development and disease using organoid technologies," Science, 2014, 345(6194): 1247125-1-247125-9, 9 pgs.

Langmead, G., et al., "Ultrafast and memory-efficient alignment of short DNA sequences to the human genome," Genome Biology, 2009, 10:R25, 10 pgs.

Lavial, F., et al., "Chicken embryonic stem cells as a non-mammalian embryonic stem cell model," Develop. Growth Diff., 2010, 52:101-114, 14 pgs.

Lê, S., et al., "FactoMineR: An R Package for Multivariate Analysis," Journal of Statistical Software, 2008, 25(1):1-18, 18 pgs.

Le Douarin, N.M., et al., "Neural crest cell plasticity and its limits," Development 131, 2004, 4637-4650, 14 pgs.

(56) References Cited

OTHER PUBLICATIONS

Le Vee, M., et al., "Polarized expression of drug transporters in differentiated human hepatoma HepaRG cells," Toxicol In Vitro, 2013, 27:1979-1986, 8 pgs.

Lechner, C., et al., "Development of a fluorescence-based assay for drug interactions with human Multidrug Resistance Related Protein (MRP2; ABCC2) in MDCKII-MRP2 membrane vesicles," Eur J Pharm Biopharm, 2010, 75:284-290, 7 pgs.

Lee, C. S., et al., "*Neurogenin 3* is essential for the proper specification of gastric enteroendocrine cells and the maintenance of gastric epithelial cell identity," Genes Dev, 2002, 16:1488-1497, 11 pgs.

Lee, G., et al., "Isolation and directed differentiation of neural crest stem cells derived from human embryonic stem cells," Nature Biotechnology, Dec. 2007, 25:1468-1475, 9 pgs.

Lee, W.M., et al., "Intravenous N-Acetylcysteine Improves Transplant-Free Survival In Early Stage Non-Acetaminophen Acute Liver Failure," Gastroenterology, 2009, 137(3):856-864, 18 pgs.

Lennerz, J.K.M., et al., "The Transcription Factor MIST1 Is a Novel Human Gastric Chief Cell Marker Whose Expression Is Lost in Metaplasia, Dysplasia, and Carcinoma," The American Journal of Pathology, 2010, 177(3):1514-1533, 20 pgs.

Leslie, E.M., et al., "Differential Inhibition of Rat and Human $Na^+$-Dependent Taurocholate Cotransporting Polypeptide (NTCP/SLC10A1) by Bosentan: A Mechanism for Species Differences in Hepatotoxicity," J Pharmacol Exp Ther, 2007, 321(3):1170-1178, 9 pgs.

Leung, A.A., et al., "Tolerance testing of passive radio frequency identification tags for solvent, temperature, and pressure conditions encountered in an anatomic pathology or biorepository setting," J Pathol Inform, 2010, 1:21, 6 pgs.

Levin, D.E., et al., "Human tissue-engineered small intestine forms from postnatal progenitor cells," Journal of Pediatric Surgery, 2013, 48:129-137, 9 pgs.

Li, H., et al., "TreeFam: a curated database of phylogenetic trees of animal gene families," Nucleic Acids Research, 2006, 34:D572-D580, 9 pgs.

Li, L., "BMP Signaling Inhibits Intestinal Stem Cell Self-Renewal Through Antagonizing Wnt Signaling," Gastroenterology, AASLD Abstracts, Abstract S1223, 2005, 128: A702, 1 pg.

Li, N., et al., "A Systematic Assessment of Mitochondrial Function Identified Novel Signatures for Drug-Induced Mitochondrial Disruption in Cells," Toxicol Sci, 2014, 142(1):261-273, 13 pgs.

Li, Y., et al., "In vitro organogenesis from pluripotent stem cells," Organogenesis, Jun. 2014, 10(2):159-163, 5 pgs.

Li, Z., et al., "SATB2 is a sensitive marker for lower gastrointestinal well-differentiated neuroendocrine tumors," Int J Clin Exp Pathol, 2015, 8(6): 7072-7082, 11 pgs.

Lim, D.A., et al., "Noggin Antagonizes BMP Signaling to Create a Niche for Adult Neurogenesis," Neuron, Dec. 2000, 28:713-726, 14 pgs.

Lin, C., et al., "The application of engineered liver tissues for novel drug discovery," Expert Opinion on Drug Discovery, 2015, 10(5):519-540, 22 pgs.

Lin, Y., et al., "Differentiation, Evaluation, and Application of Human Induced Pluripotent Stem Cell-Derived Endothelial Cells," Arterioscler Thromb Vasc Biol, 2017, 37:2014-2025, 12 pgs.

Lindley, R.M., et al., "Human and Mouse Enteric Nervous System Neurosphere Transplants Regulate the Function of Aganglionic Embryonic Distal Colon," Gastroenterology, Jul. 2008, 135(1):205-216, XP022823118, 18 pgs.

Liu, J., et al., "A Small-Molecule Agonist of the Wnt Signaling Pathway," Angew Chem Int Ed Engl., 2005, 44(13):1987-1990, 4 pgs.

Liu, L., et al., "A Review of Locomotion Systems for Capsule Endoscopy," IEEE Rev Biomed Eng, 2015, 8:138-151, 14 pgs.

Logan, C.Y., et al., "The Wnt Signaling Pathway in Development and Disease," Annu. Rev. Cell Dev. Biol., 2004, 20:781-810, 32 pgs.

Loike, J.D., et al., "Opinion: Develop Organoids, Not Chimeras, for Transplantation," The Scientist Magazine, Aug. 2019., (online: https://www.the-scientist.com/news-opinion/opinion--develop-organoids--not-chimeras--for-transplantation-66339), 3 pgs.

Longmire, T.A., et al., "Efficient Derivation of Purified Lung and Thyroid Progenitors from Embryonic Stem Cells," Stem Cell, 2012, 10:398-411, 14 pgs.

López-Díaz, L., et al., "Intestinal Neurogenin 3 directs differentiation of a bipotential secretory progenitor to endocrine cell rather than goblet cell fate," Dev Biol. 2007, 309:298-305, 8 pgs.

Love, M.I., et al., "Moderated estimation of fold change and dispersion for RNA-seq data with DESeq2," Genome Biol, 2014, 15:550, 21 pgs.

Low, L.A., et al., "Organs-on-chips: Progress, challenges, and future directions," Experimental Biology and Medicine, 2017, 242:1573-1578, 6 pgs.

Lu, Y., et al., "A Novel 3D Liver Organoid System for Elucidation of Hepatic Glucose Metabolism," Biotechnol Bioeng., Feb. 2012, 109(2):595-604, 21 pgs.

Ludwig, T.E., et al., "Derivation of human embryonic stem cells in defined conditions," Nat Biotechnol, 2006, 24:185-187, 3 pgs.

Ludwig, T.E., et al., "Feeder-independent culture of human embryonic stem cells," Nat Methods, 2006, 3:637-646, 10 pgs.

Lui, V.C., et al., "Perturbation of hoxb5 signaling in vagal neural crests down-regulates ret leading to intestinal hypoganglionosis in mice," Gastroenterology, 2008, 134:1104-1115, 12 pgs.

Luntz, J., et al., "Mechanical Extension Implants for Short-Bowel Syndrome," Smart Structures and Materials 2006: Smart Structures and Integrated Systems, Proc of SPIE, 2006, 6173:617309-1-617309-11, 11 pgs.

Luo, X., et al., "Generation of endoderm lineages from pluripotent stem cells," Regenerative Medicine, 2017, 12(1):77-89, 13 pgs.

Macparland, S.A., et al., "Single cell RNA sequencing of human liver reveals distinct intrahepatic macrophage populations," Nat Commun, 2018, 9:4383, 21 pgs.

Mahe, M.M., et al., "Establishment of gastrointestinal epithelial organoids," Current Protocols in Mouse Biology, 2013, 3(4):217-240, XP002750112, 31 pgs.

Mahe, M.M., et al., "In Vivo Model of Small Intestine," Methods Mol Biol, 2017, 1597:229-245, 17 pgs.

Majumdar, A.P.N., "Postnatal Undernutrition: Effect of Epidermal Growth Factor on Growth and Function of the Gastrointestinal Tract in Rats," J. Pediatr. Gastroenterol. Nutr., 1984, 3:618-625, 8 pgs.

Makin, A.J., et al., "A 7-Year Experience of Severe Acetaminophen-Induced Hepatotoxicity (1987-1993)," Gastroenterology, 1995, 109:1907-1916, 10 pgs.

Malinen, M.M., et al., "Differentiation of liver progenitor cell line to functional organotypic cultures in 3D nanofibrillar cellulose and hyaluronan-gelatin hydrogels," Biomaterials, 2014, 35:5110-5121, 12 pgs.

Mammoto, A., et al., "Mechanosensitive mechanisms in transcriptional regulation," Journal of Cell Science, 2012, 125:3061-3073, 13 pgs.

Marcum, Z.A., et al., "Medication Adherence to Multi-Drug Regimens," Clin Geriatr Med, 2012, 28(2):287-300, 15 pgs.

Marini, F., et al., "pcaExplorer: an R/Bioconductor package for interacting with RNA-seq principal components," BMC Bioinformatics, 2019, 20:331, 8 pgs.

Marini, F., "pcaExplorer: Interactive Visualization of RNA-seq Data Using a Principal Components Approach," bioconductor.org, R package version 2.3.0, 2017, 7 pgs.

Markova, S.M., et al., "Association of CYP2C9*2 With Bosentan-Induced Liver Injury," Clin Pharmacol Ther., Dec. 2013, 94(6):678-86, 9 pgs.

Marsh, M.N., et al., "A study of the small intestinal mucosa using the scanning electron microscope," Gut, 1969, 10:940-949, 10 pgs.

Martin, G.R., "Teratocarcinomas and Mammalian Embryogenesis," Science, 1980, 209(4458):768-776, 9 pgs.

Martin, M., et al., "Dorsal pancreas agenesis in retinoic acid-deficient *Raldh2* mutant mice," Dev Biol., 2005, 284:399-411, 13 pgs.

McCauley, H.A., et al., "Pluripotent stem cell-derived organoids: using principles of developmental biology to grow human tissues in a dish," Development, 2017, 144:958-962, 5 pgs.

(56) References Cited

OTHER PUBLICATIONS

McCracken, K.W., et al., "Generating human intestinal tissue from pluripotent stem cells in vitro," Nature Protocols, 2011, 6(12):1920-1928, 19 pgs.

McCracken, K.W., et al., "Mechanisms of embryonic stomach development," Seminars in Cell & Development Biology, 2017, 66:36-42, 7 pgs.

McCracken, K.W., "Mechanisms of endoderm patterning and directed differentiation of human stem cells into foregut tissues," Dissertation, Graduate School of the University of Cincinnati, Jun. 19, 2014, 185 pgs.

McCracken, K.W., et al., "Modeling human development and disease in pluripotent stem-cell-derived gastric organoids," Nature, Oct. 29, 2014, 516(7531):400-404, XP055210509, 30 pgs.

McCracken, K.W., et al., "Wnt/β-catenin promotes gastric fundus specification in mice and humans," Nature, 2017, 541(7636):182-187, 31 pgs.

McCracken, K.W., et al., "Erratum: Wnt/β-catenin promotes gastric fundus specification in mice and humans," Nature, 2017, 543:136, 1 pg.

McGovern, D.P.B., et al., "Genome-wide association identifies multiple ulcerative colitis susceptibility loci," Nature Genetics, 2010, 42(4):332-337, 8 pgs.

McKenzie, T.J., et al., "Artificial and Bioartificial Liver Support," Seminars in Liver Disease, 2008, 28(2):210-217, 8 pgs.

McKeown, S.J., et al., "Hirschsprung disease: a developmental disorder of the enteric nervous system," Wiley Interdisciplinary Reviews Developmental Biology, Jan./Feb. 2013, 2:113-129, 17 pgs.

McLin, V.A., et al., "Repression of Wnt/β-catenin signaling in the anterior endoderm is essential for liver and pancreas development," Development, 2007, 134:2207-2217, 11 pgs.

McLin, V.A et al., "The Role of the Visceral Mesoderm in the Development of the Gastrointestinal Tract," Gastroenterology, 2009, 136:2074-2091, 18 pgs.

McMahon, J.A., et al., "Noggin-mediated antagonism of BMP signaling is required for growth and patterning of the neural tube and somite," Genes & Development, May 1998, 12:1438-1452, 15 pgs.

McManus, M.T., et al., "Gene Silencing in Mammals by Small Interfering RNAs," Nat. Rev. Genet., Oct. 2002, 3:737-747, 13 pgs.

Meerbrey, K.L., et al., "The pINDUCER lentiviral toolkit for inducible RNA interference in vitro and in vivo," Proc Natl Acad Sci USA, 2011, 108:3665-3670, 6 pgs.

Mercaldi, C.J., et al., "Methods to Identify and Compare Parenteral Nutrition Administered From Hospital-Compounded and Premixed Multichamber Bags in a Retrospective Hospital Claims Database," J Parenter Enteral Nutr, 2012, 36(3):330-336, 7 pgs.

Merker, S.R., et al., "Gastrointestinal organoids: How they gut it out," Developmental Biology, 2016, 420:239-250, 12 pgs.

Mica, Y., et al., "Modeling neural crest induction, melanocyte specification and disease-related pigmentation defects in hESCs and patient-specific iPSCs," Cell Reports, Apr. 25, 2013, 3:1140-1152, 27 pgs.

Micallef, S.J., et al., "Endocrine cells develop within pancreatic bud-like structures derived from mouse ES cells differentiated in response to BMP4 and retinoic acid," Stem Cell Research, 2007, 1:25-36, 12 pgs.

Michaut, A., et al., "A cellular model to study drug-induced liver injury in nonalcoholic fatty liver disease: application to acetaminophen," Toxicol Appl Pharmacol, 2016, 292:40-55, 35 pgs.

Miki, T., et al., "Hepatic Differentiation of Human Embryonic Stem Cells Is Promoted by Three-Dimensional Dynamic Perfusion Culture Conditions," Tissue Eng: Part C Methods, 2011, 17(5):557-568, 12 pgs.

Mills, J.C., et al., "Gastric Epithelial Stem Cells," Gastroenterology, 2011, 140:412-424, 13 pgs.

Miyabayashi, T., et al., "Wnt/β-catenin/CBP signaling maintains long-term murine embryonic stem cell pluripotency," Proc Natl Acad Sci USA, 2007, 104(13):5668-5673, 6 pgs.

Molodecky, N.A., et al., "Increasing Incidence and Prevalence of the Inflammatory Bowel Diseases With Time, Based on Systematic Review," Gastroenterology, 2012, 142:46-54, 51 pgs.

Molotkov, A., et al., "Retinoic Acid Generated by *Raldh2* in Mesoderm is Required for Mouse Dorsal Endodermal Pancreas Development," Dev Dyn, 2005, 232:950-957, 8 pgs.

Mörk, L.M., et a., "Comparison of Culture Media for Bile Acid Transport Studies in Primary Human Hepatocytes," J Clin Exp Hepatol, 2012, 2:315-322, 8 pgs.

Moser, A.R., et al., "A dominant mutation that predisposes to multiple intestinal neoplasia in the mouse," Science, 1990, 247(4940):322-324, 3 pgs.

Mosher, J.T., et al., "Intrinsic differences among spatially distinct neural crest stem cells in terms of migratory properties, fate-determination, and ability to colonize the enteric nervous system," Dev. Biol., Mar. 2007, 303(1): 1-15, 29 pgs.

Mou, H., et al., "Generation of Multipotent Lung and Airway Progenitors from Mouse ESCs and Patient-Specific Cystic Fibrosis iPSCs," Stem Cell, 2012, 10:385-397, 13 pgs.

Mudaliar, S., et al., "Efficacy and Safety of the Farnesoid X Receptor Agonist Obeticholic Acid in Patients with Type 2 Diabetes and Nonalcoholic Fatty Liver Disease," Gastroenterology, 2013, 145:574-582, 10 pgs.

Munera, J.O., et al., "Differentiation of Human Pluripotent Stem Cells into Colonic Organoids via Transient Activation of BMP Signaling," Cell Stem Cell, Jul. 2017, 21(1):51-64.e6, 21 pgs.

Munera, J.O., et al., "Generation of Gastrointestinal Organoids from Human Pluripotent Stem Cells," Organ Regeneration, In: Tsuji, T., (eds), Organ Regeneration. Methods in Molecular Biology, vo. 1597, Humana Press, New York, NY, 2017, 11 pgs.

Muñoz, M., et al., "Conventional pluripotency markers are unspecific for bovine embryonic-derived cell-lines," Theriogenology, 2008, 69:1159-1164, 6 pgs.

Nakamura, T., et al., "Advancing Intestinal Organoid Technology Toward Regenerative Medicine," Cell Mol Gastroenterol Hepatol, 2018, 5:51-60, 10 pgs.

Nandivada, P., et al., "Treatment of Parenteral Nutrition-Associated Liver Disease: The Role of Lipid Emulsions," Advances in Nutrition, Reviews from ASN EB 2013 Symposia, pp. 711-717, 7 pgs.

Navarro, V.J., et al., "Drug-Related Hepatotoxicity," N Engl J Med, 2006, 354:731-739, 9 pgs.

Negishi, T., et al., "Retinoic Acid Signaling Positively Regulates Liver Specification by Inducing *wnt2bb* Gene Expression in Medaka," Hepatology, 2010, 51:1037-1045, 9 pgs.

Neiiendam, J.L., et al., "An NCAM-derived FGF-receptor agonist, the FGL-peptide, induces neurite outgrowth and neuronal survival in primary rat neurons," J. Neurochem., 2004, 91(4):920-935, 17 pgs.

Nelson, B.J., et al., "Microrobots for Minimally Invasive Medicine," Annual Review of Biomedical Engineering, 2010, 12(12):55-85, 33 pgs.

Nelson, C.M., "On Buckling Morphogenesis," J Biomech Eng, 2016, 138:021005-1-021005-6, 6 pgs.

Neuschwander-Tetri, B.A., et al., "Farnesoid X nuclear receptor ligand obeticholic acid for non-cirrhotic, non-alcoholic steatohepatitis (FLINT): a multicentre, randomised, placebo-controlled trial," Lancet, 2015, 385:956-965, 10 pgs.

Ni, X., et al., "Functional human induced hepatocytes (hiHeps) with bile acid synthesis and transport capacities: A novel in vitro cholestatic model," Sci Rep, 2016, 6:38694, 16 pgs.

Nielsen, C., et al., "Gizzard Formation and the Role of *Bapx1*," Developmental Biology, 2001, 231:164-174, 11 pgs.

Nishida, T., et al., "Rat liver canalicular membrane vesicles contain an ATP-dependent bile acid transport system," Proc Natl Acad Sci USA, 1991, 88:6590-6594, 5 pgs.

Noguchi, T-A.K., et al., "Generation of stomach tissue from mouse embryonic stem cells," Nature Cell Biology, 2015, 17(8):984-993, XP055225165, 20 pgs.

Nomura, S., et al., "Evidence for Repatterning of the Gastric Fundic Epithelium Associated With Ménétrier's Disease and TGFα Overexpression," Gastroenterology, 2005, 128:1292-1305, 14 pgs.

(56) References Cited

OTHER PUBLICATIONS

Obermayr, F., et al., "Development and developmental disorders of the enteric nervous system," Nature Reviews/Gastroenterology & Hepatology, Jan. 2013, 10:43-57, 15 pgs.

Ogaki, S., et al., "Wnt and Notch Signals Guide Embryonic Stem Cell Differentiation into the Intestinal Lineages," Stem Cells, 2013, 31:1086-1096, 11 pgs.

Okita, K., et al., "An Efficient Nonviral Method to Generate Integration-Free Human- Induced Pluripotent Stem Cells from Cord Blood and Peripheral Blood Cells," Stem Cells, 2013, 31:458-466, 9 pgs.

Okita, K., et al., "Generation of Mouse Induced Pluripotent Stem Cells Without Viral Vectors," Science, 2008, 322(5903):949-953, 5 pgs.

Olbe, L., et al., "A Mechanism by Which *Helicobacter pylori* Infection of the antrum Contributes to the Development of Duodenal Ulcer," Gastroenterology, 2001, 110:1386-1394, 9 pgs.

Oorts, M., et al., "Drug-induced cholestasis risk assessment in sandwich-cultured human hepatocytes," Toxicol In Vitro, 2016, 34:179-186, 8 pgs.

Ootani, A et al., "Sustained in vitro intestinal epithelial culture within a Wnt- dependent stem cell niche," Nat Med, 2009, 15:701-706, 14 pgs.

Ornitz, D.M., et al., "FGF signaling pathways in endochondral and intramembranous bone development and human genetic disease," Genes & Development, Jun. 2002, 16:1446-1465, 21 pgs.

Ornitz, D.M., et al., "The Fibroblast Growth Factor signaling pathway," WIREs Dev Biol, 2015, 4:215-266, 52 pgs.

Orso, G., et al., "Pediatric parenteral nutrition-associated liver disease and cholestasis: Novel advances in pathomechanisms-based prevention and treatment," Dig Liver Dis, 2016, 48:215-222, 8 pgs.

Ouchi, R., et al., "Modeling Steatohepatitis in Humans with Pluripotent Stem Cell-Derived Organoids," Cell Metabolism, Aug. 2019, 30:1-11, 17 pgs.

Paddison, P.J., et al., "RNA interference: the new somatic cell genetics?", Cancer Cell, 2002, 2:17-23, 7 pgs.

Pai, R., et al., "Deoxycholic Acid Activates β-Catenin Signaling Pathway and Increases Colon Cell Cancer Growth and Invasiveness," Mol Biol Cell., 2004, 15(5):2156-2163, 8 pgs.

Pan, Q., *Physiology*, University of Science and Technology of China Press, Jan. 31, 2014, pp. 149-150. [Reference unavailable, citing referencing Search Report, 3 pgs. ].

Pardal, M.L., et al., "Towards the Internet of Things: An Introduction to RFID technology," RFID Technology-Concepts, Applications, Challenges, Proceedings of the 4th International Workshop, IWRT 2010, In conjunction with ICEIS 2010, Funchal, Madeira, Portugal, Jun. 2010, pp. 69-78, 10 pgs.

Paris, D.B.B.P., et al., "Equine embryos and embryonic stem cells: Defining reliable markers of pluripotency," Theriogenology, 2010, 74:516-524, 9 pgs.

Park, H.R., et al., "Lipotoxicity of Palmitic Acid on Neural Progenitor Cells and Hippocampal Neurogenesis," Toxicol Res, 2011, 27(2):103-110, 8 pgs.

Park, J.S., et al., "Differential Effects of Equiaxial and Uniaxial Strain on Mesenchymal Stem Cells," Biotechnology and Bioengineering, 2004, 88(3):359-368, 10 pgs.

Park, J.S., et al., "The effect of matrix stiffness on the differentiation of mesenhymal stem cells in response to TGF-β," Biomaterials, 2011, 32:3921-3930, 10 pgs.

Park, K.I., et al., "Acute injury directs the migration, proliferation, and differentiation of solid organ stem cells: Evidence for the effect of hypoxia-ischemia in the CNS on clonal "reporter" neural stem cells," Experimental Neurology, 2006, 199:159-178, 23 pgs.

Park, Y.H., et al., "Review of Atrophic Gastritis and Intestinal Metaplasia as a Premalignant Lesion of Gastric Cancer," Journal of Cancer Prevention, 2015, 20(1):25-40, 16 pgs.

Parkin, D.M., "The global health burden of infection-associated cancers in the year 2002," Int. J. Cancer, 2006, 118:3030-3044, 15 pgs.

Pastor, W.A., et al., "TFAP2C regulates transcription in human naïve pluripotency by opening enhancers," Nature Cell Biology, 2018, 20:553-564, 18 pgs.

Pastula, A., et al., "Three-Dimensional Gastrointestinal Organoid Culture in Combination with Nerves or Fibroblasts: A Method to Characterize the Gastrointestinal Stem Cell Niche," Stem Cells International, 2016, 16 pgs.

Patankar, J.V., et al., "Intestinal Deficiency of Gata4 Protects from Diet-Induced Hepatic Steatosis by Suppressing De Novo Lipogenesis and Gluconeogenesis in Mice," Journal of Hepatology, Posters, Abstract 1253, 2012, 56:S496, 1 pg.

Patankar, J.V., et al., "Intestinal GATA4 deficiency protects from diet-induced hepatic steatosis," Journal of Hepatology, 2012, 57:1061-1068, 8 pgs.

Peek, R.M., Jr., "*Helicobacter pylori* infection and disease: from humans to animal models," Dis Model Mech, 2008, 1:50-55, 6 pgs.

Peek, R.M., Jr., et al., "*Helicobacter pylori* cagA+ Strains and Dissociation of Gastric Epithelial Cell Proliferation From Apoptosis," J. Natl. Cancer Inst., 1997, 89:863-868, 7 pgs.

Pennisi, C.P., Ph.D., et al., "Uniaxial Cyclic Strain Drives Assembly and Differentiation of Skeletal Myocytes," Tissue Engineering: Part A, 2011, 17(19-20):2543-2550, 8 pgs.

Pereira, C.F., et al., "Heterokaryon-Based Reprogramming of Human B Lymphocytes for Pluripotency Requires Oct4 but Not Sox2," PLoS Genet, 2008, 4(9):e1000170, 14 pgs.

Pessayre, D., et al., "Central role of mitochondria in drug-induced liver injury," Drug Metab Rev, 2012, 44(1):34-87, 54 pgs.

Pessayre, D., et al., "Mitochondrial involvement in drug-induced liver injury," in *Adverse Drug Reaction*, J. Uetrecht (ed.), Handb Exp Pharmacol 196, Springer-Verlag, Berlin, Germany, 2010, pp. 311-365, 55 pgs.

Petitte, J.N., et al., "Avian pluripotent stem cells," Mech. of Develop., 2004, 121:1159-1168, 10 pgs.

Poling, H.M., et al., "Mechanically induced development and maturation of human intestinal organoids in vivo," Nat Biomed Eng, 2018, 2(6):429-442, 31 pgs.

Polson, J., et al., "AASLD Position Paper: The Management of Acute Liver Failure," Hepatology, 2005, 41(5):1179-1197, 19 pgs.

Pompaiah, M., et al., "Gastric Organoids: An Emerging Model System to Study *Helicobacter pylori* Pathogenesis," Molecular Pathogenesis and Signal Transduction by Helicobacter pylori, Current Topics in Microbiology and Immunology, N. Tegtmeyer, et al., (eds.), 2017, pp. 149-168, 20 pgs.

Prakash, R., "Regulation of WNT Genes in Stem Cells Development and Organogenesis," IJP, Jun. 2014, 1(6):366-372, 7 pgs.

Pulikkot, S., "Establishment of a 3D Culture Model of Gastric Stem Cells Supporting Their Differentiation into Mucous Cells Using Microfibrous Polycaprolactone Scaffold," Dissertation, United Arab Emirates University, College of Medicine and Health Sciences, May 2015, 187 pgs. (4 parts: Part 1—58 pgs; Part 2—69 pgs; Part 3—31 pgs; Part 4—29 pgs.).

Purton, L.E., et al., "All-trans retinoic acid enhances the long-term repopulating activity of cultured hematopoietic stem cells," Blood, 2000, 95:470-477, 8 pgs.

Qi, M-C., et al., "Mechanical strain induces osteogenic differentiation: Cbfal and Ets-1 expression in stretched rat mesenchymal stem cells," Int J Oral Maxillofac Surg, 2008, 37:453-458, 6 pgs.

Que, J., et al., "Morphogenesis of the trachea and esophagus: current players and new roles for noggin and Bmps," Differentiation, 2006, 74:422-437, 16 pgs.

Rachek, L.I., et al., "Troglitazone, but not rosiglitazone, damages mitochondrial DNA and induces mitochondrial dysfunction and cell death in human hepatocytes," Toxicol Appl Pharmacol, 2009, 240(3):348-354, 17 pgs.

Raju, R., et al., "A Network Map of FGF-1/FGFR Signaling System," Journal of Signal Transduction, Apr. 2014, 2014:1-16, Article ID 962962, 16 pgs.

Ramachandran, S.D., et al., "In Vitro Generation of Functional Liver Organoid-Like Structures Using Adult Human Cells," PloS One, Oct. 2015, 10(10):1-14, 14 pgs.

Ramalingam, S., et al., "Distinct levels of Sox9 expression mark colon epithelial stem cells that form colonoids in culture," Am J Physiol Gastrointest Liver Physiol, 2012, 302:G10-G20, 11 pgs.

(56) References Cited

OTHER PUBLICATIONS

Ramirez-Weber, F-A., et al., "Cytonemes: Cellular Processes that Project to the Principal Signaling Center in *Drosophila* Imaginal Discs," Cell, 1999, 97:599-607, 9 pgs.
Ramsey, V.G., et al., "The maturation of mucus-secreting gastric epithelial progenitors into digestive-enzyme secreting zymogenic cells requires *Mist1*," Development, 2007, 134:211-222, 12 pgs.
Rane, A., et al., "Drug Metabolism in the Human Fetus and Newborn Infant," Pediatr Clin North Am, 1972, 19(1):37-49, 11 pgs.
Rankin, S.A., et al., "A Molecular Atlas of *Xenopus* Respiratory System Development," Developmental Dynamics, 2015, 244:69-85, 17 pgs.
Rankin, S.A., et al., "Suppression of Bmp4 signaling by the zinc-finger repressors Osr1 and Osr2 is required for Wnt/B-catenin-mediated lung specification in *Xenopus*," Development, 2012, 139:3010-3020, 11 pgs.
Rankin, S.A., et al., "Timing is everything: Reiterative Wnt, BMP and RA signaling regulate developmental competence during endoderm organogenesis," Developmental Biology, Feb. 1, 2018, 434(1):121-132, 12 pgs.
Rao, R.R., et al., "Gene Expression Profiling of Embryonic Stem Cells Leads to Greater Understanding of Pluripotency and Early Developmental Events," Biol Reprod, 2004, 71:1772-1778, 7 pgs.
Ratineau, C., et al., "Endoderm- and mesenchyme-dependent commitment of the differentiated epithelial cell types in the developing intestine of rat," Differentiation, 2003, 71:163-169, 7 pgs.
Ray, K., "Engineering human intestinal organoids with a functional ENS," Nature Reviews Gastroenterology & Hepatology, Nov. 2016, 1 pg.
Rector, R.S., et al., "Mitochondrial dysfunction precedes insulin resistance and hepatic steatosis and contributes to the natural history of non-alcoholic fatty liver disease in an obese rodent model," J Hepatol, 2010, 52(5):727-736, 20 pgs.
Reilly, G.C., et al., "Intrinsic extracellular matrix properties regulate stem cell differentiation," Journal of Biomechanics, 2010, 43:55-62, 8 pgs.
Rennert, K., et al., "A microfluidically perfused three dimensional human liver model," Biomaterials, 2015, 71:119-131, 13 pgs.
Reuben, A., et al. "Drug-Induced Acute Liver Failure: Results of a U.S. Multicenter, Prospective Study," Hepatology, 2010, 52:2065-2076, 12 pgs.
Richards, M., et al., "The Transcriptome Profile of Human Embryonic Stem Cells as Defined by SAGE," Stem Cells, 2004, 22:51-64, 14 pgs.
Riedinger, H-J, et al., "Reversible shutdown of replicon initiation by transient hypoxia in Ehrlich ascites cells: Dependence of initiation on short-lived protein," Eur J. Biochem, 1992, 210:389-398, 10 pgs.
Roberts, A., et al., "Identification of novel transcripts in annotated genomes using RNA-Seq," Bioinformatics, 2011, 27(17):2325-2329, 5 pgs.
Roberts, A., et al., "Improving RNA-Seq expression estimates by correcting for fragment bias," Genome Biol, 2011, 12:R22, 14 pgs.
Roberts, D.J., et al., "Sonic hedgehog is an endodermal signal inducing Bmp-4 and Hox genes during induction and regionalization of the chick hindgut," Development, 1995, 121:3163-3174, 12 pgs.
Rodríguez-Piñeiro, A.M., et al., "Studies of mucus in mouse stomach, small intestine, and colon. II. Gastrointestinal mucus proteome reveals Muc2 and Muc5ac accompanied by a set of core proteins," Am J Physiol Gastrointest Liver Physiol, 2013, 305:G348-G356, 9 pgs.
Rodriquez, P., et al., "BMP signaling in the development of the mouse esophagus and forestomach," Development, 2010, 137:4171-4176, 6 pgs.
Rohrschneider, M.R., et al., "Polarity and cell fate specification in the control of *C. elegans* gastrulation," Dev. Dyn., 2009, 238(4):789-796, 15 pgs.
Ronn, R.E., et al., "Retinoic Acid Regulates Hematopoietic Development from Human Pluripotent Stem Cells," Stem Cell Reports, 2015, 4:269-281, 13 pgs.
Roth, R.B., et al., "Gene expression analyses reveal molecular relationships among 20 regions of the human CNS," Neurogenetics, 2006, 7:67-80, 14 pgs.
Rouch, J.D., et al., "Scalability of an endoluminal spring for distraction enterogenesis," Journal of Pediatric Surgery, 2016, 51:1988-1992, 5 pgs.
Roy, S., et al., "Cytoneme-Mediated Contact-Dependent Transport of the *Drosophila* Decapentaplegic Signaling Protein," Science, 2014, 343:1244624-1, 11 pgs.
Russo, M.W., et al., "Liver Transplantation for Acute Liver Failure From Drug Induced Liver Injury in the United States," Liver Transpl, 2004, 10:1018-1023, 6 pgs.
Sachs, N., et al., "A Living Biobank of Breast Cancer Organoids Captures Disease Heterogeneity," Cell, 2018, 172:373-386, 25 pgs.
Saenz, J.B., et al., "Stomach growth in a dish: A protocol has been developed to grow structures that resemble the main part of the stomach in vitro from human embryonic stem cells—an advance that provides insights into stomach development," Nature, Jan. 2017, 541:160-161, 2 pgs.
Saffrey, M.J., "Cellular changes in the enteric nervous system during ageing," Developmental Biology, 2013, 382:344-355, 12 pgs.
Saha, S., et al., "Inhibition of Human Embryonic Stem Cell Differentiation by Medical Strain," Journal of Cellular Physiology, 2006, 206:126-137, 12 pgs.
Saini, A., "Cystic Fibrosis Patients Benefit from Mini Guts," Cell Stem Cell, 2016, 19:425-427, 3 pgs.
Saito, M., et al., "Reconstruction of liver organoid using a bioreactor," World J Gastroenterol, Mar. 2006, 12(12):1881-1888, 8 pgs.
Salas-Vidal, E., et al., "Imaging filopodia dynamics in the mouse blastocyst," Developmental Biology, 2004, 265:75-89, 15 pgs.
Sampaziotis, F., et al., "Potential of Human Induced Pluripotent Stem Cells in Studies of Liver Disease," Hepatology, Jul. 2015, 62(1):303-311, 9 pgs.
Sancho, E., et al., "Signaling Pathways in Intestinal Development and Cancer," Annu. Rev. Cell Dev. Biol., 2004, 20:695-723, 31 pgs.
Sartori-Rupp, A., et al., "Correlative cryo-electron microscopy reveals the structure of TNTs in neuronal cells," Nature Communications, 2019, 10:342, 16 pgs.
Sasai, Y., "Cytosystems dynamics in self-organization of tissue architecture," Nature, 2013, 493:318-326, 9 pgs.
Sasai, Y., "Next-Generation Regenerative Medicine: Organogenesis from Stem Cells in 3D Culture," Cell Stem Cell, May 2013, 12:520-530, 11 pgs.
Sasselli, V., et al., "The enteric nervous system," Developmental Biology, Jan. 2012, 366:64-73, 10 pgs.
Sato, T., et al., "Long-term expansion of epithelial organoids from human colon, adenoma, adenocarcinoma, and Barrett's epithelium," Gastroenterology, Nov. 2011, 141:1762-1772, 11 pgs.
Sato, T., et al., "Single Lgr5 stem cells build crypt-villus structures in vitro without a mesenchymal niche," Nature, 2009, 459:262-265, 5 pgs.
Sato, T., et al., "Snapshot: Growing Organoids from Stem Cells," Cell, 2015, 161:1700-1700e1, 2 pgs.
Savidge, T.C., et al., "Human intestinal development in a severe-combined immunodeficient xenograft model," Differentiation, 1995, 58:361-371, 11 pgs.
Savin, T., et al., "On the growth and form of the gut," Nature, 2011, 476:57-62, 7 pgs.
Schlieve, C.R., et al., "Created of Warm Blood and Nerves: Restoring an Enteric Nervous System in Organoids," Cell Stem Cell, Jan. 2017, 20:5-7, 3 pgs.
Schmelter, M., et al., "Embryonic stem cells utilize reactive oxygen species as transducers of mechanical strain-induced cardiovascular differentiation," The FASEB Journal, Jun. 2006, 20(8): 1182-1184, 16 pgs.
Schonhoff, S.E., et al., "Neurogenin 3-expressing progenitor cells in the gastrointestinal tract differentiate into both endocrine and non-endocrine cell types," Dev Biol, 2004, 270:443-454, 12 pgs.

(56) References Cited

OTHER PUBLICATIONS

Schumacher, M.A., et al., "Gastric Sonic Hedgehog Acts as a Macrophage Chemoattractant During the Immune Response to *Helicobacter pylori*," Gastroenterology, 2012, 142:1150-1159, 16 pgs.
Schumacher, M.A., et al., "The use of murine-derived fundic organoids in studies of gastric physiology," J. Physiol., 2015, 593(8):1809-1827, 19 pgs.
Schuppan, D., et al., "Non-alcoholic steatohepatitis: Pathogenesis and novel Therapeutic approaches," Journal of Gastroenterology and Hepatology, 2013, 28(Suppl 1):68-76, 9 pgs.
Serviddio, G., et al., "Ursodeoxycholic Acid Protects Against Secondary Biliary Cirrhosis in Rats by Preventing Mitochondrial Oxidative Stress," Hepatology, 2004, 39:711-720, 10 pgs.
Shah, S.B., et al., "Cellular self-assembly and biomaterials-based organoid models of development and diseases," Acta Biomaterialia, 2017, 53:29-45, 17 pgs.
Shahbazi, M.N., et al., "Self-organization of the human embryo in the absence of maternal tissues," Nature Cell Biology, 2016, 18(6):700-708, 20 pgs.
Shan, J., et al., "Identification of a Specific Inhibitor of the Dishevelled PDZ Domain," Biochemistry, 2005, 44(47):15495-15503, 9 pgs.
Sheehan-Rooney, K., et al., "Bmp and Shh Signaling Mediate the Expression of satb 2 in the Pharyngeal Arches," PLoS One, Mar. 2013, 8(3):e59533, 10 pgs.
Shekherdimian, S., et al., "The feasibility of using an endoluminal device for intestinal lengthening," Journal of Pediatric Surgery, 2010, 45:1575-1580, 6 pgs.
Sherwood, R.I., et al., "Transcriptional dynamics of endodermal organ formation," Dev Dyn, 2009, 238(1):29-42, 23 pgs.
Sherwood, R.I., et al., "Wnt signaling specifies and patterns intestinal endoderm," Mechanisms of Development, 2011, 128:387-400, 14 pgs.
Shi, X-L., et al., "Effects of Membrane Molecular Weight Cutoff on Performance of a Novel Bioartificial Liver," Artificial Organs, 2011, 35(3):E40-E46, 7 pgs.
Shi, X-L., et al., "Evaluation of a novel hybrid bioartificial liver based on a multi-layer flat-plate bioreactor," World J Gastroenterol, 2012, 18(28):3752-3760, 9 pgs.
Shimizu, N., et al., "Cyclic strain induces mouse embryonic stem cell differentiation into vascular smooth muscle cells by activating PDGF receptor β," J Appl Physiol, 2008, 104:766-772, 7 pgs.
Shyer, A.E., et al., "Bending Gradients: How the Intestinal Stem Cell Gets Its Home," Cell, 2015, 161:569-580, 13 pgs.
Shyer, A.E., et al., "Villification: How the Gut Gets its Villi," Science, 2013, 342:212-218, 7 pgs.
Si-Tayeb, K., et al., "Highly Efficient Generation of Human Hepatocyte-Like Cells from Induced Pluripotent Stem Cells," Hepatology, 2010, 51:297-305, 9 pgs.
Siegel, R., et al., "Colorectal Cancer Statistics, 2014," CA Cancer J Clin, 2014, 64:104-117, 14 pgs.
Sigalet, D.L., "The Role of the Enteric Neuronal System In Controlling Intestinal Function," Clinical Surgery Society Magazine, 2003, 64:214. [Reference unavailable, citing excerpt of referencing Search Report, 5 pgs.].
Sim, Y-J., et al., "2i Maintains a Naïve Ground State in ESCs through Two Distinct Epigenetic Mechanisms," Stem Cell Reports, 2017, 8:1312-1328, 17 pgs.
Simon-Assmann, P., et al., "In vitro models of intestinal epithelial cell differentiation," Cell Biol. Toxicol., 2007, 23:241-256, 16 pgs.
Sinagoga, K.L., et al., "Generating human intestinal tissues from pluripotent stem cells to study development and disease," The EMBO Journal, 2015, 34(9):1149-1163, 15 pgs.
Singh, S., et al., "Comparative Effectiveness of Pharmacological Interventions for Nonalcoholic Steatohepatitis: A Systematic Review and Network Meta-analysis," Hepatology, Nov. 2015, 62(5):1417-1432, 16 pgs.

Sitti, M., et al., "Biomedical Applications of Untethered Mobile Milli/Microrobots," Proc IEEE Inst Electr Electron Eng, 2015, 103(2):205-224, 20 pgs.
Skardal, A., et al., "Organoid-on-a-chip and body-on-a-chip systems for drug screening and disease modeling," Drug Discovery Today, Sep. 2016, 21(9):1399-1411, 13 pgs.
Slaymaker, I.M., et al., "Rationally engineered Cas9 nucleases with improved specificity," Science, 2016, 351(6268):84-88, 10 pgs.
Sloan, C.A., et al., "ENCODE data at the ENCODE portal," Nucleic Acids Res, 2016, 44:D726-D732, 7 pgs.
Sneddon, I.N., "The Relation Between Load and Penetration in the Axisymmetric Boussinesq Problem for a Punch of Arbitrary Profile," Int. J. Engng. Sci., 1965, 3:47-57, 11 pgs.
Snoeck, H-W., "Generation of Anterior Foregut Derivatives from Pluripotent Stem Cells," Stem Cells Handbook, S. Sell (ed.), 2013, pp. 161-175, 15 pgs.
Snykers, S., et al., "In Vitro Differentiation of Embryonic and Adult Stem Cells into Hepatocytes: State of the Art," Stem Cells, 2009, 27:577-605, 29 pgs.
Soffers, J.H.M., et al., "The growth pattern of the human intestine and its mesentery," BMC Dev Biol, 2015, 15:31, 16 pgs.
Song, W., et al., "Engraftment of human induced pluripotent stem cell-derived hepatocytes in immunocompetent mice via 3D co-aggregation and encapsulation," Sci Rep, 2015, 5:16884, 13 pgs.
Song, Z., et al., "Efficient generation of hepatocyte-like cells from human induced pluripotent stem cells," Cell Res, 2009, 19:1233-1242, 10 pgs.
Sonntag, F., et al., "Design and prototyping of a chip-based multi-micro-organoid culture system for substance testing, predictive to human (substance) exposure," Journal of Biotechnology, 2010, 148:70-75, 6 pgs.
Soto-Gutierrez, A., et al., "Engineering of an Hepatic Organoid to Develop Liver Assist Devices," Cell Transplant., 2010, 19(6):815-822, 12 pgs.
Spear, P.C., et al., "Interkinetic nuclear migration: A mysterious process in search of a function," Develop. Growth Differ., 2012, 54:306-316, 12 pgs.
Speer, A.L., et al., "Fibroblast Growth Factor 10-Fibroblast Growth Factor Receptor 2b Mediated Signaling Is Not Required for Adult Glandular Stomach Homeostasis," PLoS ONE, 2012, 7(11):e49127, 12 pgs.
Speer, A.L., et al., "Murine Tissue-Engineered Stomach Demonstrates Epithelial Differentiation," Journal of Surgical Research, Mar. 22, 2011, 171(1):6-14, XP028317226, 9 pgs.
Spence, J.R., et al., "Directed differentiation of human pluripotent stem cells into intestinal tissue in vitro," Nature, 2011, 470(7332):105-109, 13 pgs.
Spence, J.R., et al., "Translational Embryology: Using Embryonic Principles to Generate Pancreatic Endocrine Cells from Embryonic Stem Cells," Developmental Dynamics, 2007, 236:3218-3227, 10 pgs.
Spence, J.R., et al., "Vertebrate Intestinal Endoderm Development," Developmental Dynamics, 2011, 240:501-520, 20 pgs.
Stadtfeld, M., et al., "Induced pluripotent stem cells generated with viral integration," Science, 2008, 322(5903):945-949, 12 pgs.
Stafford, D., et al., "A conserved role for retinoid signaling in vertebrate pancreas development," Dev Genes Evol, 2004, 214:432-441, 10 pgs.
Stange, D.E., et al., "Differentiated Troy+ chief cells act as 'reserve' stem cells to generate all lineages of the stomach epithelium," Cell, 2013, 155(2):357-368, 26 pgs.
Stark, R., et al., "Development of an endoluminal intestinal lengthening capsule," Journal of Pediatric Surgery, 2012, 47:136-141, 6 pgs.
Stender, S., et al., "Adiposity Amplifies the Genetic Risk of Fatty Liver Disease Conferred by Multiple Loci," Nat Genet, 2017, 49(6):842-847, 18 pgs.
Stevens, J.L., et al., "The future of drug safety testing: expanding the view and narrowing the focus," Drug Discov Today, 2009, 14(3/4): 162-167, 6 pgs.
Stuart, T., et al., "Comprehensive Integration of Single-Cell Data," Cell, 2019, 177:1888-1902, 37 pgs.

(56) References Cited

OTHER PUBLICATIONS

Su, N., et al., "Role of FGF/FGFR signaling in skeletal development and homeostasis: learning from mouse models," Bone Research, 2014, 2:14003, 24 pgs.

Sugawara, T., et al., "Organoids recapitulate organs?" Stem Cell Investig, 2018, vol. 5, Iss. 3, 4 pgs.

Sugimoto, S., et al., "Reconstruction of the Human Colon Epithelium In Vivo," Cell Stem Cell, 2018, 22:171-176, 16 pgs.

Sui, L., et al., "Signaling pathways during maintenance and definitive endoderm differentiation of embryonic stem cells," Int J Dev Bio, 2013, 57:1-12, 12 pgs.

Sun, Y., et al., "Genome engineering of stem cell organoids for disease modeling," Protein Cell, 2017, 8(5):315-327, 13 pgs.

Suzuki, A., et al., "Clonal identification and characterization of self-renewing pluripotent stem cells in the developing liver," The Journal of Cell Biology, 2002, 156(1):173-184, 12 pgs.

Tada, M., et al., "Embryonic germ cells induce epigenetic reprogramming of somatic nucleus in hybrid cells," EMBO J, 1997, 16(21):6510-6520, 11 pgs.

Taipale, J., et al., "The Hedgehog and Wnt signalling pathways in cancer," Nature, 2001, 411:349-354, 8 pgs.

Tait, I.S., et al., "Colonic mucosal replacement by syngeneic small intestinal stem cell transplantation," The American Journal of Surgery, Jan. 1994, 167:67-72, 6 pgs.

Tait, I.S., et al., "Generation of neomucosa in vivo by transplantation of dissociated rat postnatal small intestinal epithelium," Differentiation, 1994 56:91-100, 10 pgs.

Takahashi, K et al., "Induction of Pluripotent Stem Cells from Adult Human Fibroblasts by Defined Factors," Cell, 2007, 131:861-872, 12 pgs.

Takahashi, K., et al., "Induction of Pluripotent Stem Cells from Mouse Embryonic and Adult Fibroblast Cultures by Defined Factors," Cell, 2006, 126:663-676, 14 pgs.

Takahashi, S., et al., "Epigenetic differences between naïve and primed pluripotent stem cells," Cellular and Molecular Life Sciences, 2018, 75:1191-1203, 13 pgs.

Takaki, M., et al., "In Vitro Formation of Enteric Neural Network Structure in a Gut-Like Organ Differentiated from Mouse Embryonic Stem Cells," Stem Cells, Jun. 9, 2006, 24(6):1414-1422, XP55241404, 9 pgs.

Takashima, Y., et al., "Resetting Transcription Factor Control Circuitry toward Ground-State Pluripotency in Human," Cell, 2014, 158(6):1254-1269, 32 pgs.

Takebe, T., et al., "Generation of a vascularized and functional human liver from an iPSC-derived organ bud transplant," Nat Protoc, 2014, 9(2):396-409, 14 pgs.

Takebe, T., et al., "Human iPSC-Derived Miniature Organs: A Tool for Drug Studies," Clin Pharmacol Ther, 2014, 96(3):310-313, 4 pgs.

Takebe, T., et al., "Massive and Reproducible Production of Liver Buds Entirely from Human Pluripotent Stem Cells," Cell Reports, 2017, 21:2661-2670, 11 pgs.

Takebe, T., et al., "Vascularized and Complex Organ Buds from Diverse Tissues via Mesenchymal Cell-Driven Condensation," Cell Stem Cell, 2015, 16:556-565, 10 pgs.

Takebe, T., et al., "Vascularized and functional human liver from an iPSC-derived organ bud transplant," Nature, 2013, 499:481-484, 5 pgs.

Tamm, C., et al., "A Comparative Study of Protocols for Mouse Embryonic Stem Cell Culturing," PLoS ONE, 2013, 8(12):e81156, 10 pgs.

Tamminen, K., et al., "Intestinal Commitment and Maturation of Human Pluripotent Stem Cells Is Independent of Exogenous FGF4 and R-spondin1," PLOS One, Jul. 2015, 10(7):e0134551, 19 pgs.

Tang, W., et al., "Faithful expression of multiple proteins via 2A-peptide self-processing: a versatile and reliable method for manipulating brain circuits," The Journal of Neuroscience, Jul. 8, 2009, 29:8621-8629, 9 pgs.

Teo, A.K.K., et al., "Activin and BMP4 Synergistically Promote Formation of Definitive Endoderm in Human Embryonic Stem Cells," Stem Cells, 2012, 30:631-642, 12 pgs.

Terry, B.S., et al., "Preliminary Mechanical Characterization of the Small Bowel for In Vivo Robotic Mobility," J. Biomech Eng, 2011, 133:091010-1-09101-7, 7 pgs.

Thanasupawat, T., et al., "INSL5 is a novel marker for human enteroendocrine cells of the large intestine and neuroendocrine tumours," Oncology Reports, 2013, 29:149-154, 6 pgs.

The WNT homepage, "Small molecules in Wnt signalling," Nusse Lab, Jan. 2019, 2 pgs.

Theunissen, T.W., et al., "Systematic Identification of Culture Conditions for Induction and Maintenance of Naïve Human Pluripotency," Cell Stem Cell, 2014, 15:471-487, 47 pgs.

Thomson, et al., "Embryonic Stem Cell Lines Derived from Human Blastocysts," Science, 1998, 282(5391):1145-1147, 3 pgs.

Tian, X., et al., "Modulation of Multidrug Resistance-Associated Protein 2 (Mrp2) and Mrp3 Expression and Function with Small Interfering RNA in Sandwich-Cultured Rat Hepatocytes," Mol Pharmacol, 2004, 66(4):1004-1010, 7 pgs.

Tiso, N., et al., "BMP signalling regulates anteroposterior endoderm patterning in zebrafish," Mech Dev, 2002, 118:29-37, 9 pgs.

Toivonen, S., et al., "Activin A and Wnt-dependent specification of human definitive endoderm cells," Experimental Cell Research, 2013, 319:2535-2544, 10 pgs.

Tran, K., et al. "Evaluation of regional and whole gut motility using the wireless motility capsule: relevance in clinical practice," Therap Adv Gastroenterol, 2012, 5(4):249-260, 12 pgs.

Trapnell, C., et al., "Differential gene and transcript expression analysis of RNA-seq experiments with TopHat and Cufflinks," Nat Protoc, 2013, 7(3):562-578, 39 pgs.

Trapnell, C., et al., "Transcript assembly and quantification by RNA-Seq reveals unannotated transcripts and isoform switching during cell differentiation," Nat Biotechnol, 2010, 28(5):511-515, 8 pgs.

Trisno, S.L., et al., "Esophageal Organoids from Human Pluripotent Stem Cells Delineate Sox2 Functions during Esophageal Specification," Cell Stem Cell, 2018, 23:501-515, 23 pgs.

Troy, D.B. (ed.), Remington: The Science and Practice of Pharmacy, $21^{st}$ Ed., 2006, Lippincott, Williams & Wilkens, Baltimore, MD, 6 pgs., Table of Contents Only.

Tsakmaki, A., et al., "3D intestinal organoids in metabolic research: virtual reality in a dish," Current Opinion in Pharmacology, 2017, 37:51-58, 8 pgs.

Tsedensodnom, O., et al., "ROS: Redux and Paradox in Fatty Liver Disease," Hepatology, 2013, 58(4):1210-1212, 3 pgs.

Tsukada, N., et al., "The Structure and Organization of the Bile Canalicular Cytoskeleton With Special Reference to Actin and Actin-Binding Proteins," Hepatology, 1995, 21(4):1106-1113, 8 pgs.

Tuschl, T., et al., "Targeted mRNA degradation by double-stranded RNA in vitro," Genes Dev., 1999, 13:3191-3197, 8 pgs.

Tyml, K., et al., "Lipopolysaccharide reduces intercellular coupling in vitro and arteriolar conducted response in vivo," AJP-Heart Circ Physiol, 2001, 281:H1397-H1406, 10 pgs.

The United States Pharmacopeia: The National Formulary (USP 24 NF 19), United States Pharmacopeial Convention, Inc., Rockville, MD, 1999, 4 pgs., Table of Contents Only.

Uppal, K., et al., "Meckel's Diverticulum: A Review," Clinical Anatomy, 2011, 24:416-422, 7 pgs.

Valadi, H., et al., "Exosome-mediated transfer of mRNAs and microRNAs is a novel mechanism of genetic exchange between cells," Nat Cell Biol, 2007, 9(6):654-659, 17 pgs.

Van Breemen, R.B., et al., "Caco-2 cell permeability assays to measure drug absorption," Expert Opin. Drug Metab. Toxicol., Aug. 2005, 1(2):175-185, 11 pgs.

Van De Garde, M.D., et al., "Liver Monocytes and Kupffer Cells Remain Transcriptionally Distinct during Chronic Viral Infection," PLoS One, 2016, 11(11):e0166094, 16 pgs.

Van Dop, W.A., et al., "Depletion of the Colonic Epithelial Precursor Cell Compartment Upon Conditional Activation of the Hedgehog Pathway," Gastroenterology, 2009, 136:2195-2203, 16 pgs.

(56) References Cited

OTHER PUBLICATIONS

Van Klinken, B.J-W., et al., "MUC5B is the prominent mucin in human gallbladder and is also expressed in a subset of colonic goblet cells," The American Journal of Physiology, 1998, 274:G871-G878, 8 pgs.

Venick, R.S., et al., "Unique Technical and Patient Characteristics of Retransplantation: A Detailed Single Center Analysis of Intestinal Transplantation," International Small Bowel Symposium 2013; Abstract 5.203 (online: https://www.tts.org/component/%20tts/?view=presentation&id=13190), Accessed Jun. 12, 2017, 4 pgs.

Verma, S., et al., "Diagnosis, management and prevention of drug-induced liver injury," Gut, 2009, 58:1555-1564, 10 pgs.

Verzi, M.P., et al., "Role of the Homeodomain Transcription Factor Bapx1 in Mouse Distal Stomach Development," Gastroenterology, 2009, 136:1701-1710, 10 pgs.

Vosough, M., et al., "Generation of Functional Hepatocyte-Like Cells from Human Pluripotent Stem Cells in a Scalable Suspension Culture," Stem Cells Dev, 2013, 22(20):2693-2705, 13 pgs.

Wakayama, T., et al., "Full-term development of mice from enucleated oocytes injected with cumulus cell nuclei," Nature, 1998, 394:369-374, 6 pgs.

Walker, E.M., et al., "GATA4 and GATA6 regulate intestinal epithelial cytodifferentiation during development," Developmental Biology, 2014, 392:283-294, 12 pgs.

Wallace, A.S., et al., "Development of the enteric nervous system, smooth muscle and interstitial cells of Cajal in the human gastrointestinal tract," Cell and Tissue Research, Jan. 26, 2005, 319:367-382, 16 pgs.

Walton, K.D., et al., "Epithelial Hedgehog signals direct mesenchymal villus patterning through BMP," Abstracts / Developmental Biology, Program/Abstract # 354, 2009, 331:489, 1 pg.

Walton, K.D., et al., "Hedgehog-responsive mesenchymal clusters direct patterning and emergence of intestinal villi," PNAS, 2012, 109(39):15817-15822, 6 pgs.

Walton, K.D., et al., "Villification in the mouse: Bmp signals control intestinal villus patterning," Development, 2016, 143:427-436, 10 pgs.

Wan, W., et al., "The Role of Wnt Signaling in the Development of Alzheimer's Disease: A Potential Therapeutic Target?", BioMed Research International, 2014, 2014:1-9, Article ID 301575, 9 pgs.

Wang, A., et al., "Generating cells of the gastrointestinal system: current approaches and applications for the differentiation of human pluripotent stem cells," J Mol Med, 2012, 90:763-771, 9 pgs.

Wang, F., et al., "Isolation and characterization of intestinal stem cells based on surface marker combinations and colony-formation assay," Gastroenterology, 2013, 145:383-395.e1-e21, 34 pgs.

Wang, J., et al., "Mutant Neurogenin-3 in Congenital Malabsorptive Diarrhea," New England Journal of Medicine, 2006, 355:270-280, 11 pgs.

Wang, S., (Ed.), "The role of homologous genes in the development of appendages," in Basis of Developmental Biology, Press of East China University of Science and Technology, 2014, pp. 184-185, 4 pgs.

Wang, X., et al., "Cloning and variation of ground state intestinal stem cells," Nature, 2015, 522:173-178, 18 pgs.

Wang, Y., et al., "Hepatic stellate cells, liver innate immunity, and hepatitis C virus," J Gastroenterol Hepatol, 2013, 28(Suppl 1):112-115, 8 pgs.

Wang, Z., et al., "Retinoic acid regulates morphogenesis and patterning of posterior foregut derivatives," Dev Biol, 2006, 297:433-445, 13 pgs.

Want, R., "An Introduction to RFID Technology," IEEE Pervas Comput, 2006, 5:25-33, 9 pgs.

Ward, D.F., Jr., et al., "Mechanical Strain Enhances Extracellular Matrix-Induced Gene Focusing and Promotes Osteogenic Differentiation of Human Mesenchymal Stem Cells Through an Extracellular-Related Kinase-Dependent Pathway," Stem Cells and Development, 2007, 16:467-479, 14 pgs.

Ware, C.B., "Concise Review: Lessons from Naïve Human Pluripotent Cells," Stem Cells, 2017, 35:35-41, 7 pgs.

Warlich, E., et al., "Lentiviral vector design and imaging approaches to visualize the early stages of cellular reprogramming," Mol. Ther., Apr. 2011, 19:782-789, 9 pgs.

Warren, C.R., et al., "Induced Pluripotent Stem Cell Differentiation Enables Functional Validation of GWAS Variants in Metabolic Disease," Cell Stem Cell, 2017, 20:547-557, 18 pgs.

Warren, C.R., et al., "The NextGen Genetic Association Studies Consortium: A Foray into In Vitro Population Genetics," Cell Stem Cell, 2017, 20:431-433, 3 pgs.

Watson, C.L., et al., "An in vivo model of human small intestine using pluripotent stem cells," Nature Medicine, Oct. 19, 2014, 20(11):1310-1314, XP055241417, 7 pgs.

Wehkamp, J., et al., "Paneth cell antimicrobial peptides: Topographical distribution and quantification in human gastrointestinal tissues," FEBS Letters, 2006, 580:5344-5350, 7 pgs.

Weis, V.G., et al., "Current understanding of SPEM and its standing in the preneoplastic process," Gastric Cancer, 2009, 12:189-197, 9 pgs.

Wells, J.M., et al., "Early mouse endoderm is patterned by soluble factors from adjacent germ layers," Development, 2000, 127:1563-1572, 10 pgs.

Wells, J.M., et al., "How to Make an intestine," Development, Feb. 15, 2014, 141(4):752-760, XP055241409, 9 pgs.

Wen, S. et al., "Helicobacter pylori virulence factors in gastric carcinogenesis," Cancer Lett., 2009, 282:1-8, 8 pgs.

Wernig, M., et al., "In vitro reprogramming of fibroblasts into a pluripotent ES-cell-like state," Nature, 2007, 448:318-324, 8 pgs.

Whissell, G., et al., "The transcription factor GATA6 enables self-renewal of colon adenoma stem cells by repressing BMP gene expression," Nature Cell Biology, 2014, 16(7):695-707, 24 pgs.

Wieck, M.M., et al., "Prolonged Absence of Mechanoluminal Stimulation in Human Intestine Alters the Transcriptome and Intestinal Stem Cell Niche," Cell Mol Gastroenterol Hepatol, 2017, 3(3):367-388e1, 23 pgs.

Wiley, L.A., et al., "cGMP production of patient-specific iPSCs and photoreceptors precursor cells to treat retinal degenerative blindness," Scientific Reports, 2016, 6:30742, 16 pgs.

Willet, S.G., et al., "Stomach Organ and Cell Lineage Differentiation: From Embryogenesis to Adult Homeostasis," Cellular and Molecular Gastroenterology and Hepatology, 2016, 2(5):546-559, 14 pgs.

Williamson, R.C.N., et al., "Humoral stimulation of cell proliferation in small bowel after transection and resection in rats," Gastroenterology, 1978, 75:249-254, 6 pgs.

Wills, A., et al., "Bmp signaling is necessary and sufficient for ventrolateral endoderm specification in Xenopus," Dev Dyn., 2008, 237(8):2177-2186, 18 pgs.

Wilmut, I., et al., "Viable offspring derived from fetal and adult mammalian cells," Nature, 1997, 385:810-813, 4 pgs.

Woltjen, K., et al., "piggyBac transposition reprograms fibroblasts to induced pluripotent stem cells," Nature, 2009, 458(7239):766-770, 13 pgs.

Workman, M.J., et al., "Engineered human pluripotent-stem-cell-derived intestinal tissues with a functional enteric nervous system," Nat Med, 2017, 23(1):49-59, 29 pgs.

Workman, M.J., "Generating 3D human intestinal organoids with an enteric nervous system," Thesis, Graduate School of the University of Cincinnati, Oct. 2014, 61 pgs.

Xia, H.H-X., et al. "Antral-Type Mucosa in the Gastric Incisura, Body, and Fundus (Antralization): A Link Between Helicobacter pylori Infection and Intestinal Metaplasia?", Am. J. Gastroenterol., 2000, 95:114-121, 8 pgs.

Xinaris, C., et al., "Organoid Models and Applications in Biomedical Research," Nephron, 2015, 130:191-199, 9 pgs.

Xu, R., et al., "Association Between Patatin-Like Phospholipase Domain Containing 3 Gene (PNPLA3) Polymorphisms and Nonalcoholic Fatty Liver Disease: A Huge Review and Meta-Analysis," Sci Rep, 2015, 5:9284, 11 pgs.

Xu, R., et al. (Eds.), "Retinoic acid receptor" in Basis and Clinic of Receptor, Shanghai Science and Technology Press, 1992, pp. 129-131, 2 pgs.

(56) References Cited

OTHER PUBLICATIONS

Xue, X., et al., "Endothelial PAS Domain Protein 1 Activates the Inflammatory Response in the Intestinal Epithelium to Promote Colitis in Mice," Gastroenterology, 2013, 145:831-841, 11 pgs.
Yahagi, N., et al., "Position-specific expression of Hox genes along the gastrointestinal tract," Congenital Anomalies, 2004, 44:18-26, 9 pgs.
Yamada, S., et al. "Differentiation of immature enterocytes into enteroendocrine cells by Pdxl overexpression," Am. J. Physiol. Gastrointest. Liver Pyshiol., 2001, 281:G229-G236, 8 pgs.
Yanagimachi, M.D., et al., "Robust and Highly-Efficient Differentiation of Functional Monocytic Cells from Human Pluripotent Stem Cells under Serum- and Feeder Cell-Free Conditions," PLoS One, 2013, 8(4):e59243, 9 pgs.
Yanagita, M., "Modulator of bone morphogenetic protein activity in the progression of kidney diseases," Kidney International, 2006, 70:989-993, 5 pgs.
Yang, K., et al., "Systems Pharmacology Modeling Predicts Delayed Presentation and Species Differences in Bile Acid-Mediated Troglitazone Hepatotoxicity," Clin Pharmacol Ther, 2014, 96(5):589-598, 21 pgs.
Yin, C., et al., "Hepatic stellate cells in liver development, regeneration, and cancer," The Journal of Clinical Investigation, May 2013, 123(5):1902-1910, 9 pgs.
Yoneda, M., et al., "Noninvasive assessment of liver fibrosis by measurement of stiffness in patients with nonalcoholic fatty liver disease (NAFLD)," Dig Liver Dis, 2008, 40:371-378, 8 pgs.
Young, H.M., et al., "Expression of Ret-, $p75^{NTR}$-, Phox2a-, Phox2b-, and tyrosine hydroxylase-immunoreactivity by undifferentiated neural crest-derived cells and different classes of enteric neurons in the embryonic mouse gut," Developmental Dynamics, 1999, 216:137-152, 16 pgs.
Young, H.M., et al., "GDNF is a chemoattractant for enteric neural cells," Developmental biology, Dec. 19, 2000, 229:503-516, 14 pgs.
Yu, H., et al., "The Contributions of Human Mini-Intestines to the Study of Intestinal Physiology and Pathophysiology," Annu Rev Physiol, 2017, 79:291-312, 22 pgs.
Yuan, Y., et al., "Peptic ulcer disease today," Nat Clin Pract Gastroenterol Hepatol, 2006, 3:80-89, 10 pgs.
Yui, S., et al., "Functional engraftment of colon epithelium expanded in vitro from a single adult Lgr5+ stem cell," Nature Medicine, Apr. 2012, 18:618-623, 8 pgs.
Zachos, N.C., et al., "Human Enteroids/Colonoids and Intestinal Organoids Functionally Recapitulate Normal Intestinal Physiology and Pathophysiology," The Journal of Biological Chemistry, Feb. 2016, 291(8):3759-3766, 8 pgs.
Zain, S.M., et al., "A common variant in the glucokinase regulatory gene rs780094 and risk of nonalcoholic fatty liver disease: A meta-analysis," J Gastroenterol Hepatol, 2015, 30:21-27, 7 pgs.
Zambrano, E., et al., "Total parenteral Nutrition Induced Liver Pathology: An Autopsy Series of 24 Newborn Cases," Pediatr Dev Pathol, 2004, 7:425-432, 8 pgs.
Zborowski, J., et al., "Induction of swelling of liver mitochondria by fatty acids of various chain length," Biochim Biophys Acta, 1963, 70:596-598, 3 pgs.
Zbuk, K.M., et al., "Hamartomatous polyposis syndromes," Gastroenterology & Hepatology, 2007, 4(9):492-502, 12 pgs.
Zhang, D., et a., "Neural crest regionalisation for enteric nervous system formation: implications for Hirschsprung's disease and stem cell therapy," Developmental Biology, Jan. 18, 2010, 339:280-294, 15 pgs.
Zhang, Q, et al., "Small-molecule synergist of the Wnt/β-catenin signaling pathway," Proc Natl Acad Sci USA, 2007, 104(18):7444-7448, 6 pgs.
Zhang, R-R., et al., "Human iPSC-Derived Posterior Gut Progenitors Are Expandable and Capable of Forming Gut and Liver Organoids," Stem Cell Reports, 2018, 10(3):780-793, 14 pgs.
Zhang, W., et al., "Elastomeric Free-Form Blood Vessels for Interconnecting Organs on Chip Systems," Lab Chip, Apr. 2016, 16(9):1579-1586, 19 pgs.
Zhang, Y.S., et al., "Multisensor-integrated organs-on-chips platforms for automated and continual in situ monitoring of organoid behaviors," PNAS Early Edition, 2017, 10 pgs.
Zhang, Y.S., et al., "Seeking the right context for evaluating nanomedicine: from tissue models in petri dishes to microfluidic organs-on-a-chip," Nanomedicine (Lond.), 2015, 10(5):685-688, 4 pgs.
Zhao, Y., et al., "A XEN-like State Bridges Somatic Cells to Pluripotency during Chemical Reprogramming," Cell, 2015, 163:1678-1691, 15 pgs.
Zhong, J., et al., "Continuous-wave laser-assisted injection of single magnetic nanobeads into living cells," Sensors and Actuators B: Chemical, 2016, 230:298-305, 8 pgs.
Zhou, H., et al., "Generation of Induced Pluripotent Stem Cells Using Recombinant Proteins," Cell Stem Cell, 2009, 4(5):381-384, 4 pgs.
Zhou, J., et al., "The Potential for Gut Organoid Derived Interstitial Cells of Cajal in Replacement Therapy," International Journal of Molecular Sciences, Sep. 2017, 18:1-17, 17 pgs.
Zhou, Q., et al., "In vivo reprogramming of adult pancreatic exocrine cells to β-cells," Nature, 2008, 455: 627-632, 6 pgs.
Zorn, A.M., et al., "Vertebrate Endoderm Development and Organ Formation," Annu Rev Cell Dev Biol, 2009, 25:221-251, 36 pgs.
Chinese Office Action, the First Office Action, and Preliminary Search Report, dated 01- 30-2019 for Application No. CN 201580034910.4, 11 pgs.
Chinese Office Action, the Second Office Action, and Supplementary Search Report, dated Dec. 19, 2019 for Application No. CN 201580034910.4, 11 pgs.
European Exam Report dated Sep. 28, 2017 for Application No. EP 15728704.6, 4 pgs.
European Exam Report dated Jul. 4, 2018 for Application No. EP 15728704.6, 3 pgs.
European Exam Report dated May 18, 2018 for Application No. EP 15791404.5, 3 pgs.
European Search Report and Written Opinion dated Oct. 31, 2019 for Application No. EP 17793451.0, 11 pgs.
International Search Report dated Feb. 9, 2012 for Application No. PCT/US2011/035518, 7 pgs.
International Preliminary Report on Patentability and Written Opinion dated Nov. 6, 2012 for Application No. PCT/US2011/035518, 5 pgs.
International Search Report and Written Opinion dated Dec. 15, 2015 for Application No. PCT/US2015/032626, 19 pgs.
International Search Report and Written Opinion dated Jan. 25, 2016 for Application No. PCT/US2015/055956, 16 pgs.
International Preliminary Report on Patentability dated Apr. 18, 2017 for Application No. PCT/US2015/055956, 8 pgs.
International Search Report and Written Opinion dated Aug. 14, 2017 for Application No. PCT/US2017/013109, 17 pgs.
International Search Report and Written Opinion dated Jan. 19, 2018 for Application No. PCT/US2017/059845, 13 pgs.
International Search Report and Written Opinion dated Jan. 29, 2018 for Application No. PCT/US2017/059860, 13 pgs.
International Search Report and Written Opinion dated Jan. 18, 2018 for Application No. PCT/US2017/059865, 12 pgs.
International Search Report and Written Opinion dated Feb. 21, 2018 for Application No. PCT/US2017/064600, 15 pgs.
International Search Report and Written Opinion dated Jun. 14, 2018 for Application No. PCT/US2018/018585, 14 pgs.
International Search Report and Written Opinion dated Jul. 9, 2018 for Application No. PCT/US2018/027585, 12 pgs.
International Searching Authority Invitation to Pay Additional Fees, Where Applicable, Protest Fee, dated Jun. 27, 2018 for Application No. PCT/US2018/029083, 3 pgs.
International Search Report and Written Opinion dated Sep. 28, 2018 for Application No. PCT/US2018/029083, 14 pgs.
International Search Report and Written Opinion dated Jan. 8, 2019 for Application No. PCT/US2018/054635, 16 pgs.
International Search Report and Written Opinion dated May 7, 2019 for Application No. PCT/US2018/067057, 15 pgs.
International Search Report and Written Opinion dated Oct. 29, 2019 for Application No. PCT/US2019/041985, 13 pgs.

(56) References Cited

OTHER PUBLICATIONS

International Search Report and Written Opinion dated Dec. 5, 2019 for Application No. PCT/US2019/050846, 10 pgs.
International Search Report and Written Opinion dated Dec. 13, 2019 for Application No. PCT/US2019/053408, 10 pgs.
Israeli Office Action dated Nov. 29, 2018 for Application No. IL 249253, 8 pgs.
Japanese Office Action, Notice of Reasons for Refusal, and Search Report by Registered Search Organization, dated Apr. 2, 2019 for Application No. JP 2016-569618, 42 pgs.
Japanese Office Action, Notification of Reasons for Refusal, and First Search Report by Registered Search Organization, dated May 14, 2019 for Application JP 2017-520900, 65 pgs.
Singaporean Written Opinion dated Oct. 19, 2017 for Application No. SG11201609953X, 8 pgs.
Singaporean Second Written Opinion dated Sep. 4, 2018 for Application No. SG11201609953X, 6 pgs.
Singaporean Office Action, Third Written Opinion, dated May 3, 2019 for Application No. Sg 11201609953X, 5 pgs.
U.S. Appl. No. 16/346,190, filed Apr. 30, 2019, by Takebe et al., entitled: "Liver Organoid Disease Models and Methods of Making and Using Same."
U.S. Appl. No. 16/603,611, filed Oct. 8, 2019, by Mahe et al., entitled: "Methods of Making Improved Human Intestinal Organoid Compositions Via Application of Strain and Human Intestinal Organoid Compositions Thereof."
U.S. Appl. No. 16/611,998, filed Nov. 8, 2019, by Takebe et al., entitled: "Liver Organoid Compositions and Methods of Making and Using Same."
Abe T., et al., "Reporter Mouse Lines for Fluorescence Imaging," Development, Growth & Differentiation, May 2013, vol. 55, No. 4, pp. 390-405.
Adam M., et al., Psychrophilic Proteases Dramatically Reduce Single-Cell RNA-Seq Artifacts: a Molecular Atlas of Kidney Development, Development, Oct. 1, 2017, vol. 144, No. 19, pp. 3625-3632.
Arora R., et al., Multiple Roles and Interactions of Tbx4 and Tbx5 in Development of the Respiratory System, PLoS Genetics, Aug. 2, 2012, vol. 8, No. 8, e1002866, 14 pages.
Asahina K., et al., Septum Transversum-Derived Mesothelium gives rise to Hepatic Stellate Cells and Perivascular Mesenchymal Cells in Developing Mouse Liver, Hepatology, Mar. 2011, vol. 53, No. 3, pp. 983-995.
Baptista P.M., et al., "Transplantable Liver Organoids, Too Many Cell Types to Choose: a Need for Scientific Self-Organization," Current Transplantation Reports, Feb. 15, 2020, vol. 7, pp. 18-23.
Barnes R.M., et al., "Analysis of the Hand1 Cell Lineage Reveals Novel Contributions to Cardiovascular, Neural Crest, Extra- Embryonic, and Lateral Mesoderm Derivatives," Developmental Dynamics, vol. 239, 2010, pp. 3086-3097.
Baron M., et al., A Single-Cell Transcriptomic Map of the Human and Mouse Pancreas Reveals Inter- and Intra-cell Population Structure, Cell Systems, Oct. 26, 2016, vol. 3, No. 4, pp. 346-360.
Bauwens C.L., et al., "Control of Human Embryonic Stem Cell Colony and Aggregate Size Heterogeneity Influences Differentiation Trajectories," Stem Cells, vol. 26, No. 9, Sep. 2008, pp. 2300-2310.
Brandenberg N., et al., "High-Throughput Automated Organoid Culture via Stem-Cell Aggregation in Microcavity Arrays," Nature Biomedical Engineering, 2020, vol. 4, pp. 863-874.
Briggs J.A., et al., The Dynamics of Gene Expression in Vertebrate Embryogenesis at SingleCell Resolution, Science, Jun. 1, 2018, vol. 360, No. 6392, eaar5780, 23 pages.
Bult C.J., et al., Mouse Genome Database (MGD) 2019, Nucleic Acids Research, Jan. 8, 2019, vol. 47, No. D1, pp. D801-D806.
Calder, L.E., Retinoic Acid-mediated Regulation of GLI3 Enables High Yield Motoneuron Derivation from Human Embryonic Stem Cells Independent of Extrinsic Activation of SHH Signaling, Dissertation, Jan. 2015, 24 pages.
Cao J., et al., The Single-Cell Transcriptional Landscape of Mammalian Organogenesis, Nature, Feb. 2019, vol. 566, No. 7745, pp. 496-502.
Carpenedo R.L., et al., "Homogeneous and Organized Differentiation Within Embryoid Bodies Induced by Microsphere-mediated Delivery of Small Molecules," Biomaterials, May 2009, vol. 30, No. 13, pp. 2507-2515.
Carpenedo R.L., et al., "Rotary Suspension Culture Enhances the Efficiency, Yield, and Homogeneity of Embryoid Body Differentiation," Stem Cells, 2007, vol. 25, pp. 2224-2234.
Carpenedo R.L., "Microsphere-Mediated Control of Embryoid Body Microenvironments," May 2010, 24 pages.
Chambers M. S., et al., Highly Efficient Neural Conversion of Human ES and IPS Cells by Dual Inhibition of SMAD Signaling, Nature Biotechnol., Mar. 2009, vol. 27(3), pp. 275-280.
Chen Y., et al., "Robust Bioengineered 3D Functional Human Intestinal Epithelium," Scientific Reports, vol. 5 (13708), Sep. 16, 2015, XP055454950, Doi: 10.1038/srep13708, 11 pages.
Chua C.C., et al., "Single Luminal Epithelial Progenitors Can Generate Prostate Organoids in Culture," Nature Cell Biology, Oct. 2014, vol. 16(10), 26 pages.
Cohen M., et al., Lung Single-Cell Signaling Interaction Map Reveals Basophil Role in Macrophage Imprinting, Cell, Nov. 1, 2018, vol. 175, No. 4, pp. 1031-1044.
Conley B.J., et al., "Derivation, Propagation and Differentiation of Human Embryonic Stem Cells," The International Journal of Biochemistry & Cell Biology, 2004, vol. 36, pp. 555-567.
De Soysa T.Y., et al., Single-cell Analysis of Cardiogenesis Reveals Basis for Organ-level Developmental Defects, Nature, Aug. 2019, vol. 572, No. 7767, pp. 120-124.
Dolle L., et al., "EpCAM and the Biology of Hepatic Stem/Progenitor Cells," American Journal of physiology gastrointestinal liver physiology, 2015, vol. 308, pp. G233-G250.
Dye B.R., et al., "Take a Deep Breath and Digest the Material: Organoids and Biomaterials of the Respiratory and Digestive Systems," Materials Research Society, Sep. 2017, vol. 7, No. 3, pp. 502-514.
Ei Sebae G.K., et al., "Single-Cell Murine Genetic Fate Mapping Reveals Bipotential Hepatoblasts and Novel Multi-organ Endoderm Progenitors," Development, Oct. 1, 2018, vol. 145, No. 19, dev168658, 7 pages.
Erkan M., et al., Organ-, Inflammation- and Cancer Specific Transcriptional Fingerprints of Pancreatic and Hepatic Stellate Cells,. Molecular Cancer, Dec. 2010, vol. 9, No. 1, pp. 1-15.
Farrell J.A., et al., Single-Cell Reconstruction of Developmental Trajectories During Zebrafish Embryogenesis, Science, Jun. 1, 2018, vol. 360, No. 6392, eaar3131, 18 pages.
Fattahi F., et al., Deriving Human ENS Lineages for Cell Therapy and Drug Discovery in Hirschsprung Disease, Nature, Feb. 2016, vol. 531 (7592), pp. 105-109.
Ferretti E., et al., Mesoderm Specification and Diversification: From Single Cells to Emergent Tissues,. Current Opinion in Cell Biology, Dec. 2019, vol. 61, pp. 110-116.
Forster R., et al., "Human Intestinal Tissue with Adult Stem Cell Properties Derived from Pluripotent Stem Cells," Stem Cell Reports, Jun. 3, 2014, vol. 2, No. 6, pp. 838-852.
Foulke-Abel J., et al., Human Enteroids as a Model of Upper Small Intestinal Ion Transport Physiology and Pathophysiology, Gastroenterology, Mar. 2016, vol. 150, No. 3, pp. 638-649.
Francou A., et al., Second Heart Field Cardiac Progenitor Cells in the Early Mouse Embryo, Biochimica et Biophysica Acta, Apr. 1, 2013, vol. 1833, No. 4, pp. 795-798.
Franklin V., et al., Regionalisation of the Endoderm Progenitors and Morphogenesis of the Gut Portals of the Mouse Embryo,. Mechanisms of Development, Jul. 1, 2008, vol. 125, No. 7, pp. 587-600.
Gao S., et al., Fetal Liver: An Ideal Niche for Hematopoietic Stem Cell Expansion, Science China, Life Sciences, Review, Aug. 2018, vol. 61 (8), pp. 885-892.
Gissen P et al., "Structural and Functional Hepatocyte Polarity and Liver Disease," Journal of Hepatology, 2015, vol. 63, pp. 1023-1037.
Godoy P., et al., "Recent Advances in 2D and 3D in vitro Systems Using Primary Hepatocytes, Alternative Hepatocyte Sources and

(56) References Cited

OTHER PUBLICATIONS

Non-parenchymal Liver Cells and their use in Investigating Mechanisms of Hepatotoxicity Cell Signaling and ADME," Arch Toxicol, Aug. 2013, vol. 87, 216 pages.

Graffmann N., et al., "Modeling Nonalcoholic Fatty Liver Disease With Human Pluripotent Stem Cell-Derived Immature Hepatocyte-Like Cells Reveals Activation of PLIN2 and Confirms Regulatory Functions of Peroxisome Proliferator-Activated Receptor Alpha," Stem Cells and Development, vol. 25 (15), 2016, pp. 1119-1133.

Grand R. J., et al., "Development of the Human Gastrointestinal Tract- A Review," Gastroenterology, May 1976, vol. 70, No. 5, pp. 790-810.

Grapin-Botton A., Antero-posterior Patterning of the Vertebrate Digestive Tract: 40 Years After Nicole Le Douarin's PhD Thesis, The International Journal of Developmental Biology, Jan. 1, 2005, vol. 49, Nos. 2-3, pp. 335-347.

Griffin O.D., et al., "Human B1 Cells in Umbilical Cord and Adult Peripheral Blood Express the Novel Phenotype CD20+CD27+CD43+CD70-," Journal of Experimental Medicine, 2011, vol. 208(1), pp. 67-80.

Han L., et al., Single Cell Transcriptomics Identifies a Signaling Network Coordinating Endoderm and Mesoderm Diversification during Foregut Organogenesis, Nature Communications, Aug. 2020, vol. 11, No. 4158, pp. 1-16.

Hill D R., et al., "Bacterial Colonization Stimulates a Complex Physiological Response in the Immature Human Intestinal Epithelium," Developmental Biology, Microbiology and Infectious Disease, Tools and Resources, Nov. 7, 2017, XP055822977, retrieved from the Internet: https://elifesciences.org/articles/29132,35 pages.

Hoffmann A.D., et al., Sonic Hedgehog Is required in Pulmonary Endoderm for Atrial Septation, Development, 2009, vol. 136, pp. 1761 1770.

Horie M., et al., TBX4 is involved in the Super-Enhancer-Driven Transcriptional Programs Underlying Features Specific to Lung Fibroblasts,. The American Journal of Physiology-Lung Cellular and Molecular Physiology, Jan. 1, 2018, vol. 314, No. 1, pp. L177-L191.

Huss J. M., et al., "Constitutive Activities of Estrogen-Related Receptors: Transcriptional Regulation of Metabolism by the ERR Pathways in Health and Disease," Biochimica et Biophysica Acta, 2015, vol. 1852, 2015, pp. 1912-1927.

Huynh N., et al., "61.06 Feasibility and Scalability of Spring Parameters in Distraction Enterogenesis in a Murine Model," 2017, 3 pages, Retrieved from Internet: URL: https://www.asc-abstracts.org/abs2017/61-06-feasibility-and-scalability-of-spring- parameters- in- distraction-enterogenesis-in-a-murine-model/, Retrieved on Jun. 4, 2022.

Ibarra-Soria X. et al., Defining Murine Organogenesis at Single-Cell Resolution Reveals a Role for the Leukotriene Pathway in Regulating Blood Progenitor Formation,. Nature Cell Biology, Feb. 2018, vol. 20, No. 2, pp. 127-134.

Khan J.A., et al., "Fetal Liver Hematopoietic Stem Cell Niches Associate With Portal Vessels," Science, Jan. 8, 2016, vol. 351 (6269), pp. 176-180.

Kharchenko V. P., et al., Bayesian Approach to Single-cell Differential Expression Analysis, Nature Methods, Jul. 2014, vol. 11, No. 7, pp. 740-742.

Kim E., et al., Isl1 Regulation of Nkx2.1 in the Early Foregut Epithelium Is Required for Trachea-Esophageal Separation and Lung Lobation, Developmental Cell, Dec. 16, 2019, vol. 51, No. 6, pp. 675-683.

Kimura M., et al., "Digitalized Human Organoid for Wireless Phenotyping," iScience, cell press, XP055822469, DOI: 10.1016/j.isci.2018.05.007, retrieved from the Internet: https://www.ncbi.nlm.nih.gov/pmc/articles/PMC6147234/, Jun. 29, 2018, vol. 4, pp. 294-301.

Kiselev Y. V., et al., SCmap—A Tool for Unsupervised Projection of Single Cell RNA-seq data, Nature Methods, May 2018, vol. 15 (5), pp. 359-362.

Koike H., et al., "Engineering Human Hepato-Biliary-Pancreatic Organoids from Pluripotent Stem Cells," Nature Protocols, Feb. 2021, vol. 16(2), pp. 919-936.

Koike H., et al., Modeling human hepato-biliary-pancreatic organogenesis from the foregutmidgut boundary, Nature, Oct. 2019, vol. 574(7776), pp. 112-116.

Langfelder P., et al., WGCNA: An R package for weighted correlation network analysis, BMC Bioinformatics, Dec. 2008, vol. 9 (1), pp. 1-13.

Langmead B., et al., Fast Gapped-read Alignment with Bowtie 2, Nature Methods, Apr. 2012, vol. 9 (4), pp. 357-359.

Le Douarin N., et al., Role of the Mesoderm in the Induction of the Synthesis of Glycogen During Differentiation of the Hepatic Endoderm, CR Acad Hebd Seances Acad Sci D, 1967, vol. 264, pp. 1872-1874.

Lee G., et al., "Derivation of Neural Crest Cells From Human Pluripotent Stem Cells," Nature Protocols, Mar. 18, 2010, vol. 5(4), pp. 688-701.

Li et al., RSEM: Accurate Transcript Quantification from RNA-Seq data with or without a Reference Genome, BMC Bioinformatics Aug. 2011, vol. 12, No. 323, 16 pages.

Li L.C., et al., Single-Cell Transcriptomic Analyses Reveal Distinct Dorsal/Ventral Pancreatic Programs,. EMBO Reports, Oct. 2018, vol. 19, No. 10, e46148, 14 pages.

Lis R., et al., "Conversion of Adult Endothelium to Immunocompetent Haematopoietic Stem Cells," Nature, May 2017, vol. 545 (7655), pp. 439-445.

Loh K. M., et al., Mapping the Pairwise Choices Leading From Pluripotency to Human Bone, Heart, and Other Mesoderm Cell Types, Cell, Jul. 14, 2016, vol. 166, No. 2, pp. 451-467.

Manno L. G., et al., Molecular Diversity of Midbrain Development in Mouse, Human and Stem Cells, Cell, Oct. 6, 2016, vol. 167, (2), pp. 566-580.

Mashima H., et al., INSL5 may be a Unique Marker of Colorectal Endocrine Cells and Neuroendocrine Tumors, Biochemical and Biophysical Research Communications, 2013, vol. 432, pp. 586-592.

McCann C.J., et al., "Enteric Neural Stem Cell Therapies for Enteric Neuropathies," Neurogastroenterology and Motility, vol. 30, e13369, 2018, doi: 10.1111/nmo. 13369, pp. 1-9.

McGrath P.S., et al., The Basic Helix-Loop-Helix Transcription Factor NEUROG3 Is Required for Development of the Human Endocrine Pancreas, Diabetes, Jul. 2015, vol. 64, pp. 2497-2505.

McIntyre B., et al., "Gli3-mediated hedgehog inhibition in human pluripotent stem cells initiates and augments developmental programming of adult hematopoiesis," The American Society of Hematology, Feb. 28, 2013, vol. 121 (9), pp. 1543-1552.

McKimpson W.M., et al., "A Fluorescent Reporter Assay of Differential Gene Expression Response To Insulin In Hepatocytes," Methods in Cell Physiology, American Journal of Physiology Cell Physiology, May 15, 2019, vol. 317, pp. C143-C151.

Menendez L., et al., Directed differentiation of human pluripotent cells to neural crest stem cells, Nature Protocols, Jan. 2013, vol. 8 (1), pp. 203-212.

Mitaka., et al., "Characterization of Hepatic-organoid Cultures," Drug Metabolism Reviews, 2010, vol. 42, No. 3, pp. 472-481.

Mitaka T., "Reconstruction of Hepatic Organoid by Hepatic Stem Cells," Journal of Hepatobiliary Pancreatic Surgery, 2002, vol. 9 (6), pp. 697-703.

Moignard V., et al., Decoding the Regulatory Network of Early Blood Development From Single-Cell Gene Expression Measurements, Nature Biotechnology, Mar. 2015, vol. 33, No. 3, pp. 269-276.

Montecino-Rodriguez E., et al., "Identification of a B-1 B Cell-Specified Progenitor," Natural Immunology, Mar. 2006, vol. 7(3), pp. 293-301.

Morrison A. J., et al., Single-cell transcriptome analysis of avian neural crest migration reveals signatures of invasion and molecular transitions, eLife., Dec. 2017, vol. 6, 27 pages.

Moschidou D., et al., "Human Mid-Trimester Amniotic Fluid Stem Cells Cultured under Embryonic Stem Cell Conditions with Valproic Acid Acquire Pluripotent Characteristics," Stem Cells and Development, Feb. 1, 2013, vol. 22, No. 3, pp. 444-458.

(56) References Cited

OTHER PUBLICATIONS

Nantasanti S., et al., Disease Modeling and Gene Therapy of Copper Storage Disease in Canine Hepatic Organoids, Stem Cell Reports, 2015, vol. 5, pp. 895-907.

Nasr T., et al., Endosome-Mediated Epithelial Remodeling Downstream of Hedgehog-Gli Is Required for Tracheoesophageal Separation, Developmental Cell, Dec. 16, 2019, vol. 51, No. 6, pp. 665-674.

Naujok O., et al., Cytotoxicity and Activation of the WNT/Beta-Catenin Pathway in Mouse Embryonic Stem Cells Treated with Four GSK3 Inhibitors, BMC Research Notes, 2014, vol. 7, No. 273, pp. 1-8.

Ng S., et al., "Human iPSC-Derived Hepatocyte-Like Cells Support Plasmodium Liver-Stage Infection In Vitro," Stem cell reports, Mar. 10, 2015, vol. 4, pp. 348-359.

Nowotschin S., et al., The Emergent Landscape of the Mouse Gut Endoderm at Single-Cell Resolution, Nature, May 2019, vol. 569, No. 7756, pp. 361-367.

Ogaki S., et al., A Cost-Effective System for Differentiation of Intestinal Epithelium from Human Induced Pluripotent Stem Cells, Scientific Reports, Nov. 30, 2015, 11 pages.

Payushina O.V., Hematopoietic Microenvironment in the Fetal Liver: Roles of Different Cell Populations, Review Article, International Scholarly Research Network Cell Biology, 2012, 8 pages.

Pedersen J.K., et al., Endodermal Expression of Nkx6 Genes depends differentially on Pdx1, Developmental Biology, Dec. 15, 2005, vol. 288, No. 2, pp. 487-501.

Peng T., et al., Coordination of Heart and Lung Co-development by a Multipotent Cardiopulmonary Progenitor, Nature, Aug. 2013, vol. 500, No. 7464, pp. 589-592.

Pijuan-Sala B., et al., A Single-Cell Molecular Map of Mouse Gastrulation and Early Organogenesis, Nature, Feb. 2019, vol. 566, No. 7745, pp. 490-495.

Que J., et al., Mesothelium Contributes to Vascular Smooth Muscle and Mesenchyme During Lung Development, Proceedings of the National Academy of Sciences USA, Oct. 28, 2008, vol. 105, No. 43, pp. 16626-16630.

Rana M.S., et al., A Molecular and Genetic Outline of Cardiac Morphogenesis, Acta Physiologica (Oxf), Apr. 2013, vol. 207, No. 4, pp. 588-615.

Riehl T., et al., "CD44 and TLR4 Mediate Hyaluronic Acid Regulation of Lgr5+ Stem Cell Proliferation, Crypt Fission, and Intestinal Growth in Postnatal and Adult Mice," The American Journal of Physiology-Gastrointestinal and Liver Physiology, Dec. 1, 2015, vol. 309, No. 11, pp. G874-G887.

Robert-Moreno A., et al., "Impaired Embryonic Haematopoiesis Yet Normal Arterial Development in the Absence of the Notch ligand Jagged1 ," EMBO Journal, 2008, vol. 27(13), pp. 1886-1895.

Robert-Moreno A., et al., "RBPj?—dependent Notch Function Regulates Gata2 and is Essential for the Formation of Intraembryonic Hematopoietic Cells," Development and disease, 2005, vol. 132(5), pp. 1117-1126.

Rothstein L.T., et al., "Human B-1 cells take the stage," Annals of the New York Academy of Sciences, May 2013, vol. 1285, pp. 97-114.

Rubin L.L., et al., Targeting the Hedgehog Pathway in Cancer, Nature Reviews Drug Discovery, 2006, vol. 5, pp. 1026-1033.

Sanchez-Valle V., et al., "Role of Oxidative Stress and Molecular Changes in Liver Fibrosis: A Review," Current Medicinal Chemistry, 2012, vol. 19, No. 28, pp. 4850-4860.

Sander M., et al., Homeobox Gene Nkx6.1 lies Downstream of Nkx2.2 in the major Pathway of Beta-Cell formation in the Pancreas, Development, Dec. 15, 2000, vol. 127, No. 24, pp. 5533-5540.

Sathananthan A.H., et al., "Human Embryonic Stem Cells and their Spontaneous Differentiation," Italian Journal of Anatomy and Embryology, 2005, vol. 110 (Supplement 1), No. 2, pp. 151-157.

Sauka-Spengler T et al., Snapshot: Neural Crest, Cell, Oct. 2010, vol. 143, No. 3, 486-486. e1.

Schlieve C. R., et al., Neural Crest Cell Implantation Restores Enteric Nervous System Function and Alters the Gastrointestinal Transcriptome in Human Tissue-Engineered Small Intestine, Stem Cell Reports, ISSCR, Sep. 12, 2017, vol. 9, pp. 883-896.

Scialdone A., et al., Resolving Early Mesoderm Diversification Through Single-Cell Expression Profiling, Nature, Jul. 2016, vol. 535, No. 7611, pp. 289-293.

Scott A., et al., "Repeated Mechanical Lengthening of Intestinal Segments in a Novel Model," Journal of Pediatric Surgery, Jun. 2015, vol. 50, No. 6, pp. 954-957.

Seet C.S., et al., Generation of Mature T Cells from Human Hematopoietic Stem/Progenitor Cells in Artificial Thymic Organoids, Nature Methods, May 2017, vol. 14 (5), pp. 521-530.

Semrau S., et al., Dynamics of lineage commitment revealed by single-cell transcriptomics of differentiating embryonic stem cells, Nature Communications, Oct. 2017, vol. 8 (1), pp. 1-16.

Simões F.C., et al., "The Ontogeny, Activation and Function of the Epicardium During Heart Development and Regeneration," Development, Apr. 1, 2018, vol. 145, No. 7, dev155994; 13 pages.

Simian M., et al., "Organoids: A Historical Perspective of Thinking In Three Dimensions," Journal of Cell Biology, 2017, vol. 216, No. 1, pp. 31-40.

Soldatow V. Y., et al., "In Vitro Models for Liver Toxicity Testing," Toxicology Research 2.1, 2013, vol. 2, pp. 23-39.

Sugimura R., et al., "Haemotopoietic Stem and Progenitor Cells from Human Pluripotent Stem Cells," Nature, May 25, 2017, vol. 545 (7655), pp. 432-438.

Sullins V. F., et al., "Intestinal Lengthening in an Innovative Rodent Surgical Model," Journal of Pediatric Surgery, Dec. 2014, vol. 49, No. 12, pp. 1791-1794.

Sweetman D., et al., The Migration of Paraxial and Lateral Plate Mesoderm Cells Emerging From the Late Primitive Streak Is Controlled by Different Wnt Signals, BMC Developmental Biology, Dec. 2008, vol. 8, No. 1, pp. 1-15.

Tanaka M., "Molecular and Evolutionary Basis of Limb Field Specification and Limb Initiation," Development, Growth & Differentiation, Jan. 2013, vol. 55, No. 1, pp. 149-163.

Tang X. et al. Transcriptome Regulation and Chromatin Occupancy by E2F3 and MYC in Mice, Scientific Data, Feb. 16, 2016, vol. 3, No. 1, pp. 1-8.

Testaz S., et al., Sonic hedgehog restricts adhesion and migration of neural crest cells independently of the Patched-Smoothened-Gli signaling pathway, PNAS, Oct. 23, 2001, vol. 98 (22), pp. 12521-12526.

Ueda T., et al., "Expansion of Human NOD/SCID-repopulating Cells by Stem Cell Factor Flk2/Flt3 ligand, thrombopoietin, IL-6, and soluble IL-6 receptor," Journal of Clinical Investment, 2000, vol. 105(7), pp. 1013-1021.

Uenishi I.G., et al., "NOTCH Signaling Specifies Arterial-type Definitive Hemogenic Endothelium from Human Pluripotent Stem Cells," Nature Communication, 2018, 14 pages.

Wagner D.E., et al., Lineage Tracing Meets Single-cell Omics: Opportunities and Challenges, Nature Reviews Genetics, Jul. 2020, vol. 21, No. 7, pp. 410-427.

Wang, et al., "Spatially Monitoring Oxygen Level in 3D Microfabricated Cell Culture Systems Using Optical Oxygen Sensing Beads," Lab on a Chip, 2013, vol. 13, pp. 1586-1592.

Wang J., et al., WebGestalt 2017: A more comprehensive, powerful, flexible and interactive gene set enrichment analysis toolkit, Nucleic Acids Research, Jul. 2017, vol. 45, 8 pages.

Wang L., et al., "The Maintenance and Generation of Membrane Polarity in Hepatocytes," Hepatology, 2004, vol. 39, No. 4, pp. 892-899.

Weinreb C., et al., Lineage tracing on transcriptional landscapes links state to fate during differentiation, Science, Feb. 14, 2020, vol. 367, (6479), 48 pages.

Weinreb C., et al., Spring: A Kinetic Interface for Visualizing High Dimensional Single-cell Expression Data, Bioinformatics, Apr. 2018, vol. 34 (7), pp. 1246-1248.

Weisenberg, E. M.D., "Esophagus—General Histology"; Pathology Outlines, Copyright 2003- 2023, 2023,3 Pages.

(56) References Cited

OTHER PUBLICATIONS

Wilkinson C. A., et al., "Long-term Ex-vivo Haematopoietic-stem-Cell Expansion Allows Nonconditioned Transplantation," Nature, 2019, vol. 571 (7763), pp. 117-121.
Xie T., et al., Single-Cell Deconvolution of Fibroblast Heterogeneity in Mouse Pulmonary Fibrosis, Cell Reports, Mar. 27, 2018, vol. 22, No. 13, pp. 3625-3640.
Yu G., et al., ClusterProfiler: An R package for Comparing Biological Themes Among Gene Clusters, Omics: A Journal Integrative Biology, May 2012, vol. 16 (5), pp. 284-287.
Yuelei C., et al., BMP Signaling Pathway and Colon Cancer, CNKI, Oct. 15, 2009, 1 page.
Zaret K.S., From Endoderm to Liver Bud: Paradigms of Cell Type Specification and Tissue Morphogenesis, Current Topics in Developmental Biology, Jan. 2016, vol. 117, pp. 647-669.
Zeltner N., et al., Feeder-free derivation of neural crest progenitor cells from human pluripotent stem cells, Journal of Visualized Experiments, May 2014, vol. 87, 9 pages.
Zhang C., et al., "Angiopoietin-like 5 and IGFBP2 Stimulate Ex-vivo Expansion of Human Cord Blood Hematopoietic Stem Cells as Assayed by NOD/SCID transplantation," Hematopoiesis and stem Cells, 2008, vol. 111 (7), pp. 3415-3423.
Zhang X., et al., A Comprehensive Structure-Function Study of Neurogenin3 Disease-Causing Alleles during Human Pancreas and Intestinal Organoid Development, Developmental Cell, Aug. 5, 2019, vol. 50, pp. 367-380.
Abo., K.M., et al., Human iPSC-Derived Alveolar and Airway Epithelial Cells Can Be Cultured at Air-liquid Interface and Express SARS-CoV-2 Host Factors. Biorxiv, June 4; 2020, 27 pages.
Adachi S., et al., "Three Distinctive Steps in Peyer's Patch Formation of Murine Embryo," International Immunology, Apr. 1997, vol. 9(4), pp. 507-514.
Anderson C.M.H., et al., "Inhibition of Intestinal Dipeptide Transport by the Neuropeptide VIP is an Anti-absorptive Effect via the VPAC1 Receptor in a Human Enterocyte-like Cell Line (Caco-2)," British Journal of Pharmacology, 2003, vol. 138, No. 4, pp. 564-573.
Ang L. T., et al., "A Roadmap for Human Liver Differentiation from Pluripotent Stem Cells," Cell Reports, Feb. 20, 2018, vol. 22, pp. 2190-2205.
Baker C., et al., "Hypoganglionosis in the Gastric Antrum Causes Delayed Gastric Emptying," Neurogastroenterology and Motility, May 2020, vol. 32(5): e13766, 18 pages.
Balbinot C., et al., "Fine-tuning and Autoregulation of the Intestinal Determinant and Tumor Suppressor Homeobox Gene CDX2 by Alternative Splicing," Cell Death and Differentiation, 2017, vol. 24, No. 12, pp. 2173-2186.
Barber K., et al., "Derivation of Enteric Neuron Lineages from Human Pluripotent Stem Cells," Nature Protocols, Apr. 2019, vol. 14, No. 4, pp. 1261-1279.
Bar-Ephraim Y.E., et al., "Organoids in Immunological Research,". Nature Reviews Immunology, May 2020, vol. 20(5), pp. 279-293.
Barkauskas C. E. et al. "Lung Organoids: Current Uses and Future Promise," Development, Mar. 15; 2017, vol. 144(6), pp. 986-997.
Barkauskas C.E., et al., Type 2 alveolar Cells Are Stem Cells in Adult Lung. The Journal of Clinical Investigation, Jul. 1, 2013, vol. 123(7), pp. 3025-3036.
Barnes P.J., et al., "Chronic Lung Diseases: Prospects for Regeneration and Repair," European Respiratory Review, Mar. 31, 2021, vol. 30(159), 14 pages.
Basil, M. C., et al., "The Cellular and Physiological Basis for Lung Repair and Regeneration: Past, Present, and Future," Apr. 2, 2020, vol. 26(4, pp. 482-502.
Batterham R.L., et al., "Gut Hormone PYY3-36 Physiologically Inhibits Food Intake," Nature, Aug. 8, 2002, vol. 418, pp. 650-654.
Beckett E.A.H., et al., "Inhibitory Responses Mediated by Vagal Nerve Stimulation are Diminished in Stomachs of Mice with Reduced Intramuscular Interstitial Cells of Cajal," Mar. 20, 2017, Scientific Reports, vol. 7, No. 44759, 11 pages.

Beers M.F., et al., "Alveolar Type 2 Epithelial Cell Quality Control Responses to Pulmonary Fibrosis Related SFTPC Mutations Are Dysfunctional And Substrate Specific," The FASEB Journal, Apr. 2020, vol. 34(S1), 1 page (Abstract Only).
Bergen V., et al., "Generalizing RNA Velocity to Transient Cell States Through Dynamical Modeling," Nature Biotechnology, Oct. 28, 2019, vol. 38(12), 26 pages.
Bharat A., et al., "Lung Transplantation for Patients with Severe COVID-19," Science Translational Medicine, Dec. 16, 2020, vol. 12(574):eabe4282, 13 pages.
Blanchard J.W., et al., "Reconstruction of the Human Blood-Brain Barrier in vitro reveals a Pathogenic Mechanism of APOE4 in Pericytes," Nature Medicine, Jun. 2020, vol. 26, No. 6, pp. 952-963.
Bohorquez D.V., et al., "Neuroepithelial Circuit Formed by Innervation of Sensory Enteroendocrine Cells," The Journal of Clinical Investigation, 2015, vol. 125, No. 2, pp. 782-786.
Bolte C., et al., "FOXF1 Transcription Factor Promotes Lung Regeneration After Partial Pneumonectomy," Scientific Reports, Sep. 6, 2017, vol. 7(1):10690, 14 pages.
Braegger C.P., et al., "Ontogenetic Aspects of the Intestinal Immune System in Man," International Journal of Clinical and Laboratory Research, 1992, vol. 22(1), pp. 1-4.
Breit S., et al., "Vagus Nerve as Modulator of the Brain-Gut Axis in Psychiatric and Inflammatory Disorders," Frontiers in Psychiatry, Mar. 13, 2018, vol. 9, Article. 44, 15 pages.
Brookes S.J.H., et al., "Extrinsic Primary Afferent Signaling in the Gut," Nature Rev Gastroenter Hepatol., 2013, vol. 10, No. 5, pp. 286-296.
Brosch M., et al., "Epigenomic Map of Human Liver Reveals Principles of Zonated Morphogenic and Metabolic Control," Nature Communications, 2018, vol. 9, Article. 4150, 13 pages.
Buning J.W., et al., "Higher Hydrocortisone Dose Increases Bilirubin in Hypopituitary Patients- results from an RCT," European Journal of Clinical Investigation, 2016, vol. 46, No. 5, pp. 475-480.
Burleigh D.E., et al., "Stimulation of Intestinal Secretion by Vasoactive Intestinal Peptide and Cholera Toxin," Autonomic Neuroscience: Basic and Clinical, 2007, vol. 133, pp. 64-75.
Buske., et al., "On The Biomechanics of Stem Cell Niche Formation in the Gut—Modelling Growing Organoids," The FEBS Journal, 2012, vol. 279, pp. 3475-3487.
Bykov V.L., "Paneth Cells: History of Discovery, Structural and Functional Characteristics and the Role in the Maintenance of Homeostasis in the Small Intestine," Morfologiia, 2014, vol. 145, No. 1, pp. 67-80.
Cakir B., et al., "Development of Human Brain Organoids with Functional Vascular-like System," Nature Methods, Nov. 2019, vol. 16, No. 11, pp. 1169-1176.
Cao J., et al., "A Human Cell Atlas of Fetal Gene Expression," Science, Nov. 13, 2020, vol. 370(6518), 42 pages.
Cardenas-Diaz F. L., et al., Temporal and Spatial Staging of Lung Alveolar Regeneration Is Determined by the Grainyhead Transcription Factor Tfcp2l1Cell Reports, May 30; 2023, vol. 42(5), 21 pages.
Cardoso W.V., et al., "Regulation of Early Lung Morphogenesis: Questions, Facts and Controversies," Development, 2006, vol. 133, pp. 1611-1624.
Chandrasekaran A., et al., "Astrocyte Differentiation of Human Pluripotent Stem Cells: New Tools for Neurological Disorder Research," Frontiers in Cellular Neuroscience, Sep. 26, 2016, vol. 10, Article. 215, 27 pages.
Chassaing B., et al., "Mammalian Gut Immunity," Biomedical Journal, Sep. 2014, vol. 37(5) p. 246 in 22 pages.
Chen M., et al., "Gene Ablation for PEPT1 in Mice Abolishes the Effects of Dipeptides on Small Intestinal Fluid Absorption, Short Circuit Current and Intracellular pH," American Journal of Physiology-Gastrointestinal and Liver Physiology, Apr. 29, 2010, 33 pages.
Cheng Y., et al., "Current Development Status of MEK Inhibitors," Molecules, 2017, vol. 22, pp. 1-20.
Choi J., et al., "Inflammatory Signals Induce AT2 Cell-Derived Damage-Associated Transient Progenitors that Mediate Alveolar Regeneration," Cell stem cell, Sep. 3, 2020, vol. 27(3), pp. 366-382.
Chung C., et al., "Hippo-Foxa2 Signaling Pathway Plays a Role in Peripheral Lung Maturation and Surfactant Homeostasis." Proceed-

(56) References Cited

OTHER PUBLICATIONS ings of the National Academy of Sciences of the United States of America, May 7, 2013, vol. 110(19), pp. 7732-7737.
Chung, M. I., et al., "Niche-mediated BMP/SMAD Signaling Regulates Lung Alveolar Stem Cell Proliferation and Differentiation," Development, May 1, 2018, vol. 145(9):dev 163014, 23 pages.
Cox H.M., "Neuroendocrine Peptide Mechanisms Controlling Intestinal Epithelial Function," Current Opinion in Pharmacology, 2016, vol. 31, pp. 50-56.
Cox H.M., et al., "Peptide YY Is Critical for Acylethanolamine Receptor Gpr119-Induced Activation of Gastrointestinal Mucosal Responses," Cell Metabolism, Jun. 9, 2010, vol. 11, pp. 532-542.
Creeden J.F., et al., "Bilirubin as a Metabolic Hormone: the Physiological Relevance of Low Levels," American Journal of Physiology-Endocrinology and Metabolism, 2021, vol. 320, No. 2, 59 pages.
Daviaud N., et al., "Vascularization and Engraftment of Transplanted Human Cerebral Organoids in Mouse Cortex," Disorders of the Nervous System, Nov./Dec. 2018, vol. 5, No. 6, 18 pages.
De Carvalho A.L.R.T et al., "The in Vitro Multi-Lineage Differentiation and Maturation of Lung and Airway Cells from Human Pluripotent Stem Cell-derived Lung Progenitors in 3D," Nature Protocols, Apr. 2021, 16(4), pp. 1802-1829.
De Carvalho A.L.R.T., et al., "Glycogen Synthase Kinase 3 Induces Multilineage Maturation of Human Pluripotent Stem Cell-derived Lung Progenitors in 3D Culture," Development. Jan. 1, 20195, vol. 146(2):dev171652, 34 pages.
De Lau W., et al., "Peyer's Patch M Cells Derived from Lgr5+ Stem Cells Require SpiB and are Induced by RankL in Cultured Miniguts,". Molecular and Cellular Biology, Sep. 2012, vol. 32(18), pp. 3639-3647.
De Souza H.S.P., et al., "Immunopathogenesis of IBD: Current State of the Art," Nature Reviews Gastroenterology & Hepatology, Jan. 2016, vol. 13(1), pp. 13-27.
Dekkers J.F., et al., "High-resolution 3D Imaging of Fixed and Cleared Organoids," Nature protocol, Jun. 2019, vol. 14(6), pp. 1756-1771.
Dunn, A et al., Highly Efficient In Vivo Targeting of the Pulmonary Endothelium Using Novel Modifcations of Polyethlenimine: An Importance of Charge, Adv Healthc Mater 7 (23) Dec. 2018.
Dunn, A et al., Polymeric Vectors for Strategic Delivery of Nucleic Acids, NaNo. LIFE, vol. 7, No. 2 2017.
Dunn, A et al., POLYseq A poly (B-Amino ester)-based Vector for Multifunctional Cellular Barcoding, vol. 16 2149-2158 Stem Cell Reports, Sep. 2021.
Duren Z., et al., "Modeling Gene Regulation from Paired Expression and Chromatin Accessibility Data,".Proceedings of the National Academy of Sciences of the United States of America, Jun. 2, 2017, vol. 114(25), pp. E4914-E4923.
Eberl G., et al., "An Essential Function for the Nuclear Receptor RORgamma(t) in the Generation of Fetal Lymphoid Tissue Inducer Cells," Nature Immunology, Dec. 21, 2003, vol. 5(1), pp. 64-73.
Egerod K.L., et al., "A Major Lineage of Enteroendocrine Cells Coexpress CCK, Secretin, Gip, GLP-1, PYY, and Neurotensin but Not Somatostatin," Endocrinology, Dec. 1, 2012, vol. 153, No. 12, pp. 5782-5795.
Egerod K.L., et al., "Profiling of G Protein-coupled Receptors in Vagal Afferents Reveals Novel Gut-to-brain Sensing Mechanisms," Molecular Metabolism, 2018, vol. 12, pp. 62-75.
Fan, Y et al., "Bioengineering Thymus Organoids to Restore Thymic Function and Induce Donor-Specific Immune Tolerance to Allografts," Molecular Therapy, vol. 23, No. 7, Jul. 2015, pp. 1262-1277.
Faure S., et al., "Endogenous Patterns of BMP Signaling During Early Chick Development," Developmental Biology, Apr. 1, 2002, vol. 244(1), pp. 44-65.
Faure S., et al., "Enteric Neural Crest Cells Regulate Vertebrate Stomach Patterning and Differentiation," Development, 2015, vol. 142, pp. 331-342.

Faure S., et al., "Expression Pattern of the Homeotic Gene Bapx1 During Early Chick Gastrointestinal Tract Development," Gene Expression Patterns, Dec. 2013, vol. 13(8), 7 pages.
Finn J., et al., Dlk1-Mediated Temporal Regulation of Notch Signaling Is Required for Differentiation of Alveolar Type II to Type I Cells during Repair, Cell Reports, Mar. 12, 2019, vol. 26(11), pp. 2942-2954.
Flodby P., et al., "Cell-Specific Expression of Aquaporin-5 (Aqp5) in Alveolar Epithelium Is Directed by GATA6/Sp1 via Histone Acetylation," Scientific Reports, Jun. 14, 2017, vol. 7(1):3473, 12 pages.
Fomin M.E., et al., "Human Fetal Liver Cultures Support Multiple Cell Lineages That Can Engraft Immunodeficient Mice," Open Biology, 2017, 16 pages.
Frank D. B., et al., "Emergence of a Wave of Wnt Signaling that Regulates Lung Alveologenesis by Controlling Epithelial Self-Renewal and Differentiation," Cell Reports, Nov. 22, 2016, vol. 17(9), pp. 2312-2325.
Freddo A.M., et al., "Coordination of Signaling and Tissue Mechanics During Morphogenesis of Murine Intestinal Villi: A Role for Mitotic Cell Rounding," Integrative Biol., Sep. 12, 2016;8(9): 918-928.
Fukuda M., et al., "Small Intestinal Stem Cell Identity Is Maintained with Functional Paneth Cells in Heterotopically Grafted Epithelium Onto the Colon," Genes & Development, 2014, vol. 28, No. 16, pp. 1752-1757.
Furness J.B., et al., "The Identification of Neuronal Control Pathways Supplying Effector Tissues in the Stomach," Cell and Tissue Research, Dec. 2020, vol. 382, No. 3, pp. 433-445.
Gage B.K., et al., "Generation of Functional Liver Sinusoidal Endothelial Cells from Human Pluripotent Stem-Cell Derived Venous Angioblasts," Cell Stem Cell, Aug. 6, 2020, vol. 27, pp. 254-269.
Galand G., "Brush Border Membrane Sucrase-Isomaltase, Maltase-Glucoamylase and Trehalase in Mammals. Comparative Development, Effects of Glucocorticoids, Molecular Mechanisms, and Phylogenetic Implications," Comparative Biochemistry & Physiology, 1989, vol. 94B, No. 1, 11 pages.
Gaskill C.F., et al., "Disruption of Lineage Specification in Adult Pulmonary Mesenchymal Progenitor Cells Promotes Microvascular Dysfunction," Journal of Clinical Investigation, Jun. 1, 2017, vol. 127(6), pp. 2262-2276.
Gerdes H-H., et al., "Intercellular Transfer Mediated by Tunneling Nanotubes," Current Opinion in Cell Biology, 2008, vol. 20, pp. 470-475.
Gerdes, HG et al., Tunneling Nanotubes, an Emerging Intercellular Communication Route in Development, 130, pp. 381-387, Mechanisms of Development, Dec. 2012.
Gibbs C.S., et al., "High-performance Single-cell Gene Regulatory Network Inference at Scale: the Inferelator 3.0," Bioinformatics, May 1, 2022, vol. 38(9), pp. 2519-2528.
Gilbert M.A., et al., "Protein-Elongating Mutations in MYH11 Are Implicated in a Dominantly Inherited Smooth Muscle Dysmotility Syndrome with Severe Esophageal, Gastric, and Intestinal Disease," Human Mutation, 2020, vol. 41, pp. 973-982.
Gillich A., et al., "Capillary Cell Type Specialization in the Alveolus," Nature, Oct. 2020, 586(7831), pp. 785-789.
Gokey J.J., et al., "Active Epithelial Hippo Signaling in Idiopathic Pulmonary Fibrosis," JCI insight, Mar. 3, 2018, vol. 3(6), 14 pages.
Gonzales L.W., et al., "Differentiation of Human Pulmonary Type II Cells in Vitro by Glucocorticoid Plus Cyclic Amp," AJP-Lung Articles in Press, 2002, 45 pages.
Goodwin K., et al., "Smooth Muscle Differentiation Shapes Domain Branches During Mouse Lung Development," Development, Nov. 15, 2019, 146(22), 37 pages.
Gordillo M., et al., "Orchestrating liver development," Development, Jun. 2015, vol. 142(12), pp. 2094-2108.
Gorin G., et al., "Protein Velocity and Acceleration from Single-cell Multiomics Experiments," Genome Biology, (2020)21:39, 6 pages.
Gorin G., et al., "RNA Velocity Unraveled," PLOS Computational Biology, Sep. 12, 2022, vol. 18(9):e1010492, 55 pages.
Granja J.M., et al., "ArchR is a Scalable Software Package for Integrative Single-Cell Chromatin Accessibility Analysis," Nature Genetics, Mar. 2021, vol. 53(3), pp. 403-411.

(56) References Cited

OTHER PUBLICATIONS

Grant R.A., et al., "Circuits Between Infected Macrophages and T cells in SARS-CoV-2 Pneumonia," Nature, Feb. 25, 2021, vol. 590(7847), pp. 635-641.

Green J., et al., "Diversity of Interstitial Lung Fibroblasts Is Regulated by Platelet-derived Growth Factor Receptor Alpha Kinase Activity," American Journal of Respiratory Cell and Molecular Biology, Apr. 2016, vol. 54(4), pp. 532-545.

Gribble F.M., et al., "Function and Mechanisms of Enteroendocrine Cells and Gut Hormones in Metabolism," Reviews, Apr. 2019, vol. 15, pp. 226-237.

Guo M., et al., "Single Cell RNA Analysis Identifies Cellular Heterogeneity and Adaptive Responses of the Lung at Birth," Nature Communications, Jan. 3, 2019; vol. 10(1):37, 16 pages.

Guye P., et al., "Genetically Engineering Self-organization of Human Pluripotent Stem Cells into a Liver Bud-like Tissue Using Gata6," Nature Communications, Jan. 6, 2016, 12 pages.

Ham O., et al., "Blood Vessel Formation in Cerebral Organoids Formed From Human Embryonic Stem Cells," Biochemical and Biophysical Research Communications, 2020, vol. 521, pp. 84-90.

Hamilton T.G., et al., "Evolutionary Divergence of Platelet-derived Growth Factor Alpha Receptor Signaling Mechanisms," Molecular and Cellular Biology, Jun. 1, 2003, vol. 23(11), pp. 4013-4025.

Hao Y., et al., "Integrated Analysis of Multimodal Single-cell Data," Cell, Jun. 24, 2021, vol. 184(13), pp. 3573-3587.

Harrison S.P., et al., "Liver Organoids: Recent Developments, Limitations and Potential," Frontiers in Medicine, May 2021, vol. 8, 18 pages.

Hawkins F., et al., "Prospective Isolation of NKX2-1-Expressing Human Lung Progenitors Derived from Pluripotent Stem Cells," The Journal of Clinical Investigation, Jun. 1, 2017; 127(6), pp. 2277-2294.

He B., et al., "Understanding Transcriptional Regulatory Networks Using Computational Models," Current Opinion in Genetics & Development, Apr. 1, 2016, vol. 37, pp. 101-108.

Herriges M.J., et al., "Long Noncoding RNAs are Spatially Correlated with Transcription Factors and Regulate Lung Development," Genes & Development, Jun. 15, 2014, vol. 28(12), pp. 1363-1379.

Holloway E.M., et al., "Differentiation of Human Intestinal Organoids with Endogenous Vascular Endothelial Cells," Developmental Cell, 2020, vol. 54, pp. 516-528.

Homan K.A., et al., "Flow-Enhanced Vascularization and Maturation of Kidney Organoids in Vitro," Nature Methods, 2019, 16(3), pp. 255-262.

Hu S., et al., "Wnt/-Catenin Signaling and Liver Regeneration: Circuit, Biology, and Opportunities," Gene expression, 2021, vol. 20(3), pp. 189-199.

Hu Y., et al., "Wnt/-Catenin Signaling Is Critical for Regenerative Potential of Distal Lung Epithelial Progenitor Cells in Homeostasis and Emphysema," Stem Cells, Nov. 2020, vol. 38(11), pp. 1467-1478.

Huang W-K., et al., "Generation of Hypothalamic Arcuate Organoids From Human Induced Pluripotent Stem Cells," Cell Stem Cell, 2021, pp. 1657-1670.

Huycke T.R., et al., "Genetic and Mechanical Regulation of Intestinal Smooth Muscle Development," Cell, 2019, vol. 179, No. 1, pp. 90-105.

Hyland N.P., et al., "Functional Consequences of Neuropeptide Y Y2 Receptor Knockout and Y2 Antagonism in Mouse and Human Colonic Tissues," British Journal of Pharmacology, 2003, vol. 139, pp. 863-871.

Iino S., et al., "Interstitial Cells of Cajal Are Involved in Neurotransmission in the Gastrointestinal Tract," The Japan Society of Histochemistry and Cytochemistry, 2006, 39 (6), pp. 145-153.

Ikegami, M. et al. "Surfactant Protein D Influences Surfactant Ultrastructure and Uptake by Alveolar Type II Cells," American Journal of Physiology-Lung Cellular and Molecular Physiology, Mar. 2005, vol. 288(3), pp. L552-L561.

Jacob A., et al., "Derivation of Self-Renewing Lung Alveolar Epithelial Type II Cells From Human Pluripotent Stem Cells," Nature Protocols, 2019, 14(12), pp. 3303-3332.

Jacob A., et al., "Differentiation of Human Pluripotent Stem Cells into Functional Lung Alveolar Epithelial Cells," Cell Stem Cell, Oct. 5, 2017, vol. 21(4), pp. 472-488.

Jacob F., et al., "Human Pluripotent Stem Cell-Derived Neural Cells and Brain Organoids Reveal SARS-COV-2 Neurotropism Predominates in Choroid Plexus Epithelium," Cell Stem Cell, 2020, vol. 27, pp. 937-950.

Jain R., et al., "Plasticity of Hopx (+) Type I Alveolar Cells to Regenerate Type Ii Cells in the Lung," Nature Communications, 2015, vol. 13;6(1):6727, 20 pages.

Jin S., et al., "Inference and Analysis of Cell-cell Communication Using Cellchat," Nature Communications, Feb. 17, 2021, vol. 12(1):1088, 20 pages.

Kaelberer M.M., et al., "A Gut-Brain Neural Circuit for Nutrient Sensory Transduction," Science, Sep. 21, 2018, vol. 361, No. 6408, 18 pages.

Kalucka J., et al., "Single-Cell Transcriptome Atlas of Murine Endothelial Cells," Cell, 2020, vol. 180, pp. 764-779.

Kathiriya, J.J., et al., "Human Alveolar Type 2 Epithelium Transdifferentiates into Metaplastic KRT5+ Basal Cells," Nature Cell Biology, Jan. 2022, vol. 24(1), pp. 10-23.

Khalil H.A., et al., "Intestinal Epithelial Replacement by Transplantation of Cultured Murine and Human Cells Into the Small Intestine," Plos One, May 31, 2019, vol. 14, No. 5, 13 pages.

Kim S., et al., "Engraftment Potential of Spheroid-Forming Hepatic Endoderm Derived from Human Embryonic Stem Cells," Stem Cells Development. Jun. 15, 2013, vol. 22(12), pp. 1818-1829.

Kinchen J., et al., "Structural Remodeling of the Human Colonic Mesenchyme in Inflammatory Bowel Disease," Cell, 2018, vol. 175, No. 2, pp. 372-388.

Kitano K., et al., "Bioengineering of Functional Human Induced Pluripotent Stem Cell-derived Intestinal Grafts," Nature Communications, 2017, vol. 8, No. 765, 13 pages.

Knox S.M., et al., "Parasympathetic Innervation Maintains Epithelial Progenitor Cells During Salivary Organogenesis," Science, Sep. 24, 2010, vol. 329, No. 5999, pp. 1645-1647.

Kobayashi Y., et al., "Persistence of a Regeneration-associated, Transitional Alveolar Epithelial Cell State in Pulmonary Fibrosis," Nature Cell Biology, Aug. 2020, vol. 22(8), pp. 934-946.

Koboziev I., et al., "Use of Humanized Mice to Study the Pathogenesis of Autoimmune and Inflammatory Diseases," Inflammatory Bowel Diseases, Jul. 1, 2015, 21 (7), pp. 1652-1673.

Koslowski M., et al., "MS4A12 Is a Colon-Selective Store-Operated Calcium Channel Promoting Malignant Cell Processes," Cancer Research, May 1, 2008, vol. 68, No. 9, 3458-3466.

Kotobank, "Encyclopedia—Basement Membrane," Machine translated by Google, 2023, 6 pages.

Kruitwagen HS et al., Research Communications of the 26th ECVIM-CA Congress, J Vet Intern Med, vol. 31, No. 1, pp. 203-204, Jan. 1, 2017.

Kuna L., et al., "Peptic Ulcer Disease: A Brief Review of Conventional Therapy and Herbal Treatment Options," Journal of Clinical Medicine, 2019, vol. 8, No. 2, 19 pages.

Kusakabe T., et al., "Thyroid-Specific Enhancer-binding Protein/NKX2.1 is Required for the Maintenance of Ordered Architecture and Function of the Differentiated Thyroid," Molecular Endocrinology, Aug. 2006, vol. 20(8), pp. 1796-1809.

Lacanna R., et al., "Yap/Taz Regulate Alveolar Regeneration and Resolution of Lung Inflammation," Journal of Clinical Investigation, May 1, 2019, vol. 129(5), pp. 2107-2122.

Lanas A., et al., "Peptic Ulcer Disease," vol. 390, Aug. 5, 2017, pp. 613-624.

Lange, M., et al., "CellRank for Directed Single-cell Fate Mapping," Nature Methods, Feb. 2022, vol. 19(2), pp. 159-170.

Lasrado R., et al., "Lineage-Dependent Spatial and Functional Organization of the Mammalian Enteric Nervous System," Science, 2017, vol. 356, No. 6339, pp. 722-726.

Laughney A.M., et al., "Regenerative Lineages and Immune-mediated Pruning in Lung Cancer Metastasis," Nature Medicine, Feb. 2020, vol. 26(2), pp. 259-269.

(56) References Cited

OTHER PUBLICATIONS

Le Guen L., et al., "Mesenchymal-Epithelial Interactions During Digestive Tract Development and Epithelial Stem Cell Regeneration," Cellular and Molecular Life Sciences, 2015, vol. 72, No. 20, pp. 3883-3896.
Lee J., et al., "IL-25 and CD4(+) TH2 Cells Enhance Type 2 Innate Lymphoid Cell- derived IL-13 Production, Which Promotes IgE-mediated Experimental Food Allergy," The Journal of Allergy and Clinical Immunology, Apr. 1, 2016, vol. 137(4), pp. 1216-1225.
Lee J.H et al., "Anatomically and Functionally Distinct Lung Mesenchymal Populations Marked by Lgr5 and Lgr6," Cell, Sep. 7, 2017, vol. 170(6), pp. 1149-1163.
Lehner, R. et al., "A Comparison of Plasmid DNA Delivery Efficiency and Cytotoxicity of Two Cationic Diblock Polyoxazoline Copolymers", Nanotechnology, 28, 2017, pp. 1-11.
Li N., et al., Mass cytometry reveals innate lymphoid cell differentiation pathways in the human fetal intestine. Journal of Experimental Medicine, May 7, 2018, vol. 215(5), pp. 1383-1396.
Li N., et al., "Memory CD4+ T Cells Are Generated in the Human Fetal Intestine," Nature Immunology, Mar. 2019, vol. 20(3), pp. 301-312.
Li N., et al., Early-Life Compartmentalization of Immune Cells in Human Fetal Tissues Revealed by High-Dimensional Mass Cytometry, Frontiers in Immunology, Aug. 14, 2019; vol. 10(1932), 13 pages.
Li Y., et al., "Synthesis and Characterization of an Amphiphilic Graft Polymer and its Potential as a pH-Sensitive Drug Carrier", Polymer, vol. 58, No. 15, Jul. 2011, pp. 3304-3310.
Li Z., et al., "Essential Roles of Enteric Neuronal Serotonin in Gastrointestinal Motility and the Development/Survival of Enteric Dopaminergic Neurons," The Journal of Neuroscience, Jun. 15, 2011, vol. 31, No. 24, pp. 8998-9009.
Lian X., et al., "Robust Cardiomyocyte Differentiation from Human Pluripotent Stem Cells via Temporal Modulation of Canonical Wnt Signaling," PNAS, May 29, 2012, pp. E1848-E1857.
Liang, W., et al., MEF2C Alleviates Acute Lung Injury in Cecal Ligation and Puncture (CLP)-induced Sepsis Rats by Up-regulating AQP1Allergologia et Immunopathologia, Sep. 1, 2021, vol. 49(5), pp. 117-124.
Lignitto L., et al., Nrf2 Activation Promotes Lung Cancer Metastasis by Inhibiting the Degradation of Bach 1Cell, Jul. 11, 2019, vol. 178(2), pp. 316-329.
Lino S., et al., "Interstitial Cells of Cajal Are Involved in Neurotransmission in the Gastrointestinal Tract," The Japan Society of Histochemistry and Cytochemistry, 2006, 39 (6), pp. 145-153.
Lippmann E.S., et al., "Human Blood-Brain Barrier Endothelial Cells Derived from Pluripotent Stem Cells," Nature Biotechnology, Aug. 2012, 30(8), pp. 783-791.
Little D.R., et al., "Differential Chromatin Binding of the Lung Lineage Transcription Factor NKX2-1 Resolves Opposing Murine Alveolar Cell Fates in Vivo," Nat Comm. May 2021; vol. 12, No. 1, 18 pages.
Loh K.M., et al., "Efficient Endoderm Induction from Human Pluripotent Stem Cells by Logically Directing Signals Controlling Lineage Bifurcations," Cell Stem Cell, Feb. 6, 2014, vol. 14(2), pp. 237-252.
Ma T.Y., et al., "IEC-18, A Nontransformed Small Intestinal Cell Line for Studying Epithelial Permeability," Journal of Laboratory and Clinical Medicine, Aug. 1992, vol. 120, No. 2, pp. 329-341.
Mabbott N.A., et al., "Microfold (M) Cells: Important Immunosurveillance Posts in the Intestinal Epithelium," Mucosal Immunology, Jul. 1, 2013, vol. 6(4), pp. 666-677.
Maeda Y., et al., Kras(G12D) and Nkx2-1 Haploinsufficiency Induce Mucinous Adenocarcinoma of the Lung. Journal of Clinical Investigation, Dec. 3, 2012, vol. 122(12), pp. 4388-4400.
Mahe M., et al., "Establishment of Human Epithelial Enteroids and Colonoids from Whole Tissue and Biopsy," Journal of Visualized Experiments, Mar. 6, 2015, vol. 97, 13 pages.
Manno., L.G., et al., "RNA Velocity of Single Cells," Nature, Aug. 2018, vol. 560 (7719), pp. 494-498.
Mansour A.A., et al., "An In Vivo Model of Functional and Vascularized Human Brain Organoids," Nature Biotechnology, Jun. 2018, 36(5), pp. 432-441.
Maruyama E.O., et al., "Cell-Specific Cre Strains for Genetic Manipulation in Salivary Glands," PLOS ONE, Jan. 11, 2016, vol. 11(1):e0146711,12 pages.
Mccauley H.A., "Enteroendocrine Regulation of Nutrient Absorption," The Journal of Nutrition, 2019, pp. 10-21.
McCauley H.A., et al., "Enteroendocrine Cells Couple Nutrient Sensing to Nutrient Absorption by Regulating Ion Transport," Nature Communications, 2020, vol. 11,10 pages.
McCauley K.B., et al., "Efficient Derivation of Functional Human Airway Epithelium from Pluripotent Stem Cells via Temporal Regulation of Wnt Signaling," Cell Stem Cell, 2017, vol. 20, pp. 844-857.
McCauley K.B., et al., "Single-Cell Transcriptomic Profiling of Pluripotent Stem Cell- Derived SCGB3A2+ Airway Epithelium," Stem Cell Reports, 2018, vol. 10, pp. 1579-1595.
McGinnis C.S., et al., "DoubletFinder: Doublet Detection in Single-Cell RNA Sequencing Data Using Artificial Nearest Neighbors," Cell Systems, Apr. 24, 2019, vol. 8(4), pp. 329-337.
Mellitzer G., et al., "Loss of Enteroendocrine Cells in Mice Alters Lipid Absorption and Glucose Homeostasis and Impairs Postnatal Survival," The Journal of Clinical Investigation, vol. 120, No. 5, May 2010, pp. 1708-1721.
Menoret S., et al., "Generation of Immunodeficient Rats With Rag1 and Il2rg Gene Deletions and Human Tissue Grafting Models," Transplantation, Aug. 2018, vol. 102, No. 8, pp. 1271-1278.
Mentlein R., et al., "Proteolytic Processing of Neuropeptide Y and Peptide YY by Dipeptidyl Peptidase IV," Regulatory Peptides, 1993, vol. 49, pp. 133-144.
Miraldi E.R., et al., Leveraging Chromatin Accessibility for Transcriptional Regulatory Network Inference in T Helper 17 Cells. Genome Research, Mar. 1, 2019, vol. 29(3), pp. 449-463.
Miranda J., et al., "A Novel Mutation in FOXF1 Gene Associated with Alveolar Capillary Dysplasia with Misalignment of Pulmonary Veins, Intestinal Malrotation and Annular Pancreas," Neonatology, 2013, vol. 103, pp. 241-245.
Miyoshi H., et al., "In Vitro Expansion and Genetic Modification of Gastrointestinal Stem Cells in Spheroid Culture," Nature Protocols, 2013, vol. 8(12), pp. 2471-2482.
Mizumoto H., et al., "Hybrid Artificial Liver Using Hepatocyte Organoids," Regenerative Medicine, 2006, vol. 5 No. 3, pp. 81-86.
Mollaoglu G., et al., "The Lineage-Defining Transcription Factors SOX2 and NKX2-1 Determine Lung Cancer Cell Fate and Shape the Tumor Immune Microenvironment," Immunity, Oct. 16, 2018, vol. 49(4), pp. 764-779.
Moniot B., et al., "SOX9 Specifies the Pyloric Sphincter Epithelium Through Mesenchymal- epithelial Signals," Development, Aug. 2004, vol. 131, No. 15, pp. 3795-3804.
Moodaley R., et al., "Agonism of Free Fatty Acid Receptors 1 and 4 Generates Peptide YY—Mediated Inhibitory Responses in Mouse Colon," British journal of Pharmacology, 2017, vol. 174, pp. 4508-4522.
Morrisey E.E., et al., "Preparing for the First Breath: Genetic and Cellular Mechanisms in Lung Development," Developmental Cell, Jan. 19, 2010, vol. 18, pp. 8-23.
Mowat A., et al., "Regional Specialization Within the Intestinal Immune System," Nature Reviews Immunology, Oct. 2014, vol. 14(10), pp. 667-685.
Munera, J.O et al., Generation of Gastrointestinal Organoids from Human Pluripotent Stem Cells, Methods in Molecular Biology: Chapter 12, pp. 167-177, Jan. 2017.
Nabhan A., et al., "A Single Cell Wnt Signaling Niche Maintains Stemness of Alveolar Type 2 Cells," Science, Mar. 9, 2018; vol. 359(6380), pp. 1118-1123.
Nagy N., et al., "Enteric Nervous System Development: a Crest Cell's Journey From Neural Tube to Colon," Seminars in Cell & Developmental Biology, 2017, vol. 66, pp. 94-106.
Nagy N., et al., "Sonic Hedgehog Controls Enteric Nervous System Development by Patterning the Extracellular Matrix," Development, 2016, 143(2), pp. 264-275.

(56) References Cited

OTHER PUBLICATIONS

Nakahara T., et al., "Human Papillomavirus Type 16 E1 E4 Contributes to Multiple Facets of the Papillomavirus Life Cycle," Journal of Virology, Oct. 31, 2005, vol. 79, No. 20, p. 13150-13165.
Nakamura T., et al., "Intestinal Stem Cell Transplantation," Journal of Gastroenterology, 2017, vol. 52, pp. 151-157.
Nantasanti, S et al., Concise Review: Organoids are a Powerful Tool for the Study of Liver Disease and Personalized Treatment Designs in Humans and Animals, 5:325-330, Stell Cell Translational Medicine, Jan. 2016.
Nedvetsky P.I., et al., "Parasympathetic Innervation Regulates Tubulogenesis in the Developing Salivary Gland," Developmental Cell, 2014, vol. 30, pp. 449-462.
Negretti N. M., et al., "A Single-cell Atlas of Mouse Lung Development," Development Dec. 15, 2021, vol. 148(24), 30 pages.
Nguyen J., et al., "The Next Generation of Endothelial Differentiation: Tissue-Specific ECs," Cell Stem Cell, Jul. 1, 2021, vol. 28(7), pp. 1188-1204.
Nochi T., et al., "Cryptopatches are essential for the development of human GALT," Cell Reports, Jun. 27, 2013, vol. 3(6), vol. 1874-1884.
Noel G., et al., "A Primary Human Macrophage-enteroid Co-culture Model to Investigate Mucosal Gut Physiology and Host-pathogen Interactions," Scientific Reports, Mar. 27, 2017, vol. 7(45270), 13 pages.
Norlen P., et al., "The Vagus Regulates Histamine Mobilization from Rat Stomach ECL Cells by Controlling Their Sensitivity to Gastrin," The Journal of Physiology, 2005, 564(Pt 3), pp. 895-905.
Oceguera-Yanez F., et al., "Engineering the AAVS1 Locus for Consistent and Scalable Transgene Expression in Human iPSCs and their Differentiated Derivatives," Methods, 2015, 13 pages.
Ohashi S., et al., "Epidermal Growth Factor Receptor and Mutant p53 Expand an Esophageal Cellular Subpopulation Capable of Epithelial-to-Mesenchymal Transition through ZEB Transcription Factors," Tumor and Stem Cell Biology, Apr. 27, 2010, vol. 70, No. 10, pp. 4147-4184.
Ostrin E. J., et al., "β-Catenin Maintains Lung Epithelial Progenitors After Lung Specification," Development, Mar. 1, 2018, vol. 145(5), 32 pages.
Paik D.T., et al., "Single-cell RNA-Seq Unveils Unique Transcriptomic Signatures of Organ—Specific Endothelial Cells," Circulation, Nov. 10, 2020, 142(19), pp. 1848-1862.
Palikuqi B., et al., "Adaptable Haemodynamic Endothelial Cells for Organogenesis and Tumorigenesis," Nature, Sep. 17, 2020, vol. 585, 33 pages.
Panaro B.L., et al., "The Melanocortin-4 Receptor Is Expressed in Enteroendocrine L Cells and Regulates the Release of Peptide YY and Glucagon-like Peptide 1 In Vivo," Cell Metabolism, Dec. 2, 2014, vol. 20, pp. 1018-1029.
Paris A.J., et al., "STAT3BDNF-TrkB Signaling Promotes Alveolar Epithelial Regeneration After Lung Injury," Nature Cell Biology, Oct. 2020, vol. 22(10), pp. 1197-1210.
Park, B et al, Hematopoietic Stem Cell Expansion and Generation: The Ways to Make a Breakthrough, 50, 4, pp. 194-202, Blood Research, Dec. 2015.
Penkala I.J., et al., "Age-Dependent Alveolar Epithelial Plasticity Orchestrates Lung Homeostasis and Regeneration," Cell Stem Cell, Oct. 7, 2021, vol. 28, pp. 1775-1789.
Perriot S., et al., "Differentiation of Functional Astrocytes From Human-Induced Pluripotent Stem Cells in Chemically Defined Media," STAR Protocols, Dec. 17, 2021,2(4):100902, 13 pages.
Perriot S., et al., "Human Induced Pluripotent Stem Cell-Derived Astrocytes Are Differentially Activated by Multiple Sclerosis-Associated Cytokines," Stem Cell Reports, Nov. 13, 2018, vol. 11, pp. 1199-1210.
Pless, Gesine, Artificial and Bioartificial Liver Support, vol. 3, issue 1, Organogensis, Jan. 2007.
Pradhan A., et al., "The S52F FOXF1 Mutation Inhibits STAT3 Signaling and Causes Alveolar Capillary Dysplasia," American Journal of Respiratory and Critical Care Medicine, Oct. 15, 2019, vol. 200, No. 8, pp. 1045-1056.
Qian X., et al., "Brain-Region-Specific Organoids Using Minibioreactors for Modeling ZIKV Exposure," Cell, 2016, vol. 165, pp. 1238-1254.
Qian X., et al., "Generation of Human Brain Region-specific Organoids Using a Miniaturized Spinning Bioreactor," Nature Protocols, Mar. 2018, 13(3), pp. 565-580.
Qin X., "Why is Damage Limited to the Mucosa in Ulcerative Colitis but Transmural in Crohn's Disease", World Journal of Gastrointestinal Pathophysiology, Aug. 15, 2013, vol. 4, No. 3, pp. 63-64.
Rakhilin N., et al., "Simultaneous Optical and Electrical in Vivo Analysis of the Enteric Nervous System," Nature Communications, Jun. 7, 2016, 7:11800, 7 pages.
Ran F.A., et al., "Genome Engineering using the CRISPR-Cas9 System," Nature Protocols, Nov. 2013, 8(11), pp. 2281-2308.
Ranganathan S., et al., "Evaluating Shigella Flexneri Pathogenesis in the Human Enteroid Model," Infection and Immunity, Apr. 2019, vol. 87(4), 14 pages.
Rice A.C., et al., "A New Animal Model of Hemolytic Hyperbilirubinemia-Induced Bilirubin Encephalopathy (Kernicterus)," Pediatric Research, 2008, vol. 64, No. 3, pp. 265-269.
Riemondy K. A., et al., "Single Cell RNA Sequencing Identifies TGF-β As a Key Regenerative Cue Following LPS-induced Lung Injury," JCI Insight, Apr. 4, 2019, vol. 4(8), 18 pages.
Rindler T.N., et al., "Efficient Transduction of Alveolar Type 2 Cells with Adeno-associated Virus for the Study of Lung Regeneration," American Journal of Respiratory Cell and Molecular Biology, Jul. 2021, vol. 65(1), pp. 118-121.
Roberts D.J., et al., "Epithelial-mesenchymal Signaling During the Regionalization of the Chick Gut," Development, 1998, vol. 125, No. 15, pp. 2791-2801.
Rodriguez-Castillo J. A., et al., "Understanding Alveolarization to Induce Lung Regeneration," Respiratory Research, Dec. 2018, vol. 19:1-1, 11 pages.
Rouch J.D., et al., "Development of Functional Microfold (M) Cells from Intestinal Stem Cells in Primary Human Enteroids," PLOS One . Jan. 28, 2016, vol. 11(1), 16 pages.
Ruppert C. et al., "Role of HGF in the healthy and injured lung," European Respiratory Journal, 2015, vol. 46, 2 pages.
Rydning A., et al., "Mast Cell Derived Histamine is Involved in Gastric Vasodilation During Acid Back Diffusion via Activation of Sensory Neurons," Am J Physiol Gastrointest Liver Physiol., Sep. 1, 2002, vol. 283, vol. 3, 36 pages.
Salahudeen A. A., et al., "Progenitor Identification and SARS-COV-2 Infection in Human Distal Lung Organoids," Nature, Dec. 24, 2020, vol. 588(7839), pp. 670-675.
Scavuzzo M.A., et al., "Organotypic Pancreatoids with Native Mesenchyme Develop Insulin Producing Endocrine Cells," Scientific Reports, Sep. 7, 2017, pp. 1-12.
Schuldiner et al. "Induced Neuronal Differentiation of Human Embryonic Stem Cells," Brain Research 2001, Sep. 21, 2001, vol. 913(2):201-5.
Sebrell., et al., "Live Imaging Analysis of Human Gastric Epithelial Spheroids Reveals Spontaneous Rupture, Rotation and Fusion Events,". Cell and Tissue Research, 2018, vol. 371, pp. 293-307.
Serra M., et al., "Pluripotent Stem Cell Differentiation Reveals Distinct Developmental Pathways Regulating Lung-Versus Thyroid-lineage Specification," Development, Nov. 1, 2017, vol. 144(21), pp. 3879-3893.
Shacham-Silverberg V., et al., "Generation of Esophageal Organoids and Organotypic Raft Cultures from Human Pluripotent Stem Cells," Methods of Cell Biology, May 13, 2020, vol. 159, pp. 1-23.
Shaylor L.A., et al., "Convergence of Inhibitory Neural Inputs Regulate Motor Activity in the Murine and Monkey Stomach," Am J Physiol Gastrointest Liver Physiol., Nov. 1, 2016, vol. 311, No. 5, pp. G838-G851.
Shi Y., et al., "Vascularized Human Cortical Organoids (vOrganoids) Model Cortical Development in Vivo," PloS Biology, 2020, 8(5), 29 pages.

(56) References Cited

OTHER PUBLICATIONS

Shin Y., et al., "Blood-Brain Barrier Dysfunction in a 3D In Vitro Model of Alzheimer's Disease," Advanced Science, 2019, 6(20), 10 pages.
Shinozawa T., et al., "High-Fidelity Drug-Induced Liver Injury Screen Using Human Pluripotent Stem Cell-Derived Organoids," Gastroenterology. Feb. 2021, vol. 160(3), pp. 831-846.
Singh A., et al., "Evaluation of Transplantation Sites for Human Intestinal Organoids," Plos One, Aug. 27, 2020, 15(8), 12 pages.
Singh A., et al., "Gastrointestinal Organoids: A Next-Generation Tool for Modeling Human Development," American Journal of Physiology-gastrointestinal and Liver Physiology, 2020, 319(3), pp. G375-G381.
Smith D.M., et al., "BMP Signaling Specifies the Pyloric Sphincter," Nature, Dec. 16, 1999, vol. 402, No. 6763, pp. 748-749.
Smith, S.M., et al., "Obeticholic Acid: A Farnesoid X Receptor Agonist for Primary Biliary Cholangitis", Journal of Pharmacy Technology, 2017, vol. 33 (2), pp. 66-71.
Song L., et al., "Assembly of Human Stem Cell Derived Cortical Spheroids and Vascular Spheroids to Model 3-D Brain-like Tissues," 2019, Scientific Reports, vol. 9, No. 5977, 16 pages.
Spencer J., et al., "T Cell Subclasses in Fetal Human Ileum," Clinical and Experimental Immunology, 1986, pp. 553-558.
Spencer J., et al., "The Development of Gut Associated Lymphoid Tissue in the Terminal Ileum of Fetal Human Intestine," Clinical and Experimental Immunology, 1986, pp. 536-543.
Srinivas S., et al., "Cre Reporter Strains Produced by Targeted Insertion of EYFP and ECFP into the ROSA26 Locus," BMC Developmental Biology, Dec. 2001, vol. 1 (4), 8 pages.
Srinivasan B., et al., "TEER Measurement Techniques for in Vitro Barrier Model Systems," Journal of Laboratory Automation, 2015, 20 (2), 20 pages.
Staab J.F., et al., "Co-Culture System of Human Enteroids/Colonoids with Innate Immune Cells,". Current Protocols in Immunology, Dec. 2020, vol. 131(1), 23 pages.
Stevens M.L., et al., "Genomic Integration of Wnt/-catenin and BMP/smad1 Signaling Coordinates Foregut and Hindgut Transcriptional Programs," Development, 2017, 144(7), pp. 1283-1295.
Stoeckius, M et al, "Cell Hashing with Barcoded Antibodies Enables Multiplexing and Doublet Detection for Single Cell Genomics", 19:224 Genome Biology, Dec. 2018.
Stras., et al., "Maturation of the Human Intestinal Immune System Occurs Early in Fetal Development," Developmental Cell, Nov. 4, 2019, vol. 51(3), pp. 357-373.
Strauss K.A., et al., "Crigler-Najjar Syndrome Type 1: Pathophysiology, Natural History, and Therapeutic Frontier," Hepatology, 2020, 71(6), pp. 1923-1939.
Street K., et al., "Slingshot: Cell Lineage and Pseudotime Inference for Single-cell Transcriptomics," BMC Genomics, Dec. 2018, vol. 19, pp. 1-16.
Strikoudis A., et al., "Modeling of Fibrotic Lung Disease Using 3D Organoids Derived from Human Pluripotent Stem Cells," Cell Reports, Jun. 18, 2019, vol. 27(12), pp. 3709-3723.
Strunz M., et al., "Alveolar Regeneration Through a Krt8+ Transitional Stem Cell State That Persists in Human Lung Fibrosis," Nature Communications, Jul. 16, 2020, vol. 11 (1 ):3559, 20 pages.
Sucre J. M.S., et al., "Hyperoxia Injury in the Developing Lung is Mediated by Mesenchymal Expression of Wnt5A," American Journal of Respiratory and Critical Care Medicine, May 15, 2020, vol. 201(10), pp. 1249-1262.
Sugimoto S., et al., "An Organoid-based Organ-Repurposing Approach to Treat Short Bowel Syndrome," Nature, Apr. 2021, vol. 99, 26 pages.
Sun X., et al., "A Census of the Lung: CellCards from LungMAP," Developmental Cell, Jan. 10, 2022, vol. 57(1), pp. 112-145.
Sun X-Y., et al., "Generation of Vascularized Brain Organoids to Study Neurovascular Interactions," eLife, 2022, vol. 11,28 pages.
Sung T.S., et al., "The Cells and Conductance Mediating Cholinergic Neurotransmission in the Murine Proximal Stomach," The Journal of Physiology, 2018, 596(9), pp. 1549-1574.
Sunshine, J et al, "Effects of Base Polymer Hydrophobicity and End-Group Modification on Polymeric Gene Delivery", 12, pp. 3592-3600 Biomacromolecules, Sep. 2011.
Tacer et al., "Research Resource:Comprehensive Expression Atlas of the Fibroblast Growth Factor System in Adult Mouse." Mol. Endocrinol., vol. 24(10), pp. 2050-2064, Oct. 2010.
Tan S.H., et al., "AQP5 Enriches for Stem Cells and Cancer Origins in the Distal Stomach," Nature, 2020, 578 (7795), pp. 437-443.
Tanimizu N., et al., "Generation of Functional Liver Organoids on Combining Hepatocytes and Cholangiocytes with Hepatobiliary Connections Ex Vivo," Nature Communications, Jun. 2021, 12 pages.
Tanimizu N., et al., "Tissue Structure Formation by Liver Epithelial Cells," 2012, vol. 84, No. 8, pp. 658-665.
Tata P.R., et al., "Developmental History Provides a Roadmap for the Emergence of Tumor Plasticity," Developmental Cell, Mar. 26, 2018, vol. 44(6), pp. 679-693.
Tcw J. et al., "An Efficient Platform for Astrocyte Differentiation from Human Induced Pluripotent Stem Cells," Stem Cell Reports, vol. 9, 2017, pp. 600-614.
Teixeira V., et al., "Neonatal Vitamin C and Cysteine Deficiencies Program Adult Hepatic Glutathione and Specific Activities of Glucokinase, Phosphofructokinase, and Acetyl-CoA Carboxylase in Guinea Pigs' Livers," 2021, Antioxidants, 10, 953, 17 pages.
Theodosiou N.A., et al., "Sox9 and Nkx2. 5 Determine the Pyloric Sphincter Epithelium Under the Control of BMP Signaling," Developmental Biology, 2005, 279, pp. 481-490.
Thompson C.A., et al., "GATA4 Is Sufficient to Establish Jejunal Versus Ileal Identity in the Small Intestine," Cellular and Molecular Gastroenterology and Hepatology, May 2017, 3(3), pp. 422-446.
Thwaites D.T., et al., "H+/Dipeptide Absorption Across the Human Intestinal Epithelium Is Controlled Indirectly via a Functional Na+/H+ Exchanger," Gastroenterology, 2002, vol. 122, pp. 1322-1333.
Toth A., et al., "Alveolar Epithelial Progenitor Cells Drive Lung Regeneration via Dynamic Changes in Chromatin Topology Modulated by Lineage-specific Nkx2-1 Activity," bioRxiv, 2022, 31 pages.
Toth A., et al., "Alveolar Epithelial Stem Cells in Homeostasis and Repair," Chapter 10 in Lung Stem Cells in Development, Health and Disease, European Respiratory Society, 2021, pp. 122-133.
Tough I.R., et al., "Endogenous Peptide YY and Neuropeptide Y Inhibit Colonic Ion Transport, Contractility and Transit Differentially Via Y1 and Y2 Receptors," British journal of Pharmacology, 2011, vol. 164, pp. 471-484.
Traber M.G., et al., "Vitamins C and E: Beneficial Effects from a Mechanistic Perspective," Free Radical Biology and Medicine, 2011,51 (5), pp. 1000-1013.
Travaglini K.J., et al., "A Molecular Cell Atlas of the Human Lung from Single-cell RNA Sequencing," Nature, Nov. 26, 2020, vol. 587(7835), pp. 619-625.
Tsai Y-H., et al., "In Vitro Patterning of Pluripotent Stem Cell-Derived Intestine Recapitulates in Vivo Human Development," Development, 2016, 144(6), 57 pages.
Ustiyan V., et al., "FOXF1 Transcription Factor Promotes Lung Morphogenesis by Inducing Cellular Proliferation in Fetal Lung Mesenchyme," Developmental Biology, 2018, 443(1), pp. 50-63.
Vallicelli C., et al., "Small Bowel Emergency Surgery: Literature's Review," World Journal of Emergency Surgery, 2011, vol. 6, No. 1,8 pages.
Van De Steeg E., et al., "Complete OATP1B1 and OATP1B3 Deficiency Causes Human Rotor Syndrome by Interrupting Conjugated Bilirubin Reuptake Into the Liver," The Journal of Clinical Investigation, 2012, vol. 122, No. 2, pp. 519-528.
Van Lieshout., L.P., et al., "A Novel Triple-Mutant AAV6 Capsid Induces Rapid and Potent Transgene Expression in the Muscle and Respiratory Tract of Mice," Molecular Therapy—Methods and Clinical Development, Open Access Jun. 15, 2018, vol. 9, pp. 323-329.
Vannucchi M.G., "The Telocytes: Ten Years after Their Introduction in the Scientific Literature. An Update on Their Morphology, Distribution, and Potential Roles in the Gut," International Journal of Molecular Sciences, 2020, vol. 21, 15 pages.

(56) References Cited

OTHER PUBLICATIONS

Verheyden J.M., et al., "A Transitional Stem Cell State in the Lung," Nature Cell Biology, Sep. 2020, vol. 22(9), pp. 1025-1026.
Vila Ellis L., et al., "Epithelial Vegfa Specifies a Distinct Endothelial Population in the Mouse Lung," Developmental Cell, 2020, 52, pp. 617-630.
Walsh K.T., et al., "The Enteric Nervous System for Epithelial Researchers: Basic Anatomy, Techniques, and Interactions with the Epithelium," Cellular and Molecular Gastroenterology and Hepatology, 2019, vol. 8, No. 3, pp. 369-378.
Wang Y., et al., "Loss of Lrig1 Leads to Expansion of Brunner Glands Followed by Duodenal Adenomas with Gastric Metaplasia," Am J Pathol., Apr. 2015, vol. 185, No. 4, pp. 1123-1134.
Ward S.M., et al., "Involvement of Intramuscular Interstitial Cells of Cajal in Neuroeffector Transmission in the Gastrointestinal Tract," The Journal of Physiology, 2006, vol. 576, pp. 675-682.
Weigmann B., et al., Isolation and Subsequent Analysis of Murine Lamina Propria Mononuclear Cells from Colonic Tissue, Nature Protocols, Oct. 2007, vol. 2(10), 2307-2311.
Weng A., et al., "Lung Injury Induces Alveolar Type 2 Cell Hypertrophy and Polyploidy with Implications for Repair and Regeneration," American Journal of Respiratory Cell and Molecular Biology, May 2022, vol. 66(5), pp. 564-576.
Westfal M.L., et al., "Pediatric Enteric Neuropathies: Diagnosis and Current Management," Current Opinion in Pediatrics, 2017, 29(3), pp. 347-353.
Wiel C., et al., "BACH1 Stabilization by Antioxidants Stimulates Lung Cancer Metastasis," Cell, Jul. 11, 2019, vol. 178(2), pp. 330-345.
Wimmer R.A., et al., "Generation of Blood Vessel Organoids from Human Pluripotent Stem Cells," Nature Protocols, 2019, vol. 14, pp. 3082-3100.
Wimmer R.A., et al., "Human Blood Vessel Organoids as a Model of Diabetic Vasculopathy," Nature, 2019, 565(7740), 41 pages.
Wong G.L.H., et al., "High Incidence of Mortality and Recurrent Bleeding in Patients With Helicobacter Pylori-Negative Idiopathic Bleeding Ulcers," Gastroenterology, 2009, vol. 137, pp. 525-531.
Wright E.M., et al., "Biology of Human Sodium Glucose Transporters," Physiological Reviews, 2011, vol. 91,62 pages.
Wright E.M., et al., "Regulation of Na+/Glucose Cotransporters," The Journal of Experimental Biology, 1997, vol. 200, pp. 287-293.
Wunderlich M., et al., "AML Xenograft Efficiency Is Significantly Improved in Nod/Scid- IL2RG Mice Constitutively Expressing Human SCF, GM-CSF and IL-3," Leukemia, Oct. 2010, vol. 24(10) pp. 1785-1788.
Wunderlich M., et al., "Improved Multilineage Human Hematopoietic Reconstitution and Function in NSGS Mice," PLOS One, Dec. 12, 2018, vol. 13(12), 20 pages.
Xiang., et al., "Fusion of Regionally Specified hPSC-Derived Organoids Models Human Brain Development and Interneuron Migration,". Cell Stem Cell, 2017, vol. 21, pp. 383-398.
Yamaguchi T., et al., "NKX2-1/TTF-1: An Enigmatic Oncogene That Functions As a Doubleedged Sword for Cancer Cell Survival and Progression," Cancer Cell, Jun. 10, 2013, vol. 23(6), pp. 718-723.
Yang Y., et al., "Transcription Factor C/EBP Homologous Protein in Health and Diseases," Frontiers in Immunology, Nov. 27, 2017, vol. 8:1612, 18 pages.
Yu Q., et al., "Charting Human Development Using a Multi-Endodermal Organ Atlas and Organoid Models," Cell, 2021, vol. 184, pp. 3281-3298.
Yuan T., et al., "Fgf10 Signaling in Lung Development, Homeostasis, Disease, and Repair After Injury," Frontiers in Genetics, Sep. 25, 2018, vol. 9(418), 8 pages.
Yun C.H.C., et al., "CAMP-mediated Inhibition of the Epithelial Brush Border Na +/H+ exchanger, NHE3, requires an Associated Regulatory Protein," PNAS, 1997, vol. 94, pp. 3010-3015.
Zacharias W.J., et al., "Regeneration of the Lung Alveolus by an Evolutionarily Conserved Epithelial Progenitor," Nature, Mar. 8, 2018, vol. 555(7695), pp. 251-255.
Zepp J.A., et al., "Distinct Mesenchymal Lineages and Niches Promote Epithelial Self-Renewal and Myofibrogenesis in the Lung," Cell, Sep. 7, 2017, vol. 170(6), pp. 1134-1148.
Zhang S., et al., "Vascularized Organoids on a Chip: Strategies for Engineering Organoids with Functional Vasculature," Lab Chip, 2021,21 (3), pp. 473-488.
Zhao C-M., et al., "Control of Gastric Acid Secretion in Somatostatin Receptor 2 Deficient Mice: Shift from Endocrine/Paracrine to Neurocrine Pathways," Endocrinology, 2008, 149(2), pp. 498-505.
Zheng, Y., et al., "pH-and Temperature-Senstive PCL-Grafted Poly (ß-amino ester)-Poly (ethylene glycol)-Poly (ß-amino ester) Copolymer Hydrogels, Macromolecular Research, 2010, vol. 18, No. 11, pp. 1096-1102.
Zhou B., et al., "Comprehensive Epigenomic Profiling of Human Alveolar Epithelial Differentiation Identifies Key Epigenetic States and Transcription Factor Co-regulatory Networks for Maintenance of Distal Lung Identity," BMC Genomics, Dec. 2021, vol. 22(906), 25 pages.
Ziegler B. L., et al., "KDR Receptor: A Key Marker Defining Hematopoietic Stem Cells," Science, vol. 285, No. 5433, 1999, pp. 1553-1558.
Coskun T. et al., "Activation of Prostaglandin E Receptor 4 Triggers Secretion of Gut Hormone Peptides GLP-1, GLP-2, and PYY," Endocrinology, 2013, 154, 45-53.
Cox H. M., "Endogenous PYY and NPY mediate tonic Y(1)- and Y(2)-mediated absorption in human and mouse colon," Nutrition, 2008, 24, 900-906.
Creane M., et al., "Biodistribution and Retention of Locally Administered Human Mesenchymal Stromal Cells: Quantitative Polymerase Chain Reaction-Based Detection of Human DNA in Murine Organs," Cytotherapy, 2017, vol. 19, pp. 384-394. DOI: 10.1016/j.jcyt.2016.12.003.
Crisera C. A., et al., "Expression and Role of Laminin-1 in Mouse Pancreatic Organogenesis," Diabetes, 2000, vol. 49, pp. 936-944.
Cruz, N. M., et al., "Differentiation of Human Kidney Organoids from Pluripotent Stem Cells." In Methods in Cell Biology, vol. 153, Chapter 7, 2019, pp. 133-150.
Cucullo L., et al., "The role of shear stress in Blood-Brain Barrier endothelial physiology," BMC Neurosci, 2011, 40, 15 pages.
Cuevas I., et al., "Sustained Endothelial Expression of HoxA5 In Vivo Impairs Pathological Angiogenesis and Tumor Progression," PLoS One, 2015, vol. 10, e0121720.
Cui, J., et al., "Progressive Pseudogenization: Vitamin C Synthesis and Its Loss in Bats," Molecular Biology and Evolution, 2011, vol. 28, No. 4, pp. 1025-1031.
Cunningham, R.P., et al., "Liver Zonation—Revisiting Old Questions With New Technologies," Frontiers in Physiology, 2021, vol. 12, 732929.
Dahlman et al., "Barcoded Nanoparticles for High Throughput in Vivo Discovery of Targeted Therapeutics", PNAS, U.S.A., 2017, vol. 114(8), pp. 2060-2065.
Daneman R., et al., "The Blood-Brain Barrier," Cold Spring Harbor Perspectives in Biology, 2015, vol. 7, a020412.
Daniely Y. et al., "Critical role of p63 in the development of a normal esophageal and tracheobronchial epithelium," American Journal of Physiology, Cell Physiology, 2004, 287(1), C171-C181.
Dathan N. et al., "Distribution of the titf2/foxe1 gene product is consistent with an important role in the development of foregut endoderm, palate, and hair," Dev. Dyn., 2002, 224, 450-456.
Davidson L. M., et al., "Bronchopulmonary Dysplasia: Chronic Lung Disease of Infancy and Long-Term Pulmonary Outcomes," Journal of Clinical Medicine, 2017, vol. 6, p. 20.
Davis B. P., et al., "Eosinophilic Esophagitis-Linked Calpain 14 is an IL-13-Induced Protease that Mediates Esophageal Epithelial Barrier Impairment," JCI Insight, 2016, 1(4), 11 pages.
Dawkins H.J.S., et al., "Progress in rare diseases research 2010-2016: An IRDIRC Perspective," Clinical and Translational Science. Jan. 2018; 11(1): 11-20.
De Felice, M. et al., "A mouse model for hereditary thyroid dysgenesis and cleft palate," Nat. Genet., 1998, 19, 395-398.
De Jong E. M. et al., Etiology of esophageal atresia and tracheoesophageal fistula: 'Mind the gap', Current Gastroenterology Reports, 2010, 12(3), 215-222.

(56) References Cited

OTHER PUBLICATIONS

De Paepe M. E., et al., "Growth of Pulmonary Microvasculature in Ventilated Preterm Infants," American Journal of Respiratory and Critical Care Medicine, 2006, vol. 173, pp. 204-211.

De Santa Barbara P., et al., "Molecular Etiology of Gut Malformations and Diseases," American Journal of Medical Genetics, Dec. 30, 2002; vol. 115(4), pp. 221-230.

De Santa Barbara, P., et al., "Tail gut endoderm and gut/genitourinary/tail development: a new tissue-specific role for Hoxa13," Development, 2002, vol. 129, pp. 551-561.

Demirgan E.B., et al., "AGTR1-related Renal Tubular Dysgeneses May Not Be Fatal," Kidney International Reports, 2021, vol. 6, pp. 846-852.

Distefano P.V. et al., "KRIT1 protein depletion modifies endothelial cell behavior via increased vascular endothelial growth factor (VEGF)signaling," J Biol Chem, 2014, 289, 33054-33065.

D'Mello R. J., et al., "LRRC31 is Induced by IL-13 and Regulates Kallikrein Expression and Barrier Function in the Esophageal Epithelium," Mucosal Immunology, 2016, 9(3), pp. 744-756.

Dolinay T., et al., "Integrated Stress Response Mediates Epithelial Injury in Mechanical Ventilation," American Journal of Respiratory Cell and Molecular Biology, 2017, 57, pp. 193-203.

Dollard S. C., et al., "Production of Human Papillomavirus and Modulation of the Infectious Program in Epithelial Raft Cultures." Genes & Development, 6, 1992, pp. 1131-1142.

Domyan E.T. et al., "Signaling through BMP receptors promotes respiratory identity in the foregut via repression of Sox2," Development (Cambridge, England), 2011, 138(5), 971-981.

Donati, B., et al., "The rs2294918 E434K Variant Modulates Patatin-Like Phospholipase Domain-Containing 3 Expression and Liver Damage." Hepatology, vol. 63, No. 3, Mar. 2016, pp. 787-798.

Dong R., et al., "SpatialDWLS: Accurate Deconvolution of Spatial Transcriptomic Data." Genome Biology, 22, 145, 2021, 10 pages. https://doi.org/10.1186/s13059-021-02362-7.

Dorison A., et al., "What Can We Learn from Kidney Organoids?" Kidney International, 102, 2022, pp. 1013-1029. https://doi.org/10.1016/j.kint.2022.06.032.

Dougherty, E., "Tackling the common denominator in liver disease," Novartis, Jun. 16, 2016, https://www.novartis.com/stories/tackling-common-denominator-liver-disease.

Doupe D. P. et al., "A Single Progenitor Population Switches Behavior to Maintain and Repair Esophageal Epithelium," Science, 2012, 337(6098), 1091-1093.

Draheim K. M., et al., "Cerebral Cavernous Malformation Proteins at a Glance," Journal of Cell Science, 2014, vol. 127(4), pp. 701-707.

Drukcer, D. J., "Evolving Concepts and Translational Relevance of Enteroendocrine Cell Biology," J Clin Endocrinol Metab, 2016, vol. 101, No. 3, pp. 778-786.

Du A. et al., "Arx is required for normal enteroendocrine cell development in mice and humans," Developmental biology, 2012, 365, 175-188.

Du Y., et al., "Lung Gene Expression Analysis (LGEA): An Integrative Web Portal for Comprehensive Gene Expression Data Analysis in Lung Development," Thorax, 2017, 72, pp. 481-484.

Du Y. et al., "'LungGENS': a web-based tool for mapping single-cell gene expression in the developing lung," Thorax, 2015, 70, 1092-1094.

Dubrovskyi O., et al., "Measurement of Local Permeability at Subcellular Level in Cell Models of Agonist—and Ventilator-Induced Lung Injury," Laboratory Investigation, 2013, vol. 93, pp. 254-263.

Duluc I., et al., "Changing Intestinal Connective Tissue Interactions Alters Homeobox Gene Expression in Epithelial Cells," Journal of Cell Science, 1997, vol. 110, pp. 1317-1324.

Duval, K., et al., "Revisiting the role of Notch in nephron segmentation confirms a role for proximal fate selection during mouse and human nephrogenesis," Development, 2022, vol. 149.

Dye B. R., et al., "A Bioengineered Niche Promotes In Vivo Engraftment and Maturation of Pluripotent Stem Cell Derived Human Lung Organoids," eLife 5, 2016, 18 pages.

Dye B.R. et al., "In vitro generation of human pluripotent stem cell derived lung organoids," Elife 4:e05098 (2015), 25 pages.

Efremova I., et al., "CellPhoneDB: Inferring Cell-Cell Communication from Combined Expression of Multi-Subunit Receptor-Ligand Complexes," Nature Protocols, 2020, vol. 15, pp. 1484-1506.

Eicher A.K., et al., "Functional Human Gastrointestinal Organoids Can Be Engineered from Three Primary Germ Layers Derived Separately from Pluripotent Stem Cells," Cell Stem Cell, 2022, vol. 29, pp. 36-51.e6. doi: 10.1016/j.stem.2021.10.010.

Engelstoft, M. S. et al., "Enteroendocrine Cell Types Revisited". Current Opinion in Pharmacology, 2013, vol. 13, pp. 912-921.

Everhart J. E., et al., "Fatty Liver: Think Globally," Hepatology, 2010, vol. 51, pp. 1491-1493.

Fang M., et al., "Ulinastatin Ameliorates Pulmonary Capillary Endothelial Permeability Induced by Sepsis Through Protection of Tight Junctions via Inhibition of TNFalpha and Related Pathways," Frontiers in Pharmacology, Sep. 2018, vol. 9, doi: 10.3389/fphar.2018.00823.

Fantes J. et al., "Mutations in SOX2 cause anophthalmia," Nature Genetics, 2003, 33(4), 461-463.

Fausett S. R. et al., "Compartmentalization of the foregut tube: developmental origins of the trachea and esophagus," Wiley Interdisciplinary eviews. Developmental Biology, 2012, (2), 184-202.

Fausett S.R., et al., "BMP antagonism by Noggin is required in presumptive notochord cells for mammalian foregut morphogenesis," Developmental Biology, 2014, 391(1), 111-24.

Blanchard C., et al., "Coordinate Interaction between IL-13 and Epithelial Differentiation Cluster Genes in Eosinophilic Esophagitis," The Journal of Immunology 2010, 184(7), 4033-4041.

Bochkis I.M. et al., "Genome-wide location analysis reveals distinct transcriptional circuitry by paralogous regulators Foxa1 and Foxa2," PLoS genetics, 2012, 8, 6, e1002770, 10 pages.

Boj S.F., et al., "Forskolin-induced Swelling in Intestinal Organoids: An In Vitro Assay for Assessing Drug Response in Cystic Fibrosis Patients," J Vis Exp, Feb. 11, 2017, (120):55159.

Bolger A. M. et al., "Trimmomatic: a flexible trimmer for Illumina sequence data," Bioinformatics, 2014, 30, 2114-2120.

Bolte C., et al., "Nanoparticle Delivery of Proangiogenic Transcription Factors into the Neonatal Neurotrophic Factor-Mediated Alveolar Capillary Injury and Repair Circulation Inhibits Alveolar Simplification Caused by Hyperoxia," American Journal of Respiratory and Critical Care Medicine, Jul. 2020, vol. 202, No. 1, pp. 100-111. doi: 10.1164/rccm.201906-12320C.

Boon et al., "Amino Acid Levels Determine Metabolism and CYP450 Function in Hepatocytes and Hepatoma Cell Lines," Nature Communications, 2020, vol. 11, 1393.

Bordi C. et al., "Classification of gastric endocrine cells at the light and electron microscopical levels," Microsc. Res. Tech., 2000, 48, 258-271.

Bray N. L., et al., "Near-Optimal Probabilistic RNA-Seq Quantification," Nature Biotechnology, 2016, vol. 34, pp. 525-527.

Buettner et al., "Computational Analysis of Cell-to-cell Heterogeneity in Single-cell RNA-sequencing Data reveals Hidden Subpopulations of cells", Nature Biotech, 2015, vol. 33(2), pp. 155-160.

Butler, A., et al. Integrating Single-Cell Transcriptomic Data Across Different Conditions, Technologies, and Species, Nature Biotechnology, 2018, 36(4), pp. 411-420.

Cai, W., et al., "Genetic polymorphisms associated with nonalcoholic fatty liver disease in Uyghur population: a case-control study and meta-analysis," Lipids in Health and Disease, 2019, vol. 18, 14.

Cain M.P., et al., "Quantitative Single-Cell Interactomes in Normal and Virus-Infected Mouse Lungs," Disease Models Mechanisms, May 2020, vol. 13, No. 6, doi: 10.1242/dmm.044404.

Cakir, et al., "Engineering of Human Brain Organoids with a Functional Vascular-Like System," Nature Methods, 2019, vol. 16, No. 11, 1169-1175.

Caldwell J. M., et al., "Novel Immunologic Mechanisms in Eosinophilic Esophagitis," Current Opinion in Immunology, 2017, vol. 48, pp. 114-121.

(56) References Cited

OTHER PUBLICATIONS

Candi E. et al., "Differential roles of p63 isoforms in epidermal development: selective genetic complementation in p63 null mice," Cell Death Differ, 2006, 13, 1037-1047.

Capeling M. M. et al., "Suspension culture promotes serosal mesothelial development in human intestingal organoids," Cell Reports, 2002, 38, 110379, 33 pages.

Carmona R., et al., "Conditional Deletion of WT1 in the Septum Transversum Mesenchyme Causes Congenital Diaphragmatic Hernia in Mice,". eLife, Sep. 19, 2016, vol. 5, No. e16009, pp. 1-17.

Chambers J. C., et al., "Genome-Wide Association Study Identifies Loci Influencing Concentrations of Liver Enzymes in Plasma," Nature Genetics, 2011, vol. 43, pp. 1131-1138.

Chance W.T., et al., "Preservation of Intestine Protein by Peptide YY During Total Parenteral Nutrition," Life Sciences 1996, vol. 58, No. 21, pp. 1785-1794.

Chandran S., et al., "Necrotising Enterocolitis in a Newborn Infant Treated with Octreotide for Chylous Effusion: Is Octreotide Safe?," BMJ Case Reports, 2020, 13, e232062. doi: 10.1136/bcr-2019-232062.

Char V.C. et al., "Digestion and absorption of carbohydrates by the fetal lamb in utero," Pediatr Res, 1979, 13, 1018-1023.

Charlton, V. E., et al., "Effects of Gastric Nutritional Supplementation on Fetal Umbilical Uptake of Nutrients," Am J Physiol, 1981, vol. 241, pp. E178-E185.

Chatterjee S., et al., "Tissue-Specific Gene Expression during Productive Human Papillomavirus 16 Infection of Cervical, Foreskin, and Tonsil Epithelium." Journal of Virology, 93(17), 2019, e00915-19.

Chen et al., "A Versatile Polypharmacology Platform Promotes Cryoprotection and Viability of Human Pluripotent and Differentiated Cells," Nature Methods, 2021, vol. 18, pp. 528-541.

Chen, F., et al., "Inhibition of Tgf beta signaling by endogenous retinoic acid is essential for primary lung bud induction," Development, 2007, vol. 134, pp. 2969-2979.

Chen H., et al., "Single-Cell Trajectories Reconstruction, Exploration and Mapping of Omics Data with STREAM," Nature Communications, 2019, vol. 10, Article 1903. doi: 10.1038/s41467-019-09670-4, 14 pages.

Chen H. et al., "Transcript profiling identifies dynamic gene expression patterns and an important role for Nrf2/Keap1 pathway in the developing mouse esophagus," PloS One 2012, 7(5), e36504, 10 pages.

Chen J., et al., "Improved Human Disease Candidate Gene Prioritization Using Mouse Phenotype," BMC Bioinformatics, 2007, vol. 8, p. 392.

Chen J., et al., "ToppGene Suite for Gene List Enrichment Analysis and Candidate Gene Prioritization," Nucleic Acids Research, 2009, vol. 37, pp. W305-W311.

Chen S., et al., "fastp: An Ultra-Fast All-in-One FASTQ Preprocessor," Bioinformatics, 2018, vol. 34, pp. 1884-1890.

Chen X., "Aberrant expression of Wnt and Notch signal pathways in Barrett's esophagus," Clinics and Research in Hepatology and Gastroenterology, 2012, 36(5), 473-483.

Chen Y., et al., "A Three-Dimensional Model of Human Lung Development and Disease from Pluripotent Stem Cells," Nature Cell Biology, May 2017, vol. 19, No. 5, pp. 542-557.

Chen Y. et al., "BMP Signaling pathway and colon cancer," Journal of Cell Biology 2009, 5, 6 pages (Chinese with machine translation).

Chen, Y., et al., "SOX2 expression inhibits terminal epidermal differentiation," Exp. Dermatol., 2015, vol. 24, pp. 966-982.

Chen Y., et al., "Regulation of Angiogenesis Through a MicroRNA (miR-130a) That Down-Regulates Antiangiogenic Homeobox Genes GAX and HOXA5," Blood, 2008, vol. 111, pp. 1217-1226.

Chen Y. et al., "The Molecular Mechanism Governing the Oncogenic Potential of SOX2 in Breast Cancer," Journal of Biological Chemistry 2008, 283(26), 17969-17978.

Cheung K.C.P., et al., "Preservation of Microvascular Barrier Function Requires CD31 Receptor-Induced Metabolic Reprogramming," Nature Communications, Jul. 2020, vol. 11, No. 1, doi: 10.1038/s41467-020-17329-8.

Chey, W. Y., et al., "Secretin: historical perspective and current status," Pancreas, 2014, vol. 43, pp. 162-182.

Chin, A. M., et al., "Morphogenesis and maturation of the embryonic and postnatal intestine," Seminars in Cell Developmental Biology, 2017, vol. 66, pp. 81-93.

Cho C., et al., "Reck and Gpr124 Are Essential Receptor Cofactors for Wnt7a/Wnt7b-Specific Signaling in Mammalian CNS Angiogenesis and Blood-Brain Barrier Regulation," Neuron, 2017, vol. 95, pp. 1221-1225.

Cho C. F., et al., "Blood-Brain-Barrier Spheroids as an In Vitro Screening Platform for Brain-Penetrating Agents," Nature Communications, 2017, vol. 8, p. 15623.

Choi K., et al., "iGEAK: An Interactive Gene Expression Analysis Kit for Seamless Workflow Using the R/Shiny Platform," BMC Genomics, 2019, vol. 20, p. 177.

Choudhary S., et al., "Comparison and Evaluation of Statistical Error Models for scRNA-seq," Genome Biology, 2022, vol. 23, 27. doi: 10.1186/s13059-021-02584-9.

Claesson-Welsh L., et al., "Permeability of the Endothelial Barrier: Identifying and Reconciling Controversies," Trends in Molecular Medicine, Apr. 2021, vol. 27, No. 4, pp. 314-331.

Claeys, W., et al., "A mouse model of hepatic encephalopathy: bile duct ligation induces brain ammonia overload, glial cell activation and neuroinflammation," Scientific Reports, 2022, vol. 12, 17558.

Clemmensen, C. et al., "Emerging Hormonal-Based Combination Pharmacotherapies for the Treatment of Metabolic Diseases". Nat Rev Endocrinol, 2018, 14(10), pp. 670-684.

Collier et al., "Identifying Human Nave Pluripotent Stem Cells— Evaluating State-Specific Reporter Lines and Cell-Surface Markers", BioEssays. May 2018, 40(5): 1700239 in 12 pages.

Concepcion J. P., et al., "Neonatal Diabetes, Gallbladder Agenesis, Duodenal Atresia, and Intestinal Malrotation Caused by a Novel Homozygous Mutation in RFX6," Pediatric Diabetes, 2014, vol. 15, pp. 67-72.

Coon S. D. et al., "Glucose-dependent insulinotropic polypeptide-mediated signaling pathways enhance apical PepT1 expression in intestinal epithelial cells," Am J Physiol Gastrointest Liver Physiol, 2015, 308, G56-62.

Cortina, G., et al., "Enteroendocrine Cell Dysgenesis and Malabsorption, a Histopathologic and Immunohistochemical Characterization," Human Pathology, 2007, vol. 38, pp. 570-580.

Wesley, B. T., et al., "Single-Cell Atlas of Human Liver Development Reveals Pathways Directing Hepatic Cell Fates," Nature Cell Biology, 2022, vol. 24, No. 10, pp. 14871498.

Wessel J., et al., "Do Genes Determine Our Health? Implications for Designing Lifestyle Interventions and Drug Trials," Circulation: Cardiovascular Genetics, 2016, vol. 9, pp. 2-3.

Wesson, D., et al., "The effect of intrauterine esophageal ligation on growth of fetal rabbits," J Pediatr Surg, 1984, vol. 19, pp. 398-399.

Whitehead K. J., et al., "The Cerebral Cavernous Malformation Signaling Pathway Promotes Vascular Integrity via Rho GTPases," Nature Medicine, 2009, vol. 15, pp. 177-184.

Wieland H.A., et al., "Subtype selectivity of the novel nonpeptide neuropeptide YY1 receptor antagonist BIBO3304 and its effect on feeding in rodents," Br J Pharmacol, Oct. 1998, vol. 125(3), pp. 549-555.

Williamson K. A., et al., "Mutations in SOX2 Cause Anophthalmia-Esophageal-Genital (AEG) Syndrome," Human Molecular Genetics, 2006, 15(9), pp. 1413-1422.

Woo J. et al., "Barx1 -mediated inhibition of Wnt signaling in the mouse thoracic foregut controls tracheo-esophageal septation and epithelial differentiation," PloS One, 2011, 6(7), e22493, 8 pages.

Wu H., et al., "Advantages of Single-Nucleus over Single-Cell RNA Sequencing of Adult Kidney: Rare Cell Types and Novel Cell States Revealed in Fibrosis," Journal of the American Society of Nephrology, Jan. 2019, vol. 30, No. 1, pp. 23-32.

Wu H., et al., "Comparative Analysis and Refinement of Human PSC-Derived Kidney Organoid Differentiation with Single-Cell Transcriptomics," Cell Stem Cell, 2018, vol. 23, pp. 869-881.e868.

(56) References Cited

OTHER PUBLICATIONS

Wu X., et al., "Modeling Drug-induced Liver Injury and Screening for Anti-hepatofibrotic Compounds Using Human PSC-derived Organoids,", Cell Regeneration, Biomed Central, vol. 12, No. 1, Mar. 3, 2023, pp. 1-13.
Xia, M.F., et al., "NAFLD and Diabetes: Two Sides of the Same Coin? Rationale for Gene-Based Personalized NAFLD Treatment," Frontiers in Pharmacology, 2019, vol. 10, 877.
Xia Y., et al., "Angiotensin Receptors, Autoimmunity, and Preeclampsia," Journal of Immunology, 2007, vol. 179, pp. 3391-3395.
Xiao C. et al., "Gut peptides are novel regulators of intestinal lipoprotein secretion: experimental and pharmacological manipulation of lipoprotein metabolism," Diabetes, 2015, 64, 2310-2318.
Xu, C.-R., et al., "Chromatin 'Prepattern' and Histone Modifiers in a Fate Choice for Liver and Pancreas," Science, 2011, vol. 332, pp. 963-966.
Xu R., "Basis and Clinical Applications of Receptors", edited by et al. Shanghai Science and Technology Press, 1st edition, Feb. 1992, Section of "Retinoic Acid Receptors" on pp. 129-131, published on Feb. 29, 1992.
Xu, W., et al., "Hypoxia activates Wnt/-catenin signaling by regulating the expression of BCL9 in human hepatocellular carcinoma," Scientific Reports, 2017, vol. 7, 40446, 13 pages.
Xu, Y., et al., "Ascorbate protects liver from metabolic disorder through inhibition of lipogenesis and suppressor of cytokine signaling 3 (SOCS3)," Nutrition Metabolism, 2020, vol. 17, 17.
Yanan Y., et al., "Research Progress on Hedgehog Signaling Pathway and Liver Fibrosis," Chinese Journal of Anatomy, 06, Dec. 25, 2019, pp. 589-592.
Yang M., et al., "Angiogenesis-Related Genes May Be a More Important Factor than Matrix Metalloproteinases in Bronchopulmonary Dysplasia Development," Oncotarget, 2017, vol. 8, pp. 18670-18679.
Ye D.Z. et al., "Foxa1 and Foxa2 control the differentiation of goblet and enteroendocrine L- and D-cells in mice," Gastroenterology, 2009, 137, 2052-2062.
Ye F., et al., "Fibroblast Growth Factors 7 and 10 Are Expressed in the Human Embryonic Pancreatic Mesenchyme and Promote the Proliferation of Embryonic Pancreatic Epithelial Cells," Diabetologia, 2005, vol. 48, pp. 277-281.
Yin H., et al., "Non-viral Vectors for Gene-based Therapy," Nature Reviews Genetics, 2014, vol. 15(8), pp. 541-555.
Yokobori, T., et al., "Intestinal epithelial culture under an air-liquid interface: a tool for studying human and mouse esophagi," Dis. Esophagus, 2016, vol. 29, pp. 843-847.
Younossi, Z.M., et al., "Economic and Clinical Burden of Nonalcoholic Steatohepatitis in Patients With Type 2 Diabetes in the U.S.," Diabetes Care, 2020, vol. 43, pp. 283-289.
Yu J., et al., "Induced Pluripotent Stem Cell Lines Derived from Human Somatic Cells," Science, 2007, vol. 318, pp. 1917-1920.
Yu X. et al., "Lentiviral vectors with two independent internal promoters transfer highlevel expression of multiple transgenes to human hematopoietic stem-progenitor cells," Mol Ther, 2003, 7, 827-838.
Yu, Y., Chinese Studies on Disease Signaling Pathway and Targeted Therapy, Anhui Science and Technology Press, May 31, 2013, p. 363 [Reference unavailable, citing referencing Search Report, 3 pgs.].
Yu, Y., et al., "A comparative analysis of liver transcriptome suggests divergent liver function among human, mouse and rat," Genomics, 2010, vol. 96, pp. 281-289.
Yusta B. et al., "Enteroendocrine localization of GLP-2 receptor expression in humans and rodents," Gastroenterology, 2000, 119, 744-755.
Zanini F., et al., "Developmental Diversity and Unique Sensitivity to Injury of Lung Endothelial Subtypes During Postnatal Growth," iScience, Mar. 2023, vol. 26, No. 3, doi: 10.1016/j.isci.2023.106097.
Zanini F., et al., "Phenotypic Diversity and Sensitivity to Injury of the Pulmonary Endothelium During a Period of Rapid Postnatal Growth," bioRxiv, Apr. 2021, doi: 10.1101/2021.04.27.441649.
Zeng, Q., et al., "O-Linked GlcNAcylation Elevated by HPV E6 Mediates Viral Oncogenesis." Proceedings of the National Academy of Sciences, vol. 113, No. 33, Aug. 16, 2016, pp. 9333-9338.
Zhang, D., et al., "Highly efficient differentiation of human ES cells and iPS cells into mature pancreatic insulin-producing cells," Cell Res., 2009, vol. 19, pp. 429-438.
Zhang H., et al., "Generation of Quiescent Cardiac Fibroblasts From Human Induced Pluripotent Stem Cells for In Vitro Modeling of Cardiac Fibrosis," Circulation Research, Sep. 2019, vol. 125, No. 5, pp. 552-566.
Zhang S. L., et al., "Angiotensin II Stimulates Pax-2 in Rat Kidney Proximal Tubular Cells: Impact on Proliferation and Apoptosis," Kidney International, 2004, vol. 66, pp. 2181-2192.
Zhao Z., et al., "Establishment and Dysfunction of the Blood-Brain Barrier," Cell, 2015, vol. 163(5), pp. 1064-1078.
Zheng G.X.Y., et al., "Massively Parallel Digital Transcriptional Profiling of Single Cells," Nature Communications, 2017, vol. 8(1), pp. 1-12.
Zhou C., et al., "Comprehensive Profiling Reveals Mechanisms of SOX2-Mediated Cell Fate Specification in Human ESCs and NPCs," Cell Research, 2016, 26(2), pp. 171-189. DOI: 10.1038/cr.2016.15.
Zhou H. J., et al., "Endothelial Exocytosis of Angiopoietin-2 Resulting from CCM3 Deficiency Contributes to Cerebral Cavernous Malformation," Nature Medicine, 2016, vol. 22, pp. 1033-1042.
Zhou Y., et al., "A Subtype of Oral, Laryngeal, Esophageal, and Lung Squamous Cell Carcinoma with High Levels of TrkB-T1 Neurotrophin Receptor mRNA," BMC Cancer, Jun. 2019, vol. 19, No. 1, doi: 10.1186/s12885-019-5789-8.
Zhou Z., et al., "Cerebral Cavernous Malformations Arise from Endothelial Gain of MEKK3-KLF2/4 Signaling," Nature, 2016, vol. 532, pp. 122-126.
Zhu, S., et al., "Liver Endothelial Heg Regulates Vascular/Biliary Network Patterning and Metabolic Zonation Via Wnt Signaling," Cell Molecular Gastroenterology and Hepatology, 2022, vol. 13, pp. 1757-1783.
Zhu Z. et al., "Human pluripotent stem cells: an emerging model in developmental biology," Development 140, 705-717 (2013).
Zhuo J. L., et al., "Proximal Nephron," Comprehensive Physiology, 2013, vol. 3, No. 3, pp. 1079-1123.
Zwerschke, W., et al., "Modulation of Type M2 Pyruvate Kinase Activity by the Human Papillomavirus Type 16 E7 Oncoprotein." Proceedings of the National Academy of Sciences USA, vol. 96, Feb. 1999, pp. 1291-1296.
Jin W., et al., "Regulation of BDNF-TrkB Signaling and Potential Therapeutic Strategies for Parkinson's Disease," Journal of Clinical Medicine, Jan. 2020, vol. 9, No. 1, doi: 10.3390/jcm9010257.
Jonatan D., et al., "Sox17 regulates insulin secretion in the normal and pathologic mouse beta cell," PloS one, 2014, 9, e104675, 16 pages.
Kaczmarek J. C., et al., "Polymer-Lipid Nanoparticles for Systemic Delivery of mRNA to the Lungs," Angewandte Chemie International Edition, 2016, vol. 55, pp. 13808-13812.
Kaczmarek J.C., et al., "Optimization of a Degradable Polymer-Lipid Nanoparticle for Potent Systemic Delivery of mRNA to the Lung Endothelium and Immune Cells," Nano Letters, 2018, vol. 18, No. 10, 6449-6454. doi: 10.1021/acs.nanolett.8b02917.
Kaiser J., Virus used in gene therapies may pose cancer risk, dog study hints, Science—Jan. 6, 2020 doi: 10.1126/science.aba7696 in 3 pages.
Kajiwara, K., et al., "Molecular Mechanisms Underlying Twin-to-Twin Transfusion Syndrome," Cells, 2022, vol. 11, 18 pages.
Kalabis J. et al., "A subpopulation of mouse esophageal basal cells has properties of stem cells with the capacity for self-renewal and lineage specification," Journal of Clinical Investigation, 2008, (118), 3860-3869.
Kalabis J. et al., "Isolation and characterization of mouse and human esophageal epithelial cells in 3D organotypic culture," Nature Protocols, 2012, 7(2), 235-246.
Kang, J., et al., "Simultaneous deletion of the methylcytosine oxidases Tet1 and Tet3 increases transcriptome variability in early

(56) References Cited

OTHER PUBLICATIONS embryogenesis," Proceedings of the National Academy of Sciences, 2015, vol. 112, pp. E4236-E4245.

Kang, S. D., et al., "Effect of Productive Human Papillomavirus 16 Infection on Global Gene Expression in Cervical Epithelium." Journal of Virology, vol. 92, No. 20, Oct. 15, 2018, e01261-18.

Kapadia, B., et al., "PIMT regulates Hepatic Gluconeogenesis in Mice," iScience, 2023, 106120.

Kawaguchi T., et al., "Genetic Polymorphisms of the Human PNPLA3 Gene Are Strongly Associated with Severity of Non-Alcoholic Fatty Liver Disease in Japanese," PLoS One, 2012, vol. 7, e38322.

Kazumori H. et al., "Bile acids directly augment caudal related homeobox gene Cdx2 expression in oesophageal keratinocytes in Barrett's epithelium," Gut, 2006, 55(1), 16-25.

Kazumori H. et al., "Roles of caudal-related homeobox gene Cdx1 in oesophageal epithelial cells in Barrett's epithelium development," Gut, 2009, 58(5), 620-628.

KC K. et al., "In vitro model for studying esophageal epithelial differentiation and allergic inflammatory responses identifies keratin involvement in eosinophilic esophagitis," PloS One, 2015, 10(6), e0127755.

Kearns N. A. et al., "Generation of organized anterior foregut epithelia from pluripotent stem cells using small molecules," Stem Cell Res., 2013, 11, 1003-1012.

Kebschull et al., "High-throughput mapping of single-neuron projections by sequencing of barcoded RNA", Neuron, 2016, vol. 91(5), pp. 975-987.

Keebler M. E., et al., "Fine-Mapping in African Americans of 8 Recently Discovered Genetic Loci for Plasma Lipids: The Jackson Heart Study," Circulation: Cardiovascular Genetics, 2010, vol. 3, pp. 358-364.

Keeley, T.P., et al., "Defining Physiological Normoxia for Improved Translation of Cell Physiology to Animal Models and Humans," Physiological Reviews, 2019, vol. 99, pp. 161-234.

Kennedy D., et al., "Optimal Absorptive Transport of the Dipeptide Glycylsarcosine Is Dependent on Functional Na?/ H? Exchange Activity," Pflugers Archiv, 2002, vol. 445, pp. 139-146.

Kermani P., et al., "Neurotrophins Promote Revascularization by Local Recruitment of TrkB+ Endothelial Cells and Systemic Mobilization of Hematopoietic Progenitors," Journal of Clinical Investigation, 2005, vol. 115, pp. 653-663.

Kietzmann, T., et al., "Metabolic zonation of the liver: The oxygen gradient revisited," Redox Biol, 2017, vol. 11, pp. 622-630.

Kim et al., "Recent progress in development of siRNA delivery vehicles for cancer therapy", Advanced Drug Delivery Reviews, 2016, vol. 104, pp. 61-77.

Kim M., et al., "O-Linked N-Acetylglucosamine Transferase Promotes Cervical Cancer Tumorigenesis through Human Papillomavirus E6 and E7 Oncogenes." Oncotarget, 7(28), 2016, 44596-44607.

Kim, S. G., et al., "Bilirubin Activates Transcription of HIF-1a in Human Proximal Tubular Cells Cultured in the Physiologic Oxygen Content," J Korean Med Sci, 2014, vol. 29, pp. S146-S154.

Kim Y. K., et al., "Gene-Edited Human Kidney Organoids Reveal Mechanisms of Disease in Podocyte Development," Stem Cells, 2017, vol. 35, pp. 2366-2378.

Kimura M., et al., "En Masse Organoid Phenotyping Informs Metabolic-Associated Genetic Susceptibility to NASH," Cell, Jun. 2022, vol. 185, No. 2, pp. 4216-4232.e4216.

Kitamoto A., et al., "Association of Polymorphisms in GCKR and TRIB1 with Nonalcoholic Fatty Liver Disease and Metabolic Syndrome Traits," Endocrine Journal, 2014, vol. 61, pp. 683-689.

Kleshchevnikov V., et al., "Comprehensive Mapping of Tissue Cell Architecture via Integrated Single Cell and Spatial Transcriptomics," bioRxiv, Nov. 2020, doi: 10.1101/2020.11.15.378125.

Kligerman S. J., et al., "From the Radiologic Pathology Archives: Organization and Fibrosis as a Response to Lung Injury in Diffuse Alveolar Damage, Organizing Pneumonia, and Acute Fibrinous and Organizing Pneumonia," Radiographics, 2013, 33, doi:10.1148/rg. 337130057. PMID-24224590.

Kolbe E., et al., "Mutual Zonated Interactions of Wnt and Hh Signaling Are Orchestrating the Metabolism of the Adult Liver in Mice and Human," Cell Reports, Nov. 2019, vol. 29, No. 11, pp. 4553-4567.e4557.

Kong J. et al., "Ectopic Cdx2 expression in murine esophagus models an intermediate stage in the emergence of Barrett's esophagus," PLoS One, 2011, 6(4), 1-12.

Kong J. et al., "Induction of intestinalization in human esophageal keratinocytes is a multistep process," Carcinogenesis, 2009, 30(1), 122-130.

Kormish J.D. et al., "Interactions between SOX factors and Wnt/beta-catenin signaling in development and disease," Developmental Dynamics: An Official Publication of the American Association of Anatomists, 2010, 239, 56-68.

Koui Y., et al., "An In Vitro Human Liver Model by iPSC-Derived Parenchymal and Non-Parenchymal Cells," Stem Cell Reports, 2017, 9, pp. 490-498.

Kouznetsova I. et al., Self-renewal of the human gastric epithelium: new insights from expression profiling using laser microdissection. Mol Biosyst, 2011, 7, 1105-1112.

Kowalski P.S., et al., "Delivering the messenger: Advances in Technologies for Therapeutic mRNA delivery," Molecular Therapy . Apr. 10, 2019;27(4):710-728.

Kozyra M., et al., "Human Hepatic D Spheroids As a Model for Steatosis and Insulin Resistance", Scientific Reports, vol. 8, No. 1, Sep. 24, 2018, 12 pages, Retrieved from the Internet: URL: https://www.nature.com/articles/s41598-018-32722-6.

Krishnan, U., et al., "Evaluation and Management of Pulmonary Hypertension in Children with Bronchopulmonary Dysplasia." The Journal of Pediatrics, vol. 188, Sep. 2017, pp. 24-34.e1.

Kuhnert F. et al., "Essential regulation of CNS angiogenesis by the orphan G protein-coupled receptor GPR124," Science, 2010, 330, 985-989. 10.1126/science.1196554.

Kumagai et al., "A bilirubin-inducible fluorescent protein from eel muscle," Cell (2013) 153(7): 1602-11.

Kumar A., et al., "Specification and Diversification of Pericytes and Smooth Muscle Cells from Mesenchymoangioblasts," Cell Reports, 2017, vol. 19, pp. 1902-1916.

Kumari, D., "States of Pluripotency: Nave and Primed Pluripotent Stem Cells," InTech Open, vol. 1, Chapter 3, 2016, pp. 31-45.

Kurz H., "Cell Lineages and Early Patterns of Embryonic CNS Vascularization," Cell Adhesion Migration, 2009, vol. 3, pp. 205-210.

Kuzmichev A. N. et al., "Sox2 acts through Sox21 to regulate transcription in pluripotent and differentiated cells," Current Biology, 22(18), 2012, 1705-1710.

Kwapiszewska G., et al., "BDNF/TrkB Signaling Augments Smooth Muscle Cell Proliferation in Pulmonary Hypertension," American Journal of Pathology, 2012, vol. 181, pp. 2018-2029.

L. Landsman, et al., "Pancreatic Mesenchyme Regulates Epithelial Organogenesis Throughout Development," PLoS Biology, 2011, vol. 9, Article e1001143, 14 pages.

Lammert E., "Induction of Pancreatic Differentiation by Signals from Blood Vessels," Science, 2001, vol. 294, pp. 564-567.

Lancaster M. A., et al., "Cerebral Organoids Model Human Brain Development and Microcephaly," Nature, 2013, vol. 501(7467), pp. 373-379.

Landin, B. H., et al., "Labeled Lectin Studies of Renal Tubular Dysgenesis and Renal Tubular Atrophy of Postnatal Renal Ischemia and End-Stage Kidney Disease." Pediatric Pathology, vol. 14, No. 1, 1994, pp. 87-99.

Langen U.H., et al., "Development and Cell Biology of the Blood-Brain Barrier," Annual Review of Cell and Developmental Biology, 2019, vol. 35, pp. 591-613.

Langer R., "Tissue Engineering," Science, 1990, vol. 249, pp. 1527-1533.

Lau J. Y., et al., "Systematic Review of the Epidemiology of Complicated Peptic Ulcer Disease: Incidence, Recurrence, Risk Factors and Mortality," Digestion, 2011, vol. 84, pp. 102-113. DOI: 10.1159/000323958.

(56) References Cited

OTHER PUBLICATIONS

Leblanc G. G., et al., "Biology of Vascular Malformations of the Brain," Stroke, 2009, vol. 40, pp. e694-e702.
Leedham S. J. et al., "Individual crypt genetic heterogeneity and the origin of metaplastic glandular epithelium in human Barrett's oesophagus," Gut, 2008, 57(8), 1041-1048.
Leeman K.T., et al., "Mesenchymal Stem Cells Increase Alveolar Differentiation in Lung Progenitor Organoid Cultures," Scientific reports, Apr. 23, 2019, vol. 9(1), 10 pages.
Li B., et al., "Benchmarking Spatial and Single-Cell Transcriptomics Integration Methods for Transcript Distribution Prediction and Cell Type Deconvolution," Nature Methods, Jun. 2022, vol. 19, No. 6, pp. 662-670.
Li H., et al., "Directed Differentiation of Human Embryonic Stem Cells into Keratinocyte Progenitors In Vitro: An Attempt with Promise of Clinical Use," In Vitro Cellular Developmental Biology—Animal, 2016, 52(8), pp. 885-893.
Li H. et al., "Fast and accurate short read alignment with Burrows-Wheeler transform," Bioinformatics, 2009, 25(14), 1754-1760.
Li H.J. et al., Basic helix-loop-helix transcription factors and enteroendocrine cell differentiation. Diabetes Obes Metab, 2011, 13(01), Suppl 1, 5-12, 16 pages.
Li J., et al., "An Obligatory Role for Neurotensin in High Fat Diet-Induced Obesity," Nature, 2016, vol. 533, No. 7603, pp. 411-415.
Li, Y., et al., "The Renin-Angiotensin-Aldosterone System (RAAS) Is One of the Effectors By Which Vascular Endothelial Growth Factor (VEGF)/Anti-VEGF Controls the Endothelial Cell Barrier," American Journal of Pathology, 2020, vol. 190, pp. 1971-1981.
Lin Y. C., et al., "Genetic Variants in GCKR and PNPLA3 Confer Susceptibility to Nonalcoholic Fatty Liver Disease in Obese Individuals," American Journal of Clinical Nutrition, 2014, vol. 99, pp. 869-874.
Lindstrm N. O., et al., "Integrated-catenin, BMP, PTEN, and Notch signalling patterns the nephron." eLife, 4, e04000. 2015, 29 pages. https://doi.org/10.7554/eLife.04000.
Lindstrm N. O., et al., "Spatial Transcriptional Mapping of the Human Nephrogenic Program." Developmental Cell, 56(16), 2021, pp. 2381-2398.e6. https://doi.org/10.1016/j.devcel.2021.07.017.
Lindstrom N.O., et al., "Integrated Beta-Catenin, BMP, PTEN, and Notch Signalling Patterns the Nephron," eLife, 2015, vol. 3, e04000.
Liu D., Chinese Encyclopedia of Medicine—Pathophysiology, "China Signal Pathway and Targeted Therapeutics", edited by Yu Yuanxun, Anhui Science and Technology Press, May 2013, 1st edition.
Liu K., et al.,"Sox2 Cooperates with Inflammation-Mediated Stat3 Activation in the Malignant Transformation of Foregut Basal Progenitor Cells," Cell Stem Cell, 2013, 12(3), 304-315.
Liu T., et al., "Regulation of Cdx2 expression by promoter methylation, and effects of Cdx2 transfection on morphology and gene expression of human esophageal epithelial cells," Carcinogenesis, 2007, 28(2), 488-496.
Lloyd D. J., et al., "Antidiabetic Effects of Glucokinase Regulatory Protein Small-Molecule Disruptors." Nature, 504, 2013, 16 pages.
Lois C. et al., "Germline transmission and tissue-specific expression of transgenes delivered by lentiviral vectors," Science, 2002, 295, 868-872.
Loomba, R., et al., "Combination Therapies Including Cilofexor and Firsocostat for Bridging Fibrosis and Cirrhosis Attributable to NASH." Hepatology, vol. 73, No. 2, Feb. 2021, pp. 625-643.
Loomba R., et al., "Heritability of Hepatic Fibrosis and Steatosis Based on a Prospective Twin Study," Gastroenterology, 2015, vol. 149, pp. 1784-1793.
Loquet PH., et al., "Influence Of Raising Maternal Blood Pressure With Angiotensin II On Utero-Placental And Feto-Placental Blood Velocity Indices In The Human," Clinical Science, 1990, vol. 78, pp. 95-100.
Low, J.H., et al., "Generation of Human PSC-Derived Kidney Organoids with Patterned Nephron Segments and a De Novo Vascular Network," Cell Stem Cell, 2019, vol. 25, pp. 373-387 e379.

Lu T.M., et al., "Pluripotent Stem Cell-Derived Epithelium Misidentified as Brain Microvascular Endothelium Requires ETS Factors to Acquire Vascular Fate," Proceedings of the National Academy of Sciences of the United States of America, 2021, vol. 118.
Lubinsky M. Sonic Hedgehog, VACTERL, and Fanconi anemia: Pathogenetic connections and therapeutic implications. American Journal of Medical Genetics, Part A, 2015, 167(11), 2594-2598.
Luca Selfa, I., et al., "Directed Differentiation of Human Pluripotent Stem Cells for the Generation of High-Order Kidney Organoids." Methods in Molecular Biology, vol. 2258, 2021, pp. 171-189.
Lustig B. et al., "Negative feedback loop of Wnt signaling through upregulation of conductin/axin2 in colorectal and liver tumors," Molecular and Cellular Biology, 2002, 22(4), 1184-93.
Luzio J.P. et al., "Lysosomes: fusion and function", Nature reviews Molecular cell biology, 2007, vol. 8, No. 8, pp. 622-632.
Ma, R., et al., "Metabolic and non-metabolic liver zonation is established non-synchronously and requires sinusoidal Wnts," eLife, 2020, vol. 9, e46206.
Mace O. J. et al., "Pharmacology and physiology of gastrointestinal enteroendocrine cells," Pharmacol Res Perspect, 2015 3(4), e00155, 26 pages.
Maddaluno L., et al., "EndMT Contributes to the Onset and Progression of Cerebral Cavernous Malformations." Nature, vol. 498, 2013, 7 pages.
Madisen L. et al., "A robust and high-throughput Cre reporting and characterization system for the whole mouse brain," Nat Neurosci, 2020, 13, 133-140.
Madsen K., et al., "Angiotensin II Promotes Development of the Renal Microcirculation through AT1 Receptors," Journal of the American Society of Nephrology, 2010, vol. 21, pp. 448-459.
Mahieu-Caputo D., et al., "Twin-to-Twin Transfusion Syndrome: Role of the Fetal Renin-Angiotensin System," American Journal of Pathology, 2000, vol. 156, pp. 629-636.
Mammen J. M., et al., "Mucosal Repair in the Gastrointestinal Tract," Critical Care Medicine, 2003, vol. 31, pp. S532-537. DOI: 10.1097/01.CCM.0000081429.89277.AF.
Mammoto A., et al., "Vascular Niche in Lung Alveolar Development, Homeostasis, and Regeneration," Frontiers in Bioengineering and Biotechnology, Nov. 2019, vol. 7, No. 318. doi: 10.3389/fbioe.2019.00318.
Mammoto, T., et al., "Mechanical control of tissue and organ development," Development, 2010, vol. 137, No. 9, pp. 1407-1420.
Mandegar M. A., et al., "CRISPR Interference Efficiently Induces Specific and Reversible Gene Silencing in Human iPSCs," Cell Stem Cell, 2016, 18(4), pp. 541-553.
Marable, S.S., et al., "Hnf4a deletion in the mouse kidney phenocopies Fanconi renotubular syndrome," JCI Insight, 2018, vol. 3, 12 Pages.
Mari L. et al., "A pSMAD/CDX2 complex is essential for the intestinalization of epithelial metaplasia," Cell Reports, 2014, 7(4), 1197-1210.
Marino G. et al., "Self-consumption: the interplay of autophagy and apoptosis", Nature reviews Molecular cell biology, 2014, vol. 15, No. 2, pp. 81-94.
Mariotti, V., et al., "Animal models of biliary injury and altered bile acid metabolism," Biochimica et Biophysica Acta (BBA)—Molecular Basis of Disease, 2018, vol. 1864, pp. 1254-1261.
Martin M. "Cutadapt Removes Adapter Sequences From High-Throughput Sequencing Reads," EMBnet.journal, 2011 17, 10-12.
Martindale J.L., et al., "Ribonucleoprotein Immunoprecipitation (RIP) Analysis," Bio Protoc, 2020, vol. 10, No. 2, e3488. doi: 10.21769/BioProtoc.3488.
Matrka M. C., et al., "Overexpression of the Human DEK Oncogene Reprograms Cellular Metabolism and Promotes Glycolysis," PLoS One, 2017, vol. 12, e0177952.
Matsuda S., et al., "Brain-Derived Neurotrophic Factor Induces Migration of Endothelial Cells Through a TrkB-ERK-Integrin V3-FAK Cascade." Journal of Cellular Physiology, 227, 2012, pp. 2123-2129.
Matt N. et al., "Retinoic acid-induced developmental defects are mediated by RARI3/RXR heterodimers in the pharyngeal endoderm," Development, 2003, 130(10), 2083-2093.

(56) References Cited

OTHER PUBLICATIONS

Mayor S., et al., "Pathways of Clathrin-independent Endocytosis," Nature Reviews, Molecular Cell Biology, 2007, vol. 8(8), pp. 603-612.
Aakerlund, L., et al., "Y1 receptors for neuropeptide Y are coupled to mobilization of intracellular calcium and inhibition of adenylate cyclase," FEBS Letters, 1990, vol. 260, pp. 73-78.
Abbott N.J., "Astrocyte-Endothelial Interactions and Blood-Brain Barrier Permeability," Journal of Anatomy, 2002, vol. 200, pp. 629-638.
Adams S. H. et al., "Effects of peptide YY [3-36] on short-term food intake in mice are not affected by prevailing plasma ghrelin levels," Endocrinology, 2004, 145, 4967-4975.
Aday S., et al., "Stem Cell-Based Human Blood-Brain Barrier Models for Drug Discovery and Delivery," Trends in Biotechnology, 2016, vol. 34, pp. 382-393.
Afgan E., et al., "The Galaxy Platform for Accessible, Reproducible and Collaborative Biomedical Analyses: 2016 Update," Nucleic Acids Research, 2016, vol. 44, pp. W3-W10.
Ager E. I., et al., "The Renin-Angiotensin System and Malignancy," Carcinogenesis, 2008, vol. 29, pp. 1675-1684.
Aird W.C. et al., "Endothelial cell heterogeneity," Cold Spring Harb Perspect Med, 2012, 2, a006429, 14 pages.
Aizarani N., et al., "A Human Liver Cell Atlas Reveals Heterogeneity and Epithelial Progenitors," Nature, Aug. 2019, vol. 572, No. 7770, pp. 199-204.
Akbari S., et al., "Next-Generation Liver Medicine Using Organoid Models", Frontiers in Cell and Developmental Biology, vol. 7, Dec. 20, 2019, 15 pages.
Akers A., et al., "Synopsis of Guidelines for the Clinical Management of Cerebral Cavernous Malformations: Consensus Recommendations Based on Systematic Literature Review by the Angioma Alliance Scientific Advisory Board Clinical Experts Panel," Neurosurgery, 2017, vol. 80, pp. 665-680.
Al Alam D., et al., "Contrasting expression of canonical Wnt signaling reporters Topgal, Batgal and Axin2(LacZ) during murine lung development and repair," PLoS One, 2011, 6, 8, e23139, 11 pages.
Alber A.B., et al., "Directed Differentiation of Mouse Pluripotent Stem Cells into Functional Lung-Specific Mesenchyme," bioRxiv, Aug. 2022, doi: 10.1101/2022.08.12.502651.
Alber A.B., et al., "Directed Differentiation of Mouse Pluripotent Stem Cells into Functional Lung-specific Mesenchyme," Nature Communications, Jun. 13, 2023 , vol. 14:3488. 18 pages.
Allanson J.E., et al., "Possible New Autosomal Recessive Syndrome With Unusual Renal Histopathological Changes," American Journal of Medical Genetics, 1983, vol. 16, pp. 57-60.
Almeida, L. F., et al., "Role of the Renin-Angiotensin System in Kidney Development and Programming of Adult Blood Pressure." Clinical Science, vol. 134, No. 6, Mar. 27, 2020, pp. 641-656.
Alvira C. M., "Aberrant Pulmonary Vascular Growth and Remodeling in Bronchopulmonary Dysplasia," Frontiers in Medicine (Lausanne), 2016, vol. 3, p. 21.
Alvira C. M., "Nuclear Factor-Kappa-B Signaling in Lung Development and Disease: One Pathway, Numerous Functions," Birth Defects Research Part A: Clinical and Molecular Teratology, 2014, vol. 100, pp. 202-216.
Amir et al., "Comparing the Cellular Phenotype of Nave and Primed Human Embryonic Stem Cells," Fertility and Sterility, Sep. 2018 110(4): e36 Abstract.
Amir M., et al., "Hepatic Autonomic Nervous System and Neurotrophic Factors Regulate the Pathogenesis and Progression of Non-Alcoholic Fatty Liver Disease," Frontiers in Medicine (Lausanne), 2020, vol. 7, Article 62. doi: 10.3389/fmed.2020.00062.
Amireddy N., et al., "The Unintended Mitochondrial Uncoupling Effects of the FDA-Approved Anti-Helminth Drug Nitazoxanide Mitigates Experimental Parkinsonism in Mice," Journal of Biological Chemistry, 2017, vol. 292, pp. 15731-15743.
Andl C.D. et al., "Epidermal growth factor receptor mediates increased cell proliferation, migration, and aggregation in esophageal keratinocytes in vitro and in vivo," Journal of Biological Chemistry, 2003, 278(3), 1824-1830.
Andrews T.S., et al., "Single-Cell, Single-Nucleus, and Spatial RNA Sequencing of the Human Liver Identifies Cholangiocyte and Mesenchymal Heterogeneity," Hepatology Communications, Nov. 2022, vol. 6, No. 11, pp. 821-840.
Anstee, Q.M., et al., "Genome-wide association study of non-alcoholic fatty liver and steatohepatitis in a histologically characterised cohort," Journal of Hepatology, 2020, vol. 73, pp. 505-515.
Appuhn S.V., et al., "Capillary Changes Precede Disordered Alveolarization in a Mouse Model of Bronchopulmonary Dysplasia," American Journal of Respiratory Cell and Molecular Biology, Mar. 2021, vol. 65, No. 1, pp. 81-91. doi: 10.1165/rcmb.2021-0004OC.
Arnold K. et al., "Sox2+ Adult Stem and Progenitor Cells Are Important for Tissue Regeneration and Survival of Mice," Cell Stem Cell, 2011, 9(4), 317-329.
Artegiani B., et al., "Fast and Efficient Generation of Knock-in Human Organoids Using Homology-independent CRISPRCas9 Precision Genome Editing", Nature Cell Biology, 2020, vol. 22, No. 3, pp. 321-331.
Auerbach A. D., "Fanconi anemia and its diagnosis," Mutation Research—Fundamental and Molecular Mechanisms of Mutagenesis, 2009, 668(1-2), 4-10.
Aven L., et al., "An NT4/TrkB Dependent Increase in Innervation Links Early-Life Allergen Exposure to Persistent Airway Hyperreactivity," FASEB Journal, 2014, vol. 28, pp. 897-907.
Bagnat M. et al., "Genetic control of single lumen formation in the zebrafish gut," Nat Cell Biol, 2007, 9, 954-960.
Bakker S. T. et al., "Learning from a paradox: recent insights into Fanconi anaemia through studying mouse models," Disease Models Mechanisms, 2013, 6(1), 40-47.
Baldelli, S., et al., "Glutathione and Nitric Oxide: Key Team Players in Use and Disuse of Skeletal Muscle," Nutrients, 2019, vol. 11.
Ballermann B. J., "Dependence of Renal Microvessel Density on Angiotensin II: Only in the Fetus?" Journal of the American Society of Nephrology, 2010, vol. 21, pp. 386-388.
Bamberger C. et al., "Retinoic acid inhibits downregulation of DeltaNp63alpha expression during terminal differentiation of human primary keratinocytes," The Journal of Investigative Dermatology, 2002, 118(1), 133-8.
Bandara, N., et al., "Molecular Control of Nitric Oxide Synthesis through eNOS and Caveolin-1 Interaction Regulates Osteogenic Differentiation of Adipose-Derived Stem Cells by Modulation of Wnt/-Catenin Signaling," Stem Cell Research Therapy, 2016, vol. 7, No. 182, pp. 1-15.
Barbera M. et al., "The human squamous oesophagus has widespread capacity for clonal expansion from cells at diverse stages of differentiation," Gut, 2015, 64, 11-19.
Bartl, M., et al., "Optimality in the Zonation of Ammonia Detoxification in Rodent Liver." Archives of Toxicology, vol. 89, 2015, pp. 2069-2078.
Basu-Roy U. et al., "Sox2 maintains self renewal of tumor-initiating cells in osteosarcomas," Oncogene, 2012, 31 (18), 2270-2282.
Batra S., et al., "Cavernous Malformations: Natural History, Diagnosis and Treatment." Nature Reviews Neurology, 2009, vol. 5, pp. 659-670.
Beer N. L., et al., "The P446L Variant in GCKR Associated with Fasting Plasma Glucose and Triglyceride Levels Exerts Its Effect through Increased Glucokinase Activity in Liver," Human Molecular Genetics, 2009, vol. 18, pp. 4081-4088.
Belalcazar L. M., et al., "Lifestyle Intervention for Weight Loss and Cardiometabolic Changes in the Setting of Glucokinase Regulatory Protein Inhibition: Glucokinase Regulatory Protein-Leu446Pro Variant in Look AHEAD," Circulation: Cardiovascular Genetics, 2016, vol. 9, pp. 71-78.
Bellentani, S., et al., "Epidemiology of Non-Alcoholic Fatty Liver Disease." Digestive Diseases, vol. 28, 2010, pp. 155-161.
Bergers G. et al., "The role of pericytes in blood-vessel formation and maintenance," Neuro Oncol, 2005, 7, 452-464.
Besserer-Offroy, E., et al., "The signaling signature of the neurotensin type 1 receptor with endogenous ligands," Eur J Pharmacol, 2017, vol. 805, pp. 1-13.

(56) References Cited

OTHER PUBLICATIONS

Beucher A., et al., "The homeodomain-containing transcription factors Arx and Pax4 control enteroendocrine subtype specification in mice," PLoS One, 2012, 7(5), e36449, 11 pages.

Bhatt A. J., et al., "Disrupted Pulmonary Vasculature and Decreased Vascular Endothelial Growth Factor, Flt-1, and TIE-2 in Human Infants Dying with Bronchopulmonary Dysplasia," American Journal of Respiratory and Critical Care Medicine, 2001, vol. 164, pp. 1971-1980.

Biancalani T., et al., "Deep Learning and Alignment of Spatially Resolved Single-Cell Transcriptomes with Tangram," Nature Methods, Nov. 2021, vol. 18, No. 11, pp. 1352-1362.

Bilchik A. J., et al., "Peptide YY Augments Postprandial Small Intestinal Absorption in the Conscious Dog," The American Journal of Surgery, 1994, vol. 167, pp. 570-574.

Biology Stack Exchange., "Are there situations where in vivo results work better than in vitro results would have shown?", Forum post , reply on Sep. 28, 2018; Retrieved Jul. 25, 2024 from https://biology.stackexchange.com/questions/77736/are-there-situations-where-in-vivo-results-work-better-th (Year: 2018).

Blair T.A., et al., "Mass cytometry reveals distinct platelet subtypes in healthy subjects and novel alterations in surface glycoproteins in Glanzmann thrombasthenia," Scientific Reports. Jul. 9, 2018; 8(1): 10300 in 13 pages.

Blakenberg D. et al., "Manipulation of FASTQ data with Galaxy," Bioinformatics, 2010, 26(14), 1783-1785.

McCarty, W. J., et al., "A Microfabricated Platform for Generating Physiologically-Relevant Hepatocyte Zonation," Scientific Reports, 2016, vol. 6, 26868, 10 Pages.

McMahon H.T., et al., "Molecular Mechanism and Physiological Functions of Clathrin-mediated Endocytosis," Nature Reviews Molecular Cell Biology, Aug. 2011, vol. 12(8), pp. 517-533.

McNaughton, L., et al., "Distribution of nitric oxide synthase in normal and cirrhotic human liver," Proceedings of the National Academy of Sciences, 2002, vol. 99, pp. 17161-17166.

Mendelsohn C. et al., "Developmental analsyis of the retinoic acid-inducible RARb2 promoter in transgenic animals," Development, 1991, 113, 723-734.

Miao Y., et al., "Enhancer-Associated Long Non-Coding RNA Leene Regulates Endothelial Nitric Oxide Synthase and Endothelial Function," Nature Communications, Jan. 2018, vol. 9, No. 1, doi: 10.1038/s41467-017-02113-y.

Miao Y., et al., "Intrinsic Endocardial Defects in Hypoplastic Left Heart Syndrome," Cell Stem Cell, Jul. 2020. doi: 10.1016/j.stem.2020.07.015.

Miao Z., et al., "Single Cell Regulatory Landscape of the Mouse Kidney Highlights Cellular Differentiation Programs and Disease Targets," Nature Communications, 2021, vol. 12, No. 2277.

Midendorp S., et al., "Adult Stem Cells in the Small Intestine Are Intrinsically Programmed with Their Location-Specific Function," Stem Cells, 2014, vol. 32, pp. 1083-1091. DOI: 10.1002/stem. 1655.

Miller J. L., et al., "Emergence of Oropharyngeal, Laryngeal and Swallowing Activity in the Developing Fetal Upper Aerodigestive Tract: An Ultrasound Evaluation." Early Human Development, 71, 2003, pp. 61-87.

Minoo P. et al., "Defects in tracheoesophageal and lung morphogenesis in Nkx2.1 (-/-) mouse embryos," Dev. Biol., 1999, 209, 60-71.

Mitani, S., et al., "Human ESC/iPSC-Derived Hepatocyte-like Cells Achieve Zone-Specific Hepatic Properties by Modulation of WNT Signaling," Mol Ther, 2017, vol. 25, pp. 1420-1433.

Moffett, J.R., et al., "Acetate Revisited: A Key Biomolecule at the Nexus of Metabolism, Epigenetics and OncogenesisPart 1: Acetyl-CoA, Acetogenesis and Acyl-CoA Short-Chain Synthetases," Frontiers in Physiology, 2020, vol. 11.

Moon C. et al., "Development of a primary mouse intestinal epithelial cell monolayer culture system to evaluate factors that modulate IgA transcytosis," Mucosal Immunol, 2014, 7, 818-828.

Moorefield E.C., et al., "Generation of renewable mouse intestinal epithelial cell monolayers and organoids for functional analyses," BMC Cell Biol, Aug. 15, 2018, vol. 19(1): 15.

Mootha V.K. et al., "PGC-1alpha-responsive genes involved in oxidative phosphorylation are coordinately downregulated in human diabetes," Nat Genet 34, 267-273 (2003).

Morizane R., et al., "Differentiation of Murine Embryonic Stem and Induced Pluripotent Stem Cells to Renal Lineage In Vitro." Biochemical and Biophysical Research Communications, 390, 2009, pp. 1334-1339.

Morizane R., et al., "Generation of Nephron Progenitor Cells and Kidney Organoids from Human Pluripotent Stem Cells," Nature Protocols, 2017, vol. 12, pp. 195-207.

Morizane R., et al., "Kidney Organoids: A Translational Journey," Trends in Molecular Medicine, 2017, vol. 23, pp. 246-263.

Morizane R., et al., "Nephron Organoids Derived from Human Pluripotent Stem Cells Model Kidney Development and Injury." Nature Biotechnology, 33(11), 2015, pp. 1193-1200. https://doi.org/10.1038/nbt.3392.

Morris M. E., et al., "SLC and ABC Transporters: Expression, Localization, and Species Differences at the Blood- Brain and the Blood-Cerebrospinal Fluid Barriers," AAPS Journal, 2017, vol. 19, pp. 1317-1331.

Mounier F., et al., "Ontogenesis of Angiotensin-I Converting Enzyme in Human Kidney," Kidney International, 1987, vol. 32, pp. 684-690.

Murphy C. L., et al., "HIF-Mediated Articular Chondrocyte Function: Prospects for Cartilage Repair," Arthritis Research Therapy, 2009, vol. 11, p. 213. DOI: 10.1186/ar2574.

Murphy P.A., et al., "Alternative RNA Splicing in the Endothelium Mediated in Part by Rbfox2 Regulates the Arterial Response to Low Flow," eLife, Jan. 2018, vol. 7, e29494. doi: 10.7554/eLife.29494.

Navin N., et al., "Tumor Evolution Inferred by Single-cell Sequencing," Nature, Apr. 7, 2011, vol. 472(7341), pp. 90-94.

Neal E.H., et al., "A Simplified, Fully Defined Differentiation Scheme for Producing Blood-Brain Barrier Endothelial Cells from Human iPSCs," Stem Cell Reports, 2019, vol. 12, pp. 1380-1388.

Nebert D. W., et al., "Letter to the Editor for 'Update of the Human and Mouse Fanconi Anemia Genes," Human Genomics, 2016, vol. 10, No. 1, 25 pages.

Nejak-Bowen, K., et al., "Beta-catenin regulates vitamin C biosynthesis and cell survival in murine liver," J Biol Chem, 2009, vol. 284, pp. 28115-28127.

Nelson L.J., et al., "Low-Shear Modelled Microgravity Environment Maintains Morphology and Differentiated Functionality of Primary Porcine Hepatocyte Cultures," Cells Tissues Organs, 2010, vol. 192, pp. 125-140.

Niederreither K. "Embryonic retinoic acid synthesis is essential for early mouse post-implantation development," Nature Genetics, 1999, 21(4), 444-448.

Niethamer T.K., et al., "Defining the Role of Pulmonary Endothelial Cell Heterogeneity in the Response to Acute Lung Injury," eLife, Feb. 2020, vol. 9, No. e53072. doi: 10.7554/eLife.53072.

Nishinakamura R., "Human Kidney Organoids: Progress and Remaining Challenges," Nature Reviews Nephrology, 2019, vol. 15, pp. 613-624.

Nonn, O., et al., "Maternal Angiotensin Increases Placental Leptin in Early Gestation via an Alternative Renin- Angiotensin System Pathway: Suggesting a Link to Preeclampsia," Hypertension, 2021, vol. 77, pp. 1723-1736.

Nozaki, Y., et al., "Metabolic Control Analysis of Hepatic Glycogen Synthesis In Vivo," Proceedings of the National Academy of Sciences of the United States of America, 2020, vol. 117, pp. 8166-8176.

Nyeng P. et al., FGF10 signaling controls stomach morphogenesis. Developmental Biology, 2007, 303, 295-310.

Oberg, K. C., et al., "Renal Tubular Dysgenesis in Twin-Twin Transfusion Syndrome." Pediatric Developmental Pathology, vol. 2, No. 1, 1999, pp. 25-32.

Offield M.F. et al., "PDX-1 is required for pancreatic outgrowth and differentiation of the rostral duodenum," Development, 1996, 122(3), 983-995.

(56) References Cited

OTHER PUBLICATIONS

Ohashi T., "Enzyme replacement therapy for lysosomal storage diseases," Pediatr Endocrinol Rev. Oct. 1, 2012;10(supp 1):26 34.
Ohmori T et al. "Efficient expression of a transgene in platelets using simian immunodeficiency virus based vector harboring glycoprotein Iba promoter: in vivo model for platelet targeting gene therapy," FASEB J. (2006);20(9): 1522 4.
Ohsie S. et al., "A paucity of colonic enteroendocrine and/or enterochromaftin cells characterizes a subset of patients with chronic unexplained diarrhea/malabsorption," Hum Pathol , 2009, 40(7), 1006-1014.
Ohta et al., "Hemogenic endothelium differentiation from human pluripotent stem cells in a feeder and xeno free defined condition, "Journal of Visualized Experiments. Jun. 16, 2019; 148:e59823 in 6 pages.
Oliverio M. I., et al., "Reduced Growth, Abnormal Kidney Structure, and Type 2 (AT2) Angiotensin Receptor-Mediated Blood Pressure Regulation in Mice Lacking Both AT1A and AT1B Receptors for Angiotensin II," Proceedings of the National Academy of Sciences USA, 1998, vol. 95, pp. 15496-15501.
Omer, D., et al., "Human Kidney Spheroids and Monolayers Provide Insights into SARS-Cov-2 Renal Interactions," Journal of the American Society of Nephrology, 2021, vol. 32, pp. 2242-2254.
Onaga T., et al., "Multiple Regulation of Peptide YY Secretion in the Digestive Tract," Peptides, 2002, vol. 23, pp. 279-290.
Onlilsoy Aksu A., et al., "Mutant Neurogenin-3 in a Turkish Boy with Congenital Malabsorptive Diarrhea," Pediatrics International, 2016, vol. 58, pp. 379-382.
Orho-Melander M., et al., "Common Missense Variant in the Glucokinase Regulatory Protein Gene Is Associated with Increased Plasma Triglyceride and C-Reactive Protein but Lower Fasting Glucose Concentrations," Diabetes, 2008, vol. 57, pp. 3112-3121.
Orskov C. et al., "GLP-2 stimulates colonic growth via KGF, released by subepithelial myofibroblasts with GLP-2 receptors," Regulatory peptides, 2005, 124, 105-112.
Ortiz-Meoz, R. F., et al., "A Small Molecule that Inhibits OGT Activity in Cells." ACS Chemical Biology, vol. 10, No. 6, Jun. 19, 2015, pp. 1392-1397.
Pan S., "Physiology," Science and Technology of China Press, Chapter 6, "Digestion within Large Intestine," 149-150, Jan. 2014.
Pankevich D.E. et al., "Improving and accelerating drug development for nervous system disorders," Neuron, 2014, 84, 546-553.
Paris, J., et al., "Liver zonation, revisited," Hepatology, 2022, vol. 76.
Thakur, A., et al., "Hepatocyte Nuclear Factor 4-Alpha Is Essential for the Active Epigenetic State at Enhancers in Mouse Liver," Hepatology, 2019, vol. 70, pp. 1360-1376.
The Lancet Gastroenterology, "Headway and hurdles in non-alcoholic fatty liver disease," Lancet Gastroenterology Hepatology, 2020, vol. 5, 93.
Thebaud B., et al., "Vascular Endothelial Growth Factor Gene Therapy Increases Survival, Promotes Lung Angiogenesis, and Prevents Alveolar Damage in Hyperoxia-Induced Lung Injury: Evidence that Angiogenesis Participates in Alveolarization," Circulation, 2005, vol. 112, pp. 2477-2486.
Thommensen L. et al., "Molecular mechanisms involved in gastrin-mediated regulation of cAMP-responsive promoter elements," Am J Physiol Endocrinol Metab, 2001, 281, E1316-1325.
Tomassoni-Ardori F., et al., "Rbfox1 Up-Regulation Impairs BDNF-Dependent Hippocampal LTP by Dysregulating TrkB Isoform Expression Levels," eLife, Aug. 2019, vol. 8, e49673. doi: 10.7554/eLife. 49673.
Totoson P., et al., "Activation of endothelial TrkB receptors induces relaxation of resistance arteries." Vascular Pharmacology, 106, 2018, pp. 46-53.
Touboul T. et al., "Generation of functional hepatocytes from human embryonic stem cells under chemically defined conditions that recapitulate liver development," Hepatology, 2010, 51, 1754-1765.
Traag V.A., et al., "From Louvain to Leiden: Guaranteeing Well-Connected Communities," Scientific Reports, 2019, vol. 9, 5233. doi: 10.1038/s41598-019-41695-z.
Tran M., et al., "Spatial Analysis of Ligand-Receptor Interaction in Skin Cancer at Genome-Wide and Single-Cell Resolution," bioRxiv, Sep. 2021, doi: 10.1101/2020.09.10.290833.
Trapnell C. et al., "The dynamics and regulators of cell fate decisions are revealed by pseudotemporal ordering of single cells," Nat Biotechnol, 2014, 32, 381-386.
Tsakmaki A., et al., "Diabetes Through a 3D Lens: Organoid Models," Diabetologia, Springer Berlin Heidelberg, Berlin/heidelberg, vol. 63, No. 6, Mar. 27, 2020, pp. 1093-1102.
Tsankov A. M. et al., "Transcription factor binding dynamics during human ES cell differentiation," Nature, 2015, 518 (7539), 344-9.
Tufro-McReddie, A., et al., "Angiotensin II Regulates Nephrogenesis and Renal Vascular Development." American Journal of Physiology, vol. 269, No. 1, 1995, pp. F110-F115.
Uchida H., et al., "A Xenogeneic-free System Generating Functional Human Gut Organoids from Pluripotent Stem Cells," JCI Insight, Jan. 12, 2017, vol. 2, No. 1, 13 pages.
Uchimura, K., et al., "Human Pluripotent Stem Cell-Derived Kidney Organoids with Improved Collecting Duct Maturation and Injury Modeling," Cell Reports, 2020, vol. 33, 108514.
Vales, S., et al., "In Vivo Human PSC-Derived Intestinal Organoids to Study Stem Cell Maintenance." In Methods in Molecular Biology, vol. 2171, Chapter 12, 2020, pp. 201-214.
Van Den Berg C.W., et al., "Renal Subcapsular Transplantation of PSC-Derived Kidney Organoids Induces Neo-vasculogenesis and Significant Glomerular and Tubular Maturation In Vivo," Stem Cell Reports, 2018, vol. 10, pp. 751-765. doi: 10.1016/j.stemcr.2018.01. 041.
Van Dop W. A., et al., "Hedgehog Signalling Stimulates Precursor Cell Accumulation and Impairs Epithelial Maturation in the Murine Oesophagus," Gut, 2012, 62(3), pp. 348-357.
Van Hoecke et al., "How mRNA therapeutics are entering the monoclonal antibody field," Journal of Translational Medicine . Feb. 22, 2019; 17(1):54 in 14 pages.
Van Raay T. J. et al., "Frizzled 5 signaling governs the neural potential of progenitors in the developing Xenopus retina," Neuron, 2005, 46(1), 23-36.
Van Straten, G., et al., "Aberrant Expression and Distribution of Enzymes of the Urea Cycle and Other Ammonia Metabolizing Pathways in Dogs with Congenital Portosystemic Shunts," PLOS One, 2014, vol. 9, e100077, 11 pages.
Vatine G. D., et al., "Modeling Psychomotor Retardation Using iPSCs from MCT8-Deficient Patients Indicates a Prominent Role for the Blood-Brain Barrier," Cell Stem Cell, 2017, vol. 20, pp. 831-843.e835.
Vatine G.D., et al., "Human iPSC-Derived Blood-Brain Barrier Chips Enable Disease Modeling and Personalized Medicine Applications," Cell Stem Cell, 2019, vol. 24, pp. 995-1005.
Vega M. E. et al., "Inhibition of notch signaling enhances transdifferentiation of the esophageal squamous epithelium towards a Barrett's-like metaplasia via KLF4," Cell Cycle, 2014, 13(24), 3857-3866.
Veldman, T., et al., "Human Papillomavirus E6 and Myc Proteins Associate In Vivo and Bind to and Cooperatively Activate the Telomerase Reverse Transcriptase Promoter." Proceedings of the National Academy of Sciences, vol. 100, No. 14, Jul. 8, 2003, pp. 8211-8216.
Verdera H, C., et al., AAV vector immunogenicity in humans: A long journey to successful gene transfer, Mol Thera. Mar. 4, 2020;28(3):723-746.
Verma S.K., et al., "RBFOX2 is Required for Establishing RNA Regulatory Networks Essential for Heart Development," Nucleic Acids Research, 2022, vol. 50, No. 4, 2270-2286. doi: 10.1093/nar/gkac055.
Verscheijden L.F.M., et al., "Differences in P-Glycoprotein Activity in Human and Rodent Blood-Brain Barrier Assessed by Mechanistic Modelling," Archives of Toxicology, 2021, vol. 95, pp. 3015-3029.
Vincent K.M., et al., "Expanding the Clinical Spectrum of Autosomal-Recessive Renal Tubular Dysgenesis: Two Siblings with Neonatal

(56) References Cited

OTHER PUBLICATIONS

Survival and Review of the Literature," Molecular Genetics and Genomic Medicine, 2022, vol. 10, e1920.

Vohwinkel C.U., et al., "Bronchopulmonary Dysplasia: Endothelial Cells in the Driver's Seat," American Journal of Respiratory Cell and Molecular Biology, Apr. 2021, vol. 65, No. 1, pp. 6-7. doi: 10.1165/rcmb.2021-0145ED.

Wagner N., et al., "Coronary Vessel Development Requires Activation of the TrkB Neurotrophin Receptor by the Wilms' Tumor Transcription Factor Wt1," Genes Development, 2005, vol. 19, pp. 2631-2642.

Wahlestedt C. et al., "Neuropeptide Y Receptor Subtypes, Y1 and Y2," Annals of the New York Academy of Sciences, 1990, 611, 7-26.

Wahlicht, T., et al., "Controlled Functional Zonation of Hepatocytes In Vitro by Engineering of Wnt Signaling." ACS Synthetic Biology, vol. 9, 2020, pp. 1638-1649.

Walker E.M. et al., "Characterization of the developing small intestine in the absence of either GATA4 or GATA6," BMC Res Notes, 2014, 7, 902, 12 pages.

Wang D. H., et al., "Regulation of Angiotensin Type 1 Receptor and Its Gene Expression: Role in Renal Growth," Journal of the American Society of Nephrology, 1997, vol. 8, pp. 193-198.

Wang D.H. et al., "Aberrant Epithelial-Mesenchymal Hedgehog Signaling Characterizes Barrett's Metaplasia," Gastroenterology 2010, 138(5), 1810-1822.e2.

Wang H., et al., "Recent Progress in microRNA Delivery for Cancer Therapy by Non-Viral Synthetic Vectors," Advanced Drug Delivery Reviews, 2015, vol. 81, pp. 142-160.

Wang K., et al., "ANNOVAR: Functional Annotation of Genetic Variants from High-Throughput Sequencing Data," Nucleic Acids Research, 2010, vol. 38, e164.

Wang Q. et al., "Regulatable in vivo biotinylation expression system in mouse embryonic stem cells," PloS One, 2013, 8, 5, e63532, 7 pages.

Wang S., "Fundamentals of developmental biology", edited by , East China University of 25 Technology Press, Feb. 2014, 1st edition, pp. 184-185 "Role of homologous genes in development of appendages", published on Feb. 28, 2014).

Wang T. et al. "Polypeptide Growth Factor and Spinal Cord Injury". Xinjiang Science and Technology Press, Yunnan Science and Technology Press, "Biological Effects of EGF", pp. 88-89, published on Apr. 30, 2003).

Wang X., et al., "A Tropomyosin Receptor Kinase Family Protein, NTRK2, is a Potential Predictive Biomarker for Lung Adenocarcinoma," PeerJ, Jun. 2019, vol. 7, doi: 10.7717/peerj.7125.

Wang, Y., et al., "Metformin Improves Mitochondrial Respiratory Activity through Activation of AMPK," Cell Reports, 2019, vol. 29, pp. 1511-1523 e1515.

Wang, Y., et al., "Transcriptional regulation of hepatic lipogenesis," Nat Rev Mol Cell Biol, 2015, vol. 16, pp. 678-689.

Watanabe H., et al., "SOX2 and p63 colocalize at genetic loci in squamous cell carcinomas," Journal of Clinical Investigation, 2014, 124(4), 1636-1645.

Watanabe M., et al., "Feasibility Study of NMR-Based Serum Metabolomic Profiling to Animal Health Monitoring: A Case Study on Iron Storage Disease in Captive Sumatran Rhinoceros (Dicerorhinus sumatrensis)," PLoS One, 2016, vol. 11, e0156318.

Weber R.J., et al., "Efficient Targeting of Fatty-acid modified Oligonucleotides to live Cell Membranes through Stepwise Assembly," Biomacromolecules, 2014, vol. 15(12), pp. 4621-4626.

Wei Y., et al., "Liver Homeostasis is Maintained by Midlobular Zone 2 Hepatocytes," Science, Feb. 2021, vol. 371, No. eabb1625.

Weirauch M. T. et al., "Determination and inference of eukaryotic transcription factor sequence specificity," Cell, 2014, 158, 1431-1443.

Wells J.M. et al., "Wnt/beta-catenin signaling is required for development of the exocrine pancreas," BMC Dev Biol, 2007, 7, 4, 18 pages.

Feliers D., et al., "Mechanism of VEGF Expression by High Glucose in Proximal Tubule Epithelial Cells," Molecular and Cellular Endocrinology, 2010, vol. 314, pp. 136-142.

Ferguson, D., et al., "Emerging Therapeutic Approaches for the Treatment of NAFLD and Type 2 Diabetes Mellitus," Nature Reviews Endocrinology, 2021, vol. 17, pp. 484-495.

Fermini, B., et al., "Clinical Trials in a Dish: A Perspective on the Coming Revolution in Drug Development," SLAS Discovery, 2018, vol. 23, pp. 765-776.

Fischer B., et al., "Oxygen Tension in the Oviduct and Uterus of Rhesus Monkeys, Hamsters and Rabbits," Journal of Reproduction and Fertility, 1993, vol. 99, pp. 673-679.

Freedman B.S., "Physiology Assays in Human Kidney Organoids," American Journal of Physiology—Renal Physiology, 2022, vol. 322, pp. F625-F638.

Freund J.B. et al., "Fluid flows and forces in development: functions, features and biophysical principles," Development, 2012, 139(7), 1229-1245.

Fujita Y. et al., "Pax6 and Pdx1 are required for production of glucose-dependent insulinotropic polypeptide in proglucagon-expressing L cells," Am J Physiol Endocrinol Metab, 2008, 295, E648-657.

Funakoshi, K., et al., "Highly Sensitive and Specific Alu-Based Quantification of Human Cells Among Rodent Cells," Scientific Reports, 2017, vol. 7, Article 13202. DOI: 10.1038/s41598-017-13402-3.

Furuta G. T. et al., "Eosinophilic Esophagitis," New England Journal of Medicine, 2015, 373(17), 1640-1648.

Gang, X., et al., "P300 Acetyltransferase Regulates Fatty Acid Synthase Expression, Lipid Metabolism and Prostate Cancer Growth," Oncotarget, 2016, vol. 7, No. 11, pp. 15135-15149.

Gao C., et al., "RBFox1-Mediated RNA Splicing Regulates Cardiac Hypertrophy and Heart Failure," Journal of Clinical Investigation, 2016, vol. 126, pp. 195-206.

Gao et al., "Highly Branched Poly (-amino esters) for Non-Viral Gene Delivery: High Transfection Efficiency and Low Toxicity Achieved by Increasing Molecular Weight", Biomacromolecules, 2016, vol. 17(11), pp. 3640-3647.

Gao, H., et al., "Association of GCKR Gene Polymorphisms with the Risk of Nonalcoholic Fatty Liver Disease and Coronary Artery Disease in a Chinese Northern Han Population," Journal of Clinical and Translational Hepatology, 2019, vol. 7, pp. 297-303.

Garca-Surez, O., et al., "TrkB is Necessary for the Normal Development of the Lung." Respiratory Physiology Neurobiology, vol. 167, No. 3, Jul. 31, 2009, pp. 281-291.

Garcia-Martinez, S., et al., "Mimicking physiological 02 tension in the female reproductive tract improves assisted reproduction outcomes in pig," Molecular Human Reproduction, 2018, vol. 24, pp. 260-270.

Garlanda C. et al., "Heterogeneity of endothelial cells. Specific markers" Arterioscler Thromb Vasc Biol, 1997, 17, 1193-1202.

Gazzin, S., et al., "Bilirubin Accumulation and Cyp mRNA Expression in Selected Brain Regions of Jaundiced Gunn Rat Pups," Pediatric Research, 2012, vol. 71, No. 6, pp. 653-660.

German-Diaz, M., et al., "A New Case of Congenital Malabsorptive Diarrhea and Diabetes Secondary to Mutant Neurogenin," Pediatrics, 2017, vol. 140, No. 2, 8 pages.

Ghatak S. et al., "Bile acid at low pH reduces squamous differentiation and activates EGFR signaling in esophageal squamous cells in 3-D culture," Journal of Gastrointestinal Surgery: Official Journal of the Society for Surgery of the Alimentary Tract, 2013, 17(10), 1723-31.

Ginestet C., "ggplot2: Elegant Graphics for Data Analysis," J R Stat Soc a Stat, 2011 174, 245,245.

Glass, L. L., et al., "Single-cell RNA-sequencing reveals a distinct population of proglucagon-expressing cells specific to the mouse upper small intestine," Molecular Metabolism, 2017, vol. 6, pp. 1296-1303.

Gololow N., et al., "Epitheliomesenchymal Interaction in Pancreatic Morphogenesis," Developmental Biology, 1962, vol. 4, pp. 242-255.

(56) References Cited

OTHER PUBLICATIONS

Goss A.M., "Wnt2/2b and beta-catenin signaling are necessary and sufficient to specify lung progenitors in the foregut," Developmental Cell, 2009, 17(2), 290-8.
Gotoh S. et al. "Generation of Alveolar Epithelial Spheroids via Isolated Progenitor Cells from Human Pluripotent Stem cells" Stem Cell Reports (2014) 3(3):394-403.
Greene, A. S., et al., "Microvascular Angiogenesis and the Renin-Angiotensin System." Current Hypertension Reports, vol. 4, No. 1, Feb. 2002, pp. 56-62.
Greene Y. J., et al., "Ascorbic Acid Regulation of 3-Hydroxy-3-Methylglutaryl Coenzyme A Reductase Activity and Cholesterol Synthesis in Guinea Pig Liver." Biochimica et Biophysica Acta, 834(1), 1985, pp. 134-138.
Greggio C., et al., "Artificial Three-Dimensional Niches Deconstruct Pancreas Development In Vitro," Development, 2013, vol. 140, pp. 4452-4462.
Gribble, F. M., et al., "Enteroendocrine Cells: Chemosensors in the Intestinal Epithelium," Annu Rev Physiol, 2016, vol. 78, pp. 277-299.
Gribouval O., et al., "Mutations in Genes in the Renin-Angiotensin System Are Associated with Autosomal Recessive Renal Tubular Dysgenesis," Nature Genetics, 2005, vol. 37, pp. 964-968.
Gribouval, O., et al., "Spectrum of Mutations in the Renin-Angiotensin System Genes in Autosomal Recessive Renal Tubular Dysgenesis." Human Mutation, vol. 33, No. 2, Feb. 2012, pp. 316-326.
Gu G., et al., "Global expression analysis of gene regulatory pathways during endocrine pancreatic development," Development, 2004, 131, 165-179.
Gu M., et al., "iPSC-Endothelial Cell Phenotypic Drug Screening and In Silico Analyses Identify Tyrphostin-AG1296 for Pulmonary Arterial Hypertension," Science Translational Medicine, 2021, vol. 13, No. 592. doi: 10.1126/scitranslmed.aba6480.
Gu M., et al., "Microfluidic Single-Cell Analysis Shows That Porcine Induced Pluripotent Stem Cell-Derived Endothelial Cells Improve Myocardial Function by Paracrine Activation," Circulation Research, 2012, vol. 111, pp. 882-893.
Gu M., et al., "Patient-Specific iPSC-Derived Endothelial Cells Uncover Pathways that Protect Against Pulmonary Hypertension in BMPR2 Mutation Carriers," Cell Stem Cell, 2017, vol. 20, pp. 490-504.
Gualdi R. et al., "Hepatic specification of the gut endoderm in vitro: cell signaling and transcriptional control," Genes Dev, 1996, 10, 1670-1682.
Guan X. et al., "GLP-2 receptor localizes to enteric neurons and endocrine cells expressing vasoactive peptides and mediates increased blood flow," Gastroenterology, 2006, 130, 150-164.
Guarino, M., et al., "Nicotinamide and NAFLD: Is There Nothing New Under the Sun?" Metabolites, 2019, vol. 9.
Gubler M. C., et al., "Renin-Angiotensin System in Kidney Development: Renal Tubular Dysgenesis," Kidney International, 2010, vol. 77, pp. 400-406.
Gubler M. C., et al., "Renal Tubular Dysgenesis," Pediatric Nephrology, 2014, vol. 29, pp. 51-59.
Guo L., et al., "The Adrenal Stress Response is an Essential Host Response Against Therapy-Induced Lethal Immune Activation," Science Signaling, 2023, vol. 16, eadd4900. doi: 10.1126/scisignal.add4900.
Guo M., et al., "Guided Construction of Single Cell Reference for Human and Mouse Lung," Nature Communications, Jul. 29, 2023, 14:4566, 20 pages.
Gupta A. et al., "The great divide: septation and malformation of the cloaca, and its implications for surgeons," Pediatr Surg Int, 2014, 30, 1089-1095.
Ha, T. Y., et al., "Ascorbate Indirectly Stimulates Fatty Acid Utilization in Primary Cultured Guinea Pig Hepatocytes by Enhancing Carnitine Synthesis," The Journal of Nutrition, 1994, vol. 124, pp. 732-737.

Haasdijk R. A., et al., "Cerebral Cavernous Malformations: From Molecular Pathogenesis to Genetic Counselling and Clinical Management," European Journal of Human Genetics, 2012, vol. 20, pp. 134-140.
Habib A. M. et al., "Overlap of endocrine hormone expression in the mouse intestine revealed by transcriptional profiling and flow cytometry," Endocrinology, 2012, 153, 3054-3065.
Haeussler M., et al., "Evaluation of Off-Target and On-Target Scoring Algorithms and Integration into the Guide RNA Selection Tool CRISPOR," Genome Biology, 2016, vol. 17, No. 148, 12 pages.
Hagan D.M. et al., "Mutation analysis and embryonic expression of the HLXB9 Currarino syndrome gene," Am. J. Hum. Genet., 2000, 66, 1504-1515.
Haigh J. J., et al., "Cortical and Retinal Defects Caused by Dosage-Dependent Reductions in VEGF-A Paracrine Signaling," Developmental Biology, 2003, vol. 262, pp. 225-241.
Hajal C., et al., "Biology and Models of the Blood-Brain Barrier," Annual Review of Biomedical Engineering, 2021, vol. 23, pp. 359-384.
Hale, C., et al., "Molecular Targeting of the GK-GKRP Pathway in Diabetes." Expert Opinion on Therapeutic Targets, vol. 19, No. 1, 2015, pp. 129-139.
Park E.J. et al., "System for tamoxifen-inducible expression of Cre-recombinase from the Foxa2 locus in mice," Developmental Dynamics, 2008, 237(2), 447-453.
Patel Y. C., "Somatostatin and Its Receptor Family," Frontiers in Neuroendocrinology, 1999, 20, 157-198.
Patro R., et al., "Salmon Provides Fast and Bias-Aware Quantification of Transcript Expression using Dual-Phase Inference," Nature Methods, 2017, vol. 14, pp. 417-419.
Pedersen J. et al., "The glucagon-like peptide 2 receptor is expressed in enteric neurons and not in the epithelium of the intestine," Peptides, 2015, 67, 20-28.
Peng K., et al., "Regulation of O-Linked N-Acetyl Glucosamine Transferase (OGT) Through E6 Stimulation of the Ubiquitin Ligase Activity of E6AP." Journal of Molecular Sciences, 22, 2021, 10286. https://doi.org/10.3390/ijms221910286.
Perdomo J., et al., "Megakaryocyte differentiation and platelet formation from human cord blood derived CD34+ cells," Journal of Visualized Experiments. Dec. 27, 2017; 130:e56420 in 8 pages.
Petta S., et al., "Glucokinase Regulatory Protein Gene Polymorphism Affects Liver Fibrosis in Non-Alcoholic Fatty Liver Disease," PLoS One, 2014, vol. 9, e87523.
Pham D., et al., "stLearn: Integrating Spatial Location, Tissue Morphology and Gene Expression to Find Cell Types, Cell—Cell Interactions and Spatial Trajectories Within Undissociated Tissues," bioRxiv, May 2020, doi: 10.1101/2020.05.31.125658.
Picelli S., et al., "Smart-seq2 for Sensitive Full-length Transcriptome Profiling in Single Cells," Nature Methods, Nov. 2013, vol. 10(11), pp. 1096-1098.
Pierre C., et al., "Can We Live Without a Functional Renin-Angiotensin System?" Clinical and Experimental Pharmacology and Physiology, 2008, vol. 35, pp. 431-433.
Pinney S. E. et al., "Neonatal diabetes and congenital malabsorptive diarrhea attributable to a novel mutation in the human neurogenin-3 gene coding sequence," The Journal of clinical endocrinology and metabolism, 2011, 96, 1960-1965.
Pirola, C.J., et al., "A Rare Nonsense Mutation in the Glucokinase Regulator Gene Is Associated with a Rapidly Progressive Clinical Form of Nonalcoholic Steatohepatitis," Hepatology Communications, 2018, vol. 2, pp. 1030-1036.
Podolsky D. K., "Healing the Epithelium: Solving the Problem from Two Sides," Journal of Gastroenterology, 1997, vol. 32, pp. 122-126. DOI: 10.1007/BF01213309.
Pollin T. I., et al., "Triglyceride Response to an Intensive Lifestyle Intervention Is Enhanced in Carriers of the GCKR Pro446Leu Polymorphism," Journal of Clinical Endocrinology Metabolism, 2011, vol. 96, pp. E1142-E1147.
Powell D. W., et al., "Myofibroblasts. II. Intestinal Subepithelial Myofibroblasts," American Journal of Physiology, 1999, vol. 277, pp. C183-C201. DOI: 10.1152/ajpcell.1999.277.2.C183.

(56) References Cited

OTHER PUBLICATIONS

Prakash Y., et al., "Neurotrophins in Lung Health and Disease," Expert Review of Respiratory Medicine, 2010, vol. 4, pp. 395-411.
Prakash Y. S., et al., "Brain-Derived Neurotrophic Factor in the Airways," Pharmacology Therapeutics, 2014, vol. 143, pp. 74-86.
Pupilli C., et al., "Angiotensin II Stimulates the Synthesis and Secretion of Vascular Permeability Factor/Vascular Endothelial Growth Factor in Human Mesangial Cells," Journal of the American Society of Nephrology, 1999, vol. 10, pp. 245-255.
Pyke C., et al., "GLP-1 Receptor Localization in Monkey and Human Tissue: Novel Distribution Revealed With Extensively Validated Monoclonal Antibody," Endocrinology, 2014, 155, 1280-1290.
Qian T., et al., "Directed Differentiation of Human Pluripotent Stem Cells to Blood-Brain Barrier Endothelial Cells," Science Advances, 2017, vol. 3, e1701679.
Qiu X., et al., "Single-Cell mRNA Quantification and Differential Analysis with Census," Nature Methods, 2017, vol. 14, pp. 309-315.
Qiu X., et al., "Reversed Graph Embedding Resolves Complex Single-Cell Trajectories," Nature Methods, 2017, vol. 14, pp. 979-982.
Que J. et al., "Multiple dose-dependent roles for Sox2 in the patterning and differentiation of anterior foregut endoderm," Development (Cambridge, England), 2007,134(13), 2521-31.
Que J. et al., "Multiple roles for Sox2 in the developing and adult mouse trachea," Development (Cambridge, England), 2009, 136(11), 1899-1907.
Que J., "The initial establishment and epithelial morphogenesis of the esophagus: a new model of tracheal—esophageal separation and transition of simple columnar into stratified squamous epithelium in the developing esophagus," Wiley Interdiscip. Rev. Dev. Biol., 2015, 4(4), 419-430.
Raisner, R., et al., "Enhancer Activity Requires CBP/P300 Bromodomain-Dependent Histone H3K27 Acetylation," Cell Reports, 2018, vol. 24, pp. 1722-1729.
Ramilowski J. A., et al., "A Draft Network of Ligand-Receptor-Mediated Multicellular Signalling in Human," Nature Communications, 2015, vol. 6, Article 7866, 11 pages.
Raredon M.S.B., et al., "Computation and Visualization of Cell—Cell Signaling Topologies in Single-Cell Systems Data Using Connectome," Scientific Reports, 2022, vol. 12, 4187. doi: 10.1038/s41598-022-07959-x.
Ren, X., et al., "Postnatal Alveologenesis Depends on FOXF1 Signaling in c-KIT+ Endothelial Progenitor Cells." American Journal of Respiratory and Critical Care Medicine, vol. 200, No. 9, 2019, pp. 1164-1176.
Revencu N. et al. "Cerebral cavernous malformation: new molecular and clinical insights," J Med Genet, 2006, 43, 716-721.
Reyes-Palomares A., et al., "Remodeling of Active Endothelial Enhancers is Associated with Aberrant Gene Regulatory Networks in Pulmonary Arterial Hypertension," Nature Communications, Apr. 2020, vol. 11, No. 1, 1673. doi: 10.1038/s41467-020-15463-x.
Reza H.A., et al., "Organoid Transplant Approaches for the Liver," Transplant International, Nov. 2021, vol. 34, No. 11, pp. 2031-2045.
Reza, H.A., et al., "Synthetic augmentation of bilirubin metabolism in human pluripotent stem cell-derived liver organoids," Stem Cell Reports, 2023.
Rhoads, K., et al., "A Role for Hox A5 in Regulating Angiogenesis and Vascular Patterning." Lymphatic Research and Biology, vol. 3, No. 4, 2005, pp. 240-252.
Rich, N.E., et al., "Racial and Ethnic Disparities in Nonalcoholic Fatty Liver Disease Prevalence, Severity, and Outcomes in the United States: A Systematic Review and Meta-Analysis," Clinical Gastroenterology and Hepatology, 2018, vol. 16, pp. 198-210 e192.
Robbins D. J. et al., "The Hedgehog Signal Transduction Network," Science Signaling 2012, 5(246), re6-re6, 28 pages.
Robinson B.D., et al., "Measurement of Microvascular Endothelial Barrier Dysfunction and Hyperpermeability In Vitro," Methods in Molecular Biology, Feb. 2018, vol. 1717, pp. 237-242.
Rochman M., et al., "Profound Loss of Esophageal Tissue Differentiation in Patients with Eosinophilic Esophagitis," Journal of Allergy and Clinical Immunology, 2017, 140(3), pp. 738-749.e3.
Roitbak T., et al., "Neural Stem/Progenitor Cells Promote Endothelial Cell Morphogenesis and Protect Endothelial Cells against Ischemia via HIF-1a-Regulated VEGF Signaling," Journal of Cerebral Blood Flow Metabolism, 2008, vol. 28, pp. 1530-1542.
Rosekrans S. L. et al., "Esophageal development and epithelial homeostasis," American Journal of Physiology—Gastrointestinal and Liver Physiology, 2015, 309(4), G216-228.
Ross M.G. et al., "Development of ingestive behavior.," Am J Physiol, 1998, 274, R879-893.
Rossi J.M. et al., "Distinct mesodermal signals, including BMPs from the septum transversum mesenchyme, arc required in combination for hepatogenesis from the endoderm," Genes Dev, 2001, 15, 1998-2009.
Rubio-Cabezas O., et al., "Permanent Neonatal Diabetes and Enteric Anendocrinosis Associated with Biallelic Mutations in NEUROG3," Diabetes, 2011, vol. 60, pp. 1349-1353.
Sahdeo S., et al., "High-Throughput Screening of FDA-Approved Drugs Using Oxygen Biosensor Plates Reveals Secondary Mitofunctional Effects," Mitochondrion, 2014, vol. 17, pp. 116-125.
Saili K. S., et al., "Blood-Brain Barrier Development: Systems Modeling and Predictive Toxicology," Birth Defects Research, 2017, vol. 109, pp. 1680-1710.
Sajiki T., et al., "Transmission Electron Microscopic Study of Hepatocytes in Bioartificial Liver," Tissue Engineering, 2000, vol. 6, No. 6, pp. 627-640.
Samson A. et al., "Effect of somatostatin on electrogenic ion transport in the duodenum and colon of the mouse, Mus domesticus," Comparative Biochemistry and Physiology Part A: Molecular Integrative Physiology, 2000, 125, 459-468.
Samuel, V.T., et al., "Nonalcoholic Fatty Liver Disease, Insulin Resistance, and Ceramides," New England Journal of Medicine, 2019, vol. 381, pp. 1866-1869.
Santoro N., et al., "Variant in the Glucokinase Regulatory Protein (GCKR) Gene Is Associated with Fatty Liver in Obese Children and Adolescents," Hepatology, 2012, vol. 55, pp. 781-789.
Sarkar A., et al., "Sox2 Suppresses Gastric Tumorigenesis in Mice," Cell Reports, 2016, 16(7), pp. 1929-1941.
Han L., et al., "Osr1 Functions Downstream of Hedgehog Pathway to Regulate Foregut Development," Developmental Biology, 2017, 427, pp. 72-83.
Hansmann G., et al., "Pulmonary Hypertension in Bronchopulmonary Dysplasia," Pediatric Research, Jun. 2020, No. 10.1038/s41390-020-0993-4.
Harris-Johnson K.S. et al., "l3-Catenin promotes respiratory progenitor identity in mouse foregut," Proc. Natl. Acad. Sci. U. S. A., 2009, 106, 16287-16292.
Harrison S.A., et al., "Selonsertib for Patients with Bridging Fibrosis or Compensated Cirrhosis Due to NASH: Results from Randomized Phase III Stellar Trials," Journal of Hepatology, 2020, vol. 73, pp. 26-39.
Haussinger, D., "Nitrogen metabolism in liver: structural and functional organization and physiological relevance," Biochem J, 1990, vol. 267, pp. 281-290.
He, L., et al., "Proliferation tracing reveals regional hepatocyte generation in liver homeostasis and repair," Science, 2021, vol. 371, eabc4346.
Heinz S. et al., "Simple combinations of lineage-determining transcription factors prime cis-regulatory elements required for macrophage and B cell identities," Mol Cell, 2010, 38, 576-589.
Hernaez R., et al., "Association Between Variants in or near PNPLA3, Gckr, and PPP1R3B with Ultrasound-Defined Steatosis Based on Data from the Third National Health and Nutrition Examination Survey," Clinical Gastroenterology and Hepatology, 2013, vol. 11, pp. 1183-1190.e1182.
Hilgers K. F., et al., "Aberrant Renal Vascular Morphology and Renin Expression in Mutant Mice Lacking Angiotensin-Converting Enzyme," Hypertension, 1997, vol. 29, pp. 216-221.
Hill, D. R., et al., "Gastrointestinal Organoids: Understanding the Molecular Basis of the Host-Microbe Interface," Cell Mol Gastroenterol Hepatol, 2017, vol. 3, pp. 138-149.

(56) References Cited

OTHER PUBLICATIONS

Hirschhorn, J. N., et al., "Genome-Wide Association Studies for Common Diseases and Complex Traits." Nature Reviews Genetics, vol. 6, 2005, pp. 95-108.
Hirsh A. J., et al., "Effect of Cholecystokinin and Related Peptides on Jejunal Transepithelial Hexose Transport in the Sprague-Dawley Rat," American Journal of Physiology—Gastrointestinal and Liver Physiology, 1996, vol. 271, No. G755-G761.
Hoffmeister K.M., "Desialylated Platelets: A Missing Link in Hepatic Thrombopoietin Regulation," The Hematologist 2015; 12(3), 7 pages.
Hoffmeister K.M., "The role of lectins and glycans in platelet clearance," Journal of Thrombosis and Haemostasis. Jul. 2011;9 (supp1), pp. 35-43.
Hohwieler H., et al., "Human Pluripotent Stem Cell-Derived Acinar/Ductal Organoids Generate Human Pancreas upon Orthotopic Transplantation and Allow Disease Modelling," Gut, 2017, vol. 66, pp. 473-486.
Holt L.M., et al., "Astrocyte Morphogenesis is Dependent on BDNF Signaling via Astrocytic TrkB.T1," eLife, Aug. 2019, vol. 8, No. e44667. doi: 10.7554/eLife.44667.
Homayun B., et al., "Challenges and Recent Progress in Oral Drug Delivery Systems for Biopharmaceuticals," Pharmaceutics, Mar. 19, 2019, vol. 11(3): 129.
Hoskins E. E., et al., Fanconi anemia deficiency stimulates HPV-associated hyperplastic growth in organotypic epithelial raft culture. Oncogene, 2009, 28(5), 674-685.
Hotta K., et al., "Association of the rs738409 Polymorphism in PNPLA3 with Liver Damage and the Development of Nonalcoholic Fatty Liver Disease," BMC Medical Genetics, 2010, vol. 11, p. 172.
Hu H., et al., "AnimalTFDB 3.0: A Comprehensive Resource for Annotation and Prediction of Animal Transcription Factors," Nucleic Acids Research, 2019, 47(D1), pp. D33-D38.
Hu Y. et al., "Targeted disruption of peptide transporter Pept1 gene in mice significantly reduces dipeptide absorption in intestine," Molecular pharmaceutics, 2008, 5(6), 1122-1130.
Hu Z. et al., "Generation of Naivetropic Induced Pluripotent Stem Cells from Parkinson's Desease Patients for High- Efficiency Genetic Manipulation oand Disease Modeling," Stem Cells and Development, 2015, vol. 24, No. 21, 2591-2604.
Huang H., et al., "p300-Mediated Lysine 2-Hydroxyisobutyrylation Regulates Glycolysis," Molecular Cell, 2018, vol. 70, pp. 663-678. e666. doi: 10.1016/j.molcel.2018.04.011.
Huang J., et al., "Activation of Wnt/-Catenin Signalling via GSK3 Inhibitors Direct Differentiation of Human Adipose Stem Cells into Functional Hepatocytes," Nature Scientific Reports, 2017, 7, Article No. 40716, 12 pages.
Huang, S. X. L., et al., "Efficient generation of lung and airway epithelial cells from human pluripotent stem cells," Nat. Biotechnol., 2014, vol. 32, No. 1, pp. 84-91.
Hudert, C. A., et al., "Genetic Determinants of Steatosis and Fibrosis Progression in Paediatric NonAlcoholic Fatty Liver Disease." Liver International, vol. 39, 2019, pp. 540-556.
Huo X. et al., "Acid and Bile Salt-Induced CDX2 Expression Differs in Esophageal Squamous Cells From Patients With and Without Barrett's Esophagus," Gastroenterology, 2010, 139(1), 194-203.e1.
Hurr, C., et al., "Liver Sympathetic Denervation Reverses Obesity-Induced Hepatic Steatosis." The Journal of Physiology, vol. 597, No. 17, Sep. 2019, pp. 4565-4580.
Hurskainen M., et al., "Single Cell Transcriptomic Analysis of Murine Lung Development on Hyperoxia-Induced Damage," Nature Communications, Mar. 2021, vol. 12, No. 1565. doi: 10.1038/s41467-021-21865-2.
Husson, A., et al., "Argininosuccinate synthetase from the urea cycle to the citrulline-NO cycle," European Journal of Biochemistry, 2003, vol. 270, pp. 1887-1899.
Iansante, V., et al., "Human hepatocyte transplantation for liver disease: current status and future perspectives," Pediatric Research, 2018, vol. 83, pp. 232-240.

Ikeda, Y., et al., "Bilirubin exerts pro-angiogenic property through Akt-eNOS787 dependent pathway," Hypertension Research, 2015, vol. 38, pp. 733-740.
Illig R. et al., "Spatio-temporal expression of HOX genes in human hindgut development," Developmental dynamics: an official publication of the American Association of Anatomists, 2013, 242, 53-66.
Isosaari L., et al., "Simultaneous Induction of Vasculature and Neuronal Network Formation on a Chip Reveals a Dynamic Interrelationship Between Cell Types," Cell Communication and Signaling, 2023, vol. 21, 132. doi: 10.1186/s12964-023-01159-4.
Iwafuchi-Doi, M. et al., "Pioneer transcription factors in cell reprogramming," Genes Dev 2014, 28, 2679-2692.
Iwasawa K., et al., "Organogenesis In Vitro," Current Opinion in Cell Biology, 2021, 73, pp. 84-91.
Jackerott M. et al., "Immunocytochemical localization of the NPY/PYY Y1 receptor in enteric neurons, endothelial cells, and endocrine-like cells of the rat intestinal tract," J Histochem Cytochem, 1997, 45(12), 1643-1650.
Jang S. W., et al., "A Selective TrkB Agonist with Potent Neurotrophic Activities by 7,8-Dihydroxyflavone," Proceedings of the National Academy of Sciences of the United States of America, 2010, vol. 107, pp. 2687-2692.
Jaramillo M., et al., "Endothelial Cells Mediate Islet-Specific Maturation of Human Embryonic Stem Cell-Derived Pancreatic Progenitor Cells," Tissue Engineering Part A, 2015, vol. 21, pp. 14-25.
Jarmas, A.E., et al., "Progenitor translatome changes coordinated by Tsc1 increase perception of Wnt signals to end nephrogenesis," Nature Communications, 2021, vol. 12.LOW, J.H., et al., "Generation of Human PSC-Derived Kidney Organoids with Patterned Nephron Segments and a De Novo Vascular Network," Cell Stem Cell, 2019, vol. 25, pp. 373-387.
Jennings R. E., et al., "Development of the Human Pancreas from Foregut to Endocrine Commitment," Diabetes, 2013, vol. 62, pp. 3514-3522.
Jennings R. E., et al., "Human Pancreas Development," Development, 2015, vol. 142, pp. 3126-3137.
Jensen E. A., et al., "Epidemiology of Bronchopulmonary Dysplasia," Birth Defects Research Part A: Clinical and Molecular Teratology, 2014, vol. 100, pp. 145-157.
Jensen K. J., et al., "Hepatic Nervous System and Neurobiology of the Liver," Comprehensive Physiology, 2013, vol. 3, pp. 655-665.
Jeong, Y., et al., "Identification and genetic manipulation of human and mouse oesophageal stem cells," Gut, 2015, pp. 1-10.
Jho E. et al., "Wnt/beta-catenin/Tcf signaling induces the transcription of Axin2, a negative regulator of the signaling pathway," Molecular and Cellular Biology, 2002, 22(4), 1172-83.
Jiang C., et al., "Comparative Transcriptomics Analyses in Livers of Mice, Humans, and Humanized Mice Define Human-Specific Gene Networks," Cells, Nov. 2020, vol. 9, No. 2566.
Jiang H., et al., "Tyrosine Kinase Receptor B Protects Against Coronary Artery Disease and Promotes Adult Vasculature Integrity by Regulating Ets1-Mediated VE-Cadherin Expression," Arteriosclerosis, Thrombosis, and Vascular Biology, 2015, vol. 35, pp. 580-588.
Jiang M. et al., "BMP-driven NRF2 activation in esophageal basal cell differentiation and eosinophilic esophagitis," The Journal of Clinical Investigation, 2015, 125(14), 1-12.
Jiang M., et al., "Transitional Basal Cells at the Squamous-Columnar Junction Generate Barrett's Oesophagus," Nature, 2017, 550(7677), pp. 529-533.
Sato T., et al., "Growing Self-Organizing Mini-Guts from a Single Intestinal Stem Cell: Mechanism and Applications," Science, 2013, vol. 340, pp. 1190-1194. DOI: 10.1126/science. 1234852.
Saunders N. R., et al., "Barrier Mechanisms in the Developing Brain," Frontiers in Pharmacology, 2012, vol. 3, Article 46, 18 pages.
Sayar E., et al., "Chromogranin—A Staining Reveals Enteric Anendocrinosis in Unexplained Congenital Diarrhea," Journal of Pediatric Gastroenterology and Nutrition, 2013, vol. 57, No. 4, pp. e21.

(56) References Cited

OTHER PUBLICATIONS

Sayar E., et al., "Extremely Rare Cause of Congenital Diarrhea: Enteric Anendocrinosis," Pediatrics International, 2013, vol. 55, pp. 661-663.

Scheidecker, B., et al., "Induction of in vitro Metabolic Zonation in Primary Hepatocytes Requires Both Near-Physiological Oxygen Concentration and Flux," Frontiers in Bioengineering and Biotechnology, 2020, vol. 8.

Schreiber R., et al., "Inherited Renal Tubular Dysgenesis May Not Be Universally Fatal," Pediatric Nephrology, 2010, vol. 25, pp. 2531-2534.

Schreiber R., et al., "Renal Tubular Dysgenesis Secondary to Mutations in Genes Encoding the Renin-Angiotensin System," Harefuah, 2021, vol. 160, pp. 822-826.

Schupp J.C., et al., "Integrated Single-Cell Atlas of Endothelial Cells of the Human Lung," Circulation, May 2021, vol. 144, No. 4, 286-302. doi: 10.1161/CIRCULATIONAHA.120.052318.

Sekar R. and Chow B. K. C., "Secrelin Receptor—Knockout Mice Are Resistant to High-Fat Diet-Induced Obesity and Exhibit Impaired Intestinal Lipid Absorption," The FASEB Journal, 2014, vol. 28, pp. 3494-3505.

Self M. et al., "Six2 activity is required for the formation of the mammalian pyloric sphincter," Dev Biol, 2009, 334, 409-417.

Shaham O. et al., "Pax6 is essential for lens fiber cell differentiation," Development (Cambridge, England), 2009, 136 (15), 2567-2578.

Shankar A.S., et al., "Human Kidney Organoids Produce Functional Renin," Kidney International, 2021, vol. 99, pp. 134-147.

Shao Z. et al., "MAnorm: a robust model for quantitative comparison of ChIP-Seq data sets," Genome Biol, 2012, 13, R16, 17 pages.

Shapiro E., et al., "Single-cell Sequencing-based Technologies will Revolutionize Whole Organism Science," Nature Reviews Genetics, 2013, vol. 14(9), pp. 618-630.

Shen H., et al., "Glucokinase Regulatory Protein Gene Polymorphism Affects Postprandial Lipemic Response in a Dietary Intervention Study," Human Genetics, 2009, vol. 126, pp. 567-574.

Shoyaib A.A., et al., "Intraperitoneal Route of Drug Administration: Should it Be Used in Experimental Animal Studies?," Pharm Res, Dec. 23, 2019, vol. 37(1): 12.

Simon, M., et al., "Expression of Vascular Endothelial Growth Factor and Its Receptors in Human Renal Ontogenesis and in Adult Kidney." American Journal of Physiology, vol. 268, No. 2, Feb. 1995, pp. F240-F250.

Simon T.G., et al., "Mortality in Biopsy-Confirmed Nonalcoholic Fatty Liver Disease: Results from a Nationwide Cohort," Gut, 2021, vol. 70, pp. 1375-1382. doi: 10.1136/gutjnl-2020-322786.

Sinagoga K. L., et al., "Distinct Roles for the mTOR Pathway in Postnatal Morphogenesis, Maturation and Function of Pancreatic Islets," Development, 2017, vol. 144, pp. 2402-2414.

Sinagoga K.L., et al., "Deriving Functional Human Enteroendocrine Cells from Pluripotent Stem Cells," Development, 2018, vol. 145.

Singh A., et al., "Transplanted Human Intestinal Organoids: A Resource for Modeling Human Intestinal Development," Development, 2023, vol. 150, dev201416. doi: 10.1242/dev.201416.

Singh S. K., et al., "Glucose-Dependent Insulinotropic Polypeptide (GIP) Stimulates Transepithelial Glucose Transport," Obesity, 2008, vol. 16, pp. 2412-2416.

Sinner D. et al. "Sox17 and Sox4 differentially regulate beta-catenin/T-cell factor activity and proliferation of colon carcinoma cells," Molecular and Cellular Biology, 27(22), 2007, 7802-7815.

Sloan S. A., et al., "Human Astrocyte Maturation Captured in 3D Cerebral Cortical Spheroids Derived from Pluripotent Stem Cells," Neuron, 2017, vol. 95, pp. 779-790.e1-e6.

Sloth B. et al., "Effect of subcutaneous injections of PYY1-36 and PYY3-36 on appetite, ad libitum energy intake, and plasma free fatty acid concentration in obese males," American Journal of Physiology Endocrinology and Metabolism, 2007, 293, E604-E609.

Sluch V.M., et al., "Highly Efficient Scarless Knock-in of Reporter Genes into Human and Mouse Pluripotent Stem Cells via Transient Antibiotic Selection", PLOS One, vol. 13, No. 11, Nov. 29, 2018.

18 pages, Retrieved from the Internet: URL :https://www.ncbi.nlm.nih.gov/pmc/articles/PMC6264506/pdf/pone.0201683.pdf.

Snellings D.A., et al., "Cerebral Cavernous Malformation: From Mechanism to Therapy," Circulation Research, 2021, vol. 129, pp. 195-215. doi: 10.1161/CIRCRESAHA.121.318174.

Snowball J. et al., "Endodermal Wnt signaling is required for tracheal cartilage formation," Dev Biol 405, 56-70 (2015).

Soneson C., et al., "Differential Analyses for RNA-Seq: Transcript-Level Estimates Improve Gene-Level Inferences," F1000Research, 2015, vol. 4, p. 1521.

Song H.W., et al., "Transcriptomic Comparison of Human and Mouse Brain Microvessels," Scientific Reports, 2020, vol. 10, 12358. doi: 10.1038/s41598-020-69096-7.

Spangle, J. M., et al., "The Human Papillomavirus Type 16 E6 Oncoprotein Activates mTORC1 Signaling and Increases Protein Synthesis." Journal of Virology, vol. 84, No. 18, Sep. 2010, pp. 9398-9407.

Sparrow D. B., et al., "A Mechanism for Gene-Environment Interaction in the Etiology of Congenital Scoliosis," Cell, 2012, vol. 149, pp. 295-306.

Speliotes E. K., et al., "Genome-Wide Association Analysis Identifies Variants Associated with Nonalcoholic Fatty Liver Disease That Have Distinct Effects on Metabolic Traits," PLoS Genetics, 2011, vol. 7, e1001324.

Spencer-Dene B. et al.," Stomach development is dependent on fibroblast growth factor 10/fibroblast growth factor receptor 2b-mediated signaling," Gastroenterology, 2006, 130, 1233-1244.

Sreter K.B., et al., "Plasma Brain-Derived Neurotrophic Factor (BDNF) Concentration and BDNF/TrkB Gene Polymorphisms in Croatian Adults with Asthma," Journal of Personalized Medicine, Oct. 2020, vol. 10, No. 4, doi: 10.3390/jpm10040189.

Stoffers D. A., et al., "Pancreatic Agenesis Attributable to a Single Nucleotide Deletion in the Human IPF1 Gene Coding Sequence," Nature Genetics, 1997, vol. 15, pp. 106-110.

Stoll B. J., et al., "Neonatal Outcomes of Extremely Preterm Infants from the NICHD Neonatal Research Network," Pediatrics, 2010, vol. 126, pp. 443-456.

Subramanian, A. et al., "Gene set enrichment analysis: A knowledge-based approach for interpreting genome-wide expression profiles," Proceedings of the National Academy of Sciences, 2005, 102(43), 15545-15550.

Suprynowicz, F. A., et al., "HPV-16 E5 Oncoprotein Upregulates Lipid Raft Components Caveolin-1 and Ganglioside GM1 at the Plasma Membrane of Cervical Cells." Oncogene, vol. 27, 2008, pp. 1071-1078.

Suzuki, et al., "Directed differentiation of human induced pluripotent stem cells into mature stratified bladder urothelium," Scientific Reports, 2019, vol. 9, 10506.

Takasato M., et al., "Kidney Organoids from Human iPS Cells Contain Multiple Lineages and Model Human Nephrogenesis," Nature, 2016, vol. 536, p. 238.

Tam P. P., and Loebel D. A., "Gene Function in Mouse Embryogenesis: Get Set for Gastrulation," Nature Reviews Genetics, 2007, 8, pp. 368-381.

Tanaka K., et al., "Structure and Functional Expression of the Cloned Rat Neurotensin Receptor," Neuron, 1990, vol. 4, pp. 847-854.

Tanii, H., et al., "Induction of Cytochrome P450 2A6 by Bilirubin in Human Hepatocytes," Pharmacology Pharmacy, 2013, vol. 04, pp. 182-190.

Tannenbaum, S.E. et al., "Derivation of Xeno-Free and GMP-Grade Human Embryonic Stem Cells—Platforms for Future Clinical Applications," PLoS One, Jun. 2012, vol. 7, No. 6, 16 pages.

Tanwar S. et al., "Validation of terminal peptide of procollagen III for the detection and assessment of nonalcoholic steatohepatitis in patients with nonalcoholic fatty liver disease," Hepatology, 2013, 57, 103-111.

Tarlungeanu D. C., et al., "Impaired Amino Acid Transport at the Blood Brain Barrier Is a Cause of Autism Spectrum Disorder," Cell, 2016, vol. 167, pp. 1481-1494.e1418.

Terry, N. A. et al., "Lipid Malabsorption from Altered Hormonal Signaling Changes Early Gut Microbial Responses". Am J Physiol—Gastrointest Liver Physiol, 2018, 315(6), pp. G990-G1000.

(56) References Cited

OTHER PUBLICATIONS

Terry N.A. et al., "Dysgenesis of enteroendocrine cells in Aristaless-Related Homeobox polyalanine expansion mutationsm," J Pediatr Gastroenterol Nutr, 2015, 60, 2, 192-199.
Tessarollo L., et al., "TrkB Truncated Isoform Receptors as Transducers and Determinants of BDNF Functions," Frontiers in Neuroscience, Mar. 2022, vol. 16, doi: 10.3389/fnins.2022.847572.

\* cited by examiner

ALB/CDX2/PDX1
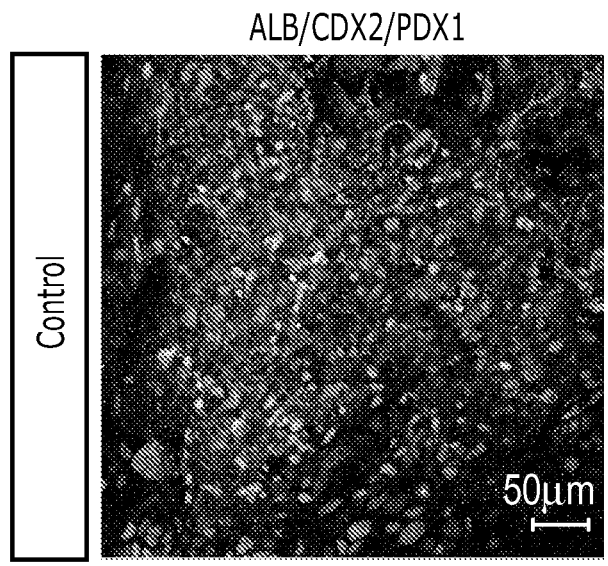
FIGURE 1b — Control
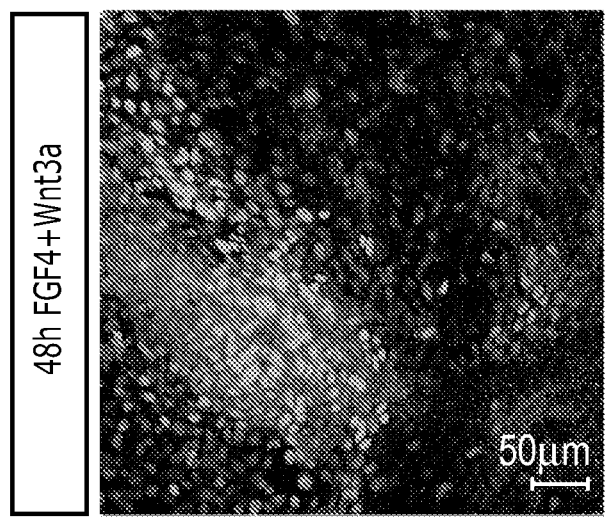
FIGURE 1c — 48h FGF4+Wnt3a
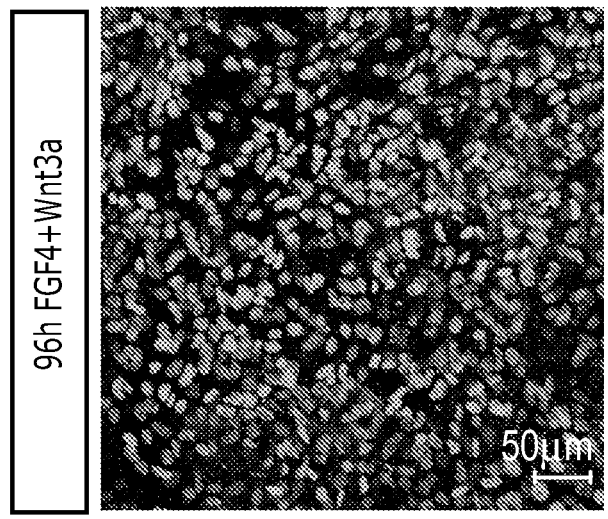
FIGURE 1d — 96h FGF4+Wnt3a

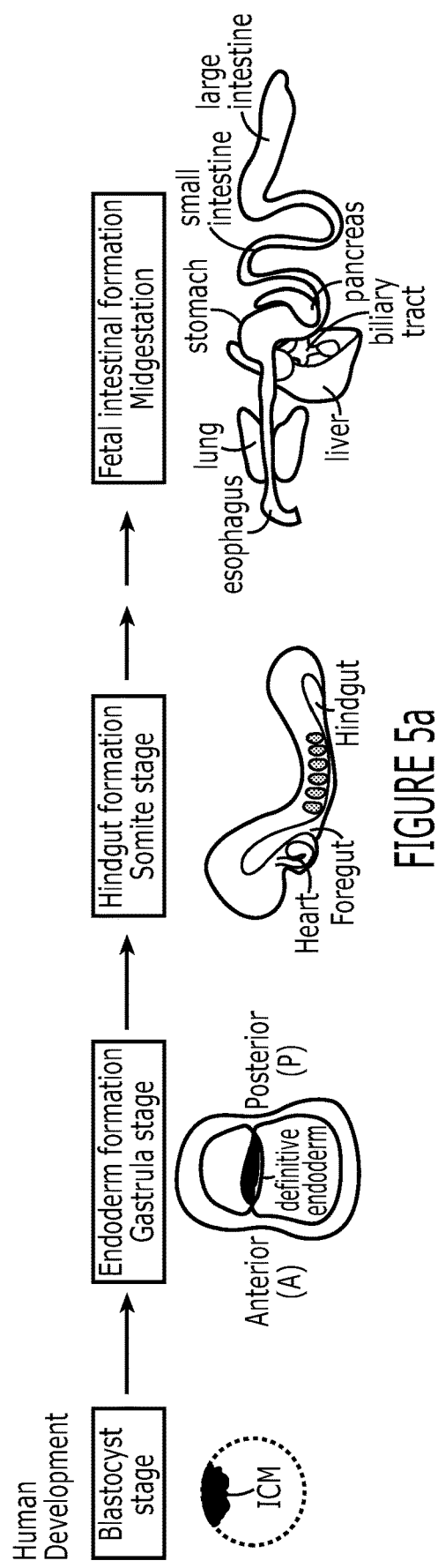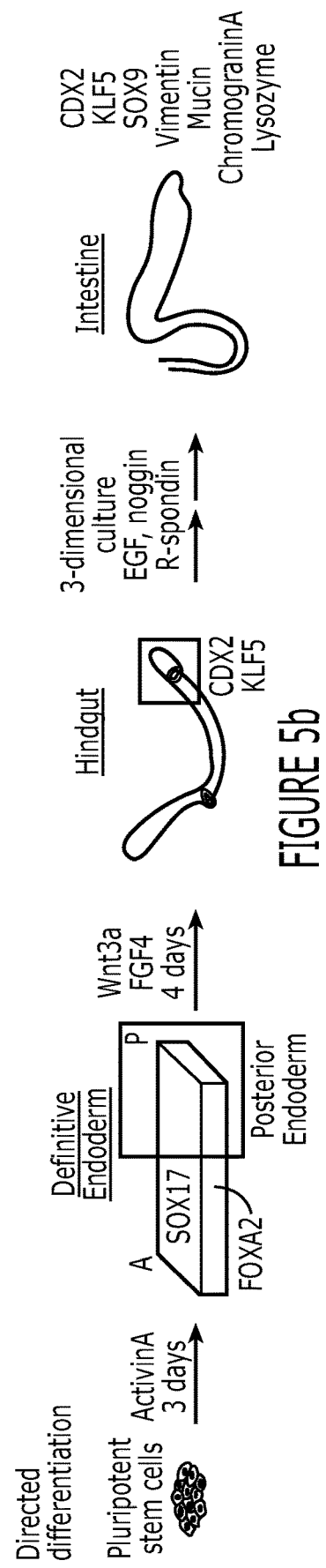
FIGURE 5a
FIGURE 5b

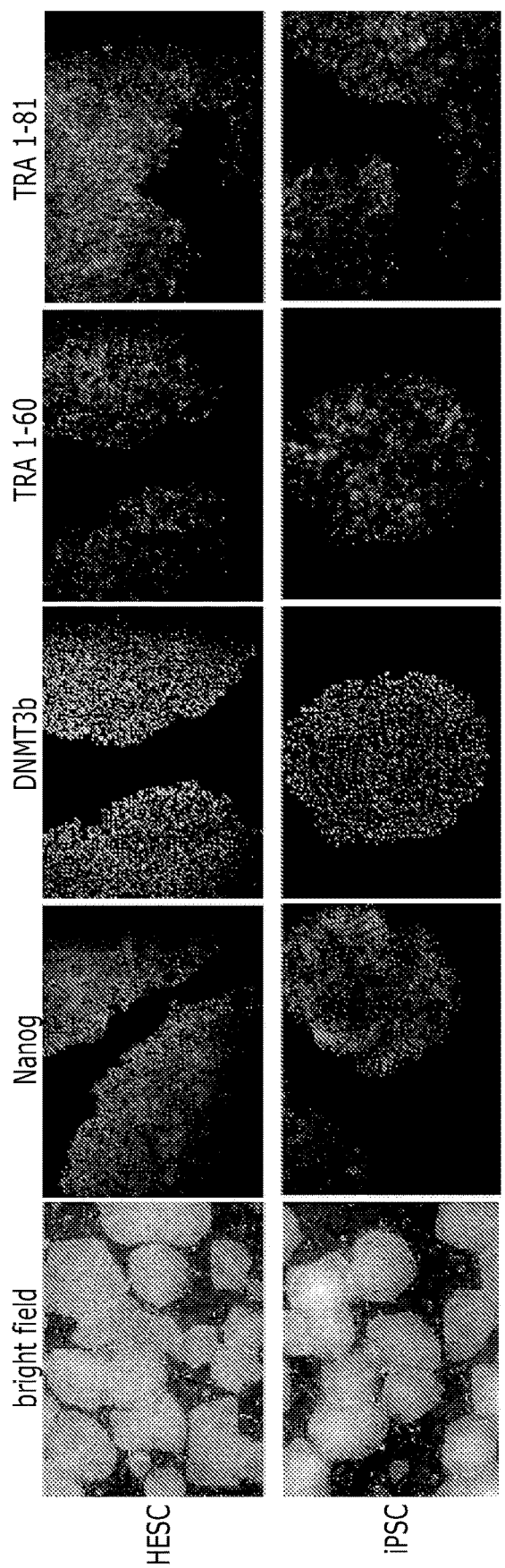
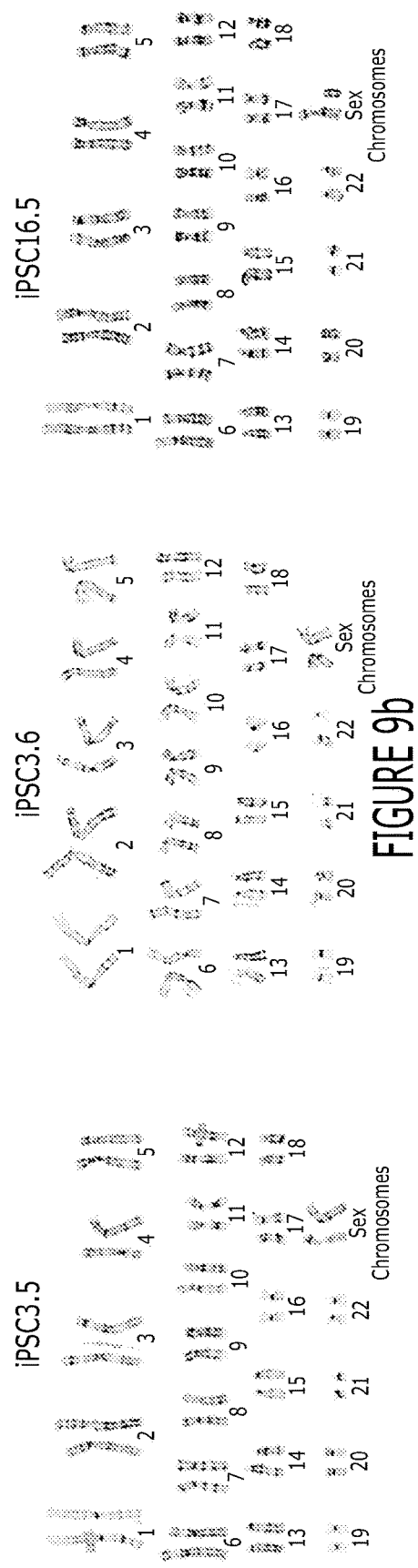
FIGURE 9a
FIGURE 9b

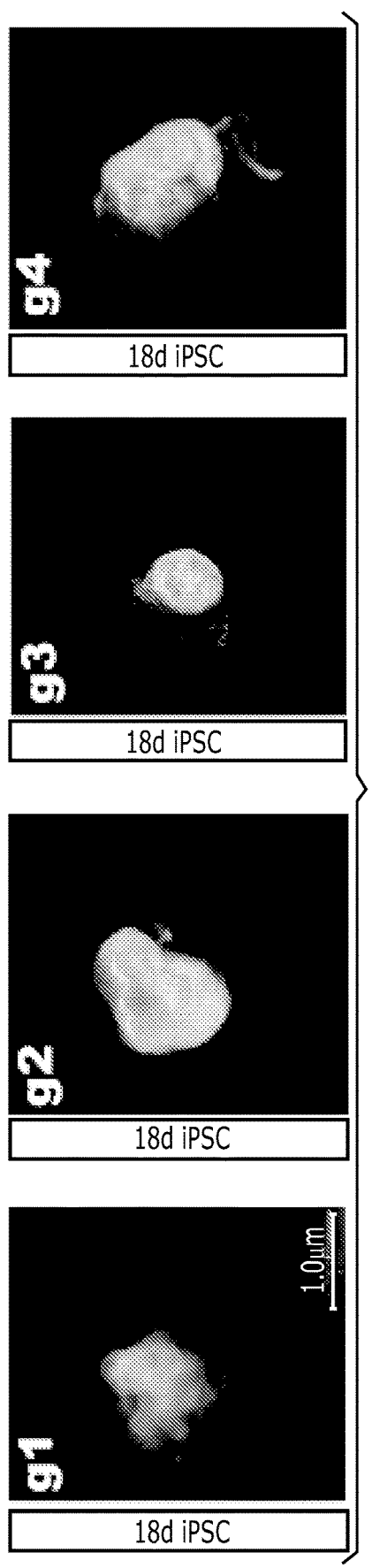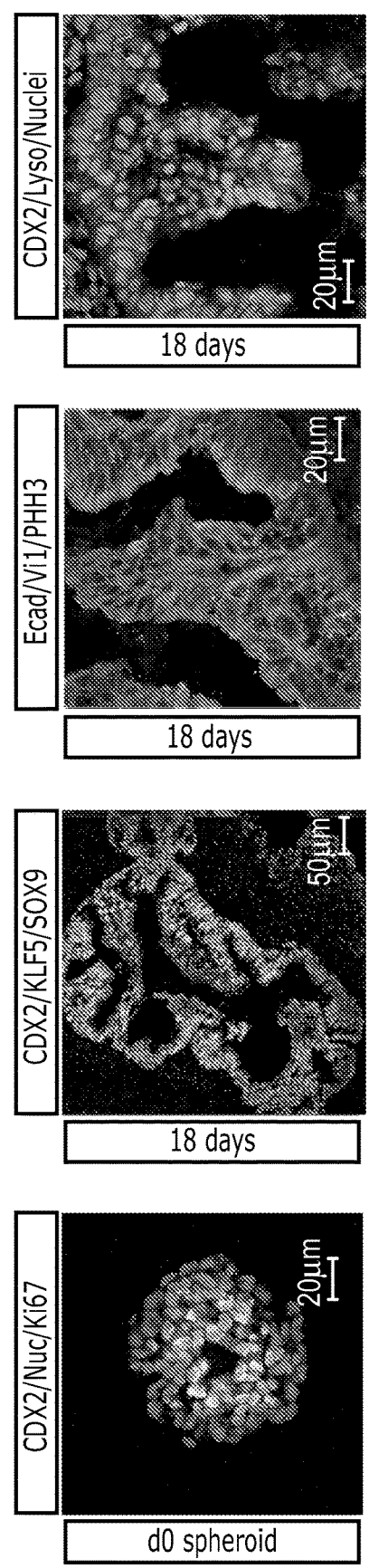

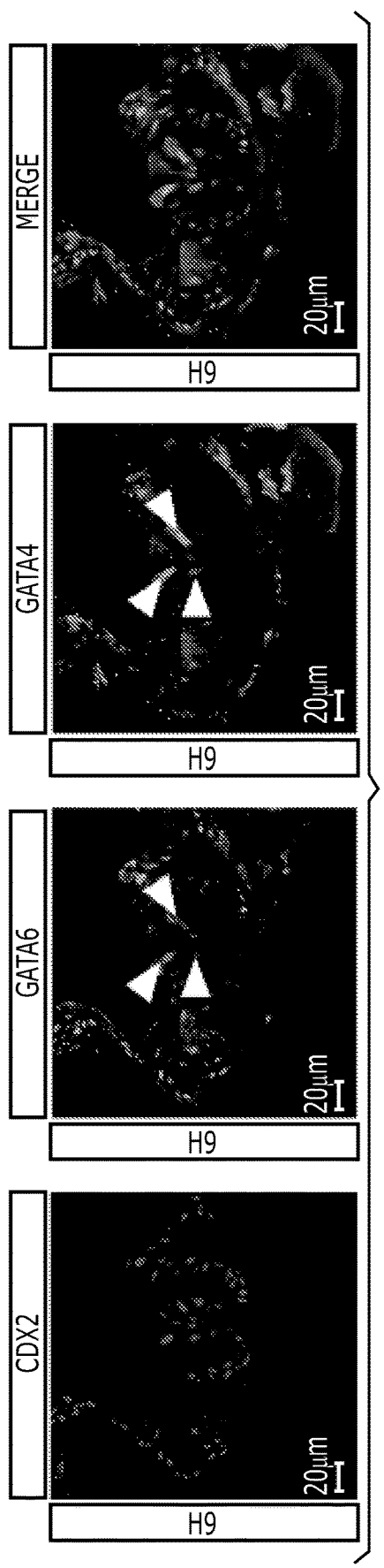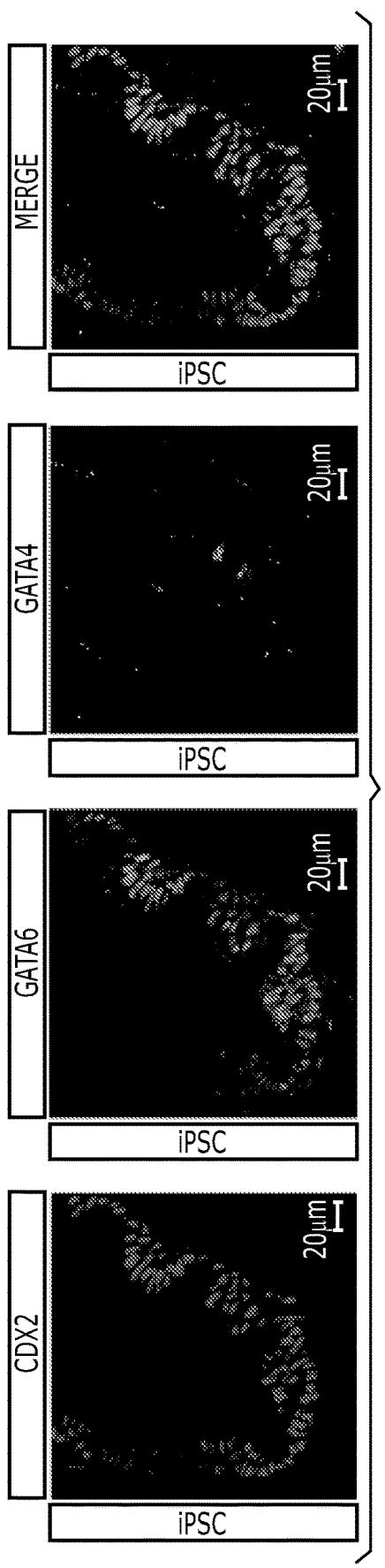
FIGURE 12a
FIGURE 12b

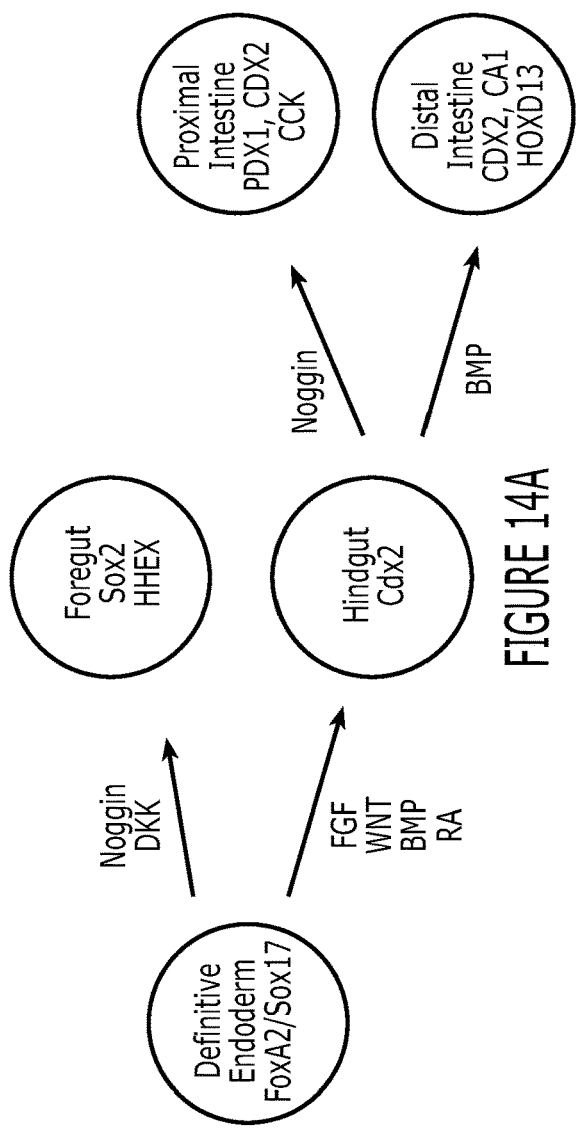
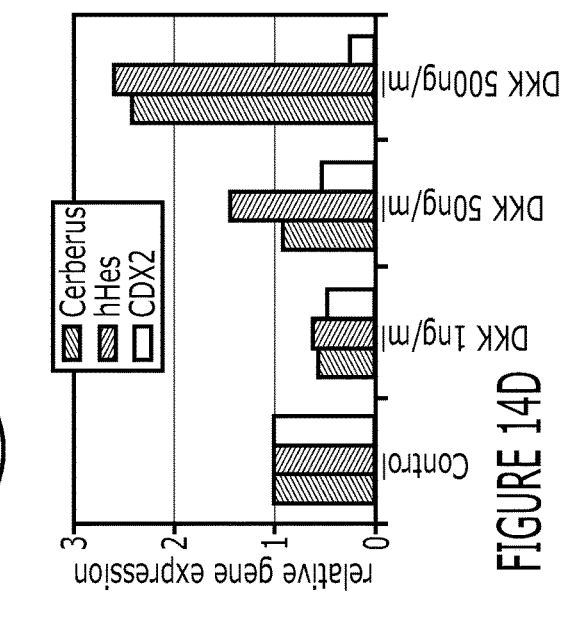
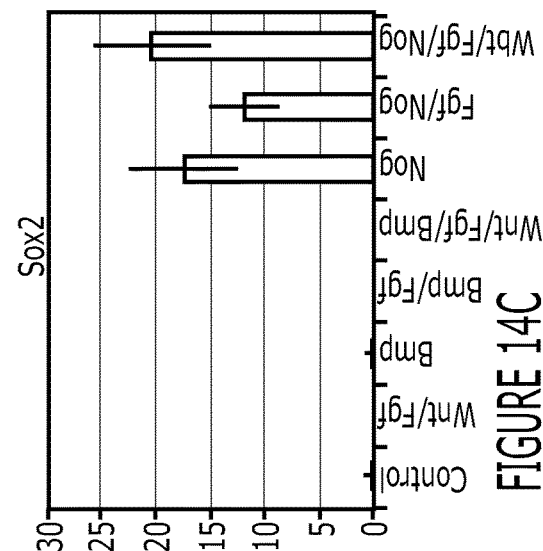
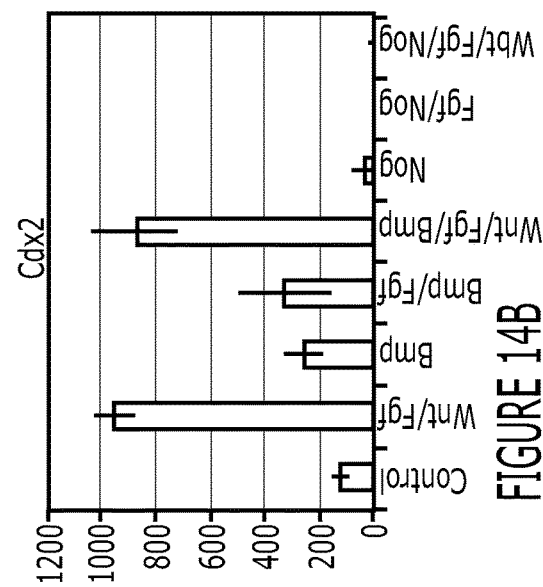
FIGURE 14A
FIGURE 14B
FIGURE 14C
FIGURE 14D

METHODS AND SYSTEMS FOR CONVERTING PRECURSOR CELLS INTO INTESTINAL TISSUES THROUGH DIRECTED DIFFERENTIATION

CROSS-REFERENCE TO RELATED APPLICATIONS

This application is a continuation of U.S. patent application Ser. No. 15/627,588, filed Jun. 20, 2017, which is a continuation of U.S. patent application Ser. No. 13/695,887, filed Nov. 2, 2012, which is a U.S. National Stage Entry of PCT/US11/35518, filed May 6, 2011, which is based on and claims priority from U.S. Provisional Patent Application Ser. No. 61/332,178, filed May 6, 2010, the contents of which are incorporated by reference in their entirety for all purposes.

STATEMENT REGARDING FEDERALLY-SPONSORED RESEARCH

This invention was made with government support under GM072915, DK080823, DK084167, CA142826, DK083202, and HD007463 awarded by the National Institutes of Health. The government has certain rights in the invention.

FIELD OF THE INVENTION

The invention disclosed herein generally relates to methods and systems for converting stem cells into specific tissue(s) or organ(s) through directed differentiation. In particular, the invention disclosed herein relates to methods and systems for promoting definitive endoderm formation from pluripotent stem cells. The invention disclosed herein further relates to methods and systems for promoting intestinal organoids or tissue formations from differentiated definitive endoderm.

BACKGROUND

Stem cells are found in all multi cellular organisms. They are characterized by the ability to renew themselves through mitotic cell division and differentiate into a diverse range of specialized cell types. The two broad types of mammalian stem cells are: embryonic stem cells that are isolated from the inner cell mass of blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin, or intestinal tissues.

Stem cells can now be grown and transformed into specialized cells with characteristics consistent with cells of various tissues such as muscles or nerves through cell culture. Highly plastic adult stem cells from a variety of sources, including umbilical cord blood and bone marrow, are routinely used in medical therapies. Embryonic cell lines and autologous embryonic stem cells generated through therapeutic cloning have also been proposed as promising candidates for future therapies.

The classical definition of a stem cell is typically indicative of two properties: self-renewal, the ability to go through numerous cycles of cell division while maintaining the undifferentiated state, and potency, the capacity to differentiate into specialized cell types. In some embodiments, stem cells are either totipotent or pluripotent, i.e. they are able to give rise to any mature cell type, although multipotent or unipotent progenitor cells are sometimes referred to as stem cells.

Potency specifies the differentiation potential (the potential to differentiate into different cell types) of the stem cell:

Totipotent stem cells (also known as omnipotent stem cells) can differentiate into embryonic and extraembryonic cell types. These cells can construct a complete, viable, organism. The cells are produced from the fusion of an egg and sperm cell. Cells produced by the first few divisions of the fertilized egg are also totipotent.

Pluripotent stem cells (PSCs) are the descendants of totipotent cells and can differentiate into nearly all cells, i.e., cells derived from any of the three germ layers, including endoderm (interior stomach lining, gastrointestinal tract, the lungs), mesoderm (muscle, bone, blood, urogenital), and ectoderm (epidermal tissues and nervous system).

Multipotent stem cells can differentiate into a number of cells, but only those of a closely related family of cells.

Oligopotent stem cells can differentiate into only a few cells, such as lymphoid or myeloid stem cells.

Unipotent cells can produce only one cell type, their own, but have the property of self-renewal which distinguishes them from non-stem cells (e.g., muscle stem cells).

Embryonic and induced pluripotent stem cells have had an unprecedented impact on our ability to study human diseases and to generate replacement tissues that are therapeutically effective in animal models.

In developmental biology, cellular differentiation is the process by which a less specialized cell becomes a more specialized cell type. Most successful efforts to direct the differentiation of human PSCs into therapeutic cell types have been based on studies of embryonic organ development. Examples include the generation of liver hepatocytes and pancreatic endocrine cells, which have shown functional potential in animal models of liver disease and diabetes. Similarly, differentiation of PSCs into intestine may provide therapeutic benefit for diseases such as necrotizing enterocolitis, inflammatory bowel diseases and short gut syndromes.

As discussed above, a pluripotent stem cell has the potential to differentiate into any of the three germ layers: endoderm (interior stomach lining, gastrointestinal tract, the lungs), mesoderm (muscle, bone, blood, urogenital), and ectoderm (epidermal tissues and nervous system). As such, pluripotent stem cells can give rise to any fetal or adult cell type. However, the fate of the particular pluripotent stem cells is controlled by numerous cellular signaling pathway and numerous factors. Further, the pluripotent stem cells alone cannot develop into a fetal or adult animal because they lack the potential to contribute to extraembryonic tissue, such as the placenta.

What is needed in the art are methods and systems for accurately controlling the destination of the pluripotent stem cells in order to create the specific type of tissue or organism of desire.

SUMMARY OF THE INVENTION

In some embodiments, a method of inducing formation of an intestinal tissue is provided, comprising: activating one or more signaling pathways within a precursor cell.

In some embodiments, the one or more signaling pathways are selected from the group consisting of the Wnt signaling pathway, Wnt/APC signaling pathway, FGF signaling pathway, TGF-beta signaling pathway, shh signaling pathway, BMP signaling pathway, Notch signaling pathway, Hedgehog signaling pathway, LKB signaling pathway, and Par polarity signaling pathway; and obtaining an intestinal tissue descended from said precursor cell.

In some embodiments, the method further comprises: providing said precursor cell. In some embodiments, the method further comprises: culturing, after said activating step, said activated precursor cell in vitro to form a 3-dimensional tissue structure.

In some embodiments, the activating and obtaining steps are conducted in vitro.

In some embodiments, the one or more signaling pathways comprise the Wnt signaling pathway and FGF signaling pathway.

In some embodiments, the Wnt signaling pathway is activated by contacting the precursor cell with one or more molecules selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

In some embodiments, the FGF signaling pathway is activated by contacting the precursor cell with one or more molecules selected from the group consisting of FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23.

In some embodiments, the activating step comprises contacting said precursor cell with both Wnt3a and FGF4 over a specified activation period.

In some embodiments, the precursor cell is contacted by Wnt3a during a first activation period and by FGF4 during a second activation period. In some embodiments, the first activation period and the second activation period overlap. In some embodiments, the first activation period and said second activation period do not overlap.

In some embodiments, the specified activation period is between 24 and 120 hours.

In some embodiments, the precursor cell is contacted with Wnt3a at a concentration between 50-1500 ng/ml.

In some embodiments, the said precursor cell is elected from the group consisting of an embryonic stem cell, an embryonic germ cell, an induced pluripotent stem cell, a mesoderm cell, a definitive endoderm cell, a posterior endoderm cell, and a hindgut cell.

In some embodiments, the definitive endoderm cell is derived from a pluripotent stem cell.

In some embodiments, the pluripotent stem cell is an embryonic stem cell, an embryonic stem cell, an adult stem cell, or an induced pluripotent stem cell.

In some embodiments, the definitive endoderm cell is derived by contacting the pluripotent stem cell with one or more molecules selected from the group consisting of Activin, the BMP subgroups of the TGF-beta superfamily of growth factors; Nodal, Activin A, Activin B, BMP4, Wnt3a, and a combinations thereof.

In some embodiments, the pluripotent stem cell is a mammalian pluripotent stem cell, including but not limited to human pluripotent stem cell or a mouse pluripotent stem cell.

In some embodiments, the human pluripotent stem cell is selected from the group consisting of a human embryonic stem cell, a human embryonic germ cell, and an induced human pluripotent stem cell.

In some embodiments, an intestinal tissue produced in vitro from one or more precursor cells is provided.

In some embodiments, the one or more precursor cells are selected from the group consisting of an embryonic stem cell, an embryonic germ cell, an induced pluripotent stem cell, a mesoderm cell, a definitive endoderm cell, a posterior endoderm cell, and a hindgut cell.

In some embodiments, a kit comprising an intestinal tissue produced in vitro from one or more precursor cells is provided.

In some embodiments, a method for identifying the absorption effect of intestinal cells or tissues is provided, comprising: contacting intestinal cells or tissues with a compound, wherein said intestinal cells or tissues are produced in vitro from one or more precursor cells; and detecting a level of absorption of said compound by said intestinal cells or tissues.

BRIEF DESCRIPTION OF THE DRAWINGS

Those of skill in the art will understand that the drawings, described below, are for illustrative purposes only. The drawings are not intended to limit the scope of the present teachings in any way.

FIG. 1 illustrates exemplary embodiments of the present invention. FIGS. 1b through 1d illustrate immunofluorescence images showing the same.

FIG. 2 illustrates exemplary embodiments in accordance with the present invention. FIG. 2a includes bright field images of definitive endoderm (DE) treated with FGF4 and Wnt3a. FIG. 2b shows immunofluorescent images of the same DE cultures illustrated in FIG. 2a.

FIG. 3 illustrates exemplary embodiments in accordance with the present invention.

FIG. 4 illustrates exemplary embodiments in accordance with the present invention.

FIG. 5 illustrates exemplary embodiments in accordance with the present invention. FIGS. 5a and 5b are schematic illustrations of human intestinal development and directed differentiation of PSCs into intestinal tissue, respectively.

FIG. 6 illustrates exemplary embodiments in accordance with the present invention.

FIG. 7 includes bar charts illustrating exemplary embodiments in accordance with the present invention. The bar charts depict time and concentration dependent induction of CDX2 by FGF4 and Wnt3a.

FIG. 9 illustrates exemplary embodiments in accordance with the present invention. FIG. 9a includes both bright field and immunofluorescent images which illustrate the characterization of induced pluripotent stem cell lines. FIG. 9b includes examples of karyotypic analysis of iPSC lines 3.5, 3.6 and 16.5.

FIGS. 10 a through 10g are microscopic images showing the morphologic comparison of hESC and iPSC organoid formation.

FIG. 11 illustrates exemplary embodiments in accordance with the present invention. FIGS. 11a through 11f are immunofluorescent images showing the molecular analysis of stages of epithelial growth, maturation and cytodifferentiation.

FIG. 12 illustrates exemplary embodiments in accordance with the present invention. FIGS. 12a and 12b are immunofluorescent images showing GATA factor expression in H9 hESC derived organoids and human iPSC derived organoids, respectively.

FIG. 13 illustrates exemplary embodiments in accordance with the present invention.

FIG. 14 illustrates exemplary embodiments in accordance with the present invention. FIG. 14A is a schematic illustration depicting the signaling network that regulates hindgut and intestinal development. FIGS. 14B through 14D are bar charts depicting the effects of FGF, WNT, and BMP signaling on differentiation of definitive endoderm into foregut and hindgut.

FIG. 15 illustrates exemplary embodiments in accordance with the present invention.

FIG. 16 illustrates exemplary embodiments in accordance with the present invention.

DETAILED DESCRIPTION OF THE INVENTION

Definitions

Figure 1A:
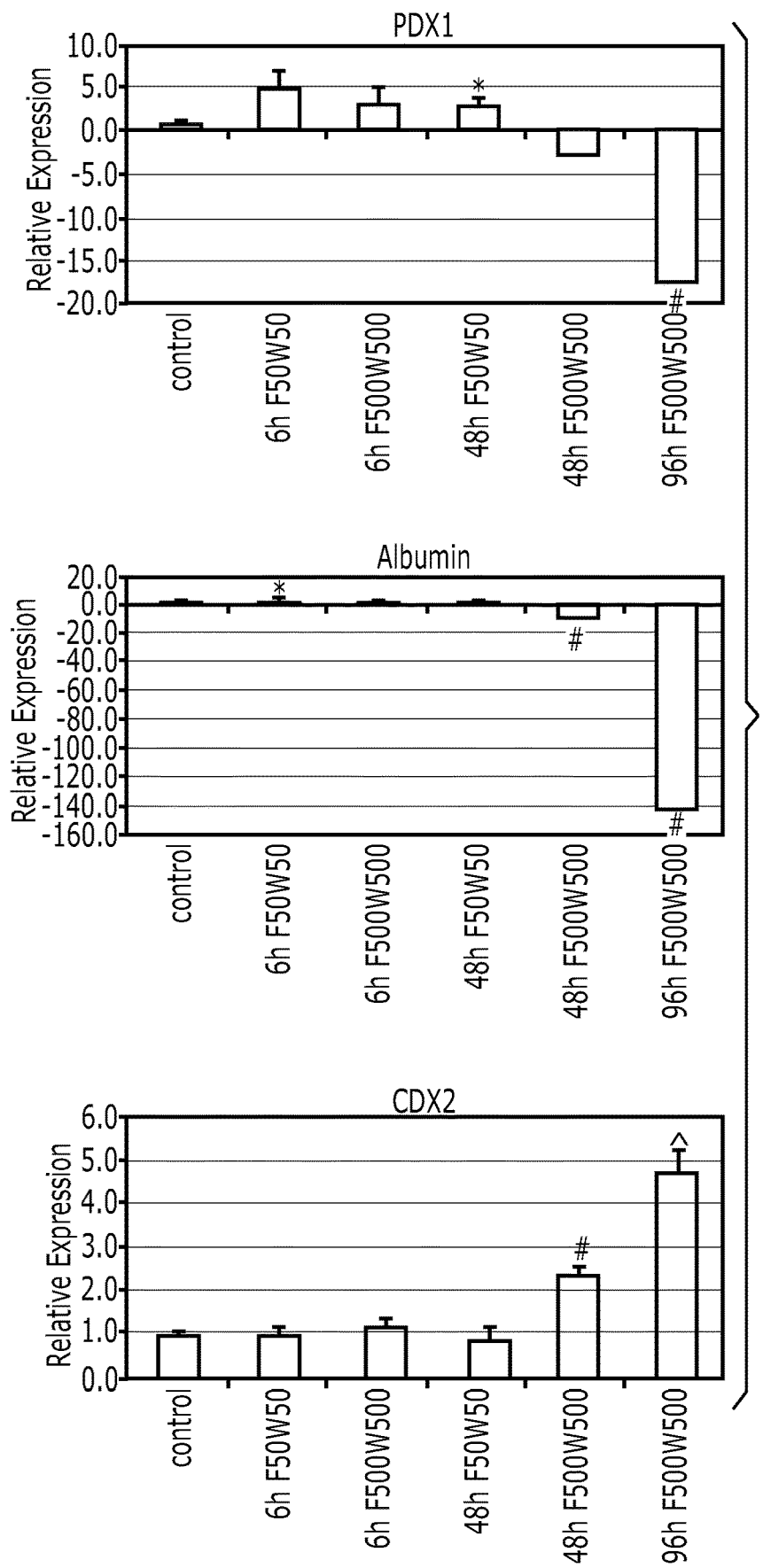
FIG. 1a includes bar charts that illustrate that FGF4 and Wnt3a act synergistically in a temporal and dose-dependent manner to specify stable posterior endoderm fate.

Unless otherwise noted, terms are to be understood according to conventional usage by those of ordinary skill in the relevant art.

As used herein, the term "totipotent stem cells" (also known as omnipotent stem cells) are stem cells that can differentiate into embryonic and extra-embryonic cell types. Such cells can construct a complete, viable, organism. These cells are produced from the fusion of an egg and sperm cell. Cells produced by the first few divisions of the fertilized egg are also totipotent.

As used herein, the term "pluripotent stem cells (PSCs)," also commonly known as PS cells, encompasses any cells that can differentiate into nearly all cells, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of totipotent cells, derived from embryonic stem cells (including embryonic germ cells) or obtained through induction of a non-pluripotent cell, such as an adult somatic cell, by forcing the expression of certain genes.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "embryonic stem cells (ESCs)," also commonly abbreviated as ES cells, refers to cells that are pluripotent and derived from the inner cell mass of the blastocyst, an early-stage embryo. For purpose of the present invention, the term "ESCs" is used broadly sometimes to encompass the embryonic germ cells as well.

As used herein, the term "precursor cell" encompasses any cells that can be used in methods described herein, through which one or more precursor cells acquire the ability to renew itself or differentiate into one or more specialized cell types. In some embodiments, a precursor cell is pluripotent or has the capacity to becoming pluripotent. In some embodiments, the precursor cells are subjected to the treatment of external factors (e.g., growth factors) to acquire pluripotency. In some embodiments, a precursor cell can be a totipotent (or omnipotent) stem cell; a pluripotent stem cell (induced or non-induced); a multipotent stem cell; an oligopotent stem cells and a unipotent stem cell. In some embodiments, a precursor cell can be from an embryo, an infant, a child, or an adult. In some embodiments, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

As used herein, the term "cellular constituents" are individual genes, proteins, mRNA expressing genes, and/or any other variable cellular component or protein activities such as the degree of protein modification (e.g., phosphorylation), for example, that is typically measured in biological experiments (e.g., by microarray or immunohistochemistry) by those skilled in the art. Significant discoveries relating to the complex networks of biochemical processes underlying living systems, common human diseases, and gene discovery and structure determination can now be attributed to the application of cellular constituent abundance data as part of the research process. Cellular constituent abundance data can help to identify biomarkers, discriminate disease subtypes and identify mechanisms of toxicity.

As described herein, methods and systems are established using a temporal series of growth factor manipulations to mimic embryonic intestinal development in culture. In particular, methods and systems are established to direct in vitro the differentiation of PSCs, both human embryonic stem cells (hESC) and induced pluripotent stem cells (iPSC), into intestinal tissue (for example, as depicted in FIGS. 5a and 5b). These factors directed human intestinal development in vitro in stages that approximate fetal gut development: activin-induced definitive endoderm (DE) formation; FGF/Wnt induced posterior endoderm pattering, hindgut specification and morphogenesis; and finally a pro-intestinal culture system that promoted intestinal growth, morphogenesis and cytodifferentiation into functional intestinal cell types including enterocytes, goblet, Paneth and enteroendocrine cells.

Pluripotent Stem Cells Derived from Embryonic Cells

In some embodiments, an important step is to obtain stem cells that are pluripotent or can be induced to become pluripotent. In some embodiments, pluripotent stem sells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. For example, three cell lines (H1, H13, and H14) had a normal XY karyotype, and two cell lines (H7 and H9) had a normal XX karyotype. Human embryonic stem cells H9 (H9-hESCs) are used in the exemplary embodiments described in the present application, but it would be understood by one of skill in the art that the methods and systems described herein are applicable to any stem cells.

Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, California); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Exemplary embryonic stem cells that can be used in embodiments in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (I3); TE04 (I4); TE06 (I6); UC01 (HSF1); UC06 (HSF6); WA01 (H1); WA07 (H7); WA09 (H9); WA13 (H13); WA14 (H14).

In some embodiments, the stem cells are further modified to incorporate additional properties. Exemplary modified cell lines include but not limited to H1 OCT4-EGFP; H9 Cre-LoxP; H9 hNanog-pGZ; H9 hOct4-pGZ; H9 inGFPhES; and H9 Syn-GFP.

More details on embryonic stem cells can be found in, for example, Thomson et al., 1998, "Embryonic Stem Cell Lines Derived from Human Blastocysts," Science 282 (5391):1145-1147; Andrews et al., 2005, "Embryonic stem (ES) cells and embryonal carcinoma (EC) cells: opposite sides of the same coin," Biochem Soc Trans 33:1526-1530; Martin 1980, "Teratocarcinomas and mammalian embryogenesis,". Science 209 (4458):768-776; Evans and Kaufman, 1981, "Establishment in culture of pluripotent cells from mouse embryos," Nature 292(5819): 154-156; Klimanskaya et al., 2005, "Human embryonic stem cells derived without feeder cells," Lancet 365 (9471): 1636-1641; each of which is hereby incorporated herein in its entirety.

Alternative, pluripotent stem cells can be derived from embryonic germ cells (EGCs), which are the cells that give rise to the gametes of organisms that reproduce sexually. EGCs are derived from primordial germ cells found in the gonadal ridge of a late embryo, have many of the properties of embryonic stem cells. The primordial germ cells in an embryo develop into stem cells that in an adult generate the reproductive gametes (sperm or eggs). In mice and humans it is possible to grow embryonic germ cells in tissue culture under appropriate conditions. Both EGCs and ESCs are pluripotent. For purpose of the present invention, the term "ESCs" is used broadly sometimes to encompass EGCs.

Induced Pluripotent Stem Cells (iPSCs)

In some embodiments, iPSCs are derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs include but are not limited to first generation iPSCs, second generation iPSCs in mice, and human induced pluripotent stem cells. In some embodiments, a retroviral system is used to transform human fibroblasts into pluripotent stem cells using four pivotal genes: Oct3/4, Sox2, Klf4, and c-Myc. In alternative embodiments, a lentiviral system is used to transform somatic cells with OCT4, SOX2, NANOG, and LIN28. Genes whose expression are induced in iPSCs include but are not limited to Oct-3/4 (e.g., Pou5fl); certain members of the Sox gene family (e.g., Sox1, Sox2, Sox3, and Sox15); certain members of the Klf family (e.g., Klf1, Klf2, Klf4, and Klf5), certain members of the Myc family (e.g., C-myc, L-myc, and N-myc), Nanog, and LIN28.

In some embodiments, non-viral based technologies are employed to generate iPSCs. In some embodiments, an adenovirus can be used to transport the requisite four genes into the DNA of skin and liver cells of mice, resulting in cells identical to embryonic stem cells. Since the adenovirus does not combine any of its own genes with the targeted host, the danger of creating tumors is eliminated. In some embodiments, reprogramming can be accomplished via plasmid without any virus transfection system at all, although at very low efficiencies. In other embodiments, direct delivery of proteins is used to generate iPSCs, thus eliminating the need for viruses or genetic modification. In some embodiment, generation of mouse iPSCs is possible using a similar methodology: a repeated treatment of the cells with certain proteins channeled into the cells via poly-arginine anchors was sufficient to induce pluripotency. In some embodiments, the expression of pluripotency induction genes can also be increased by treating somatic cells with FGF2 under low oxygen conditions.

More details on embryonic stem cells can be found in, for example, Kaji et al., 2009, "Virus free induction of pluripotency and subsequent excision of reprogramming factors," *Nature* 458:771-775; Woltjen et al., 2009, "piggyBac transposition reprograms fibroblasts to induced pluripotent stem cells," *Nature* 458:766-770; Okita et al., 2008, "Generation of Mouse Induced Pluripotent Stem Cells Without Viral Vectors," *Science* 322(5903):949-953; Stadtfeld et al., 2008, "Induced Pluripotent Stem Cells Generated without Viral Integration," *Science* 322(5903):945-949; and Zhou et al., 2009, "Generation of Induced Pluripotent Stem Cells Using Recombinant Proteins," *Cell Stem Cell* 4(5):381-384; each of which is hereby incorporated herein in its entirety.

In some embodiments, exemplary iPS cell lines include but not limited to iPS-DF19-9; iPS-DF19-9; iPS-DF4-3; iPS-DF6-9; iPS(Foreskin); iPS(IMR90); and iPS(IMR90).

It has been shown that iPSCs were capable of differentiation in a fashion similar to ESCs into fully differentiated tissues. For example, iPSCs were differentiated into neurons, expressing βIII-tubulin, tyrosine hydroxylase, AADC, DAT, ChAT, LMX1B, and MAP2. The presence of catecholamine-associated enzymes may indicate that iPSCs, like hESCs, may be differentiable into dopaminergic neurons. Stem cell-associated genes were shown to be down-regulated after differentiation. It was also shown that iPSCs were differentiated into cardiomyocytes that spontaneously began beating. Cardiomyocytes expressed TnTc, MEF2C, MYL2A, MYHCβ, and NKX2.5. Stem cell-associated genes were down-regulated after differentiation.

Intestinal Organ and Development

No systems were available prior to the present invention for converting embryonic stem cells and/or iPSCs into intestinal tissues. In anatomy, the intestine (or bowel) is the segment of the alimentary canal extending from the stomach to the anus and, in humans and other mammals, consists of two segments, the small intestine and the large intestine. In humans, the small intestine is further subdivided into the duodenum, jejunum and ileum while the large intestine is subdivided into the cecum and colon. The structure of an intestinal organ is described herein using the human organ as an example. It will be understood by one of ordinary skill in the art that the methods and systems described herein are applicable to the intestinal systems of all mammals.

The intestinal tract can be broadly divided into two different parts, the small and large intestine. Grayish-purple in color and about 35 millimeters (1.5 inches) in diameter, the small intestine is the first and longer, measuring 6 to 7 meters (20-23 feet) long average in an adult man. Shorter and relatively stockier, the large intestine is a dark reddish color, measuring roughly 1.5 meters (5 feet) long on average.

The lumen is the cavity where digested food passes through and from where nutrients are absorbed. Both intestines share a general structure with the whole gut, and are composed of several layers.

Going from inside the lumen radially outwards, one passes the mucosa (glandular epithelium and muscularis mucosa), submucosa, muscularis externa (made up of inner circular and outer longitudinal), and lastly serosa. Along the whole length of the gut in the glandular epithelium are goblet cells. These secrete mucus which lubricates the passage of food and protects the gut from digestive enzymes. Villi are vaginations of the mucosa and increase the overall surface area of the intestine while also containing a lacteal, which is connected to the lymph system and aids in the removal of lipids and tissue fluid from the blood supply. Microvilli are present on the epithelium of a villus and further increase the surface area over which absorption can take place. The muscularis mucosa is a layer of smooth muscle that aids in the action of continued peristalsis and catastalsis along the gut. The submucosa contains nerves (e.g., Meissner's plexus), blood vessels and elastic fibre with collagen that stretches with increased capacity but maintains the shape of the intestine. The muscularis externa comprises longitudinal and smooth muscle that again helps with continued peristalsis and the movement of digested material out of and along the gut. In between the two layers of muscle lies Auerbach's plexus. The serosa is made up of loose connective tissue and coated in mucus so as to prevent friction damage from the intestine rubbing against other tissue. Holding all this in place are the mesenteries which suspend the intestine in the abdominal cavity and stop it from being disturbed when a person is physically active.

In some embodiments, PSCs, such as ESCs and iPSCs, undergo directed differentiation in a step-wise manner first into definitive endoderm (DE) then into posterior/hindgut epithelium (e.g., hindgut spheroids), and then into intestinal tissue.

In some embodiments, PSCs, such as ESCs and iPSCs, undergo directed differentiation in a non step-wise manner where molecules (e.g., growth factors, ligands) for promoting DE formation and those for subsequent tissue formation are added at the same time.

Definitive Endoderm

The epithelium of the intestine is derived from a simple sheet of cells called the definitive endoderm (DE). The anterior DE forms the foregut and its associated organs including the liver and pancreas and the posterior DE forms the midgut and hindgut, which forms the small and large intestines and parts of the genitourinary system. Studies using mouse, chick and frog embryos suggest that establishing the anterior-posterior pattern in DE at the gastrula stage is a prerequisite for subsequent foregut and hindgut development. The Wnt and FGF signaling pathways are critical for this process and act to promote posterior endoderm and hindgut fate and suppress anterior endoderm and foregut fate. The simple cuboidal epithelium of the hindgut first develops into a pseudostratified columnar epithelium, then into villi containing a polarized columnar epithelium and a proliferative zone at the base of the villi, which corresponds with the presumptive progenitor domain.

A robust and efficient process is established to direct the differentiation of DE into intestinal tissue in vitro. In some embodiments, directed differentiation is achieved by selectively activating certain signaling pathways in the iPSCs and/or DE cells. In some embodiments, the signaling pathways are those active in intestinal development, including but not limited to the Wnt signaling pathway; Wnt/APC signaling pathway; FGF signaling pathway; TGF-beta signaling pathway; BMP signaling pathway; Notch signaling pathway; Hedgehog signaling pathway; LKB signaling pathway; and Par polarity signaling pathway.

Additional details of pathways relating to intestinal development in general are found in, for example, Sancho et al., 2004, "Signaling Pathways in Intestinal Development and Cancer," *Annual Review of Cell and Developmental Biology* 20:695-723; Logan and Nusse, 2004, "The Wnt Signaling Pathway in Development and Disease," *Annual Review of Cell and Developmental Biology* 20:781-810; Taipalel and Beachyl, 2001, "The Hedgehog and Wnt signalling pathways in cancer," *Nature* 411:349-354; Gregorieff and Clevers, 2005, "Wnt signaling in the intestinal epithelium: from endoderm to cancer," *Genes & Dev.* 19: 877-890; each of which is hereby incorporated by reference herein in its entirety.

More details on the functions of signaling pathways relating to DE development can be found in, for example, Zorn and Wells, 2009, "Vertebrate endoderm development and organ formation," *Annu Rev Cell Dev Biol* 25:221-251; Dessimoz et al., 2006, "FGF signaling is necessary for establishing gut tube domains along the anterior-posterior axis in vivo," *Mech Dev* 123:42-55; McLin et al., 2007, "Repression of Wnt/{beta}-catenin signaling in the anterior endoderm is essential for liver and pancreas development. Development," 134:2207-2217; Wells and Melton, 2000, *Development* 127:1563-1572; de Santa Barbara et al., 2003, "Development and differentiation of the intestinal epithelium," *Cell Mol Life Sci* 60(7): 1322-1332; each of which is hereby incorporated herein in its entirety.

Any methods for producing definitive endoderm from pluripotent cells (e.g., iPSCs or ESCs) are applicable to the methods described herein. In some embodiments, pluripotent cells are derived from a morula. In some embodiments, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some embodiments, human embryonic stem cells are used to produce definitive endoderm. In some embodiments, human embryonic germ cells are used to produce definitive endoderm. In some embodiments, iPSCs are used to produce definitive endoderm.

In some embodiments, one or more growth factors are used in the differentiation process from pluripotent stem cells to DE cells. The one or more growth factors used in the differentiation process can include growth factors from the TGF-beta superfamily. In such embodiments, the one or more growth factors comprise the Nodal/Activin and/or the BMP subgroups of the TGF-beta superfamily of growth factors. In some embodiments, the one or more growth factors are selected from the group consisting of Nodal, Activin A, Activin B, BMP4, Wnt3a or combinations of any of these growth factors.

In some embodiments, the embryonic stem cells or germ cells and iPSCs are treated with the one or more growth factors for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; or 240 or more hours.

In some embodiments, the embryonic stem cells or germ cells and iPSCs are treated with the one or more growth factors at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of the growth factor is maintained at a constant level throughout the treatment. In other embodiments, concentration of the growth factor is varied during the course of the treatment. In some embodiments, the growth factor is suspended in media that include fetal bovine serine (FBS) with varying HyClone concentrations. One of skill in the art would understand that the regimen described herein is applicable to any known growth factors, alone or in combination. When two or more growth factors are used, the concentration of each growth factor may be varied independently.

In some embodiments, populations of cells enriched in definitive endoderm cells are used. In some embodiments, the definitive endoderm cells are isolated or substantially purified. In some embodiments, the isolated or substantially purified definitive endoderm cells express the SOX17, FOXA2, and/or the CXRC4 marker to a greater extent than the OCT4, AFP, TM, SPARC and/or SOX7 markers.

Methods for enriching a cell population with definitive endoderm are also contemplated. In some embodiments, definitive endoderm cells can be isolated or substantially purified from a mixed cell population by contacting the cells with a reagent that binds to a molecule that is present on the surface of definitive endoderm cells but which is not present on the surface of other cells in the mixed cell population, and then isolating the cells bound to the reagent. In certain embodiments, the cellular constituent that is present on the surface of definitive endoderm cells is CXCR4.

Still other embodiments of the present invention relate to CXCR4 antibodies, SDF-1 ligands or other ligands for CXCR4 can be used to obtain definitive endoderm cells in an enriched, isolated or substantially purified form. For example, a CXCR4 antibody, an SDF-1 ligand or another ligand for CXCR4 can be used as a reagent in a method, such as affinity-based separation or magnetic-based separation, to enrich, isolate or substantially purify preparations of definitive endoderm cells that bind to the reagent.

In some embodiments of the present invention, definitive endoderm cells and hESCs are treated with one or more growth factors. Such growth factors can include growth factors from the TGF-beta superfamily. In such embodiments, the one or more growth factors comprise the Nodal/Activin and/or the BMP subgroups of the TGF-beta superfamily of growth factors. In some embodiments, the one or more growth factors are selected from the group consisting of Nodal, Activin A, Activin B, BMP4, Wnt3a or combinations of any of these growth factors.

Additional methods for obtaining or creating DE cells that can be used in the present invention include but are not limited to those described in U.S. Pat. No. 7,510,876 to D'Amour et al.; U.S. Pat. No. 7,326,572 to Fisk et al.; Kubol et al., 2004, "Development of definitive endoderm from embryonic stem cells in culture," Development 131:1651-1662; D'Amour et al., 2005, "Efficient differentiation of human embryonic stem cells to definitive endoderm," Nature Biotechnology 23:1534-1541; and Ang et al., 1993, "The formation and maintenance of the definitive endoderm lineage in the mouse: involvement of HNF3/forkhead proteins," *Development* 119:1301-1315; each of which is hereby incorporated by reference herein in its entirety.

Directed Differentiation of Posteriorized DE

In some embodiments, activin-induced definitive endoderm (DE) can further undergo FGF/Wnt induced posterior endoderm pattering, hindgut specification and morphogenesis, and finally a pro-intestinal culture system that promoted intestinal growth, morphogenesis and cytodifferentiation into functional intestinal cell types including enterocytes, goblet, Paneth and enteroendocrine cells. In some embodiments, human PSCs are efficiently directed to differentiate in vitro into intestinal epithelium that includes secretory, endocrine and absorptive cell types. It will be understood that molecules such as growth factors can be added to any stage of the development to promote a particular type of intestinal tissue formation.

In some embodiments, posteriorized endoderm cells of the DE are further developed into one or more specialized cell types.

In some embodiments, soluble FGF and Wnt ligands are used to mimic early hindgut specification in culture to convert, through directed differentiation, DE developed from iPSCs or ESCs into hindgut epithelium that efficiently gives rise to all the major intestinal cell types. In human, directed differentiation of DE is achieved through selective activating certain signaling pathways that are important to intestinal development.

Human intestinal development in vitro occurs in stages that approximate fetal gut development; endoderm formation, posterior endoderm patterning, hindgut morphogenesis, fetal gut development, epithelial morphogenesis, formation of a presumptive progenitor domain, and differentiation into functional cell types of the intestine. For example, in human, genes that encode Wnt signaling proteins include but are not limited to Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

It will be understood by one of skill in the art that altering the expression of any Wnt signaling protein in combination with any FGF ligand can give rise to directed differentiation in accordance of the present invention. In some embodiments, the alteration is over-expression of Wnt3, in particular Wnt3a. In some embodiments, the alternation is over-expression of Wnt1.

It will be understood by one of skill in the art that altering the signaling activity of the Wnt signaling pathway in combination with altering the signaling activity of the FGF signaling pathway can give rise to directed differentiation in accordance of the present invention. In some embodiments, the alteration is through the use of small molecule modulators that activate the aforementioned pathways. For example, Small molecule modulators of the Wnt pathway included, but is not limited to Lithium Chloride; 2-amino-4,6-disubstituted pyrimidine (hetero) arylpyrimidines; IQ1; QS11; NSC668036; DCA beta-catenin; 2-amino-4-[3,4-(methylenedioxy)-benzyl-amino]-6-(3-methoxyphenyl) pyrimidine.

In alternative embodiments, cellular constituents associated with the Wnt and/or FGF signaling pathways, for example, natural inhibitors or antagonist of the pathways can be inhibited to result in activation of the Wnt and/or FGF signaling pathways.

In some embodiment, the cellular constituents are inhibited by other cellular constituents or extrinsic molecules. Exemplary natural inhibitors of Wnt signaling include but are not limited to Dkk1, SFRP proteins and FrzB. In some embodiments, the extrinsic molecules includes but are not limited to small molecules such as WAY-316606; SB-216763; or BIO (6-bromoindirubin-3'-oxime).

More details are found, for example, in Liu et al., "A small-molecule agonist of the Wnt signaling pathway," *Angew Chem Int Ed Engl.* 44(13):1987-1990 (2005); Miyabayashi et al., "Wnt/beta-catenin/CBP signaling maintains long-term murine embryonic stem cell pluripotency," *Proc Natl Acad Sci USA.* 104(13):5668-5673 (2007); Zhang et al., "Small-molecule synergist of the Wnt/beta-catenin signaling pathway," *Proc Natl Acad Sci USA.* 104(18):7444-7448 (2007); Neiiendam et al., "An NCAM-derived FGF-receptor agonist, the FGL-peptide, induces neurite outgrowth and neuronal survival in primary rat neurons," *J Neurochem.* 91(4):920-935 (2004); Shan et al., "Identification of a specific inhibitor of the dishevelled PDZ domain," *Biochemistry* 44(47):15495-15503 (2005); Coghlan et al., "Selective small molecule inhibitors of glycogen synthase kinase-3 modulate glycogen metabolism and gene transcription," *Chem Biol.* 7(10):793-803 (2000); Coghlan et al., "Selective small molecule inhibitors of glycogen synthase kinase-3 modulate glycogen metabolism and gene transcription," Chemistry & Biology 7(10):793-803; and Pai et al., "Deoxycholic acid activates beta-catenin signaling pathway and increases colon cell cancer growth and invasiveness," *Mol Biol Cell.* 15(5):2156-2163 (2004); each of which is hereby incorporated by reference in its entirety.

In some embodiments, siRNA and/or shRNA targeting cellular constituents associated with the Wnt and/or FGF signaling pathways are used to activate these pathways. It would be understood by one of skill in the art that the target cellular constituents include but are not limited to SFRP proteins; GSK3, Dkk1, and FrzB.

More details about RNAi based technologies can be found, for example, inCouzin, 2002, *Science* 298:2296-2297; McManus et al., 2002, *Nat. Rev. Genet.* 3, 737-747; Hannon, G. J., 2002, *Nature* 418, 244-251; Paddison et al., 2002, *Cancer Cell* 2, 17-23; Elbashir et al., 2001. *EMBO J.* 20:6877-6888; Tuschl et al., 1999, *Genes Dev.* 13:3191-3197; Hutvagner et al., *Sciencexpress* 297:2056-2060; each of which is hereby incorporated by reference in its entirety.

Fibroblast growth factors (FGFs) are a family of growth factors involved in angiogenesis, wound healing, and embryonic development. The FGFs are heparin-binding proteins and interactions with cell-surface associated heparan sulfate proteoglycans have been shown to be essential for FGF signal transduction. FGFs are key players in the processes of proliferation and differentiation of wide variety of cells and tissues. In humans, 22 members of the FGF family have been identified, all of which are structurally related signaling molecules. Members FGF1 through FGF10 all bind fibroblast growth factor receptors (FGFRs). FGF1 is also known as acidic, and FGF2 is also known as basic fibroblast growth factor. Members FGF11, FGF12, FGF13, and FGF14, also known as FGF homologous factors 1-4 (FHF1-FHF4), have been shown to have distinct functional differences compared to the FGFs. Although these factors possess remarkably similar sequence homology, they do not bind FGFRs and are involved in intracellular processes unrelated to the FGFs. This group is also known as "iFGF." Members FGF16 through FGF23 are newer and not as well characterized. FGF15 is the mouse ortholog of human FGF19 (hence there is no human FGF15). Human FGF20 was identified based on its homology to Xenopus FGF-20 (XFGF-20). In contrast to the local activity of the other FGFs, FGF15/FGF19, FGF21 and FGF23 have more systemic effects.

In some embodiments, it will be understood by one of skill in the art that any of the FGFs can be used in conjunction with a protein from the Wnt signaling pathway. In some embodiments, soluble FGFs include and but are not limited to FGF4, FGF2, and FGF3.

In some embodiment, the cellular constituents of the FGF signaling pathway are inhibited by other cellular constituents or extrinsic molecules. Exemplary natural inhibitors of FGF signaling include but are not limited to the Sprouty family of proteins and the Spred family of proteins. As discussed above, proteins, small molecules, nucleic acids can be used to activating the FGF signaling pathway.

It will be understood by one of skill in the art that the methods and compositions described herein in connection with the Wnt and FGF signaling pathways are provided by way of examples. Similar methods and compositions are applicable to other signaling pathways disclosed herein.

In some embodiments, DE culture is treated with the one or more molecules of a signaling pathway described herein for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; 200 or more hours, 240 or more hours; 270 or more hours; 300 or more hours; 350 or more hours; 400 or more hours; 500 or more hours; 600 or more hours; 700 or more hours; 800 or more hours; 900 or more hours; 1,000 or more hours; 1,200 or more hours; or 1,500 or more hours.

In some embodiments, DE culture is treated with the one or more molecules of a signaling pathway described herein at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of signaling molecule is maintained at a constant throughout the treatment. In other embodiments, concentration of the molecules of a signaling pathway is varied during the course of the treatment. In some embodiments, a signaling molecule in accordance with the present invention is suspended in media comprising DMEM and fetal bovine serine (FBS). The FBS can be at a concentration of 2% and more; 5% and more; 10% or more; 15% or more; 20% or more; 30% or more; or 50% or more. One of skill in the art would understand that the regiment described herein is applicable to any known molecules of the signaling pathways described herein, alone or in combination, including but not limited to any molecules in the Wnt and FGF signaling pathways.

In embodiments where two or more signaling molecules are used to treat the DE culture, the signaling molecules can be added simultaneously or separately. When two or more molecules are use, the concentration of each may be varied independently.

Differentiation of PSCs into DE culture and subsequently into various intermediate mature intestinal cell types can be determined by the presence of stage-specific cell markers. In some embodiments, expression of representative cellular constituents is used to determine DE formation. The representative cellular constituents include but are not limited to CMKOR1, CXCR4, GPR37, RTN4RL1, SLC5A9, SLC40A1, TRPA1, AGPAT3, APOA2, C20orf56, C21orf129, CALCR, CCL2, CER1, CMKOR1, CRIP1, CXCR4, CXorf1, DIO3, DIO3OS, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

Additional cellular constituents suitable for detecting DE formation can be found in, for example, in U.S. patent application Ser. No. 11/165,305, filed Jun. 23, 2005; U.S. patent application Ser. No. 11/317,387, filed Dec. 22, 2005; U.S. patent Ser. No. 11/021,618, filed Dec. 23, 2004; U.S. patent application Ser. Nos. 11/021,618, 11/115,868 filed on Apr. 26, 2005; U.S. patent application Ser. No. 11/317,387, filed on Dec. 22, 2005; U.S. patent application Ser. No. 11/474,211, filed on Jun. 23, 2006; U.S. patent application Ser. No. 11/165,305, filed on Jun. 23, 2005; U.S. patent application Ser. No. 11/587,735 filed on Aug. 29, 2008; U.S. patent application Ser. No. 12/039,701, filed on Feb. 28, 2008; U.S. patent application Ser. No. 12/414,482, filed on Mar. 30, 2009; U.S. patent application Ser. No. 12/476,570, filed on Jun. 2, 2009; U.S. patent application Ser. No. 12/093,590 filed on Jul. 21, 2008; U.S. patent application Ser. No. 12/582,600 filed on Oct. 20, 2009; each of which is hereby incorporated by reference herein in its entirety.

In some embodiments, expression of CDX2 is used to reveal tendency of hindgut formation after DE have been incubated with FGF4 and Wnt3a for a period of time, for example, for 12 hours or longer; 18 hours or longer; 24 hours or longer; 36 hours or longer; 48 hours or longer; 60 hours or longer; or 90 hours or longer. In some embodiments, longer periods of incubation are needed to achieve a stable posterior endoderm phenotype as measured by prolonged expressed of CDX2. In such embodiments, the periods of incubation can be for 60 hours or longer; 72 hours or longer; 84 hours or longer; 96 hours or longer; 108 hours or longer; 120 hours or longer; 140 hours or longer; 160 hours or longer; 180 hours or longer; 200 hours or longer; 240 hours or longer; or 300 hours or longer.

Alternatively, in some embodiments, the absence of cellular constituents, such as foregut markers Pdx1 and Albumin, can be used to reveal directed hindgut formation. In some embodiments, intestinal transcription factors CDX2, KLF5 and SOX9 can be used to represent intestinal development. In some embodiments, GATA4 and/or GATA6 protein expression can be used to represent intestinal development. In these embodiments, the periods of incubation can be for 12 hours or longer; 18 hours or longer; 24 hours or longer; 36 hours or longer; 48 hours or longer; 60 hours or longer; or 90 hours or longer. Alternatively, the periods of incubation can be for 60 hours or longer; 72 hours or longer; 84 hours or longer; 96 hours or longer; 108 hours or longer; 120 hours or longer; 140 hours or longer; 160 hours or longer; 180 hours or longer; 200 hours or longer; 240 hours or longer; or 300 hours or longer.

In some embodiments, abundance data of cellular constituents, for example, protein and/or gene expression levels, are determined by immunohistochemistry using primary and/or secondary antibodies targeting molecules in the relevant signaling pathways. In other embodiments, abundance data of cellular constituents, for example, protein and/or gene expression levels, are determined by microarray analyses.

Still alternatively, morphological changes can be used to represent the progress of directed differentiation. In some embodiments, hindgut spheroids are further subject to 3-dimensional culture conditions for further maturation. In other embodiments, a highly convoluted epithelium surrounded by mesenchymal cells can be observed following hindgut spheroids formation. Additionally, intestinal organoids; polarized columnar epithelium; goblet cells; or smooth muscle cells can be observed in 6 days or longer; 7 days or longer; 9 days or longer; 10 days or longer; 12 days or longer; 15 days or longer; 20 days or longer; 25 days or longer; 28 days or longer; 32 days or longer; 36 days or longer; 40 days or longer; 45 days or longer; 50 days or longer; or 60 days or longer.

Directed Differentiation of Pluripotent Stem Cells

In some embodiments, pluripotent stem cells are converted into intestinal cell types via a "one step" process. For example, one or more molecules that can differentiate pluripotent stem cells into DE culture (e.g., ActivinA) are combined with additional molecules that can promote directed differentiation of DE culture (e.g., Wnt3a and FGF4) to directly treat pluripotent stem cells.

Utilities and Kits Embodiments

In some embodiments, intestinal tissue or related cell types described herein can be used to screen drugs for intestinal uptake and mechanisms of transport. For example, this can be done in a high throughput manner to screen for the most readily absorbed drugs, and can augment Phase 1 clinical trials that are done to study drug intestinal uptake and intestinal toxicity. This includes pericellular and intracellular transport mechanisms of small molecules, peptides, metabolites, salts.

In some embodiments, intestinal tissue or related cell types described herein can be used to identify the molecular basis of normal human intestinal development.

In some embodiments, intestinal tissue or related cell types described herein can be used to identify the molecular basis of congenital defects affecting human intestinal development.

In some embodiments, intestinal tissue or related cell types described herein can be used to correct intestinal congenital defects caused by genetic mutations. In particular, mutation affecting human intestinal development can be corrected using iPSC technology and genetically normal Intestinal tissue or related cell types described herein. In some embodiments, intestinal tissue or related cell types described herein can be used to generate replacement tissue. Examples of genetic diseases include but are not limited to Neurog3 mutations and Enteric anendocrinosis, PTF1a mutations and neonatal diabetes, PDX1 mutations that effect enteroendocrine cells of the intestine.

In some embodiments, intestinal tissue or related cell types described herein can be used to generate replacement intestinal tissue for Inflamatory Bowel Disease (IBD), Crohn's Disease, Short Gut syndrome, intestinal cancer patients.

In some embodiments, intestinal tissue or related cell types described herein can be used to study microbiotic interactions with the human host epithelium and host immunity.

In some embodiments, intestinal tissue or related cell types described herein, in particular the enteroendocrine cells can be used to study hormonal regulation of feeding behavior, metabolism, mediated by intestinal endocrine hormones, for example the incretin response.

In some embodiments, intestinal tissue or related cell types described herein, in particular the enteroendocrine cells that produce the hormone GLP-1 can be used to study and improve pancreatic beta-cell mass and function and for treatment of diabetes.

In some embodiments, intestinal tissue or related cell types described herein can be used to replace any damaged or removed intestinal tissue such as that removed from colon cancer.

In some embodiments, intestinal tissue or related cell types described herein can be used to screen for toxicity and efficacy of any drug that acts on the intestine, for example, for diarrhea drugs, drugs that regulate secretion and absorption of the intestinal epithelium.

In some embodiments where intestinal tissue or related cell types described herein are used to determine the absorption level of a compound, the compound will be contacted with the intestinal cells or tissues with a compound; and a level of absorption of the compound by the intestinal cells or tissues detecting can be quantified. In some embodiments, the compound is labeled with a radio-isotope, a fluorescent label and or a primary or secondary visible marker.

In some embodiments, a diagnostic kit or package is developed to include the intestinal tissue or related cell types described herein and based on one or more of the aforementioned utilities.

Additional Embodiments Based on Microarray Analysis

In some embodiments, a reverse-engineering type of approach is taken to achieve directed differentiation of pluripotent stem cells. For example, microarray analyses of human ESCs, iPSCs and DE cultures, in both differentiated and undifferentiated states, are performed to identify cellular constituents that are differentially expressed in these different cell types. In some embodiments, only cellular constituents that are differentially expressed above a pre-determined level are identified as target cellular constituents. In particular, genes that are significantly differentially expressed are identified as targets. In some embodiments, significant differential expression occurs when a cellular constituent in a differentiated state in a particular cell type (e.g., as ESCs, iPSCs and DE) is expressed more than n folds than the expression level of the same cellular constituent in an undifferentiated state in the same cell type. In some embodiments, n is equal or greater than 2; equal or greater than 3; equal or greater than 5; equal or greater than 7; equal or greater than 10; equal or greater than 15; equal or greater than 18; equal or greater than 20; equal or greater than 23; or equal or greater than 28.

In some embodiments, selected cellular constituents from Table 2 are used as the target cellular constituents. For example, one or more cellular constituents that are differentially expressed above a pre-determined level are identified as target cellular constituents. In some embodiments, molecules capable of modulating the abundance levels of the target cellular constituents are used to treat cells at a certain development stage in order to achieve the desired directed differentiation results. In some embodiments, the target cellular constituents comprise 3 or more cellular constituents from Table 2; 5 or more cellular constituents from Table 2; 6 or more cellular constituents from Table 2; 8 or more cellular constituents from Table 2; 10 or more cellular constituents from Table 2; 12 or more cellular constituents from Table 2; 15 or more cellular constituents from Table 2; 18 or more cellular constituents from Table 2; 20 or more cellular constituents from Table 2; or 25 or more cellular constituents from Table 2.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Directing Hindgut Development of PSCs

Maintenance of PSCs. Human embryonic stem cells and induced pluripotent stem cells were maintained on Matrigel (BD Biosciences) in mTesR1 media. Cells were passaged approximately every 5 days, depending on colony density. To passage PSCs, they were washed with DMEM/F12 media (no serum)(Invitrogen) and incubated in DMEM/F12 with 1 mg/mL dispase (Invitrogen) until colony edges started to detach from the dish. The dish was then washed 3 times with DMEM/F12 media. After the final wash, DMEM/F12 was replaced with mTesR1. Colonies were scraped off of the dish with a cell scraper and gently triturated into small clumps and passaged onto fresh Matrigel-coated plates.

Differentiation of PSCs into Definitive Endoderm (DE). Differentiation into Definitive Endoderm was carried out as previously described. Briefly, a 3 day ActivinA (R&D systems) differentiation protocol was used. Cells were treated with ActivinA (100 ng/ml) for three consecutive days in RPMI 1640 media (Invitrogen) with increasing concentrations of 0%, 0.2%, 2% HyClone defined FBS (dFBS) (Thermo Scientific).

Differentiation of DE in Permissive Media (Differentiation Protocol for FIG. 1). After differentiation into definitive endoderm, cells were incubated in DMEM/F12 plus 2% defined fetal bovine serum (dFBS) with either 0, 50, or 500 ng/ml of FGF4 and/or 0, 50, or 500 ng/ml of Wnt3a (R&D Systems) for 6, 48, or 96 hours. Cultures were then grown in permissive media consisting of DMEM plus 10% fetal bovine serum (FBS) for an additional 7 days.

Figure 6A:
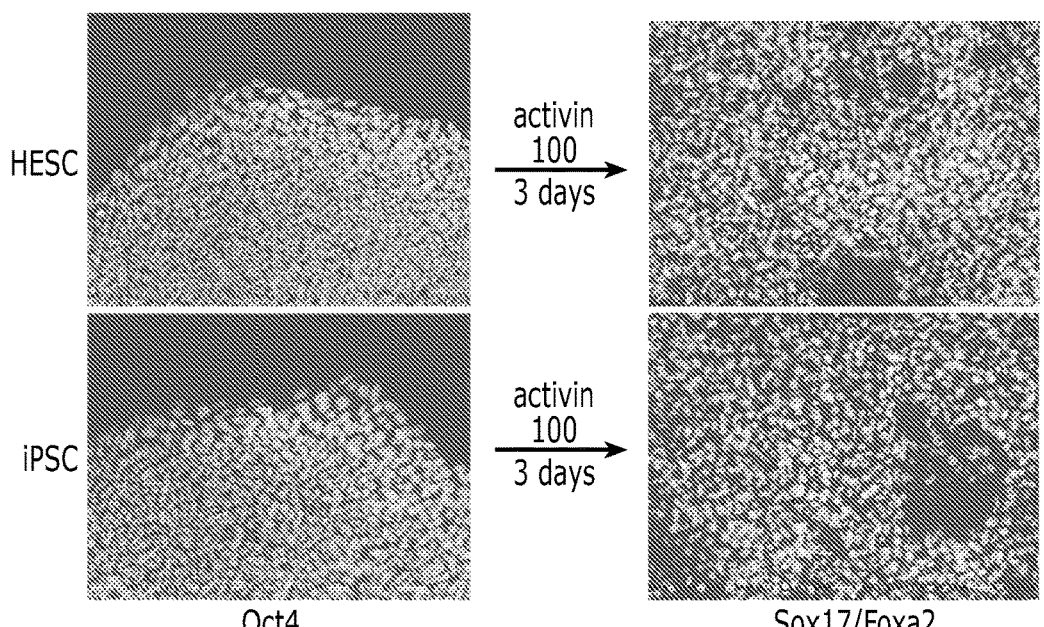
FIG. 6a includes immunofluorescent images depicting characterization of DE formation from hESC and iPSC lines.

Directing Hindgut Development of PSCs. As a first step to generating intestinal tissue, nodal-related TGFβ molecule activinA was used to promote differentiation of PSCs into DE as previously published. Activin-mediated differentiation routinely resulted in up to 90% of the cells co-expressing the DE markers SOX17 and FOXA2 (FIG. 6a). A robust activation of the DE transcriptional program (FIG. 6b and Table 2) was observed by using microarray analysis. It was also observed that cultures treated with activinA for only 3-days were competent to develop into both foregut (Albumin+ and Pdx1+) and hindgut (Cdx2) lineages when cultured for seven days in permissive conditions (FIG. 1b, control). In contrast, prolonged activin treatment for 4-5 days (common in many protocols) resulted in DE cultures that were intrinsically anterior in character and not as competent to form posterior lineages.

After the window of time when DE fate was plastic was identified, growth factors that are known to posteriorize endoderm, Wnt3a and FGF4, were used to direct the DE into a hindgut lineage. While neither factor alone was sufficient to robustly promote a posterior fate we determined that high concentrations of both FGF4+Wnt3a (500 ng/ml each) were able to induce robust expression of the hindgut marker CDX2 in the DE after 24-48 hours (FIG. 7). However 48 hours of FGF4+Wnt3a treatment was not sufficient to induce stable posterior, hindgut identity since CDX2 expression was not maintained and anterior fates, as measured by Pdx1 and Albumin expression, persisted following growth factor removal (FIG. 1a, c). In contrast, 96 hours of exposure to FGF4+Wnt3a conferred a stable posterior endoderm phenotype following growth factor removal with maintained CDX2 expression and complete absence of anterior markers (FIGS. 1a and d). Thus prolonged activity of FGF4 and Wnt3a resulted in a robust posteriorization of DE into CDX2+ hindgut endoderm.

Figure 2A:
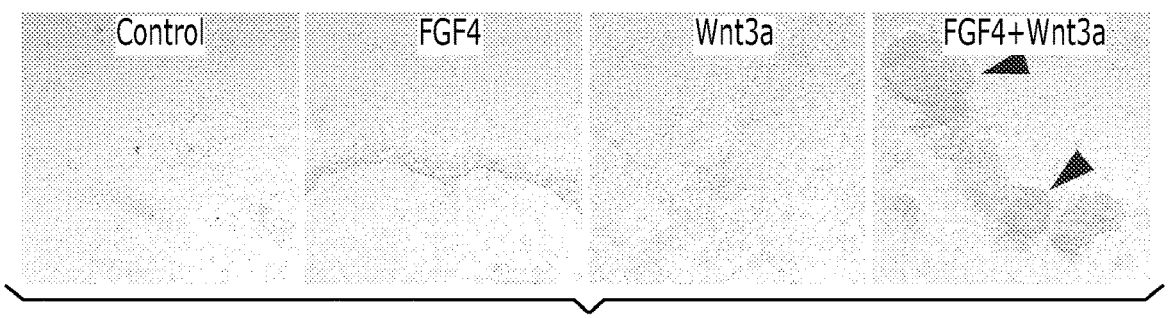
Figure 2B:
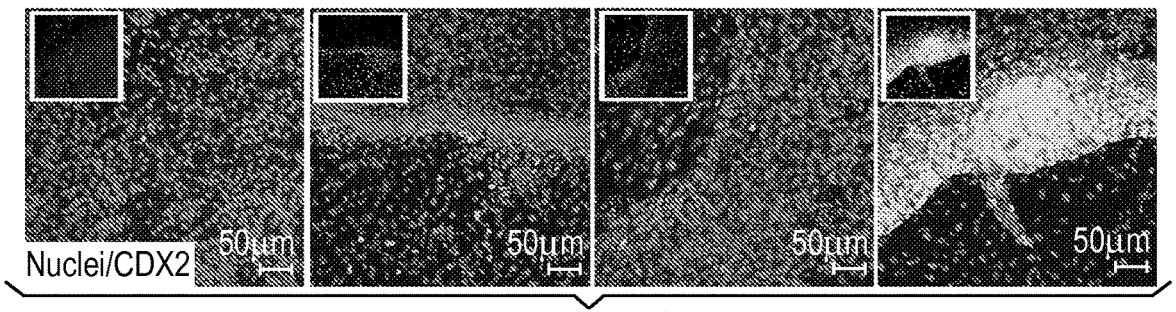
Figure 2C:
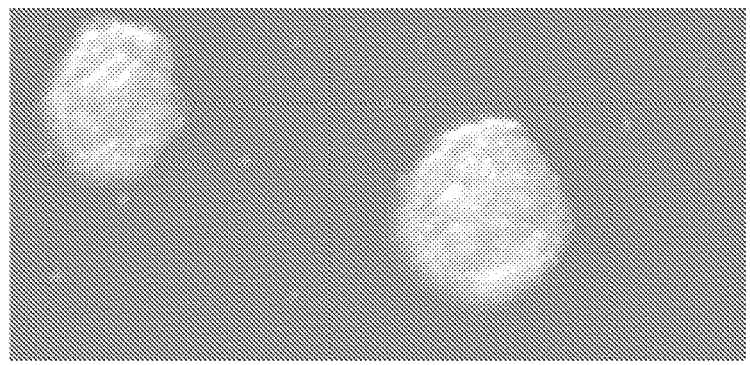
FIG. 2c includes bright field images of hindgut-like spheroids.
Figure 2D:
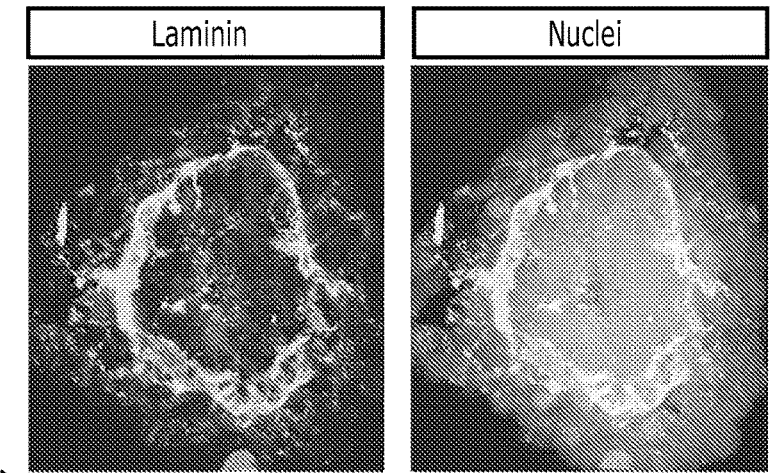
FIGS. 2d through 2f shows immunofluorescent images of CDX2, basal-lateral lamina ("laminin") and E-Cadherin expression in hindgut-like spheroids.
Figure 2E:
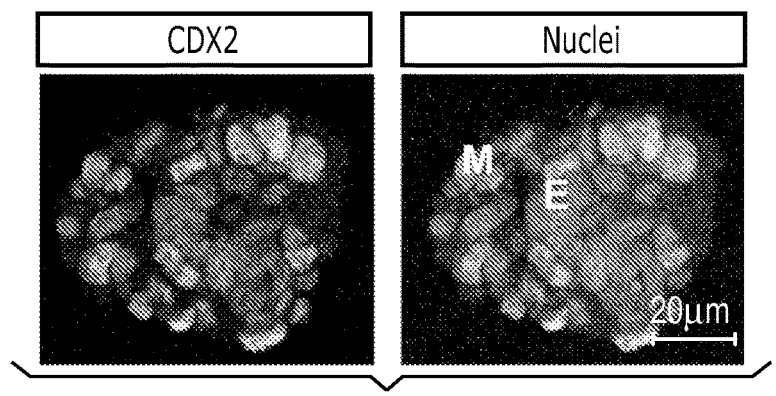
Figure 2F:
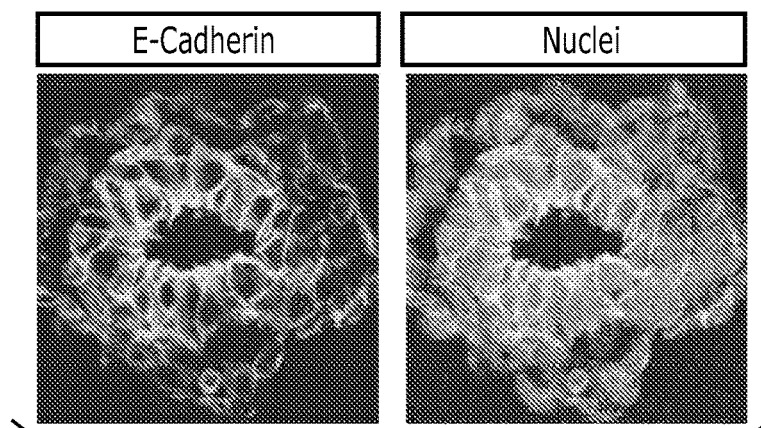
Figure 2G:
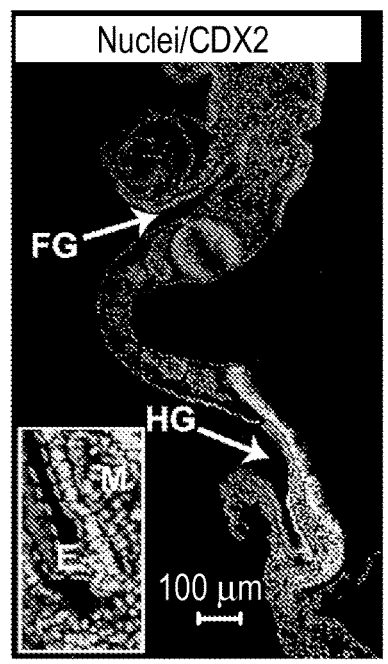
FIG. 2g is an immunofluorescent image of CDX2 expression in an e8.5 mouse embryo (sagittal section).
Figure 2H:
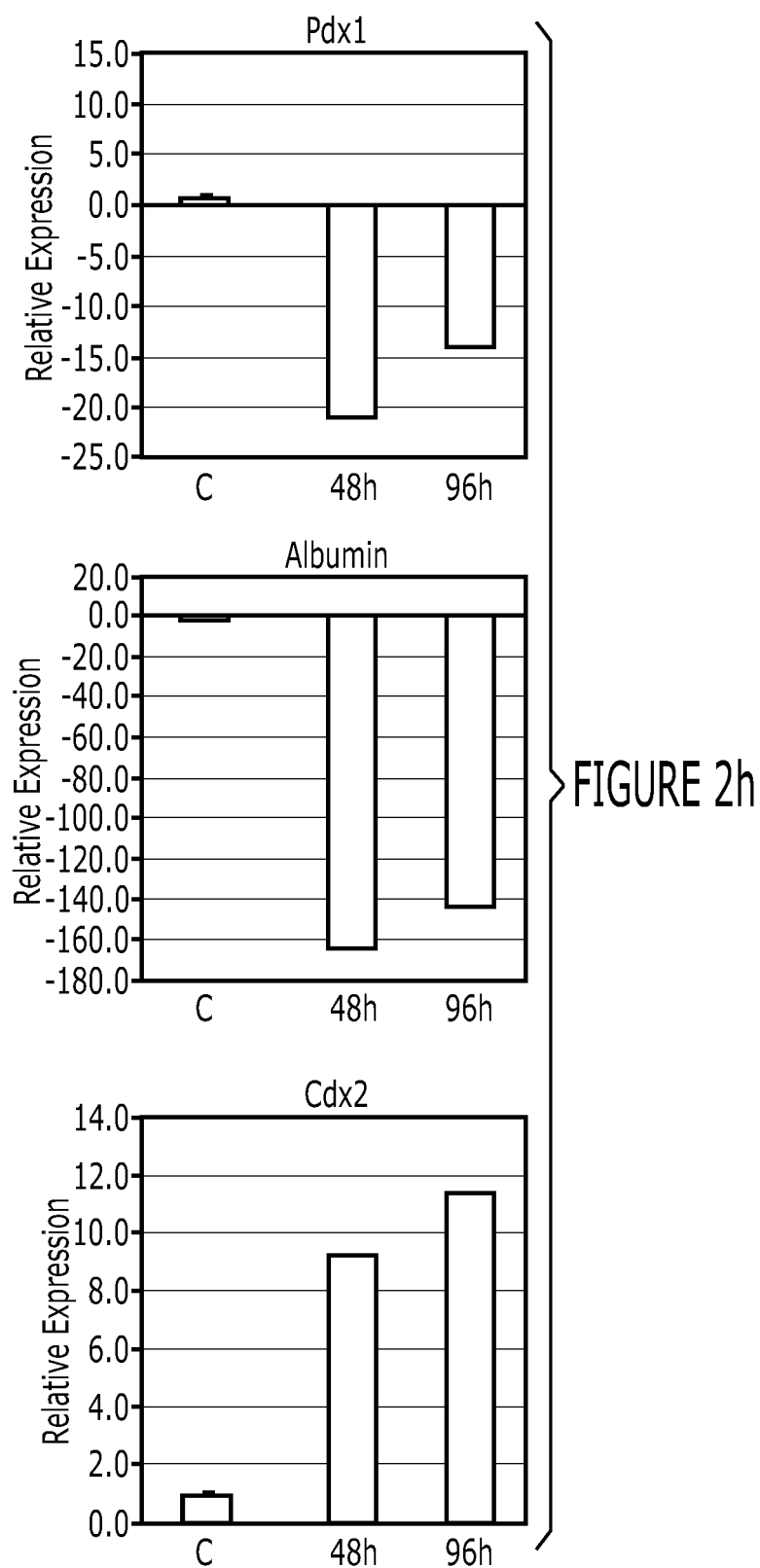
FIG. 2h includes bar charts that illustrate RT-qPCR analysis of hindgut-like spheroids for Pdx1, Albumin and CDX2 expression.

Not only were the molecular features of hindgut formation in vitro similar to hindgut development in vivo, FGF4+Wnt3a treated cultures underwent a morphogenesis similar to embryonic gut tube formation. Between 2 and 5 days of FGF4+Wnt3a treatment, flat cell sheets condensed into CDX2+ epithelial tubes, many of which budded off to form floating hindgut spheroids (FIG. 2a-c, FIG. 10a-10f) (Table 2a). Spheroids (FIG. 2c-f) were similar to e8.5 mouse hindgut (FIG. 2g) containing CDX2+ polarized epithelium (E) surrounded by CDX2+ mesenchyme (M). Spheroids were completely devoid of A1b- and Pdx1-expressing foregut cells (FIG. 2h). This in vitro gut-tube morphogenesis was never observed in control or Wnt3a-only treated cultures and FGF4 treated cultures generated 4-10 fold fewer spheroids (Table 1A), which were weakly CDX2+ and did not undergo further expansion. The similarity of the hindgut spheroids to mouse embryonic hindgut suggests that the morphological differentiation induced by FGF4+Wnt3 is a key event in the specification of the intestinal lineage.

The following tables illustrate the effects of growth factor treatment of hESCs and iPSCs. Generation of hindgut spheroids was tracked for (Table 1A) days 2-5 following growth factor treatment for H9 hESCs or (Table 1B) days 2-4 of growth factor treatment for iPSCs. Definitive endoderm was treated with either 500 ng/ml of FGF4 alone or 500 ng/ml of FGF4+Wnt3a. For both HESCs and iPSCs, hindgut spheroids formed much more robustly under FGF4+Wnt3a conditions. Control cultures or ones treated with Wnt3a alone never formed spheroids. Over the course of 4 days, FGF4+Wnt3a treated H9 endoderm generated an average of 4.5 fold more spheroids than that treated with FGF4 alone. Similarly, FGF4+Wnt3a treated iPSC endoderm generated an average of 7.25 fold more spheroids than that treated with FGF4 alone.

TABLE 1A

Growth factor treatment of hESCs: frequency of spheroid formation from hESC-H9.

| Days of GF treatment (H9 hESCs) | Total # organoids FGF4 treated (# organoids/ wells counted) | Average # organoids per well FGF4 treated | Total # organoids FGF4 + Wnt3a treated (# organoids/wells counted) | Average # organoids per well FGF4 + Wnt3a treated |
|---|---|---|---|---|
| 2 days (48 h) | 0/5 | 0 | 10/10 | 1 |
| 3 days (72 h) | 0/5 | 0 | 150/10 | 15 |
| 4 days (96 h) | 44/5 | 8.8 | 322/10 | 32.2 |
| 5 days (120 h) | 19/4 | 4.75 | 100/8 | 12.5 |

TABLE 1B

Growth factor treatment of iPSCs: frequency of spheroid formation from iPSC-3.5.

| Days of GF treatment (iPSCs) | Total # organoids FGF4 treated (# organoids/ wells counted) | Average # organoids per well FGF4 treated | Total # organoids FGF4 + Wnt3a treated (# organoids/wells counted) | Average # organoids per well FGF4 + Wnt3a treated |
|---|---|---|---|---|
| 2 days (48 h) | 0/4 | 0 | 0/10 | 0 |
| 3 days (72 h) | 10/4 | 2.5 | 229/10 | 22.9 |
| 4 days (96 h) | 14/4 | 3.5 | 206/10 | 20.6 |

Frequencies of spheroid formation in response to FGF4 and Wnt3a were studied, as shown in Tables 1A and 1B. Generation of hindgut spheroids was tracked for days 2-5 of growth factor treatment (H9 hESCs, Table 1A) or days 2-4 of growth factor treatment (iPSCs, Table 1B) for endoderm being given either 500 ng/ml FGF4 alone or 500 ng/ml FGF4+Wnt3a. In both cell lines, hindgut spheroids were much more robustly generated in FGF4+Wnt3a conditions. Over the course of 4 days, FGF4+Wnt3a treated H9 endoderm generated an average of 4.5 fold more spheroids than FGF4 treated alone. Similarly, FGF4+Wnt3a treated iPSC endoderm generated an average of 7.25 fold more spheroids than FGF4 treated alone.

Not only were the molecular features of hindgut formation in vitro similar to hindgut development in vivo, FGF4+Wnt3a treated cultures underwent a morphogenesis similar to embryonic gut tube formation. Between 2 and 5 days of FGF4+Wnt3a treatment, flat cell sheets condensed into CDX2+ epithelial tubes, many of which budded off to form floating hindgut spheroids (FIG. 2a-c, FIG. 10a-f) (table 1A). Spheroids (FIG. 2c-f) were similar to e8.5 mouse hindgut (FIG. 2g) containing CDX2+ polarized epithelium (E) surrounded by CDX2+ mesenchyme (M). Spheroids were completely devoid of Alb– and Pdx1-expressing foregut cells (FIG. 2h). This in vitro gut-tube morphogenesis was not observed in control or Wnt3a-only treated cultures and FGF4 treated cultures generated 4-10 fold fewer spheroids (Table 1A), which were weakly CDX2+ and did not undergo further expansion (not shown). The similarity of the hindgut spheroids to mouse embryonic hindgut suggests that the morphological differentiation induced by FGF4+Wnt3 is a key event in the specification of the intestinal lineage.

More details can be found in, for example, D'Amour, K. A., et al. Efficient differentiation of human embryonic stem cells to definitive endoderm. *Nat Biotechnol* 23, 1534-1541 (2005); Beck, F., Erler, T., Russell, A. & James, R. Expression of Cdx-2 in the mouse embryo and placenta: possible role in patterning of the extra-embryonic membranes. *Dev Dyn* 204, 219-227 (1995); Dessimoz, J., Opoka, R., Kordich, J. J., Grapin-Botton, A. & Wells, J. M. FGF signaling is necessary for establishing gut tube domains along the anterior-posterior axis in vivo. *Mech Dev* 123, 42-55 (2006); McLin, V. A., Rankin, S. A. & Zorn, A. M. Repression of Wnt/{beta}-catenin signaling in the anterior endoderm is essential for liver and pancreas development. *Development* 134, 2207-2217 (2007); Wells, J. M. & Melton, D. A. Early mouse endoderm is patterned by soluble factors from adjacent germ layers. *Development* 127, 1563-1572. (2000); each of which is incorporated herein in its entirety.

FIGS. 1a through 1d illustrate exemplary embodiments of the present invention. FGF4 and Wnt3a act synergistically in a temporal and dose-dependent manner to specify stable posterior endoderm fate. ActivinA (100 ng/ml) was used to differentiate H9-HES cells into definitive endoderm (DE). DE was treated with the posteriorizing factors FGF4 (50, 500 ng), Wnt3a (50, 500 ng) or both for 6, 48 or 96 hours. Cells were then cultured in a permissive medium without growth factors for an additional seven days and analyzed for expression of foregut markers (ALB, PDX1) and the hindgut marker (CDX2) by RT-qPCR (a) and immunofluorescence (b-d). FGF4/Wnt-mediated changes in marker expression in (a) is relative to 3-day activin treated DE cultures that were grown for identical lengths of time in the absence of FGF4 or Wnt3a (control). Only high levels of FGF4+Wnt3a for 96 hours gave cultures with stable CDX2 expression that lack foregut marker expression. Error bars denote standard deviation of triplicates. Significance is shown by; * (p<0.05), ^ (p<0.001), # (p<0.0001).

FIGS. 2a through 2h illustrate exemplary embodiments in accordance with the present invention in which posterior endoderm is shown developing into 3-dimensional, hindgut-like organoids. Morphogenesis of posterior endoderm into three-dimensional, hindgut-like organoids is depicted. (a) Bright field images of DE that was treated with FGF4+

Wnt3a 96 hours formed numerous 3D epithelial structures including tubes and free-floating spheres (black arrows) relative to control DE, Wnt3a or FGF4 cultures (see Table 1A and 1B). (b) CDX2 immunostaining (Green) and nuclear stain (Draq5—blue) on cultures shown in (a). 3D structures in FGF4+Wnt3a treated cultures were largely CDX2 positive. Insets—green channel only showing CDX2 staining. (c) Bright field image of hindgut-like spheroids. (d-f) Analysis of CDX2, basal-lateral lamina and E-Cadherin expression demonstrate that spheroids contain an inner layer of polarized, cuboidal, CDX2 positive epithelium surrounded by non-polarized mesenchyme-like CDX2 cells. (g) CDX2 expression in an e8.5 mouse embryo (sagittal section) shows that both hindgut endoderm (E) and adjacent mesenchyme (M) are CDX2 positive (green), similar to hindgut spheroids (Inset shows a magnified view of CDX2 staining in the hindgut endoderm and mesoderm; FIG—foregut, HG—hindgut. (h) RT-qPCR analysis of hindgut-like spheroids did not detect foregut markers (PDX1, Albumin) but detected robust expression of hindgut markers (CDX2). Expression levels shown in (h) is relative to 3-day activin treated DE cultures that were grown for identical lengths of time in the absence of FGF4 or Wnt3a (C=control; 48 h=spheroids generated after 48 hours; 96 h=spheroids generated after 96 hours). Error bars denote standard deviation of triplicates.

Figure 7A:
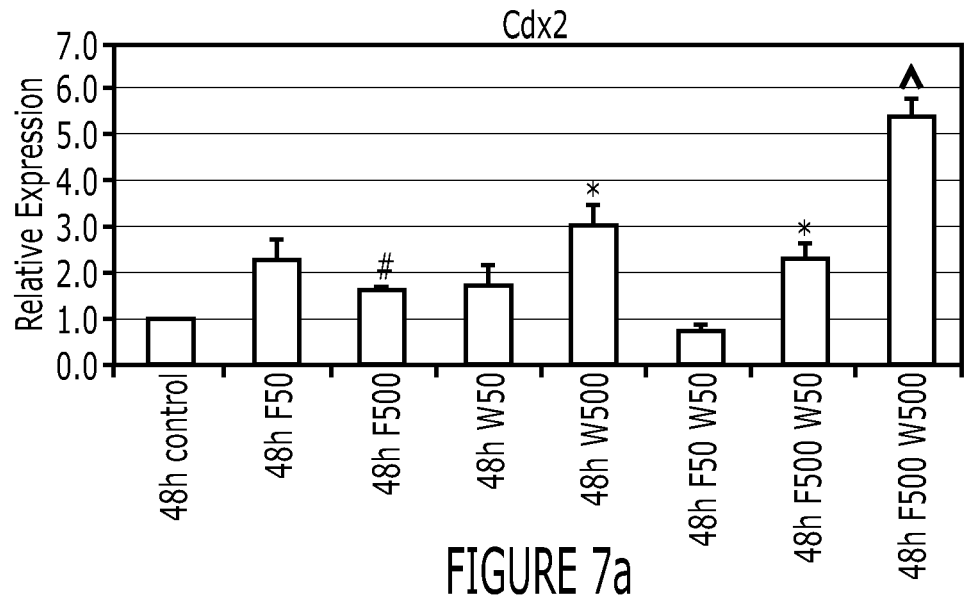
Figure 7B:
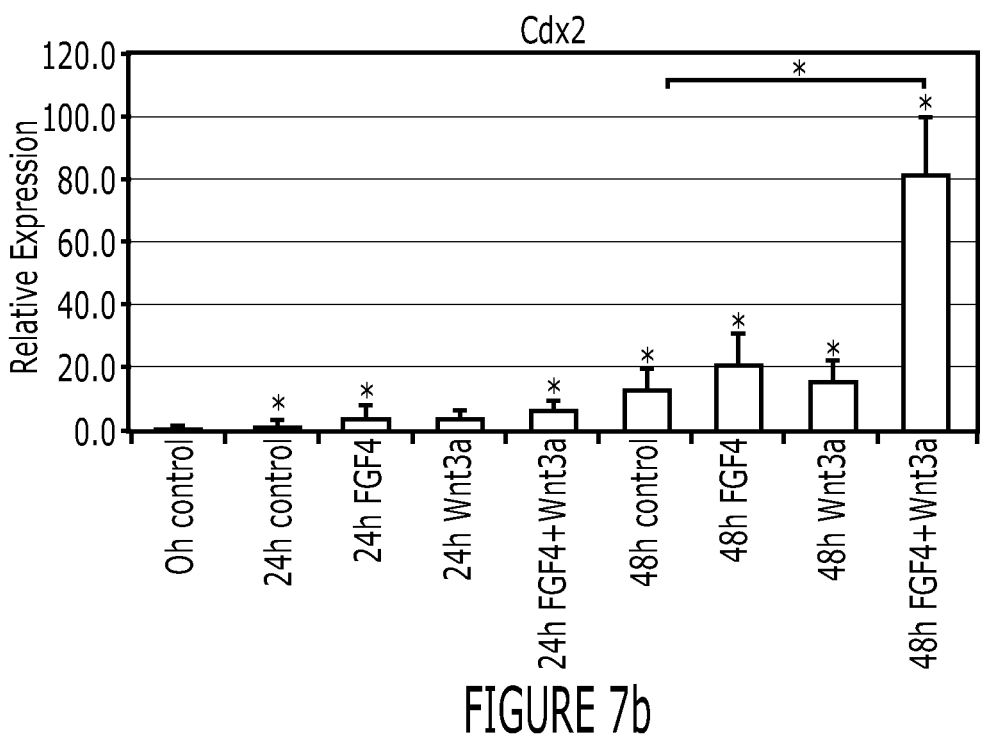

FIGS. 7a and 7b illustrate exemplary embodiments in accordance with the present invention, depicting time and concentration dependent induction of CDX2 by FGF4 and Wnt3a. (a) FGF4 and Wnt3a up-regulate CDX2 in a concentration dependant manner. 3-day ActivinA treated hESCs were treated for 48 hours with Wnt3a at 50 ng/ml or 500 ng/ml or FGF4 at 50 ng/ml or 500 ng/ml, or increasing concentrations of FGF4+Wnt3a. Cells were analyzed after 48 hours of treatment. FGF4 or Wnt3a alone caused modest changes in CDX2 expression at different doses. FGF4+Wnt3a at the highest dose (500 ng/ml each) induced robust CDX2 expression. CDX2 expression was normalized to the internal control beta-tubulin, and is shown relative to a 48 hour control cultured in the absence of growth factors. (b) FGF4 and Wnt3a up-regulate CDX2 in a time dependant manner. 48 hours of exposure to FGF4+Wnt3a was required for the most robust induction of CDX2. All time points shown are set relative to a 0 hour no growth factor control. 500 ng/ml of FGF4, Wnt3a or FGF4+Wnt3a was used for all time points. Note that 24 hour and 48 controls, in the absence of growth factors, show a significant and spontaneous up-regulation of CDX2. Error bars denote standard deviation of triplicates. Significance is shown by; * ($p<0.05$)

Example 2

Directing Hindgut Spheroids into Intestinal Tissue In Vitro

Directed differentiation into hindgut and intestinal organoids. After differentiation into definitive endoderm, cells were incubated in 2% dFBS-DMEM/F12 with either 50 or 500 ng/ml FGF4 and/or 50 or 500 ng/ml Wnt3a (R&D Systems) for 2-4 days. After 2 days with treatment of growth factors, 3-dimensional floating spheroids were present in the culture. 3-dimensional spheroids were transferred into an in vitro system previously described to support intestinal growth and differentiation. Briefly, spheroids were embedded in Matrigel (BD Bioscience #356237) containing 500 ng/ml R-Spondin1 (R&D Systems), 100 ng/ml Noggin (R&D Systems) and 50 ng/ml EGF (R&D Systems). After the Matrigel solidified, media (Advanced DMEM/F12 (Invitrogen) supplemented with L-Glutamine, 10 µM Hepes, N2 supplement (R&D Systems), B27 supplement (Invitrogen), and Pen/Strep containing growth factors was overlaid and replaced every 4 days.

Figure 3A:
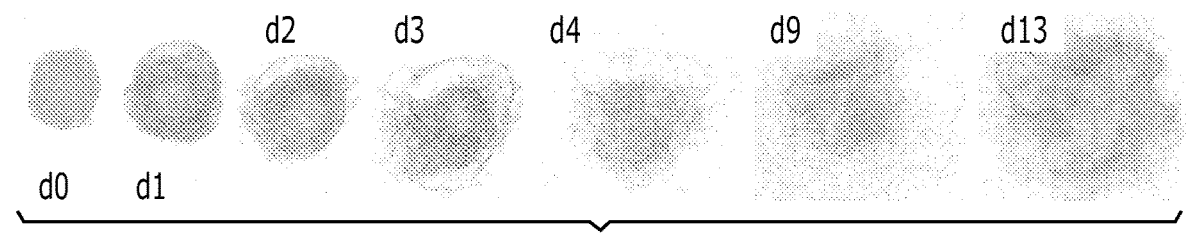
FIG. 3a includes images that illustrate the time course of organoid growth for 13 days.
Figure 3B:
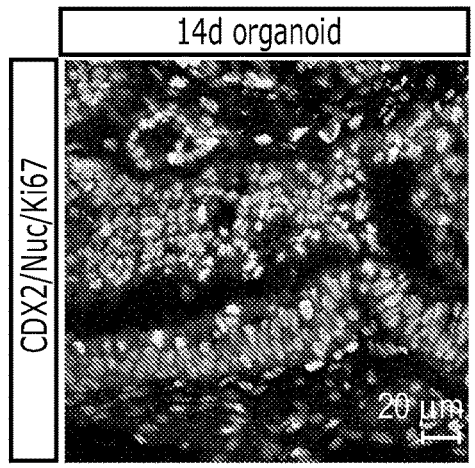
FIGS. 3b through 3e are immunofluorescent images of characteristic intestinal transcription factor expression and cell proliferation in organoids after 14 and 28 days of culture.
Figure 3C:
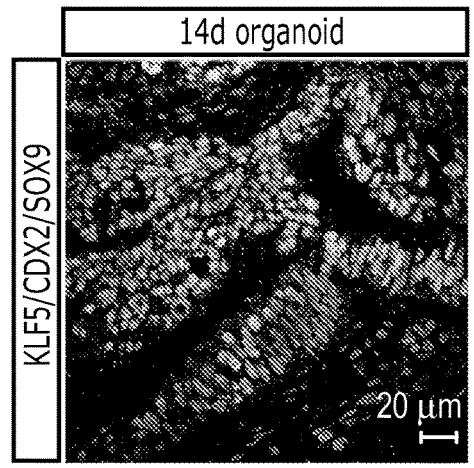
Figure 3D:
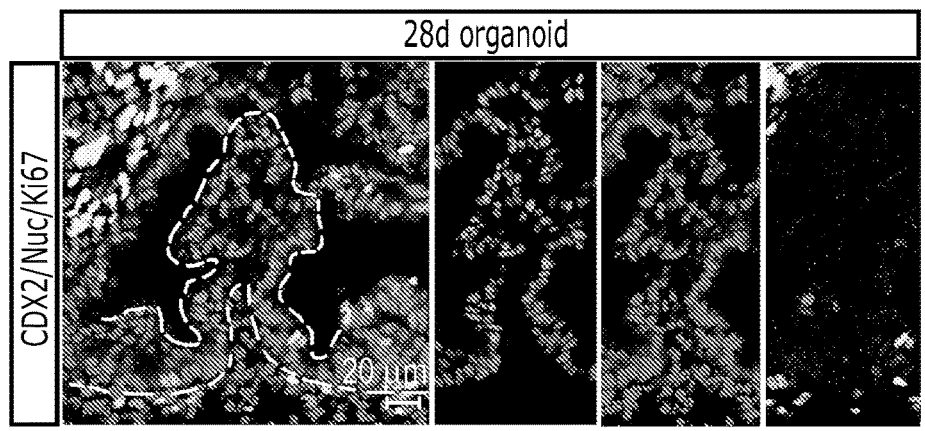
Figure 3E:
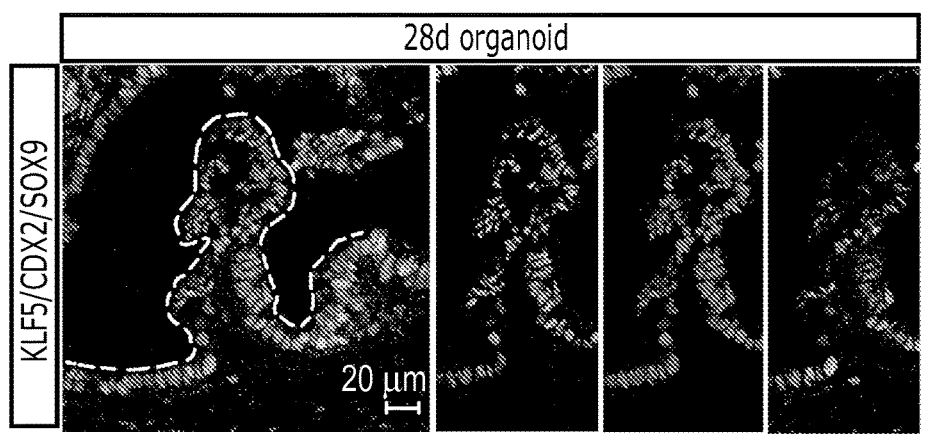
Figure 3F:
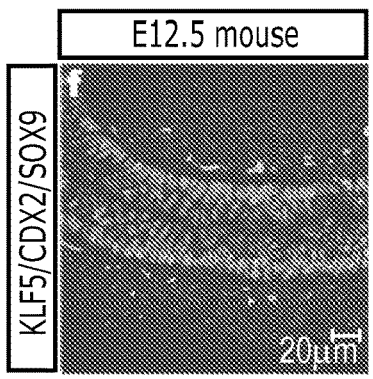
FIGS. 3f and 3g are immunofluorescent images of KLF5, CDX2 and SOX9 expression in mouse fetal intestine at e14.5.
Figure 3G:
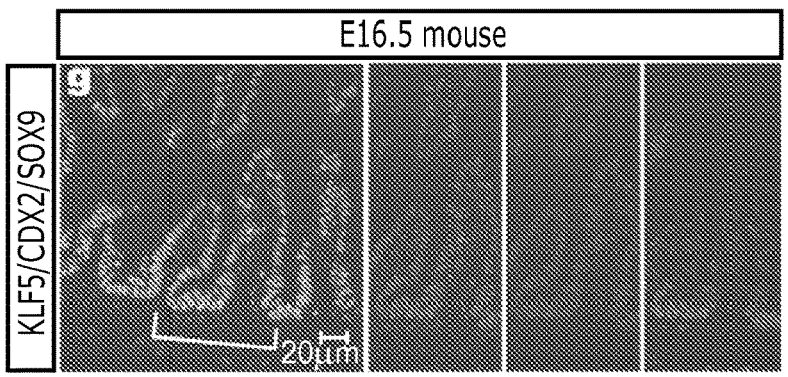
Figure 3H:
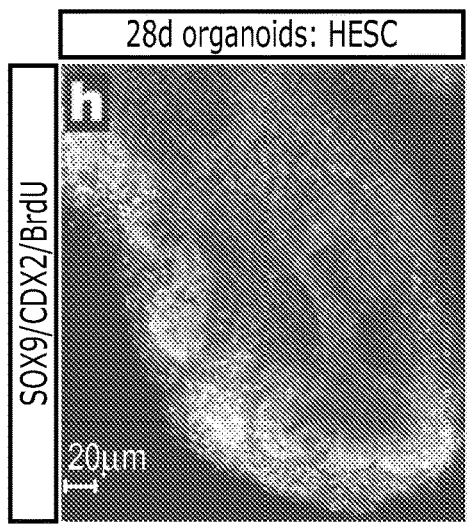
FIGS. 3h and 3i are whole mount immunofluorescent z-stack images of two different organoids for BrdU, CDX3 and SOX9 expression.
Figure 8:
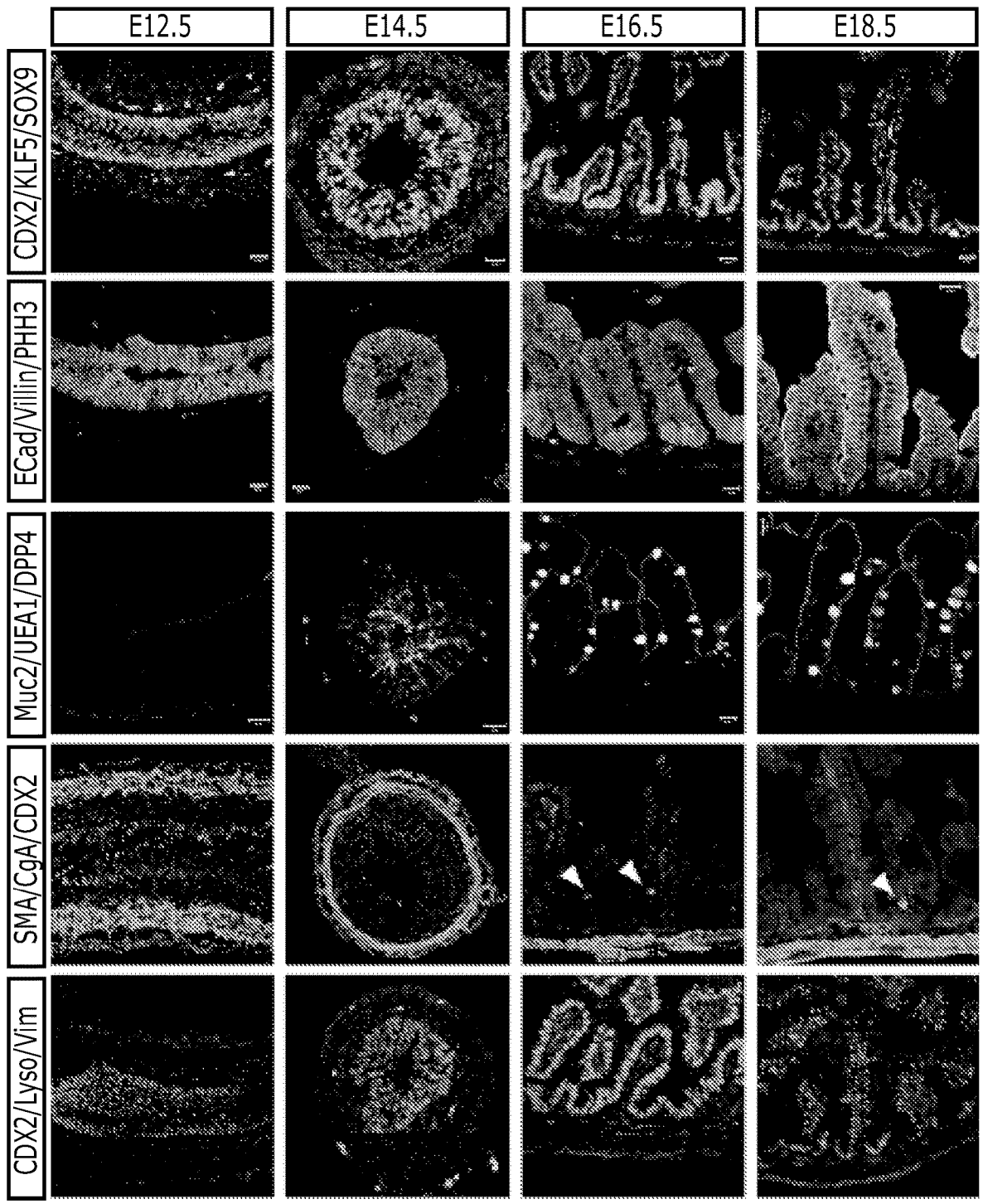
FIG. 8 includes immunofluorescent images illustrating exemplary embodiments in accordance with the present invention. The images depict molecular marker expression during mouse intestinal development at embryonic stages include e12.5, e14.5, e16.5 and e18.5.

Directing Hindgut Spheroids into Intestinal Tissue In Vitro. While in vivo engraftment of PSC-derived cell types, such as pancreatic endocrine cells, has been used to promote maturation, maturation in vivo is a poorly defined process and is experimentally intractable. Primitive hindgut spheroids were sjpwm matured into intestine in vitro using the recently described 3-dimensional culture conditions that support growth and renewal of the adult intestinal epithelia. When placed into this culture system, hindgut spheroids developed into intestinal organoids in a staged manner that was strikingly similar to fetal gut development (FIG. 3 and FIG. 8). In the first 14 days the simple cuboidal epithelium of the spheroid expanded and formed a highly convoluted pseudostratified epithelium surrounded by mesenchymal cells (FIG. 3a-c). After 28 days, the epithelium matured into a columnar epithelium with villus-like involutions that protrude into the lumen of the organoid (FIG. 3d, e). Comparable transitions were observed during mouse fetal intestinal development (FIG. 3f, g and FIG. 8). The spheroids expanded up to 40 fold in mass as they formed organoids (data not shown). Moreover, 28-day organoids were split and passaged up to 5 additional times and cultured for over 100 days. The cellular gain during that time was up to 1,000 fold (data not shown), resulting in a total cellular expansion of 40,000 fold per hindgut spheroid.

Figure 3I:
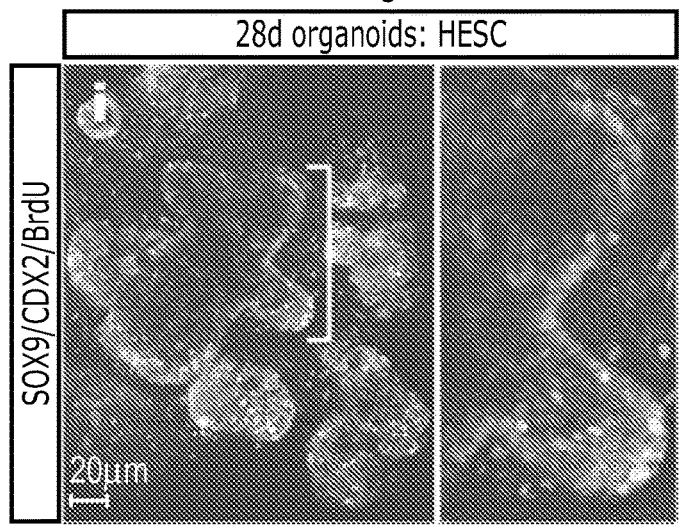
Figure 3J:
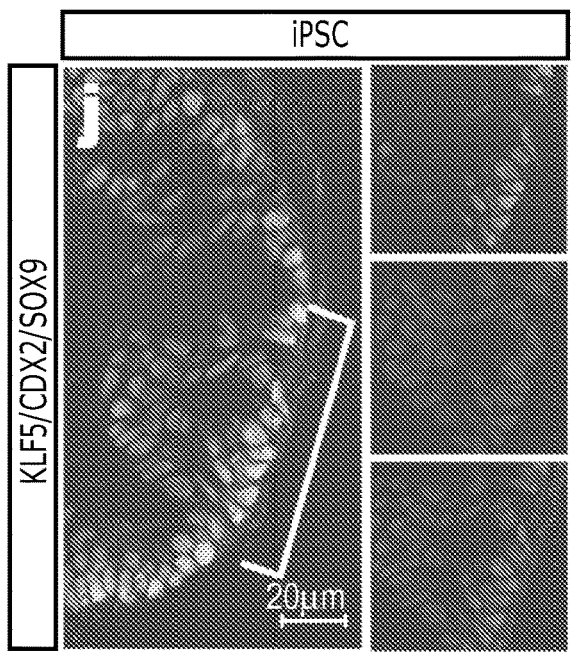
FIG. 3j is an immunofluorescent image of human induced pluripotent stem cells ("iPSCs") in which KLF5, CDX2 and localized SOX9 expression is detected.
Figure 4A:
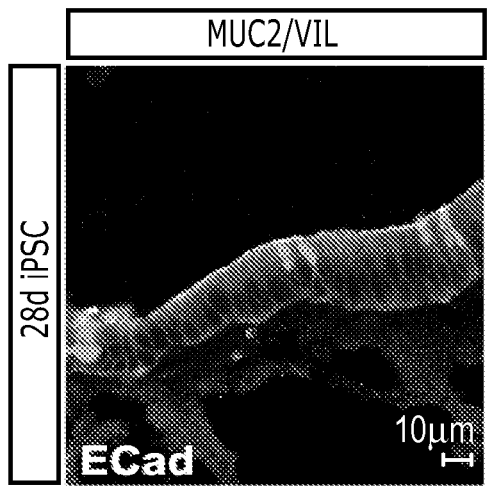
FIGS. 4a through 4c are immunofluorescent images of 28 day iPSC-derived and 38 day H9 HES-derived organoids analyzed for villin (VIL), mucin (MUC2), lysozyme (LYSO) and chromogranin A (CGA).
Figure 4A:
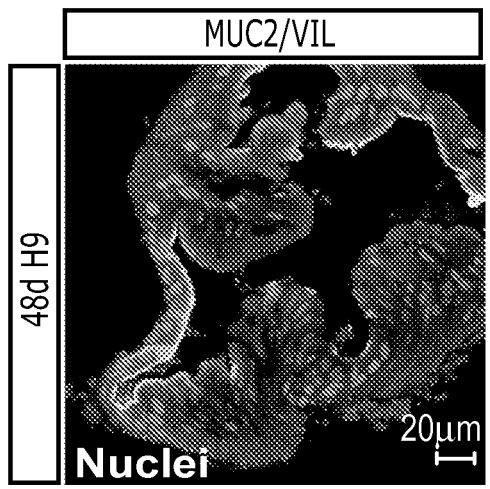
Figure 4B:
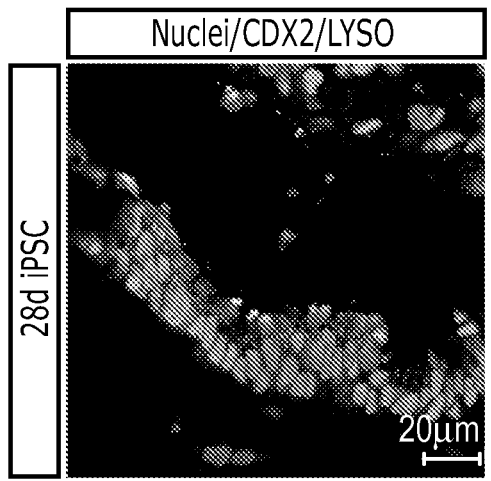
Figure 4B:
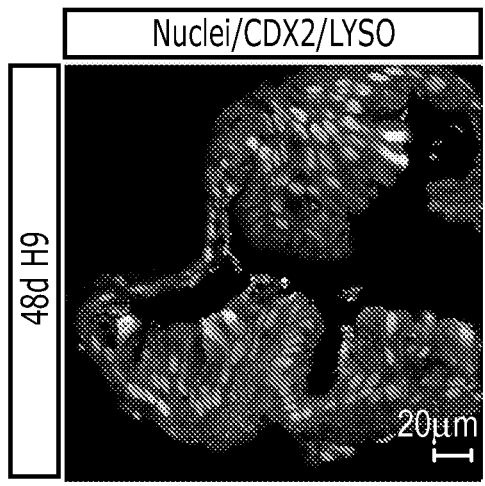
Figure 4C:
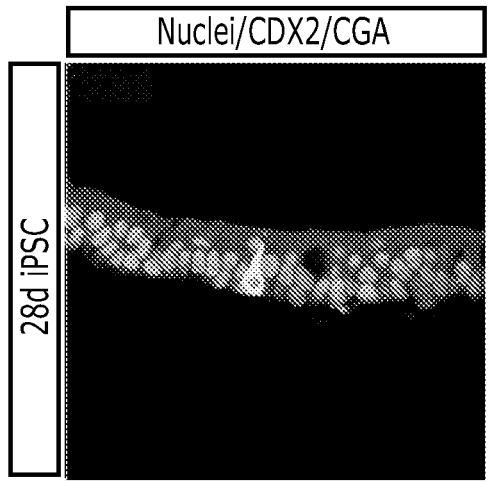
Figure 4C:
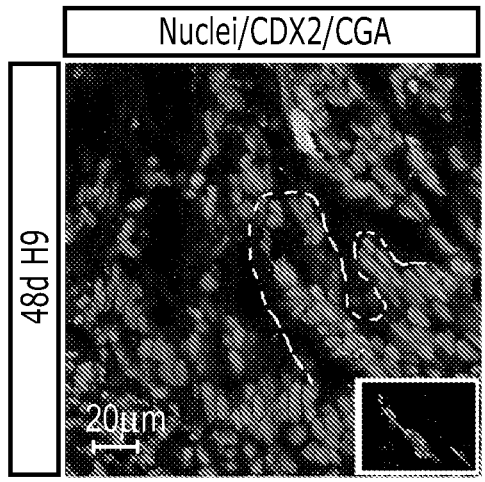
Figure 4D:
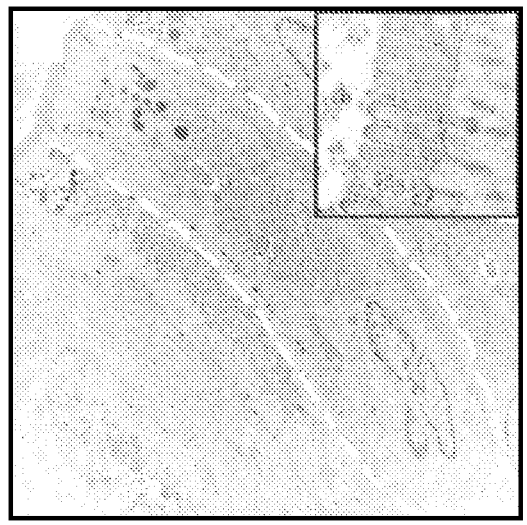
FIG. 4d is an electron micrograph image showing an enterocyte cell with a characteristic brush border with microvilli.
Figure 4E:
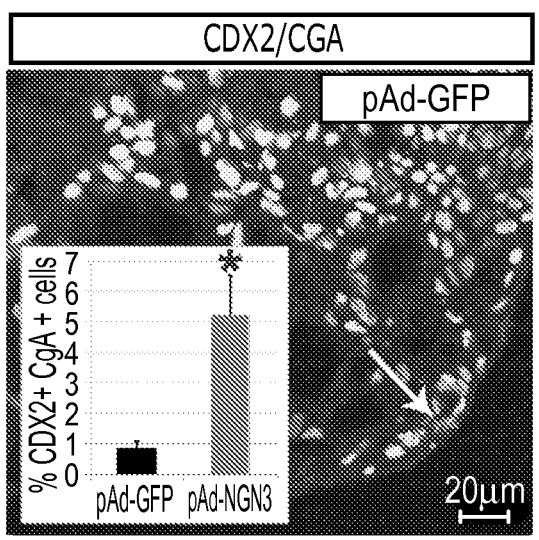
FIGS. 4e and 4f are immunofluorescent images of endocrine cell lineage development through adenoviral-mediated expression of Neurogenin 3 (NEUROG3).
Figure 4F:
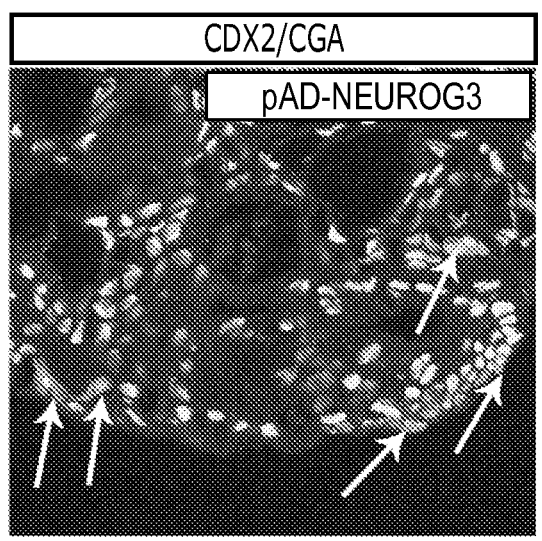

Marker analysis showed that after 14 days in culture, virtually all of the epithelium expressed the intestinal transcription factors CDX2, KLF5 and SOX9 broadly and was highly proliferative (FIG. 3b, c). By 28 days CDX2 and KLF5 remained broadly expressed, while SOX9 became localized to pockets of proliferating cells at the base of the villus-like protrusions (FIG. 3d, e, h, i). Three-dimensional rendering of a series of confocal microscopic images further revealed that the proliferative zone was in a crypt-like structure that penetrated into the underlying mesenchyme (FIG. 3 h, i). The dynamic spatial expression of CDX2, KLF5 and SOX9 in maturing, 14-28 day intestinal organoids was similar to that of the developing fetal mouse intestines between e12.5 and e16.5 (FIG. 3i, j and FIG. 8). In particular, the restriction of SOX9 to the inter-villus proliferative zone is characteristic of the developing progenitor domain, which ultimately gives rise to the intestinal stem cell niche in the crypt of Lieberkühn.

Importantly, this method for directed differentiation into intestine should be broadly applicable to other PSC lines as intestinal tissues were generated from 2 hESC and 6 iPSC lines. The kinetics of differentiation and the formation of a patterned intestinal epithelium were indistinguishable between iPSCs and hESCs (FIG. 3j, FIGS. 6, 9, 10 and Table 1B). Additional data for information on generating and analyzing iPSC lines and for DNA microarray data comparing differentiation between H9 and iPSC lines can be found in Table 2.

Maintenance and directed differentiation of human ESCs and iPSCs into intestinal tissue. Human embryonic stem cells and induced pluripotent stem cells were maintained on Matrigel (BD Biosciences) in mTesR1 media without feeders. Differentiation into Definitive Endoderm was carried out as previously described. Briefly, a 3 day ActivinA (R&D systems) differentiation protocol was used. Cells were treated with ActivinA (100 ng/ml) for three consecutive days in RPMI 1640 media (Invitrogen) with increasing concentrations of 0%, 0.2%, 2% HyClone defined FBS (dFBS) (Thermo Scientific). For hindgut differentiation, DE cells were incubated in 2% dFBS-DMEM/F12 with 500 ng/ml FGF4 and 500 ng/ml Wnt3a (R&D Systems) for 2-4 days. After 2 days with treatment of growth factors, 3-dimensional floating spheroids were present and then transferred into three-dimensional cultures previously shown to promote intestinal growth and differentiation. Briefly, spheroids were embedded in Matrigel (BD Bioscience) containing 500 ng/mL R-Spondin1 (R&D Systems), 100 ng/ml Noggin (R&D Systems) and 50 ng/ml EGF (R&D Systems). After the Matrigel solidified, media (Advanced DMEM/F12 (Invitrogen) supplemented with L-Glutamine, 10 μM Hepes, N2 supplement (R&D Systems), B27 supplement (Invitrogen), and Pen/Strep containing growth factors was overlaid and replaced every 4 days.

More details can be found in, for example, Gracz, A. D., Ramalingam, S. & Magness, S. T. Sox9-Expression Marks a Subset of CD24-expressing Small Intestine Epithelial Stem Cells that Form Organoids in vitro. *Am J Physiol Gastrointest Liver Physiol* 298, G590-600 (2010); Sato, T., et al. Single Lgr5 stem cells build crypt-villus structures in vitro without a mesenchymal niche. *Nature* 459, 262-265 (2009); Kroon, E., et al. Pancreatic endoderm derived from human embryonic stem cells generates glucose-responsive insulin-secreting cells in vivo. *Nat Biotechnol* (2008); Ludwig, T. E., et al. Feeder-independent culture of human embryonic stem cells. *Nat Methods* 3, 637-646 (2006); Ludwig, T. E., et al. Derivation of human embryonic stem cells in defined conditions. *Nat Biotechnol* 24, 185-187 (2006); D'Amour, K. A., et al. Efficient differentiation of human embryonic stem cells to definitive endoderm. *Nat Biotechnol* 23, 1534-1541 (2005); each of which is incorporated herein in its entirety.

FIGS. 3a through 3j illustrate exemplary embodiments in accordance with the present invention, showing the formation of intestine-like organoids from hESCs and hiPSCs. a, Time course of organoid growth for 13 days. (a) Organoids underwent epithelial growth and budding, forming highly convoluted epithelial structures by day 9. (b-e) Analysis of characteristic intestinal transcription factor expression (KLF5, CDX2, SOX9) and cell proliferation on serial sections of organoids after 14 and 28 days of culture (serial sections are b and c, d and e). (f) and (g) Expression of KLF5, CDX2, and SOX9 in mouse fetal intestine at e14.5 (f) and e16.5 (g) is similar to developing intestinal organoids. (h) and (i), whole mount immunofluorescence z-stacks of two different organoids for BrDU, CDX2, and SOX9 showing proliferative zones in crypt-like structures associated with the mesenchyme. (j) human iPSCs derived from keratinocytes form intestinal organoids in an identical manner to hESCs as measured by KLF5, CDX2, and localized SOX9 expression. The insets to the right in (d), (e), (g) and (j) show separated color channels.

Figure 6B:
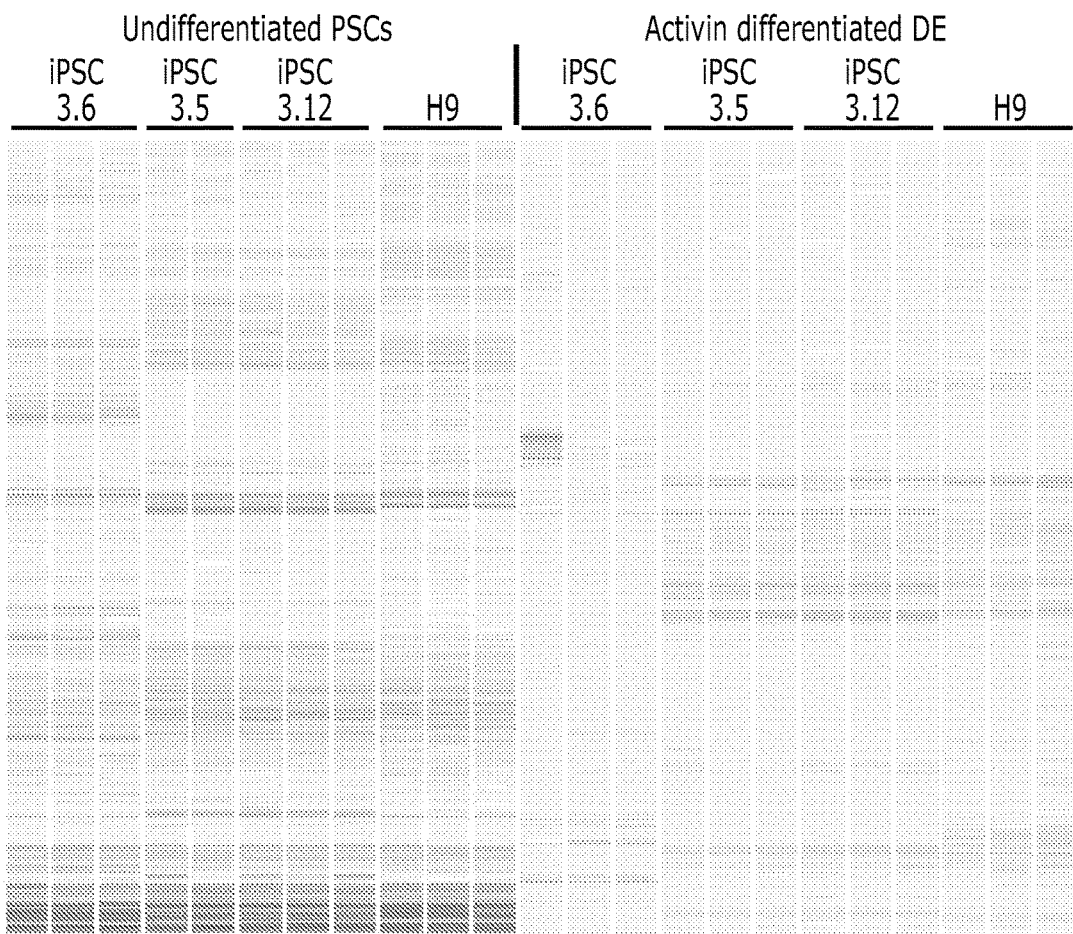
FIG. 6b is a microarray analysis of the transcriptional profile of DE induction in hESC-H9 and iPSC lines before and after DE formation.

FIGS. 6a and 6b illustrate exemplary embodiments in accordance with the present invention, depicting characterization of DE formation from hESC and iPSC lines by immuno-fluorescence (IF) and Microarray analysis. (a) Undifferentiated hESCs stained with the pluripotency marker OCT4 (green) were treated for 3 days with ActivinA. This DE induction protocol routinely results in 80-90% SOX17 (green)/FOXA2 (red) double positive cells in both hESCs and iPSCs. (b) Transcriptional profile of DE induction. hESC-H9 and iPSC lines 3.5, 3.6 and 3.12 were analyzed before and after DE formation (activin differentiation) by Affymetrix DNA microarray analysis. Clustering analysis of transcripts that were differentially regulated during DE formation indicated that iPSC lines 3.5 and 3.12 differentiate in manner that is highly similar to hESC-H9 cells (see Tables 1A and 1B for gene list and fold expression changes). iPSC line 3.6 had a more divergent transcriptional profile and was therefore not used for subsequent experiments.

FIG. 8 illustrates exemplary embodiments in accordance with the present invention, depicting molecular marker expression during mouse intestinal development. Embryonic stages include e12.5, e14.5, e16.5 and e18.5. Transcription factors detected were CDX2, KLF5, and SOX9. Epithelial markers used were E-cadherin (Ecad), Villin and DPP4. Vimentin (Vim) and Smooth Muscle Actin (SMA) were used as mesenchymal markers. Differentiation markers used were Lysozyme (Lyso) for paneth cells, Mucin (Muc2) and UEA-1 for goblet cells, Chromogranin A (CgA) for enteroendocrine cells. Phosphohistone H3 (PHH3) shows mitotic cells.

FIGS. 9a and 9b illustrate exemplary embodiments in accordance with the present invention, showing the characterization of induced pluripotent stem cell lines. All cell lines were compared to either hESC-H9 or hESC-H1 for morphology, pluripotency marker expression and karyotype. (a) Example of hESC and iPSC morphology and expression of pluripotency markers NANOG, DNMT3b, TRA 1-60 and TRA 1-81. (b) Examples of karyotypic analysis of iPSC lines 3.5, 3.6 and 16.5.

Figure 10C:
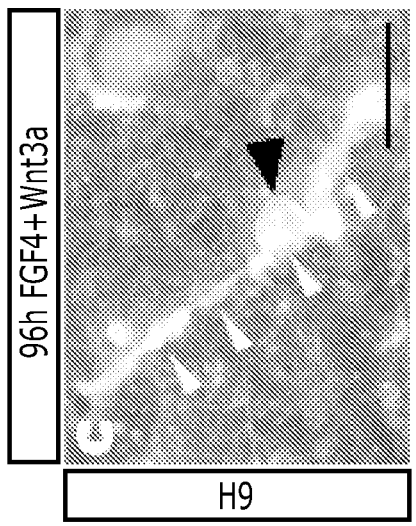
FIG. 10 illustrates exemplary embodiments in accordance with the present invention.
Figure 10F:
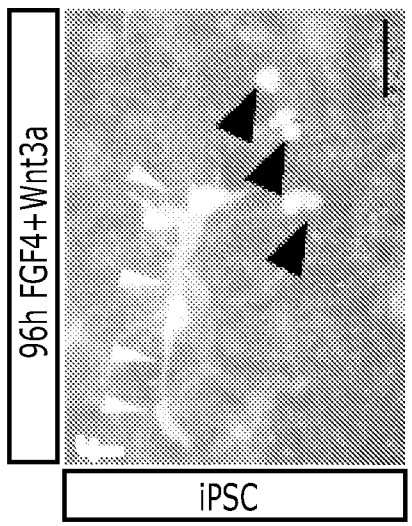
Figure 10B:
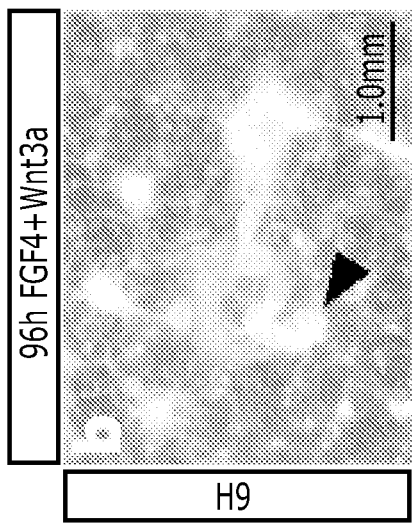
Figure 10E:
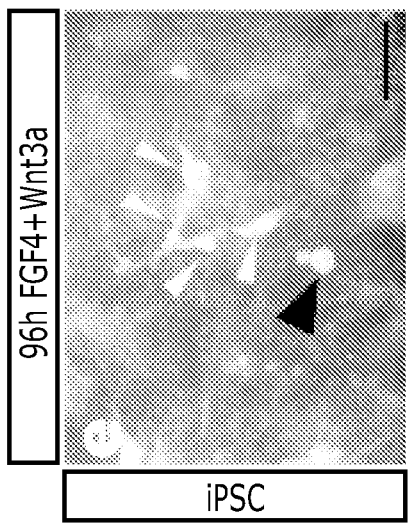
Figure 10A:
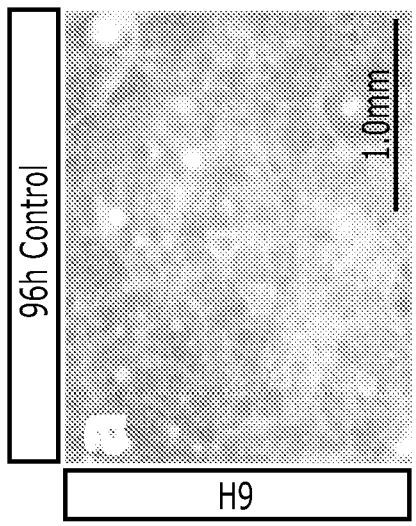
Figure 10D:
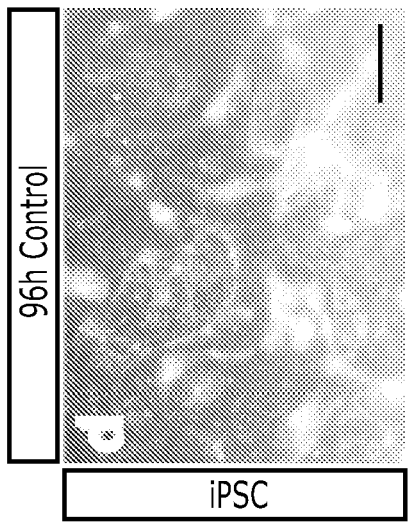
Figure 11I:
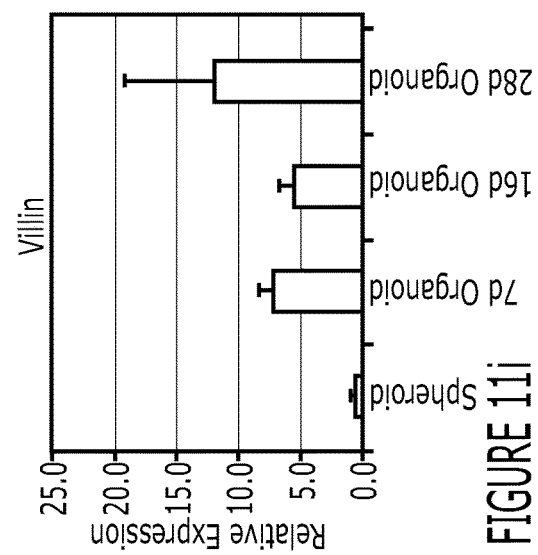
FIGS. 11g through 11m are bar charts of RT-qPCR results illustrating quantitative analysis of intestinal markers SOX9, Villin (enterocytes), Lysozyme (Paneth cells), HOXA13, IFABP (enterocytes) and MMP7 (Paneth cells) during intestinal organoid development by RT-qPCR.
Figure 11F:
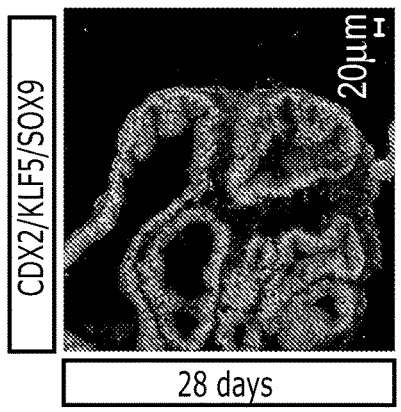
Figure 11H:
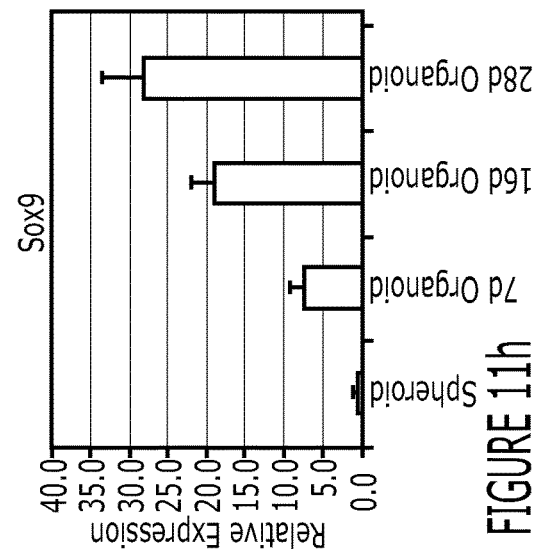
Figure 11E:
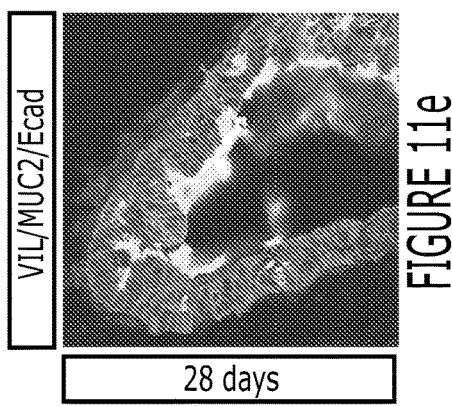
Figure 11G:
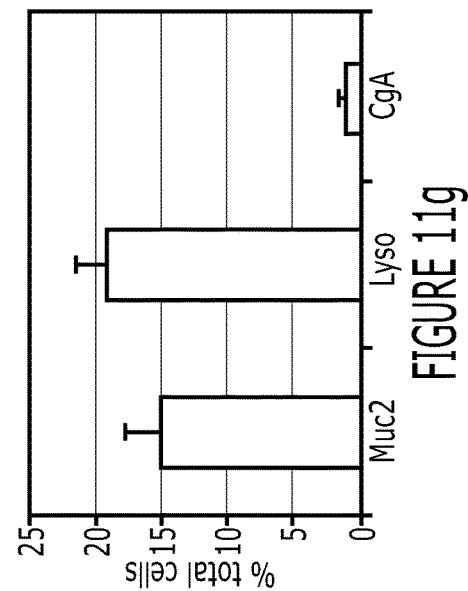
Figure 11L:
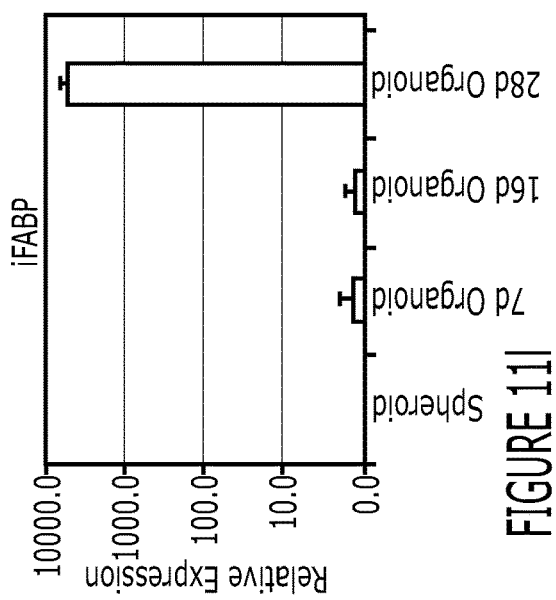
Figure 11K:
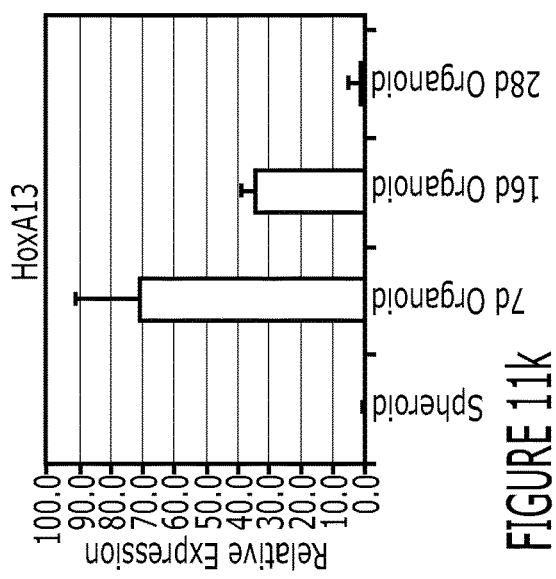
Figure 11J:
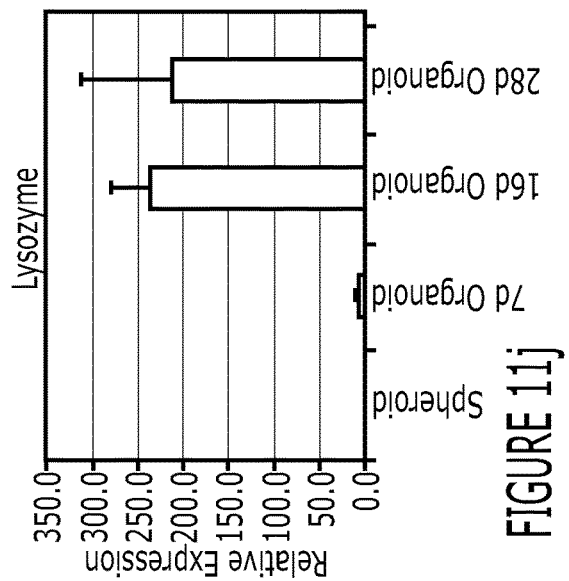
Figure 11M:
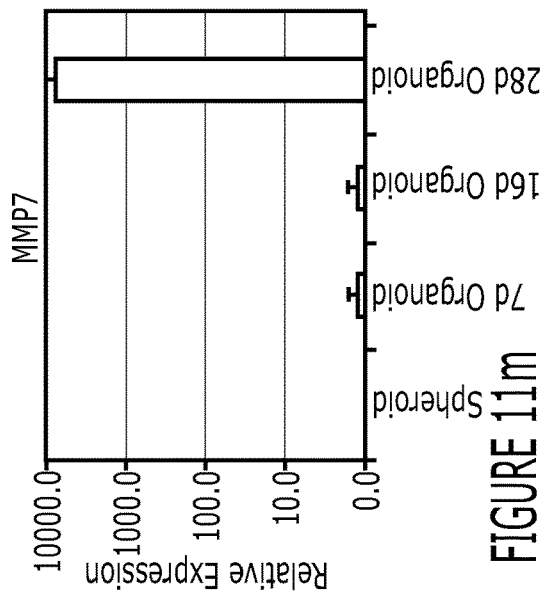

FIGS. 10a through 10g4 illustrate exemplary embodiments in accordance with the present invention, showing the morphologic comparison of hESC and iPSC organoid formation. (a)-(f) Hindgut spheroid formation from H9 human ESCs (a)-(c) or iPSCs (d)-(f) that were differentiated into endoderm and cultured without growth factors, see (a) and (d); or with 500 ng/mL FGF4+Wnt3a, see (b), (c), (e), and (f), for 96 hours. Control cultures contained little evidence of three dimensional structures (a,d) whereas FGF4+Wnt3a treated cultures contained tube like structures (yellow arrowheads; (c), (e), (f)) and free floating spheroids (black arrowheads; (b), (c), (e), (f)). (g) Examples of four different iPSC spheroids that were expanded in matrigel for 18 days (g1)-(g4). As with hESC-derived organoids, iPSC organoids contain an internal epithelium surrounded by mesenchyme.

Example 3

Cytodifferentiation of PSCs into Mature Intestinal Cell Types

Between 18 and 28 days in vitro, it was observed that cytodifferentiation of the stratified epithelium into a columnar epithelium containing brush borders and all of the major cell lineages of the gut as determined by immunofluorescence and RT-qPCR (FIG. 4 and FIG. 11). By 28 days of culture Villin (FIG. 4a, a') and DPPIV were localized to the apical surface of the polarized columnar epithelium and transmission electron microscopy revealed a brush border of apical microvilli indistinguishable from those found in mature intestine (FIG. 4d and FIG. 5). Cell counting revealed that the epithelium contained approximately 15% MUC2+ goblet cells (FIG. 4a, a'), which secrete mucin into the lumen of the organoid (FIG. 11e), 18% lysozyme positive cells that are indicative of Paneth cells (FIG. 4b, b') and about 1% chromogranin A-expressing enteroendocrine cells (FIG. 4 c, c'; and FIG. 11). RT-qPCR confirmed presence of additional markers of differentiated enterocytes (iFABP) and Paneth cells (MMP7). The analysis of GATA4 and GATA6 and HOX factors suggested that individual organoids are a mix of proximal (GATA4+/GATA6+) and distal (GATA4-/GATA6+)(HOXA13-expressing) intestine (FIG. 12).

The molecular basis of congenital malformations in humans is often inferred from studies in model organisms. For example, Neurogenin 3 (NEUROG3) was investigated as a candidate gene responsible for congenital loss of intestinal enteroendocrine cells in humans because of its known role in enteroendocrine cell development in mouse. Since it has not yet been possible to directly determine if NEUROG3 regulates cytodifferentiation during human intestinal development, a NEUROG3-GFP fusion protein or a GFP-only control was expressed in 28 day human organoids using Adenoviral-mediated transduction. After six days, Ad-NEUROG3 infected organoids contained 5-fold more chromograninA+ endocrine cells than control organoids (Ad-EGFP) (FIG. 4e, f), demonstrating that NEUROG3 expression was sufficient to promote an enteroendocrine cell fate. The fact that cells that maintained NEUROG3-GFP expression did not differentiate into chromograninA+ endocrine cells is consistent with need to down regulate NEUROG3 prior to terminal differentiation.

More details can be found in, for example, Haveri, H., et al. Transcription factors GATA-4 and GATA-6 in normal and neoplastic human gastrointestinal mucosa. *BMC Gastroenterology* 8, 9 (2008); Wang, J., et al. Mutant neurogenin-3 in congenital malabsorptive diarrhea. [see comment]. *New England Journal of Medicine* 355, 270-280 (2006); Jenny, M., et al. Neurogenin3 is differentially required for endocrine cell fate specification in the intestinal and gastric epithelium. *Embo J* 21, 6338-6347 (2002); Lee et al., Neurogenin 3 is essential for the proper specification of gastric enteroendocrine cells and the maintenance of gastric epithelial cell identity. *Genes Dev* 16, 1488-1497 (2002); Lopez-Diaz, L., et al. Intestinal Neurogenin 3 directs differentiation of a bipotential secretory progenitor to endocrine cell rather than goblet cell fate. *Dev Biol* 309, 298-305 (2007); Ootani, A., et al. Sustained in vitro intestinal epithelial culture within a Wnt-dependent stem cell niche. *Nat Med* 15, 701-706 (2009); Zhou, Q., Brown, J., Kanarek, A., Rajagopal, J. & Melton, D. A. In vivo reprogramming of adult pancreatic exocrine cells to beta-cells. *Nature* 455, 627-632 (2008); each of which is incorporated herein in its entirety.

FIGS. 4a through 4f illustrate exemplary embodiments in accordance with the present invention, showing the formation of all major intestinal cell types and directed differentiation of the endocrine lineage with Neurogenin 3 (NEUROG3). 28 day iPSC-derived or 48 day H9 HES-derived organoids were analyzed for villin (VIL) (a) and (a'), the goblet cell marker mucin (MUC2); (b) and (b'), the paneth cell marker lysozyme (LYSO); or (c) and (c'), the endocrine cell marker chromogranin A (CGA). (d) Electron micrograph showing an enterocyte cell with a characteristic brush border with microvilli (inset). (e) and (f) Promoting endocrine cell lineage development using adenoviral-mediated expression of Neurogenin 3 (NEUROG3). pAd-NEUROG3 causes a 5-fold increase in the percent of CGA+ cells compared to a control adenovirus (pAd-GFP). Error bars denote standard error mean. Significance is shown by; *(p=0.005)

Figure 5C:
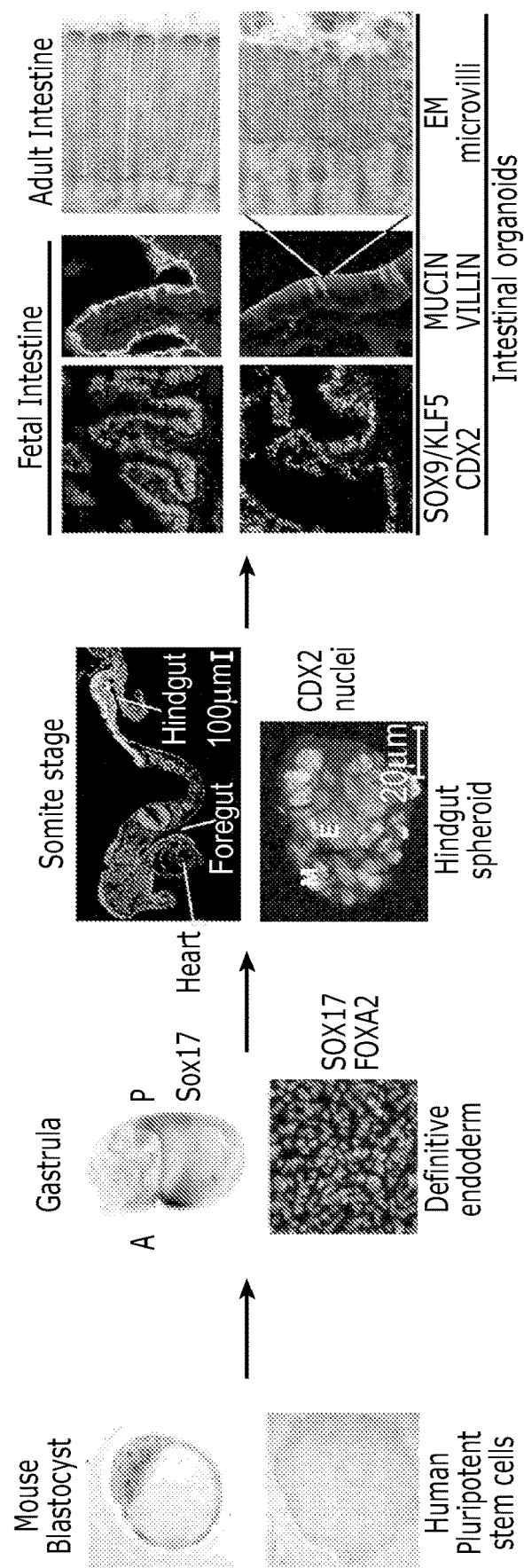
FIG. 5c includes microscopic and immunofluorescent images of mouse embryonic intestinal development (top) and human intestinal organoid development (bottom) in a side-by-side comparison.

FIGS. 5a-5c illustrate exemplary embodiments, showing a model comparing embryonic intestinal development versus directed differentiation of human PSCs into intestinal tissue in vitro. (a) Schematic of human intestinal development. At the blastocyst stage, the inner cell mass (ICM) gives rise to the entire embryo. The ICM is also the source of embryonic stem cells. At the gastrula stage, the embryo contains the three germ layers including the embryonic/definitive endoderm (yellow). The definitive endoderm forms a primitive gut tube, with the hindgut forming in the posterior region of the embryo. The hindgut undergoes intestinal morphogenesis forming the small and large intestines. (b) Schematic of directed differentiation of PSCs into intestinal tissue. PSCs cultured for 3 days in ActivinA form definitive endoderm (DE) co-expressing SOX17 and FOXA2. DE cultured for 4 days in FGF4 and Wnt3a (500 ng/ml each) form three-dimensional hindgut spheroids expressing the posterior marker CDX2. Spheroids formed intestinal organoids when grown in three dimensional conditions that favor expansion and differentiation of intestinal precursors (matrigel with 500 ng/ml R-Spondin1, 100 ng/ml Noggin and 50 ng/ml EGF. (c) Side-by-side comparison of mouse embryonic intestinal development (top) and human intestinal organoid development (bottom). PSCs underwent staged differentiation in a manner that was highly reminiscent of embryonic intestinal development and formed intestinal tissue. Stages of development in c are the same as schematically shown in (a) and (b).

FIGS. 11a through 11m illustrate exemplary embodiments in accordance with the present invention, showing the molecular analysis of stages of epithelial growth, maturation and cytodifferentiation. (a) 96 hours after FGF4+Wnt3a exposure, hindgut spheroids contained a highly proliferative cuboidal epithelium that expressed CDX2. (b)-(d) 18 day iPSC-derived organoids contained a pseudostratified epithelium that broadly expressed CDX2, KLF5 and SOX9 (b), had weak apical villin staining (c), and had begun expressing markers of cytodifferentiation including lysozyme (Lyso) (d). (e) and (f) At 28 days, organoids secreted mucin into the lumen (e-green), broadly expressed CDX2 and KLF5 and showed restricted expression of SOX9 (f). (g) The number of cells that expressed cytodifferentiation markers ChromograninA (ChA), lysozyme (Lyso) or Mucin (Muc2) was quantified and represented as a percent of total CDX2+ epithelial cells in 28d hESC organoids. (h)-(m) Quantitative analysis of intestinal markers SOX9, Villin (enterocytes), Lysozyme (Paneth cells), HOXA13, IFABP (enterocytes) and MMP7 (Paneth cells) during intestinal organoid development by RT-qPCR. Error bars denote standard deviation of triplicates.

FIGS. 12a and 12b illustrate exemplary embodiments in accordance with the present invention, showing GATA factor expression. (a) H9 hESC derived organoids show that most Cdx2 (blue) positive nuclei express Gata6 (red), whereas only a few nuclei express Gata4 (green, white arrowheads). Gata4/6 double positive cells (white arrowheads) are indicative of proximal intestine, where as Gata6+/Gata4− cells are indicative of distal intestine. (b) human iPSC derived organoids show that almost all Cdx2 positive cells (blue) are Gata6 positive (red). In this example, the organoid did not express Gata4 (green) in this section of tissue, indicating that this intestinal tissue is distal intestine.

Example 4

Mesenchymal Differentiation into Smooth Muscle

Figure 13C:
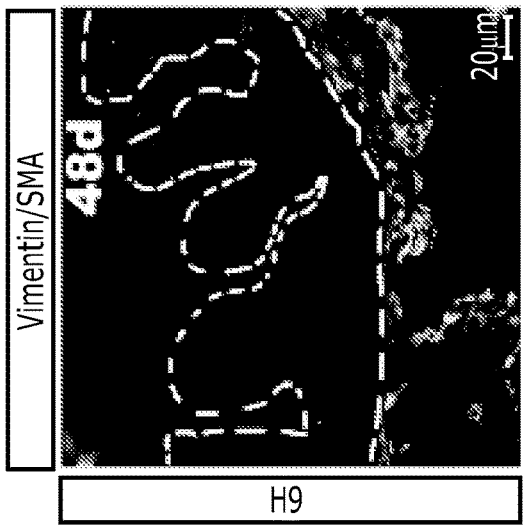
FIGS. 13a through 13f are immunofluorescent images showing mesenchymal development, in particular expression of the pan-mesenchymal markers Collagen IV (ColIV, red) and Vimentin (Vim, green) and the mesenchymal differentiation marker smooth muscle actin (SMA) during organoid development.
Figure 13F:
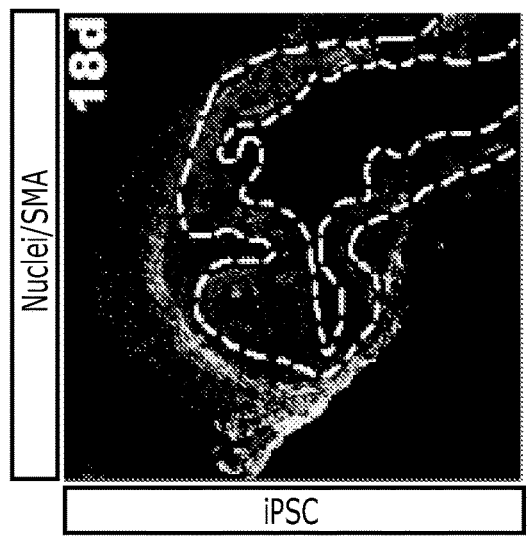
Figure 13B:
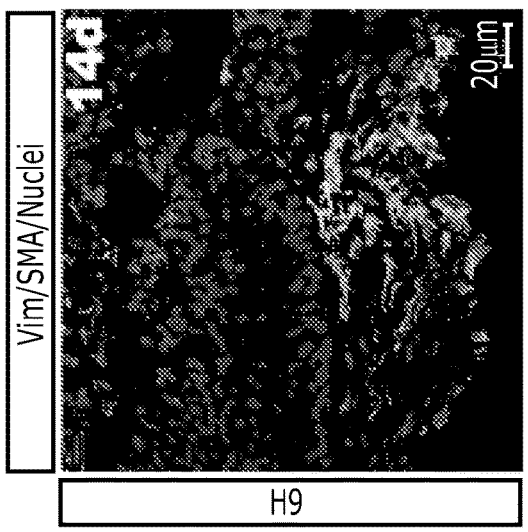
Figure 13E:
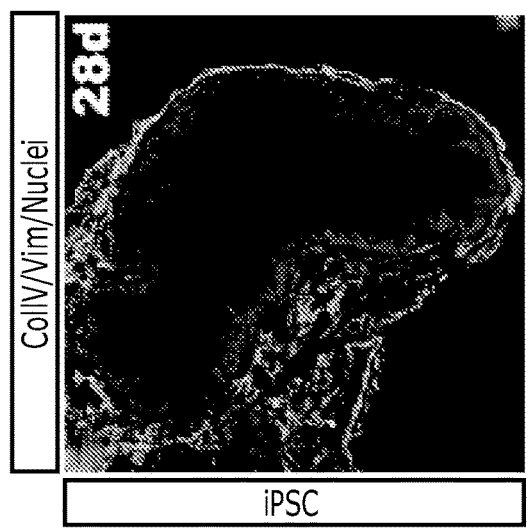

During intestinal development, epithelial and mesenchymal differentiation is regulated via a series of reciprocal signaling events. In PSC-derived cultures, the gut mesenchyme, which likely arises from the few mesoderm cells found in DE cultures, underwent stereotypic differentiation similar to developing mesenchyme in vivo. In the early stages of culture the mesenchyme underwent extensive proliferation (FIG. 3) and formed a homogeneous vimentin+/collagenIV+ layer around the epithelium (FIG. 13) similar to an e12.5 embryonic intestine (FIG. 8). By 18 days there was evidence of regional expression collagen IV, vimentin, or smooth muscle actin (SMA) in different mesenchymal layers (FIGS. 13d and 13f). By 28 days SMA+ cells had further expanded around the epithelium and by 48 days became one of several thin layers of cells adjacent to the epithelium (FIG. 13c). The fact that intestinal mesenchyme differentiation coincided with overlying epithelium suggests that epithelial-mesenchymal crosstalk may be important in the development of PSC-derived intestinal organoids.

In conclusion, this is the first report demonstrating that human PSCs can be efficiently directed to differentiate in vitro into intestinal tissue that includes multiple secretory and absorptive cell types. These findings establish an accessible and genetically tractable system to investigate the molecular basis of human congenital gut defects in vitro and to generate intestinal tissue for transplantation. Moreover human intestinal cultures are a potentially powerful tool for mechanistic studies of drug transport and absorption.

More details can be found in, for example, Zorn, A. M. & Wells, J. M. Vertebrate Endoderm Development and Organ Formation. *Annu Rev Cell Dev Biol* 25, 1-31 (2009); McLin, V. A., Henning, S. J. & Jamrich, M. The role of the visceral mesoderm in the development of the gastrointestinal tract. *Gastroenterology* 136, 2074-2091 (2009); Spence, J. R. & Wells, J. M. Translational embryology: Using embryonic principles to generate pancreatic endocrine cells from embryonic stem cells. *Developmental Dynamics* 236, 3218-3227. (2007); each of which is incorporated herein in its entirety.

Figure 13A:
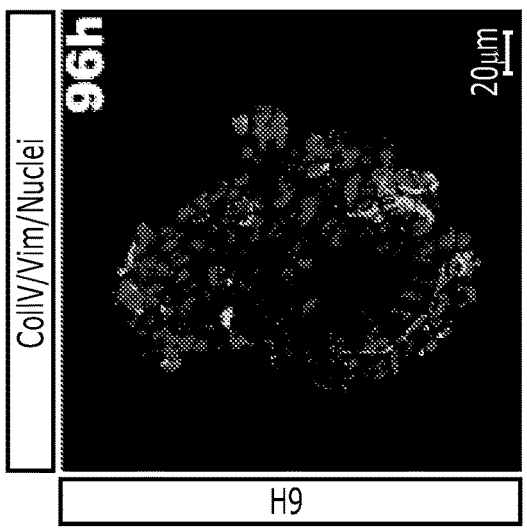
Figure 13D:
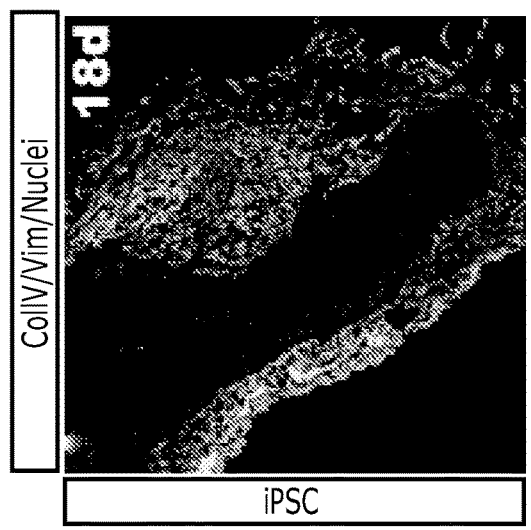

FIGS. 13a and 13f illustrate exemplary embodiments in accordance with the present invention, showing mesenchymal development. (a)-(f) Expression of the pan-mesenchymal markers Collagen IV (ColIV, red) and Vimentin (Vim, green) and the mesenchymal differentiation marker smooth muscle actin (SMA) during organoid development. a, 96 hour H9 spheroid showed Collagen IV staining (red) in the basal layer under the epithelium and weak expression of vimentin (green). b and d, By 14 to 18 days Vimentin and Collagen IV was broadly expressed in the mesenchyme surrounding the organoid epithelium. (b), (c), (f) Smooth muscle actin (SMA) was broadly expressed in 14 day organoids (b) but was restricted to a ring of cells in the 18 day organoid (f). SMA progressively became restricted to a thin layer of mesenchyme surrounding the epithelium at 48 days (c). Nuclei are stained with Draq5 and pseudo-colored blue where indicated.

Example 5

Generation and Characterization of Human iPSC Lines

For preparation of primary keratinocytes from human foreskins, tissues were cultured in dispase to remove the dermis from the epidermis, then trypsinized and cultured in serum-free low calcium medium (Epilife medium, Cascade Biologics, Portland, OR) and antibiotics. For generating iPSC lines, human keratinocytes were transduced with recombinant retroviruses expressing Oct4, Sox2, Klf4 and c-Myc and plated onto mouse embryonic fibroblast (MEF) feeders in the presence of the HDAC inhibitor valproic acid. After 2-4 weeks, iPSC colonies were picked and expanded into cell lines. The iPSC lines were expanded and passaged and analyzed for hESC-like morphology, expression of pluripotency markers (SSEA3 and Tra1-81), and karyotype. iPSC lines were maintained on MEFs or in feeder-free, defined conditions.

Example 6

Generation and Characterization of Induced Pluripotent Stem Cell Lines

Normal human skin keratinocytes (NHSK) were obtained from donors with informed consent (CCHMC IRB protocol CR1_2008-1331). NHSKs were isolated from punch biopsies following trypsinization and subsequent culture on irradiated NIH3T3 feeder cells in F media. For iPSC generation, NHSKs were transduced on two consecutive days with a 1:1:1:1 mix of recombinant RD114-pseudotyped retroviruses expressing Oct4, Sox2, Klf4 and cMyc in the presence of 8 μg/mL polybrene. Twenty-four hours after the second transduction the virus mix was replaced with fresh F media and cells were incubated for an additional three days. Cells were then trypsinized and seeded into 6 well dishes containing $1.875 \times 10^5$ irradiated mouse fibroblasts per well and Epilife medium. On the following day, media was replaced with DMEM/F12 50:50 media supplemented with 20% knockout serum replacement, 1 mM L-glutamine, 0.1 mM β-mercaptoethanol, 1× non-essential amino acids, 4 ng/mL basic fibroblast growth factor, and 0.5 mM valproic acid. Morphologically identifiable iPSC colonies arose after 2-3 weeks and were picked manually, expanded and analyzed for expression of human pluripotent stem cell markers Nanog, DNMT3b, Tra1-60 and Tra1-81. Early passage iPSC lines were adapted to feeder-free culture conditions consisting of maintenance in mTeSR1 (Stem Cell Technologies) in culture dishes coated with matrigel (BD Biosciences) and lines were karyotyped.

More details can be found in, for example, Lambert, P. F., et al. Using an immortalized cell line to study the HPV life cycle in organotypic "raft" cultures. *Methods in molecular medicine* 119, 141-155 (2005); Takahashi et al. Induction of pluripotent stem cells from adult human fibroblasts by defined factors. *Cell* 131, 861-872 (2007); Takahashi, K. & Yamanaka, S. Induction of pluripotent stem cells from mouse embryonic and adult fibroblast cultures by defined factors. Cell 126, 663-676 (2006); D'Amour et al., Production of pancreatic hormone-expressing endocrine cells from human embryonic stem cells. *Nat Biotechnol* 24, 1392-1401 (2006); Richards et al., The transcriptome profile of human embryonic stem cells as defined by SAGE. *Stem Cells* 22, 51-64 (2004); Thomson, J. A., et al. Embryonic stem cell lines derived from human blastocysts. *Science* 282, 1145-1147 (1998); each of which is incorporated herein in its entirety.

Example 7

Microarray Analysis of Human ESCs, iPSCs and DE Cultures

For microarray analysis, RNA was isolated from undifferentiated and 3-day activin treated hESC and iPSC cultures and used create target DNA for hybridization to Affymetrix Human 1.0 Gene ST Arrays using standard procedures (Affymetrix, Santa Clara, CA). Independent biological triplicates were performed for each cell line and condition. Affymetrix microarray Cel files were subjected to Robust Multichip Average (RMA) normalization in GeneSpring 10.1. Probe sets were first filtered for those that are overexpressed or underexpressed and then subjected to statistical analysis for differential expression by 3 fold or more between undifferentiated and differentiated cultures with $p<0.05$ using the Students T-test. This procedure generated a list of 530 probe sets, as shown in Table 2. Log 2 gene expression ratios were then subjected to hierachical clustering using the standard correlation distance metric as implemented in GeneSpring.

TABLE 2

Variations of Transcript levels (2-fold or more) during
DE formation in hESC-H9 and iPSC lines 3.12, 3.5, and 3.6

| GENE SYMBOL | D<sub>IFF'D</sub>-H9] VS [IFF'D-H9] (folds) | [DIFF'D-IPSC3.12] VS [IFF'D-IPSC3.12] (folds) | [Diff'd-iPSC3.4] vs [Undiff d-iPSC3.4] (folds) | GENE DESCRIPTION |
|---|---|---|---|---|
| CER1 | 137.61 | 67.98 | 66.76 | cerberus 1, cysteine knot superfamily, homolog (Xenopus laevis) |
| HAS2 | 32.29 | 15.27 | 13.43 | hyaluronan synthase 2 |
| PRDM1 | 30.35 | 24.92 | 21.56 | PR domain containing 1, with ZNF domain |
| SEMA3E | 30.17 | 21.66 | 19.36 | sema domain, immunoglobulin domain (Ig), short basic domain, secreted, (semaphorin) 3E |
| MFAP4 | 28.35 | 29.08 | 35.47 | microfibrillar-associated protein 4 |
| EOMES | 28.31 | 19.85 | 27.72 | eomesodermin homolog (Xenopus laevis) |
| CYP26A1 | 28.12 | 41.18 | 47.21 | cytochrome P450, family 26, subfamily A, polypeptide 1 |
| SLC40A1 | 27.82 | 33.13 | 34.77 | solute carrier family 40 (iron-regulated transporter), member 1 |
| CXCR4 | 24.73 | 23.19 | 19.91 | chemokine (C-X-C motif) receptor 4 |
| FGF17 | 17.92 | 15.78 | 19.00 | fibroblast growth factor 17 |
| TRPA1 | 17.40 | 25.46 | 23.50 | transient receptor potential cation channel, subfamily A, member 1 |
| ANKRD1 | 17.20 | 11.45 | 8.97 | ankyrin repeat domain 1 (cardiac muscle) |
| LOC100132916 | 15.91 | 12.59 | 9.65 | similar to hCG1811192 |
| PCDH10 | 15.88 | 18.81 | 23.07 | protocadherin 10 |
| RHOBTB3 | 15.76 | 12.01 | 8.61 | Rho-related BTB domain containing 3 |
| LGR5 | 15.44 | 12.18 | 12.88 | leucine-rich repeat-containing G protein-coupled receptor 5 |
| CD48 | 14.69 | 18.02 | 15.22 | |
| ST8SIA4 | 14.68 | 10.83 | 9.75 | ST8 alpha-N-acetyl-neuraminide alpha-2,8-sialyltransferase 4 |
| COL5A2 | 14.57 | 13.25 | 15.28 | collagen, type V, alpha 2 |
| COLEC12 | 13.69 | 11.08 | 12.98 | collectin sub-family member 12 |
| FLRT3 | 12.96 | 15.64 | 11.19 | fibronectin leucine rich transmembrane protein 3 |
| CHL1 | 12.67 | 2.89 | 3.63 | cell adhesion molecule with homology to L1CAM (close homolog of L1) |
| ELOVL2 | 12.67 | 6.73 | 6.61 | elongation of very long chain fatty acids (FEN1/Elo2, SUR4/Elo3, yeast-like 2 |
| CCL2 | 12.64 | 18.30 | 14.69 | chemokine (C-C motif) ligand 2 |
| MIXL1 | 12.51 | 7.17 | 8.06 | Mix1 homeobox-like 1 (Xenopus laevis) |
| MGST2 | 11.94 | 15.71 | 13.68 | microsomal glutathione S-transferase 2 |
| EHHADH | 11.32 | 9.12 | 8.12 | enoyl-Coenzyme A, hydratase/3-hydroxyacyl Coenzyme A dehydrogenase |
| PLXNA2 | 11.05 | 9.37 | 9.50 | plexin A2 |
| DIO3 | 10.97 | 9.31 | 7.22 | deiodinase, iodothyronine, type III |
| KLF8 | 10.94 | 6.17 | 5.97 | Kruppel-like factor 8 |
| PEG10 | 10.92 | 3.35 | 3.97 | paternally expressed 10 |
| TDRD7 | 10.91 | 9.40 | 9.32 | tudor domain containing 7 |
| MANEA | 10.90 | 8.67 | 8.97 | mannosidase, endo-alpha |
| UPK1B | 10.83 | 5.46 | 5.74 | uroplakin 1B |
| ROR2 | 10.22 | 8.35 | 8.35 | receptor tyrosine kinase-like orphan receptor 2 |
| CCKBR | 9.79 | 12.68 | 9.37 | cholecystokinin B receptor |
| DKK1 | 9.66 | 6.27 | 7.27 | dickkopf homolog 1 (Xenopus laevis) |
| SERPINB9 | 9.32 | 10.27 | 10.52 | serpin peptidase inhibitor, clade B (ovalbumin), member 9 |
| OR5P2 | 9.18 | 5.08 | 6.24 | olfactory receptor, family 5, subfamily P, member 2 |
| OVCH2 | 9.06 | 6.77 | 7.92 | ovochymase 2 |
| FRZB | 8.79 | 5.92 | 5.20 | frizzled-related protein |
| SAMD3 | 8.40 | 8.88 | 7.82 | sterile alpha motif domain containing 3 |
| HHEX | 8.37 | 15.27 | 10.62 | hematopoietically expressed homeobox |
| PPAPDC1A | 8.00 | 4.50 | 3.94 | phosphatidic acid phosphatase type 2 domain containing 1A |
| MYL7 | 7.96 | 6.41 | 7.32 | myosin, light chain 7, regulatory |
| PLSCR4 | 7.87 | 7.11 | 8.62 | phospholipid scramblase 4 |

TABLE 2-continued

Variations of Transcript levels (2-fold or more) during
DE formation in hESC-H9 and iPSC lines 3.12, 3.5, and 3.6

| GENE SYMBOL | D$_{IFF'D}$-H9] VS [IFF'D-H9] (folds) | [DIFF'D-IPSC3.12] VS [IFF'D-IPSC3.12] (folds) | [Diff'd-iPSC3.4] vs [Undiff d-iPSC3.4] (folds) | GENE DESCRIPTION |
|---|---|---|---|---|
| ITAG5 | 7.82 | 4.31 | 4.38 | integrin, alpha 5 (fibronectin receptor, alpha polypeptide) |
| ENC1 | 7.76 | 3.37 | 3.08 | ectodermal-neural cortex (with BTB-like domain) |
| TNC | 7.73 | 6.30 | 9.01 | tenascin C (hexabrachion) |
| C5 | 7.59 | 14.18 | 14.56 | complement component 5 |
| SOX17 | 7.34 | 7.29 | 7.58 | SRY (sex determining region Y)-box 17 |
| RLBP1L2 | 7.31 | 6.87 | 6.65 | retinaldehyde binding protein 1-like 2 |
| VAMP8 | 7.30 | 3.74 | 4.09 | vesicle-associated membrane protein 8 (endobrevin) |
| PLCE1 | 7.11 | 7.55 | 6.70 | phospholipase C, epsilon 1 |
| NTN4 | 7.09 | 6.11 | 5.15 | netrin 4 |
| PROS1 | 7.01 | 4.02 | 4.07 | protein S (alpha) |
| LRIG3 | 6.97 | 9.55 | 9.18 | leucine-rich repeats and immunoglobulin-like domains 3 |
| CDH2 | 6.89 | 8.08 | 7.38 | cadherin 2, type 1, N-cadherin (neuronal) |
| CFLAR | 6.84 | 6.90 | 6.63 | CASP8 and FADD-like apoptosis regulator |
| ARHGAP24 | 6.74 | 5.33 | 5.92 | Rho GTPase activating protein 24 |
| C6ORF60 | 6.67 | 7.85 | 6.40 | chromosome 6 open reading frame 60 |
| MCC | 6.48 | 3.48 | 3.37 | mutated in colorectal cancers |
| GPR177 | 6.42 | 5.21 | 4.84 | G protein-coupled receptor 177 |
| CPE | 6.36 | 7.33 | 6.89 | carboxypeptidase E |
| C9ORF19 | 6.14 | 5.15 | 5.52 | chromosome 9 open reading frame 19 |
| PLSCR1 | 5.99 | 4.35 | 3.70 | phospholipid scramblase 1 |
| BMP2 | 5.95 | 7.43 | 6.96 | bone morphogenetic protein 2 |
| OR5P3 | 5.80 | 3.50 | 4.65 | olfactory receptor, family 5, subfamily P, member 3 |
| FN1 | 5.77 | 3.80 | 3.73 | fibronectin 1 |
| TBC1D9 | 5.72 | 5.94 | 5.11 | TBC1 domain family, member 9 (with GRAM domain) |
| VWF | 5.69 | 5.27 | 5.12 | von Willebrand factor |
| NODAL | 5.66 | 5.77 | 5.00 | nodal homolog (mouse) |
| GSC | 5.57 | 5.37 | 5.22 | goosecoid homeobox |
| SMAD6 | 5.53 | 2.54 | 2.97 | SMAD family member 6 |
| S100Z | 5.52 | 4.68 | 4.36 | S100 calcium binding protein Z |
| ARHGAP29 | 5.52 | 4.47 | 4.19 | Rho GTPase activating protein 29 |
| LHX1 | 5.51 | 4.72 | 4.60 | LIM homeobox 1 |
| ARSE | 5.42 | 5.47 | 5.25 | arylsulfatase E (chondrodysplasia punctata 1) |
| CNGA4 | 5.39 | 4.06 | 4.78 | cyclic nucleotide gated channel alpha 4 |
| AHNAK | 5.34 | 4.93 | 4.71 | |
| SEPP1 | 5.28 | 5.27 | 4.42 | selenoprotein P, plasma, 1 |
| PROS1 | 5.23 | 3.60 | 3.95 | protein S (alpha) |
| CALCR | 5.20 | 3.44 | 3.13 | calcitonin receptor |
| IER3 | 5.14 | 6.06 | 5.38 | immediate early response 3 |
| MAN1A1 | 5.12 | 4.60 | 4.23 | mannosidase, alpha, class 1A, member 1 |
| KCNG1 | 5.09 | 3.70 | 4.11 | potassium voltage-gated channel, subfamily G, member 1 |
| BNIP3 | 5.08 | 3.56 | 3.35 | BCL2/adenovirus E1B 19 kDa interacting protein 3 |
| H2AFY2 | 5.05 | 7.17 | 6.81 | H2A histone family, member Y2 |
| FAM122C | 5.03 | 4.61 | 4.20 | family with sequence similarity 122C |
| FMN2 | 5.03 | 3.77 | 4.77 | formin 2 |
| PPFIBP2 | 5.03 | 4.02 | 4.10 | PTPRF interacting protein, binding protein 2 (liprin beta 2) |
| ARRDC3 | 4.99 | 4.14 | 3.33 | arrestin domain containing 3 |
| GATM | 4.99 | 4.95 | 3.94 | glycine amidinotransferase (L-arginine: glycine amidinotransferase) |
| C21ORF129 | 4.97 | 10.33 | 8.83 | chromosome 21 open reading frame 129 |
| KRT8 | 4.96 | 2.41 | 2.50 | keratin 8 |
| ADAM19 | 4.96 | 4.37 | 4.36 | ADAM metallopeptidase domain 19 (meltrin beta) |

TABLE 2-continued

Variations of Transcript levels (2-fold or more) during
DE formation in hESC-H9 and iPSC lines 3.12, 3.5, and 3.6

| GENE SYMBOL | D<sub>IFF'D</sub>-H9] VS [IFF'D-H9] (folds) | [DIFF'D-IPSC3.12] VS [IFF'D-IPSC3.12] (folds) | [Diff'd-iPSC3.4] vs [Undiff d-iPSC3.4] (folds) | GENE DESCRIPTION |
|---|---|---|---|---|
| BTG2 | 4.90 | 3.29 | 3.20 | BTG family, member 2 |
| ARRB1 | 4.90 | 2.66 | 3.03 | arrestin, beta 1 |
| AGL | 4.90 | 3.65 | 3.09 | amylo-1, 6-glucosidase, 4-alpha-glucanotransferase (glycogen debranching enzyme, glycogen storage disease type III) |
| IFLTD1 | 4.86 | 2.44 | 2.79 | intermediate filament tail domain containing 1 |
| TIPARP | 4.84 | 4.13 | 3.77 | TCDD-inducible poly(ADP-ribose) polymerase |
| NFKBIA | 4.83 | 4.56 | 4.41 | nuclear factor of kappa light polypeptide gene enhancer in B-cells inhibitor, alpha |
| RNF19A | 4.79 | 5.77 | 4.63 | ring finger protein 19A |
| PDZK1 | 4.77 | 3.94 | 3.57 | PDZ domain containing 1 |
| RNF152 | 4.77 | 4.66 | 4.52 | ring finger protein 152 |
| RPRM | 4.76 | 4.83 | 4.58 | reprimo, TP53 dependent G2 arrest mediator candidate |
| TGFB1 | 4.74 | 2.98 | 3.54 | transforming growth factor, beta 1 |
| CAMK2D | 4.64 | 4.00 | 3.77 | calcium/calmodulin-dependent protein kinase (CaM kinase) II delta |
| ARL4D | 4.62 | 4.07 | 3.95 | ADP-ribosylation factor-like 4D |
| ARHGAP28 | 4.60 | 3.54 | 3.27 | Rho GTPase activating protein 28 |
| C8ORF49 | 4.59 | 4.09 | 3.45 | chromosome 8 open reading frame 49 |
| MATN3 | 4.57 | 4.36 | 5.19 | matrilin 3 |
| DUSP10 | 4.54 | 4.45 | 4.76 | dual specificity phosphatase 10 |
| PTPRM | 4.51 | 5.04 | 5.21 | protein tyrosine phosphatase, receptor type, M |
| RNF125 | 4.49 | 3.53 | 3.28 | ring finger protein 125 |
| ACOX3 | 4.48 | 5.42 | 5.45 | acyl-Coenzyme A oxidase 3, pristanoyl |
| SLC22A3 | 4.40 | 4.27 | 5.11 | solute carrier family 22 (extraneuronal monoamine transporter), member 3 |
| IER3 | 4.39 | 4.79 | 4.34 | immediate early response 3 |
| NR0B1 | 4.39 | 11.17 | 9.41 | nuclear receptor subfamily 0, group B, member 1 |
| S1PR3|C9ORF47 | 4.39 | 3.21 | 4.05 | sphingosine-1-phosphate receptor 3 | chromosome 9 open reading frame 47 |
| IER3 | 4.39 | 4.80 | 4.34 | immediate early response 3 |
| C8ORF79 | 4.32 | 3.02 | 2.86 | chromosome 8 open reading frame 79 |
| EPSTI1 | 4.32 | 4.91 | 4.62 | epithelial stromal interaction 1 (breast) |
| KRT19 | 4.27 | 2.48 | 2.56 | keratin 19 |
| USP53 | 4.26 | 3.53 | 3.00 | ubiquitin specific peptidase 53 |
| GPSM2 | 4.21 | 5.06 | 4.09 | G-protein signaling modulator 2 (AGS3-like, *C. elegans*) |
| PRSS35 | 4.19 | 5.55 | 5.36 | protease, serine, 35 |
| RELN | 4.13 | 3.02 | 3.30 | reelin |
| RBM24 | 4.12 | 4.75 | 3.60 | RNA binding motif protein 24 |
| RASGEF1B | 4.05 | 3.15 | 3.59 | RasGEF domain family, member IB |
| MERTK | 4.01 | 3.13 | 3.67 | c-mer proto-oncogene tyrosine kinase |
| OTX2 | 4.01 | 5.22 | 5.32 | orthodenticle homeobox 2 |
| MAML3 | 4.00 | 3.41 | 3.52 | mastermind-like 3 (*Drosophila*) |
| PDE10A | 3.98 | 4.60 | 4.58 | phosphodiesterase 10A |
| PLCXD3 | 3.98 | 3.34 | 2.49 | phosphatidylinositol-specific phospholipase C, X domain containing 3 |
| GREM2 | 3.97 | 3.14 | 3.50 | gremlin 2, cysteine knot superfamily, homolog (*Xenopus laevis*) |
| MYO3A | 3.93 | 4.17 | 4.62 | myosin IIIA |
| NEK7 | 3.92 | 3.53 | 3.02 | NIMA (never in mitosis gene a)-related kinase 7 |
| LEPREL1 | 3.92 | 6.42 | 6.24 | leprecan-like 1 |
| MOBP | 3.92 | 2.68 | 2.52 | myelin-associated oligodendrocyte basic protein |
| KCNH8 | 3.87 | 4.09 | 3.76 | potassium voltage-gated channel, subfamily H (eag-related), member 8 |
| FAM20A | 3.84 | 4.69 | 5.21 | family with sequence similarity 20, member A |
| MID2 | 3.83 | 2.46 | 2.43 | midline 2 |
| SETD7 | 3.82 | 3.65 | 3.68 | SET domain containing (lysine methyltransferase) 7 |

TABLE 2-continued

Variations of Transcript levels (2-fold or more) during
DE formation in hESC-H9 and iPSC lines 3.12, 3.5, and 3.6

| GENE SYMBOL | D$_{IFF'D}$-H9] VS [IFF'D-H9] (folds) | [DIFF'D-IPSC3.12] VS [IFF'D-IPSC3.12] (folds) | [Diff'd-iPSC3.4] vs [Undiff d-iPSC3.4] (folds) | GENE DESCRIPTION |
|---|---|---|---|---|
| MYCT1 | 3.79 | 6.63 | 6.07 | myc target 1 |
| KIAA0825 | 3.75 | 4.30 | 4.73 | |
| FLRT2 | 3.74 | 2.88 | 3.40 | fibronectin leucine rich transmembrane protein 2 |
| PREX1 | 3.73 | 2.87 | 3.03 | phosphatidylinositol 3,4,5-trisphosphate-dependent RAC exchanger 1 |
| ASAM | 3.73 | 3.68 | 3.58 | adipocyte-specific adhesion molecule |
| CYP1B1 | 3.71 | 2.20 | 2.15 | cytochrome P450, family 1, subfamily B, polypeptide 1 |
| YPEL5 | 3.70 | 2.91 | 2.95 | yippee-like 5 (Drosophila) |
| SEMA5A | 3.69 | 5.53 | 5.37 | sema domain, seven thrombospondin repeats (type 1 and type 1-like), transmembrane domain (TM) and short cytoplasmic domain, (semaphorin) 5A |
| LEFTY2 | 3.68 | 8.55 | 6.11 | left-right determination factor 2 |
| C9ORF52 | 3.62 | 3.58 | 3.12 | chromosome 9 open reading frame 52 |
| SLITRK2\|LOC100129095 | 3.62 | 3.66 | 3.73 | SLIT and NTRK-like family, member 2 \| similar to CXorf2 protein |
| SERPINE2 | 3.61 | 3.78 | 3.80 | serpin peptidase inhibitor, clade E (nexin, plasminogen activator inhibitor type 1), member 2 |
| B3GNT5 | 3.57 | 2.85 | 2.91 | UDP-GlcNAc:betaGal beta-1,3-N-acetylglucosaminyltransferase 5 |
| SLCO2A1 | 3.57 | 2.32 | 2.14 | solute carrier organic anion transporter family, member 2A1 |
| SLC35F3 | 3.55 | 3.21 | 3.38 | solute carrier family 35, member F3 |
| SOX5 | 3.55 | 4.09 | 3.99 | SRY (sex determining region Y)-box 5 |
| NUDT4P1 | 3.54 | 2.88 | 2.42 | nudix (nucleoside diphosphate linked moiety X)-type motif 4 pseudogene 1 |
| ANGPT2 | 3.54 | 5.23 | 3.90 | angiopoietin 2 |
| CAP2 | 3.53 | 2.97 | 3.00 | CAP, adenylate cyclase-associated protein, 2 (yeast) |
| NETO2 | 3.50 | 2.25 | 2.21 | neuropilin (NRP) and tolloid (TLL)-like 2 |
| TRY6\|PRSS2\|PRSS1\|PRSS3\|LOC100134294 | 3.50 | 3.12 | 3.59 | trypsinogen C \| protease, serine, 2 (trypsin 2) \| protease, serine, 1 (trypsin 1) \| protease, serine, 3 \| hypothetical protein LOC100134294 |
| ANGPT1 | 3.49 | 3.56 | 3.37 | angiopoietin 1 |
| VANGL1 | 3.48 | 2.94 | 2.79 | vang-like 1 (van gogh, Drosophila) |
| CDA | 3.48 | 4.14 | 3.63 | cytidine deaminase |
| MCF2l2 | 3.46 | 3.33 | 3.11 | MCF.2 cell line derived transforming sequence-like 2 |
| C9ORF95 | 3.44 | 2.28 | 2.13 | chromosome 9 open reading frame 95 |
| GATA4 | 3.42 | 2.89 | 2.77 | GAT A binding protein 4 |
| MAGI3 | 3.39 | 3.20 | 3.13 | membrane associated guanylate kinase, WW and PDZ domain containing 3 |
| WNT3 | 3.39 | 2.97 | 3.36 | wingless-type MMTV integration site family, member 3 |
| APOBEC3G\|APOBEC3F | 3.36 | 2.79 | 2.90 | apolipoprotein B mRNA editing enzyme, catalytic polypeptide-like 3G \|apolipoprotein B mRNA editing enzyme, catalytic polypeptide-like 3F |
| FOXA2 | 3.36 | 3.08 | 3.93 | forkhead box A2 |
| BRDT | 3.34 | 2.82 | 2.33 | bromodomain, testis-specific |
| TCAG7.1177 | 3.33 | 2.60 | 3.10 | opposite strand transcription unit to STAG3 |
| LOC389523\|LOC729438\|LOC730322 | 3.33 | 2.59 | 3.10 | similar to opposite strand transcription unit to Stag3 |
| ZSWIM5 | 3.32 | 2.79 | 2.75 | zinc finger, SWIM-type containing 5 |
| COCH | 3.32 | 2.08 | 2.53 | coagulation factor C homolog, cochlin (Limulus polyphemus) |
| EPHA4 | 3.31 | 4.54 | 4.66 | EPH receptor A4 |
| C1ORF61 | 3.30 | 3.51 | 3.49 | chromosome 1 open reading frame 61 |
| KEL | 3.29 | 4.02 | 4.07 | Kell blood group, metallo-endopeptidase |

TABLE 2-continued

Variations of Transcript levels (2-fold or more) during
DE formation in hESC-H9 and iPSC lines 3.12, 3.5, and 3.6

| GENE SYMBOL | D_IFF'D-H9] VS [IFF'D-H9] (folds) | [DIFF'D-IPSC3.12] VS [IFF'D-IPSC3.12] (folds) | [Diff'd-iPSC3.4] vs [Undiff d-iPSC3.4] (folds) | GENE DESCRIPTION |
|---|---|---|---|---|
| PPM1K | 3.29 | 3.71 | 3.74 | protein phosphatase 1K (PP2C domain containing) |
| SORCS1 | 3.29 | 3.64 | 4.01 | sortilin-related VPS10 domain containing receptor 1 |
| SLC46A3 | 3.28 | 2.01 | 2.00 | solute carrier family 46, member 3 |
| BHLHB2 | 3.23 | 2.26 | 2.43 | basic helix-loop-helix domain containing, class B, 2 |
| BMPR2 | 3.23 | 3.64 | 3.57 | bone morphogenetic protein receptor, type II (serine/threonine kinase) |
| CAMKK2 | 3.21 | 2.94 | 3.14 | calcium/calmodulin-dependent protein kinase kinase 2, beta |
| DAB2 | 3.21 | 2.38 | 2.30 | disabled homolog 2, mitogen-responsive phosphoprotein (*Drosophila*) |
| ELMO1 | 3.20 | 5.68 | 4.76 | engulfment and cell motility 1 |
| SEMA6D | 3.20 | 6.82 | 6.05 | sema domain, transmembrane domain (TM), and cytoplasmic domain, (semaphorin) 6D |
| CXCR7 | 3.20 | 3.18 | 3.21 | chemokine (C-X-C motif) receptor 7 |
| P4HA1 | 3.20 | 2.63 | 2.45 | procollagen-proline, 2-oxoglutarate 4-dioxygenase (proline 4-hydroxylase), alpha polypeptide I |
| YAF2 | 3.17 | 2.48 | 2.87 | YY1 associated factor 2 |
| TMOD1 | 3.16 | 2.61 | 2.62 | tropomodulin 1 |
| RALB | 3.16 | 2.41 | 2.11 | v-ral simian leukemia viral oncogene homolog B (ras related; GTP binding protein) |
| FBN2 | 3.13 | 3.58 | 4.30 | fibrillin 2 (congenital contractural arachnodactyly) |
| KIAA1161 | 3.10 | 2.84 | 3.74 | |
| LTB4DH | 3.10 | 3.08 | 2.77 | leukotriene B4 12-hydroxydehydrogenase |
| DUSP4 | 3.10 | 3.14 | 2.43 | dual specificity phosphatase 4 |
| GPR39 | 3.09 | 5.74 | 6.56 | G protein-coupled receptor 39 |
| CNTN4 | 3.08 | 2.58 | 2.54 | contactin 4 |
| FRRS1 | 3.06 | 2.21 | 2.07 | ferric-chelate reductase 1 |
| PGM1 | 3.03 | 2.67 | 2.67 | phosphoglucomutase 1 |
| PDK1 | 3.03 | 4.84 | 5.36 | pyruvate dehydrogenase kinase, isozyme 1 |
| SOAT1 | 3.03 | 3.19 | 2.88 | sterol O-acyltransferase (acyl-Coenzyme A: cholesterol acyltransferase) 1 |
| CCDC92 | 3.00 | 2.79 | 2.97 | coiled-coil domain containing 92 |
| ZNF792 | 3.00 | 2.44 | 2.22 | zinc finger protein 792 |
| SLC35A3 | 3.00 | 3.55 | 2.83 | solute carrier family 35 (UDP-N-acetylglucosamine (UDP-GlcNAc) transporter), member A3 |
| SMAD7 | 3.00 | 2.23 | 2.07 | SMAD family member 7 |
| CEP55 | 2.99 | 2.02 | 2.08 | centrosomal protein 55 kDa |
| DDAH2 | 2.99 | 2.14 | 2.44 | dimethylarginine dimethylaminohydrolase 2 |
| DDAH2 | 2.98 | 2.15 | 2.44 | dimethylarginine dimethylaminohydrolase 2 |
| APOC1 | 2.97 | 2.73 | 2.14 | apolipoprotein C-I |
| TMEM133 | 2.95 | 3.63 | 3.12 | transmembrane protein 133 |
| HNF1B | 2.95 | 2.25 | 2.64 | HNF1 homeobox B |
| FLJ32810 | 2.94 | 3.55 | 2.92 | |
| RAP1GDS1 | 2.91 | 2.27 | 2.38 | RAP1, GTP-GDP dissociation stimulator 1 |
| DDAH2 | 2.90 | 2.08 | 2.29 | dimethylarginine dimethylaminohydrolase 2 |
| C5ORF36 | 2.90 | 2.59 | 2.45 | chromosome 5 open reading frame 36 |
| GCNT1 | 2.89 | 4.78 | 5.38 | glucosaminyl (N-acetyl) transferase 1, core 2 (beta-1,6-N-acetylglucosaminyltransferase) |
| APOBEC3D | 2.89 | 2.21 | 2.03 | apolipoprotein B mRNA editing enzyme, catalytic polypeptide-like 3D |
| NPPB | 2.88 | 3.62 | 3.57 | natriuretic peptide precursor B |
| MLYCD | 2.87 | 2.89 | 2.78 | malonyl-CoA decarboxylase |
| AADAT | 2.86 | 2.49 | 2.25 | aminoadipate aminotransferase |
| STMN2 | 2.85 | 5.88 | 5.04 | stathmin-like 2 |

TABLE 2-continued

Variations of Transcript levels (2-fold or more) during
DE formation in hESC-H9 and iPSC lines 3.12, 3.5, and 3.6

| GENE SYMBOL | D_IFF'D-H9] VS [IFF'D-H9] (folds) | [DIFF'D-IPSC3.12] VS [IFF'D-IPSC3.12] (folds) | [Diff'd-iPSC3.4] vs [Undiff d-iPSC3.4] (folds) | GENE DESCRIPTION |
|---|---|---|---|---|
| SULF2 | 2.85 | 3.19 | 2.99 | sulfatase 2 |
| ANKRA6 | 2.84 | 3.01 | 3.06 | ankyrin repeat domain 6 |
| TBX3 | 2.84 | 2.18 | 2.16 | T-box 3 (ulnar mammary syndrome) |
| APOA2 | 2.83 | 3.62 | 3.42 | apolipoprotein A-II |
| PPFIBP1 | 2.83 | 2.60 | 2.45 | PTPRF interacting protein, binding protein 1 (liprin beta 1) |
| ALDH1A1 | 2.82 | 2.46 | 2.18 | aldehyde dehydrogenase 1 family, member Al |
| LIFR | 2.82 | 2.31 | 2.51 | leukemia inhibitory factor receptor alpha |
| ID1 | 2.81 | 2.49 | 2.73 | inhibitor of DNA binding 1, dominant negative helix-loop-helix protein |
| MTUS1 | 2.81 | 2.72 | 2.99 | mitochondrial tumor suppressor 1 |
| MYL4 | 2.80 | 2.45 | 2.05 | myosin, light chain 4, alkali; atrial, embryonic |
| YPEL2 | 2.80 | 2.68 | 2.30 | yippee-like 2 (*Drosophila*) |
| FZD5 | 2.80 | 6.24 | 5.60 | frizzled homolog 5 (*Drosophila*) |
| TNNC1 | 2.80 | 2.31 | 2.03 | troponin C type 1 (slow) |
| TMPRSS11E\|TMPRSS11E2 | 2.79 | 3.23 | 3.04 | transmembrane protease, serine 11E transmembrane protease, serine 11E2 |
| CCDC75 | 2.78 | 2.47 | 2.15 | coiled-coil domain containing 75 |
| EGF | 2.78 | 4.20 | 3.94 | epidermal growth factor (beta-urogastrone) |
| KIT | 2.78 | 4.03 | 3.60 | v-kit Hardy-Zuckerman 4 feline sarcoma viral oncogene homolog |
| TMPRSS11E\|TMPRSS11E2 | 2.76 | 3.23 | 2.97 | transmembrane protease, serine 11E transmembrane protease, serine 11E2 |
| KCNG1 | 2.72 | 2.33 | 2.68 | potassium voltage-gated channel, subfamily G, member 1 |
| CUGBP2 | 2.72 | 2.54 | 2.11 | CUG triplet repeat, RNA binding protein 2 |
| CDH10 | 2.71 | 3.23 | 4.02 | cadherin 10, type 2 (T2-cadherin) |
| LEFTY1 | 2.70 | 4.86 | 5.04 | left-right determination factor 1 |
| C20ORF95 | 2.68 | 3.26 | 3.35 | chromosome 20 open reading frame 95 |
| ACSS3 | 2.67 | 2.12 | 2.10 | acyl-CoA synthetase short-chain family member 3 |
| FAM126B | 2.67 | 2.27 | 2.00 | family with sequence similarity 126, member B |
| PERP | 2.66 | 2.40 | 2.73 | |
| GATA6 | 2.65 | 3.93 | 4.05 | GAT A binding protein 6 |
| ANKS1B | 2.64 | 2.39 | 2.26 | ankyrin repeat and sterile alpha motif domain containing 1B |
| CA2 | 2.61 | 2.48 | 2.36 | carbonic anhydrase II |
| TMEM135 | 2.58 | 2.71 | 2.72 | transmembrane protein 135 |
| CCDC3 | 2.58 | 2.68 | 2.84 | coiled-coil domain containing 3 |
| JAKMIP1 | 2.57 | 2.02 | 2.07 | janus kinase and microtubule interacting protein 1 |
| APOBEC3C\|APOBEC3D | 2.55 | 2.40 | 2.44 | apolipoprotein B mRNA editing enzyme, catalytic polypeptide-like 3C apolipoprotein B mRNA editing enzyme, catalytic polypeptide-like 3D |
| FZD8 | 2.54 | 3.57 | 3.26 | frizzled homolog 8 (*Drosophila*) |
| SYNJ1 | 2.54 | 2.43 | 2.33 | synaptojanin 1 |
| GATA3 | 2.54 | 2.04 | 2.15 | GAT A binding protein 3 |
| QPCT | 2.53 | 3.59 | 3.29 | glutaminyl-peptide cyclotransferase (glutaminyl cyclase) |
| C8ORF79 | 2.52 | 2.17 | 2.90 | chromosome 8 open reading frame 79 |
| ZNF702 | 2.52 | 2.41 | 2.01 | zinc finger protein 702 |
| EDNRA | 2.52 | 2.69 | 2.27 | endothelin receptor type A |
| MAGED1 | 2.51 | 2.89 | 2.99 | melanoma antigen family D, 1 |
| DTWD2 | 2.50 | 2.53 | 2.32 | DTW domain containing 2 |
| KITLG | 2.48 | 2.12 | 2.82 | KIT ligand |
| APOBEC3F\|APOBEC3G | 2.48 | 2.48 | 2.29 | apolipoprotein B mRNA editing enzyme, catalytic polypeptide-like 3F apolipoprotein B mRNA editing enzyme, catalytic polypeptide-like 3G |
| ETS2 | 2.47 | 2.17 | 2.05 | v-ets erythroblastosis virus E26 oncogene homolog 2 (avian) |

TABLE 2-continued

Variations of Transcript levels (2-fold or more) during
DE formation in hESC-H9 and iPSC lines 3.12, 3.5, and 3.6

| GENE SYMBOL | D_IFF'D-H9] VS [IFF'D-H9] (folds) | [DIFF'D-IPSC3.12] VS [IFF'D-IPSC3.12] (folds) | [Diff'd-iPSC3.4] vs [Undiff d-iPSC3.4] (folds) | GENE DESCRIPTION |
|---|---|---|---|---|
| GNAL | 2.46 | 3.70 | 3.72 | guanine nucleotide binding protein (G protein), alpha activating activity polypeptide, olfactory type |
| ZNF518B | 2.45 | 3.00 | 2.39 | zinc finger protein 518B |
| HGSNAT | 2.45 | 2.95 | 2.90 | heparan-alpha-glucosaminide N-acetyltransferase |
| B4GALT4 | 2.42 | 2.12 | 2.05 | UDP-Gal: betaGlcNAc beta 1,4-galactosyltransferase, polypeptide 4 |
| ATP8A1 | 2.42 | 2.91 | 2.77 | ATPase, aminophospholipid transporter (APLT), class I, type 8A, member 1 |
| SYT10 | 2.41 | 2.13 | 2.26 | synaptotagmin X |
| EFNA5 | 2.41 | 2.62 | 2.83 | ephrin-A5 |
| SMARCD3 | 2.40 | 2.70 | 2.39 | SWI/SNF related, matrix associated, actin dependent regulator of chromatin, subfamily d, member 3 |
| WDR44 | 2.40 | 2.48 | 2.26 | WD repeat domain 44 |
| EPHA2 | 2.39 | 2.03 | 2.12 | EPH receptor A2 |
| BCAR3 | 2.38 | 2.41 | 2.31 | breast cancer anti-estrogen resistance 3 |
| UNC50 | 2.36 | 3.44 | 3.34 | unc-50 homolog (C. elegans) |
| LY6E | 2.36 | 2.35 | 2.14 | lymphocyte antigen 6 complex, locus E |
| SLC5A9 | 2.34 | 7.86 | 6.18 | solute carrier family 5 (sodium/glucose cotransporter), member 9 |
| COL4A1 | 2.33 | 2.20 | 2.15 | collagen, type IV, alpha 1 |
| KIAA0825 | 2.32 | 2.72 | 2.49 | |
| NSUN3 | 2.32 | 2.41 | 2.15 | NOL1/NOP2/Sun domain family, member 3 |
| HEBP2 | 2.32 | 2.58 | 2.45 | heme binding protein 2 |
| COL6A1 | 2.32 | 2.20 | 2.52 | collagen, type VI, alpha 1 |
| PMEPA1 | 2.31 | 2.35 | 2.24 | prostate transmembrane protein, androgen induced 1 |
| STC1 | 2.30 | 2.94 | 3.30 | stanniocalcin 1 |
| MBNL3 | 2.29 | 2.65 | 2.47 | muscleblind-like 3 (Drosophila) |
| FST | 2.29 | 2.59 | 2.99 | follistatin |
| TNRC18 LOC27320 | 2.28 | 2.09 | 2.17 | trinucleotide repeat containing 18 hypothetical protein LOC27320 |
| LRRC3 | 2.25 | 2.18 | 2.53 | leucine rich repeat containing 3 |
| INPP4A | 2.25 | 2.50 | 2.55 | inositol polyphosphate-4-phosphatase, type I, 107 kDa |
| RRAGB | 2.25 | 2.26 | 2.21 | Ras-related GTP binding B |
| SLC9A9 | 2.25 | 2.70 | 3.10 | solute carrier family 9 (sodium/hydrogen exchanger), member 9 |
| TMEM123 | 2.25 | 2.26 | 2.27 | transmembrane protein 123 |
| GPR151 | 2.24 | 5.25 | 4.07 | G protein-coupled receptor 151 |
| NR3C1 | 2.24 | 2.58 | 2.64 | nuclear receptor subfamily 3, group C, member 1 (glucocorticoid receptor) |
| FAM9A | 2.22 | 2.14 | 2.32 | family with sequence similarity 89, member A |
| SHISA3 | 2.21 | 3.03 | 2.52 | shisa homolog 3 (Xenopus laevis) |
| GLT1D1 | 2.21 | 2.71 | 2.37 | glycosyltransferase 1 domain containing 1 |
| NRIP1 | 2.21 | 2.18 | 2.02 | nuclear receptor interacting protein 1 |
| WNT8A | 2.21 | 3.19 | 2.99 | wingless-type MMTV integration site family, member 8A |
| AKAP13 | 2.20 | 2.05 | 2.08 | A kinase (PRKA) anchor protein 13 |
| GPR37 | 2.20 | 2.36 | 2.53 | G protein-coupled receptor 37 (endothelin receptor type B-like) |
| COL4A6 | 2.19 | 2.76 | 3.25 | collagen, type IV, alpha 6 |
| DMN | 2.19 | 2.05 | 2.34 | desmuslin |
| PHF10 | 2.17 | 2.02 | 2.05 | PHD finger protein 10 |
| CCDC46 | 2.17 | 2.06 | 2.09 | coiled-coil domain containing 46 |
| TBX20 | 2.15 | 2.06 | 2.21 | T-box 20 |
| RCAN3 | 2.15 | 2.42 | 2.48 | RCAN family member 3 |
| ATP2B4 | 2.15 | 2.96 | 2.97 | ATPase, Ca++ transporting, plasma membrane 4 |
| FBXO34 | 2.15 | 2.05 | 2.19 | F-box protein 34 |
| C1ORF97 | 2.15 | 2.13 | 2.08 | chromosome 1 open reading frame 97 |

TABLE 2-continued

Variations of Transcript levels (2-fold or more) during DE formation in hESC-H9 and iPSC lines 3.12, 3.5, and 3.6

| GENE SYMBOL | D$_{IFF'D}$-H9] VS [IFF'D-H9] (folds) | [DIFF'D-IPSC3.12] VS [IFF'D-IPSC3.12] (folds) | [Diff'd-iPSC3.4] vs [Undiff d-iPSC3.4] (folds) | GENE DESCRIPTION |
|---|---|---|---|---|
| MAPK10 | 2.14 | 2.59 | 2.41 | mitogen-activated protein kinase 10 |
| CCNG2 | 2.13 | 2.17 | 2.08 | cyclin G2 |
| CYP27A1 | 2.12 | 3.89 | 3.49 | cytochrome P450, family 27, subfamily A, polypeptide 1 |
| FUT8 | 2.12 | 3.09 | 2.80 | fucosyltransferase 8 (alpha (1,6) fuco sy ltransferase) |
| CTBS | 2.11 | 2.58 | 2.41 | chitobiase, di-N-acetyl- |
| ODZ4 | 2.10 | 2.46 | 2.76 | odz, odd Oz/ten-m homolog 4 (Drosophila) |
| TRAF5 | 2.10 | 2.09 | 2.02 | TNF receptor-associated factor 5 |
| FZD4 | 2.09 | 2.40 | 2.63 | frizzled homolog 4 (Drosophila) |
| PCDH7 | 2.09 | 3.85 | 4.19 | protocadherin 7 |
| IL18R1 | 2.09 | 2.89 | 2.88 | interleukin 18 receptor 1 |
| PLXNA4 | 2.06 | 2.09 | 2.27 | plexin A4 |
| KCNK12 | 2.06 | 2.44 | 2.20 | potassium channel, subfamily K, member 12 |
| GPM6A | 2.04 | 5.17 | 5.20 | glycoprotein M6A |
| MAGED2 | 2.04 | 2.12 | 2.28 | melanoma antigen family D, 2 |
| PDGFC | 2.04 | 2.14 | 2.30 | platelet derived growth factor C |
| IFI16 | 2.03 | 4.18 | 3.33 | interferon, gamma-inducible protein 16 |
| ABCC4 | 2.03 | 3.31 | 2.93 | ATP-binding cassette, sub-family C (CFTR/MRP), member 4 |
| C4ORF35 | 2.02 | 2.19 | 2.01 | chromosome 4 open reading frame 35 |
| ELMOD2 | 2.01 | 2.42 | 2.07 | ELMO/CED-12 domain containing 2 |
| SH3RF1 | 2.01 | 2.35 | 2.34 | SH3 domain containing ring finger 1 |

Example 8

Tissue Processing, Immunohistochemistry and Microscopy

Tissues were fixed for 1 hour to overnight in 4% paraformaldehyde or 3% glutaraldehyde for transmission electron microscopy (TEM). Cultured PSCs and DE cells were stained directly. Hindgut and intestinal organoids were, embedded in paraffin, epoxy resin LX-112 (Ladd Research, Burlington, VT), or frozen in OCT. Sections were cut 6-10 micrometers for standard microscopy and 0.1 micrometers for TEM. TEM sections were stained with uranyl acetate. Parrafin sections were deparaffinized, subjected to antigen retrieval, blocked in the appropriate serum (5% serum in 1×PBS+0.5% triton-X) for 30 minutes, and incubated with primary antibody overnight at 4 degrees Celsius. Slides were washed and incubated in secondary antibody in blocking buffer for 2 hours at room temperature. For a list of antibodies used and dilutions, see Table 3A and 3B. Slides were washed and mounted using Fluormount-G. Confocal images were captured on a Zeiss LSM510 and Z-stacks were analyzed and assembled using AxioVision software. A Hitachi H7600 transmission electron microscope was used to capture images.

TABLE 3A

Primary Antibodies.

| PRIMARY ANTIBODY | SOURCE | DILUTION |
|---|---|---|
| Mouse anti-Phosphohistone H3 | Abcam | 1:500 |
| Rat anti-BrdU | Abcam | 1:500-1:1000 |
| Rabbit anti-Ki67 | Dako | 1:500 |
| Goat anti-Sox 17 | R&D Systems | 1:500 |
| Mouse anti-FoxA2 | Novus Biologicals | 1:500 |
| Goat anti-Villin | Santa Cruz | 1:200-1:500 |
| Mouse anti-Cdx2 | BioGenex | 1:500 |
| Rabbit anti-ChromograninA | Immuno Star | 1:1000 |
| Rabbit anti-Mucin (MUC2) | Santa Cruz | 1:200 |
| Rabbit anti-Lysozyme | Zymed Laboratories | 1:1000 |
| Rat anti-Klf5 | Dr. Ichiro Manabe | 1:2000 |
| Rabbit anti-Sox9 | Millipore | 1:1000 |
| Rabbit anti-Albumin | Sigma | 1:1000 |
| Rabbit anti-Laminin | Abcam | 1:500 |
| Mouse anti-E-Cadherin | BD Biosciences | 1:500 |
| Mouse anti-Smooth Muscle Actin | Millipore | 1:500 |
| Mouse anti-Neurogenin 3 | DSHB | 1:100 |
| Goat anti-Vimentin | Santa Cruz | 1:1000 |
| Goat anti-Pdx1 | Abcam | 1:5000 |
| Goat anti-Dpp4 | R&D Systems | 1:500 |
| Rabbit anti-Phosphohistone H3 | Cell Signaling | 1:500 |
| Goat anti-Gata4 | Santa Cruz | 1:200 |
| Rabbit anti-Gata6 | Santa Cruz | 1:200 |
| Rabbit anti-Nanog | Cosmo Bio. Co. | 1:2500 |
| Chicken anti-DNMT3b | Millipore | 1:1000 |
| Mouse anti-Tra 1-60 | Millipore | 1:500 |
| Mouse anti-Tra 1-81 | Millipore | 1:500 |

TABLE 3B

Secondary Antibodies.

| Secondary Antibody | Source | Dilution |
|---|---|---|
| Goat anti-guinea pig Cy5 | Jackson Immuno | 1:500 |
| Goat anti-rabbit Cy5 | Jackson Immuno | 1:500 |
| Goat anti-rabbit Cy3 | Jackson Immuno | 1:500 |
| Goat anti-mouse Cy3 | Jackson Immuno | 1:500 |
| Goat anti-mouse 488 | Invitrogen | 1:500 |

TABLE 3B-continued

Secondary Antibodies.

| Secondary Antibody | Source | Dilution |
|---|---|---|
| Goat anti-rabbit 488 | Invitrogen | 1:500 |
| Donkey anti-guinea pig Cy5 | Jackson Immuno | 1:500 |
| Donkey anti-rabbit Cy5 | Jackson Immuno | 1:500 |
| Donkey anti-rabbit Cy3 | Jackson Immuno | 1:500 |
| Donkey anti-mouse Cy3 | Jackson Immuno | 1:500 |
| Donkey anti-rabbit 488 | Invitrogen | 1:500 |
| Donkey anti-mouse 488 | Invitrogen | 1:500 |

Example 9

Adenovirus Production and Transduction

Adenoviral plasmids were obtained from Addgene and particles were generated according to the manufacturers protocol (Invitrogen—ViraPower Adenoviral Gateway Expression System) as previously described. 28 day organoids were removed from Matrigel and manually bisected with a scalpal. One half of each organoid was then incubated in Ad-GFP or Ad-Neurog3 viral supernatant and media at a 1:1 ratio for approximately 4 hours. Organoids were then re-embedded in Matrigel and incubated overnight with viral supernatant and media at a 1:1 ratio. The next day, fresh organoid media was placed on the cultures and was changed as described until the end of the experiment.

Adenoviral-Mediated expression of NEUROG3. Adenoviral plasmids were obtained from Addgene and particles were generated as previously described. Transduction was done on 28 day organoids that were removed from Matrigel, manually bisected then incubated in Ad-GFP or Ad-Neurog3 viral supernatant and media at a 1:1 ratio for approximately 4 hours. Organoids were then re-embedded in Matrigel and incubated overnight with viral supernatant and media at a 1:1 ratio, then transferred to fresh media until the end of the experiment.

More details can be found, for example, in Zhou et al., "In vivo reprogramming of adult pancreatic exocrine cells to beta-cells," Nature 455, 627-632 (2008); which is incorporated herein in its entirety.

Example 10

RNA Isolation, Reverse Transcription and Quantitative PCR (qPCR)

RNA was isolated using the Nucleospin II RNA isolation kit (Clonetech). Reverse Transcription was carried out using the SuperScriptIII Supermix (Invitrogen) according to manufacturers protocol. Finally, qPCR was carried out using Quantitect SybrGreen MasterMix (Qiagen) on a Chromo4 Real-Time PCR (BioRad). PCR primers sequences were typically obtained from qPrimerDepot (http://primerdepot<dot>nci<dot>nih<dot>gov/). Exemplary primers (SEQ ID NO.: 1-16 used can be found in the following Table 4.

TABLE 4

Exemplary primers used.

| GENES | FORWARD PRIMERS | REVERSE PRIMERS |
|---|---|---|
| Beta-Tubulin | GATACCTCACCGTGGCTGCT (SEQ ID NO.: 1) | AGAGGAAAGGGGCAGTTGAG T(SEQ ID NO.: 2) |
| Pdx1 | CGTCCGCTTGTTCTCCTC (SEQ ID NO.: 3) | CCTTTCCCATGGATGAAGTC (SEQ ID NO.: 4) |
| Albumin | AACGCCAGTAAGTGACAGAG TC(SEQ ID NO.: 5) | AGGTCTCCTTATCGTCAGCC T(SEQ ID NO.: 6) |
| Cdx2 | GGGCTCTCTGAGAGGCAGGT (SEQ ID NO.: 7) | GGTGACGGTGGGGTTTAGCA (SEQ ID NO.: 8) |
| Sox9 | GTACCCGCACTTGCACAAC (SEQ ID NO.: 9) | GTGGTCCTTCTTGTGCTGC (SEQ ID NO.: 10) |
| Villin | CCAAAGGCCTGAGTGAAATC (SEQ ID NO.: 11) | CCTGGAGCAGCTAGTGAACA (SEQ ID NO.: 12) |
| Lysozyme | ACAAGCTACAGCATCAGCGA (SEQ ID NO.: 13) | GTAATGATGGCAAAACCCCA (SEQ ID NO.: 14) |
| HoxA13 | GCACCTTGGTATAAGGCACG (SEQ ID NO.: 15) | CCTCTGGAAGTCCACTCTGC (SEQ ID NO.: 16) |

Example 11

Regulation of Formation of Foregut and Hindgut from Human Embryonic and Induced Pluripotent Stem Cells Results and mechanisms for signaling network that regulates foregut, hindgut and intestinal development are shown in FIGS. 14-16. A summary of the pathways involved is shown in FIG. 14A.

Following definitive endoderm (DE) induction with activin (100 ng/ml) for 3 days, a 2-4 day treatment was performed with the indicated combination of factors: Wnt3a (500 ng/ml) and Fgf4 (500 ng/ml), Retinoic acid (RA) in a range of 0.2-20 µM the BMP antagonist Noggin (50 ng/ml), the WNT antagonist DU (1-500 ng/ml).

The Noggin completely abolishes the Wnt/Fgf-induced Cdx2 expression (FIG. 14B). Retinoic acid (2 µM) can posteriorize newly-formed definitive endoderm, especially in the first two days following DE induction. The Retinoic acid (RA)-induced posteriorization is also dependent on endogenous BMP signaling, as the addition of Noggin potently inhibits Cdx2 expression.

For investigating the impact of BMP signaling on intestinal regionalization after hindgut formation, hindgut spheroids were plated in matrigel and BMP or noggin were added to EGF/Rspondid1 containing media. Intestinal organoids were analyzed after 28 days.

It has been identified that, in addition to FGF and WNT signaling, BMP and RA signaling are capable of promoting a posterior/hindgut fate and repressing foregut fate. Additionally, BMP signaling regulates formation of distinct regional types of intestine. Inhibition of BMP with noggin after the hindgut stage promotes a proximal intestinal fate (duodenum/jejunum). Activation of BMP signaling after the hindgut stage promotes a more distal intestinal cell fate (cecum/colon).

FIGS. 14B-14D demonstrate the effects of FGF, WNT, and BMP signaling on differentiation of Definitive endoderm into foregut and hindgut. In particular, FIGS. 14B and 14D depict the activation of FGF/WNT/BMP signaling promotes posterior/hindgut fate as indicated by expression of Cdx2. Repression of BMP signaling with noggin suppresses hindgut fate and promotes foregut fate. Activation of FGF/WNT/BMP signaling represses foregut fate as indicated by expression of Sox2 (FIG. 14C). Repression of WNT signaling with DU promotes anterior gene expression (HHex and Cerberus) and represses posterior/hindgut fate (Cdx2) (FIG. 14D).

Figure 15A:
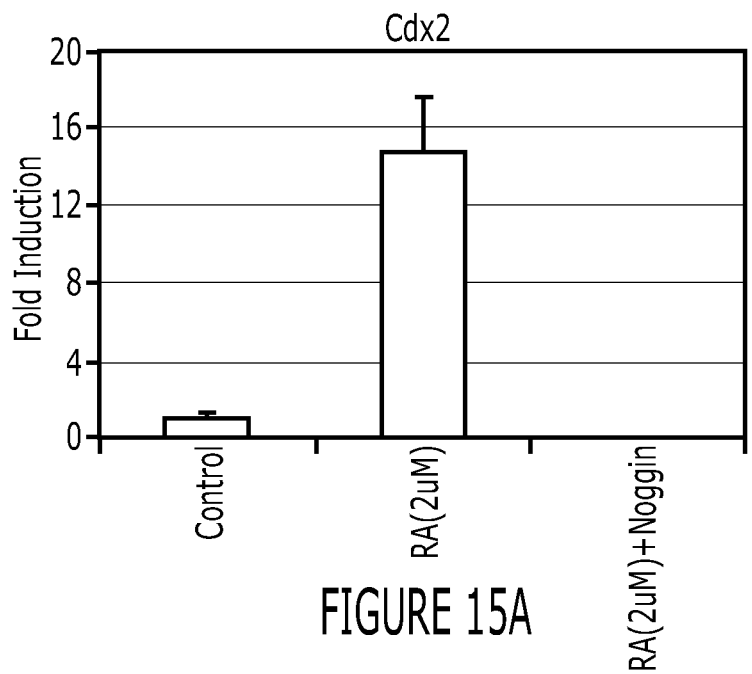
FIGS. 15A, 15C and 15D are bar charts that illustrate hindgut differentiation in a BMP dependent manner as a result of retinoic acid administration.
Figure 15B:
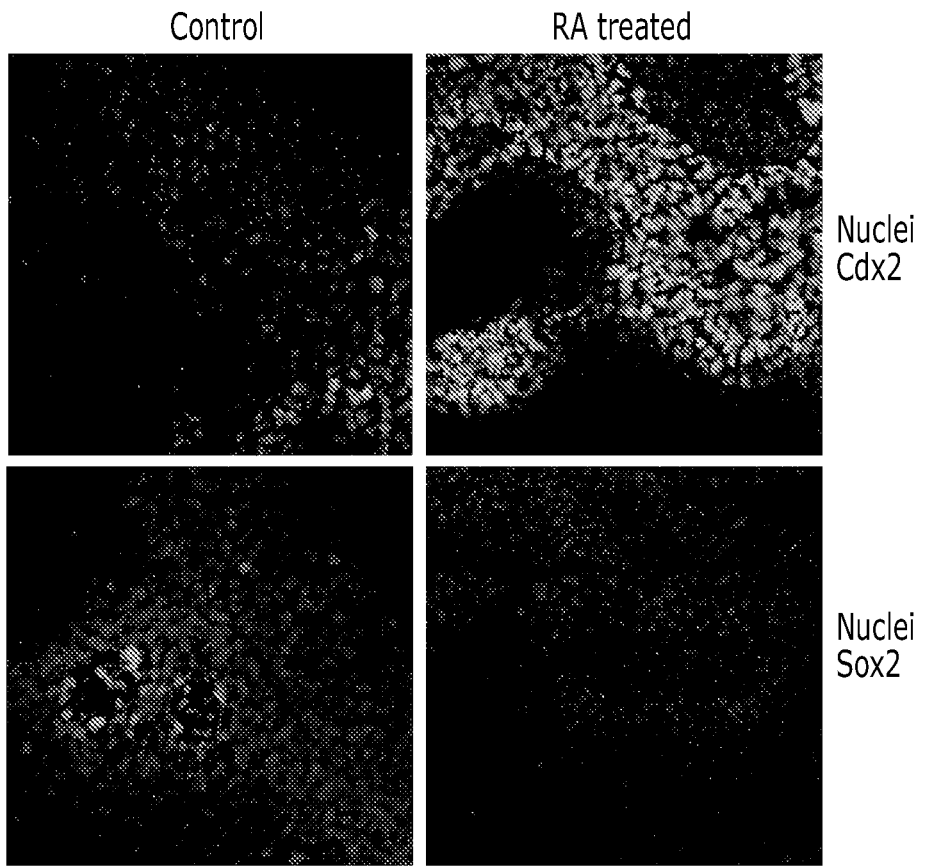
FIG. 15B is an immunofluorescent image illustrating the effects of Retinoic Acid and inhibition of BMP on differentiation of definitive endoderm into foregut and hindgut.
Figure 15C:
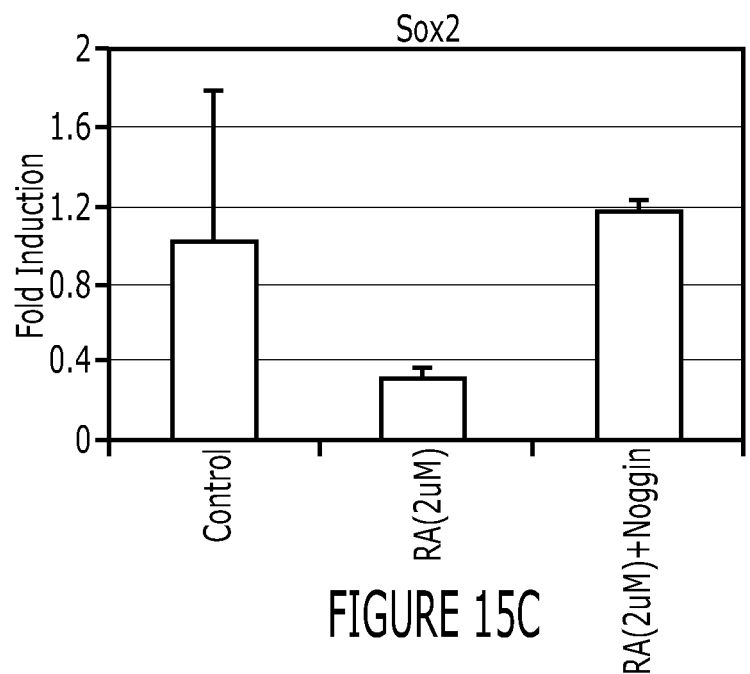
Figure 15D:
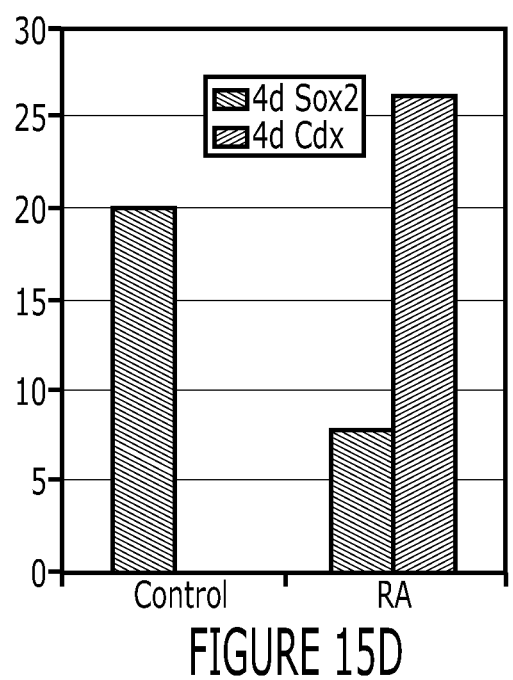

The effects of Retinoic Acid in promoting hindgut differentiation in a BMP dependent manner (FIGS. 15A-15D). Quantitative realtime PCR was used to compare the effects of Retinoic Acid and inhibition of BMP on differentiation of Definitive endoderm into foregut and hindgut (FIGS. 15A and 15B). Similar comparison was also performed by immunostaining (FIGS. 15C and 15D). Activation of RA signaling promotes posterior/hindgut fate as indicated by expression of Cdx2 and represses foregut fate as indicated by expression of Sox2. Immunostaining in FIG. 15C is quantified in FIG. 15D using an automated cell counting program.

Figure 16A:
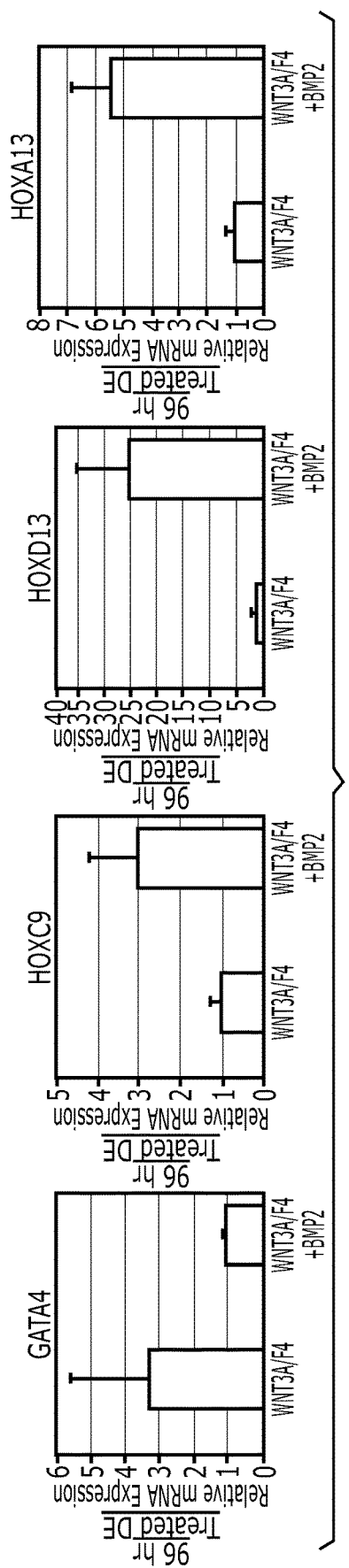
FIGS. 16A and 16B are bar charts that depict BMP signaling in regulating formation of proximal and distal intestine formation from human embryonic and induced pluripotent stem cells.
Figure 16B:
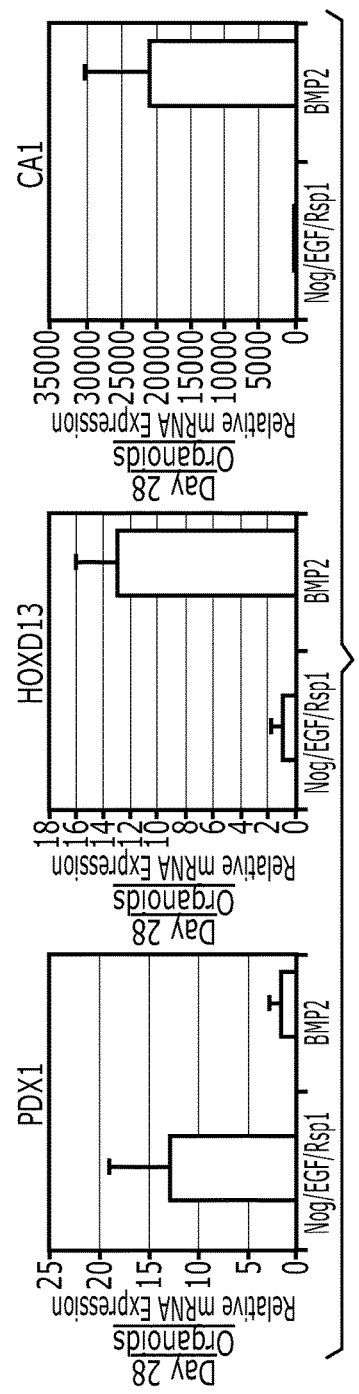
Figure 16C:
FIG. 16C includes immunofluorescent images of Noggin/EGF/Rspondid1-treated organoids that express CCK in the epithelium, thus indicating a proximal small bowel fate.
Figure 16C:

FIGS. 16A through 16C demonstrate that BMP signaling regulates formation of proximal and distal intestine formation from human embryonic and induced pluripotent stem cells. FIG. 16A shows that BMP2 promotes a posterior fate for monolayers when added during 96-hour WNT/FGF (W/F) treatment as shown by decreased expression of GATA4 compared to W/F alone and by increased expression of HOXC9 (distal small bowel and proximal colon), HOXD13, and HOXA13 compared to W/F alone.

FIG. 16B shows that, after formation of hindgut sphereoids, addition of BMP2 to 3D cultures promotes patterning of developing intestinal organoids to a distal fate after 28 days compared to the Nog/EGF/Rspo1 cocktail without BMP2 as shown by decreased relative expression of PDX1 and increased expression of HOXD13 and CA1 (carbonic anhydrase-colonocyte marker).

FIG. 16C shows that Day 138 Noggin/EGF/Rspondid1 treated organoids express CCK in the epithelium by immunostaining thus indicating a proximal small bowel fate.

FIGS. 14A-14D depict formation of foregut and hindgut from human embryonic and induced pluripotent stem cells is regulated by WNT, FGF, BMP and Retinoic acid (RA) signaling. A) Summary of the signaling network that regulates hindgut and intestinal development. B-D) Effects of FGF, WNT, and BMP signaling on differentiation of definitive endoderm into foregut and hindgut. B) and D). Activation of FGF/WNT/BMP signaling promotes posterior/hindgut fate as indicated by expression of Cdx2. Repression of BMP signaling with noggin suppresses hindgut fate and promotes foregut fate. C) Activation of FGF/WNT/BMP signaling represses foregut fate as indicated by expression of Sox2. D) Repression of WNT signaling with DU promotes anterior gene expression (HHex and Cerberus) and represses posterior/hindgut fate (Cdx2).

FIGS. 15A-15D depict retinoic acid promotes hindgut differentiation in a BMP dependent manner. Comparing the effects of Retinoic Acid and inhibition of BMP on differentiation of Definitive endoderm into foregut and hindgut by quantitative realtime PCR A) and B) or by immunostaining C) and D). Activation of RA signaling promotes posterior/hindgut fate as indicated by expression of Cdx2 and represses foregut fate as indicated by expression of Sox2. Immunostaining in C is quantified in D using an automated cell counting program.

FIGS. 16A-16C depict BMP signaling regulates formation of proximal and distal intestine formation from human embryonic and induced pluripotent stem cells. A) BMP2 promotes a posterior fate for monolayers when added during 96-hour WNT/FGF (W/F) treatment as shown by decreased expression of GATA4 compared to W/F alone and by increased expression of HOXC9 (distal small bowel and proximal colon), HOXD13, and HOXA13 compared to W/F alone. B) After formation of hindgut sphereoids, addition of BMP2 to 3D cultures promotes patterning of developing intestinal organoids to a distal fate after 28 days compared to the Nog/EGF/Rspo1 cocktail without BMP2 as shown by decreased relative expression of PDX1 and increased expression of HOXD13 and CA1 (carbonic anhydrase—colonocyte marker). C) Day 138 Noggin/EGF/Rspondid1 treated organoids express CCK in the epithelium by immunostaining thus indicating a proximal small bowel fate.

The various methods and techniques described above provide a number of exemplary ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof. Many variations and alternative elements have been disclosed in embodiments of the present invention. Still further variations and alternate elements will be apparent to one of skill in the art.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

REFERENCES CITED

All references cited are incorporated herein by reference in their entireties and for all purposes to the same extent as if each individual publication or patent or patent application was specifically and individually indicated to be incorporated by reference in its entirety for all purposes.

What is claimed is:

1. A method of obtaining an intestinal organoid comprising a) contacting definitive endoderm (DE) with FGF4 and a Wnt signaling pathway activator to form hindgut endoderm (HE) which expresses CDX2, wherein the HE maintains expression of CDX2 following removal of the FGF4 and Wnt signaling pathway activator, and b) contacting the HE with EGF and a BMP signaling pathway inhibitor to produce one or more intestinal organoid, wherein said DE is derived from an induced human pluripotent stem cell (iPSC).

2. The method of claim 1, wherein said Wnt signaling pathway activator is a small molecule inhibitor of glycogen synthase kinase-3 (GSK-3).

3. The method of claim 1, wherein the intestinal organoid is embedded in a basement membrane-like matrix.

4. The method of claim 1, wherein the intestinal organoid comprises MUC2+ goblet cells.

5. The method of claim 4, wherein the intestinal organoid comprises a lumen, and wherein mucin is secreted into the lumen.

6. The method of claim 2, wherein the concentration of Wnt signaling pathway activator is 500 ng/ml to 1,500 ng/ml.

7. The method of claim 1, wherein the concentration of FGF4 is 50 ng/ml to 500 ng/ml.

8. The method of claim 6, wherein the concentration of FGF4 is 50 ng/ml to 500 ng/ml.

9. The method of claim 1, wherein the concentration of EGF is 20 ng/ml to 75 ng/ml.

10. The method of claim 6, wherein the concentration of EGF is 20 ng/ml to 75 ng/ml.

11. The method of claim 7, wherein the concentration of EGF is 20 ng/ml to 75 ng/ml.

12. The method of claim 8, wherein the concentration of EGF is 20 ng/ml to 75 ng/ml.

13. The method of claim 1, wherein the concentration of BMP signaling pathway inhibitor is 75 ng/ml to 150 ng/ml.

14. The method of claim 6, wherein the concentration of BMP signaling pathway inhibitor is 75 ng/ml to 150 ng/ml.

15. The method of claim 7, wherein the concentration of BMP signaling pathway inhibitor is 75 ng/ml to 150 ng/ml.

16. The method of claim 8, wherein the concentration of BMP signaling pathway inhibitor is 75 ng/ml to 150 ng/ml.

17. The method of claim 9, wherein the concentration of BMP signaling pathway inhibitor is 75 ng/ml to 150 ng/ml.

18. The method of claim 10, wherein the concentration of BMP signaling pathway inhibitor is 75 ng/ml to 150 ng/ml.

19. The method of claim 11, wherein the concentration of BMP signaling pathway inhibitor is 75 ng/ml to 150 ng/ml.

20. The method of claim 12, wherein the concentration of BMP signaling pathway inhibitor is 75 ng/ml to 150 ng/ml.

21. The method of claim 20, wherein the BMP signaling pathway inhibitor is Noggin.

22. The method of claim 1, wherein removal of the FGF4 and Wnt signaling pathway activators comprises transferring to a three-dimensional culture system and/or providing with fresh media.

23. The method of claim 22, wherein the three-dimensional culture system comprises a basement membrane matrix.

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Beta-Tubulin Forward Primer

<400> SEQUENCE: 1
gatacctcac cgtggctgct                                               20

<210> SEQ ID NO 2
<211> LENGTH: 21
<212> TYPE: DNA
<213> ORGANISM: Artificial Sequence
<220> FEATURE:
<223> OTHER INFORMATION: Beta-Tubulin Reverse Primer

<400> SEQUENCE: 2
agaggaaagg ggcagttgag t                                             21

<210> SEQ ID NO 3
<211> LENGTH: 18
<212> TYPE: DNA
<213> ORGANISM: Artificial Sequence
<220> FEATURE:
<223> OTHER INFORMATION: Pdx1 Forward Primer

<400> SEQUENCE: 3
```
cgtccgcttg ttctcctc                                                 18

<210> SEQ ID NO 4
<211> LENGTH: 20
<212> TYPE: DNA
<213> ORGANISM: Artificial Sequence
<220> FEATURE:
<223> OTHER INFORMATION: Pdx1 Reverse Primer

<400> SEQUENCE: 4
cctttcccat ggatgaagtc                                               20

<210> SEQ ID NO 5
<211> LENGTH: 22
<212> TYPE: DNA
<213> ORGANISM: Artificial Sequence
<220> FEATURE:
<223> OTHER INFORMATION: Albumin Forward Primer

<400> SEQUENCE: 5
aacgccagta agtgacagag tc                                            22

<210> SEQ ID NO 6
<211> LENGTH: 21
<212> TYPE: DNA
<213> ORGANISM: Artificial Sequence
<220> FEATURE:
<223> OTHER INFORMATION: Albumin Reverse Primer

<400> SEQUENCE: 6
aggtctcctt atcgtcagcc t                                             21

<210> SEQ ID NO 7
<211> LENGTH: 20
<212> TYPE: DNA
<213> ORGANISM: Artificial Sequence
<220> FEATURE:
<223> OTHER INFORMATION: Cdx2 Forward Primer

<400> SEQUENCE: 7
gggctctctg agaggcaggt                                               20

<210> SEQ ID NO 8
<211> LENGTH: 20
<212> TYPE: DNA
<213> ORGANISM: Artificial Sequence
<220> FEATURE:
<223> OTHER INFORMATION: Cdx2 Reverse Primer

<400> SEQUENCE: 8
ggtgacggtg gggtttagca                                               20

<210> SEQ ID NO 9
<211> LENGTH: 19
<212> TYPE: DNA
<213> ORGANISM: Artificial Sequence
<220> FEATURE:
<223> OTHER INFORMATION: Sox9 Forward Primer

<400> SEQUENCE: 9
gtacccgcac ttgcacaac                                                19

<210> SEQ ID NO 10
<211> LENGTH: 19
<212> TYPE: DNA
<213> ORGANISM: Artificial Sequence

```
<220> FEATURE:
<223> OTHER INFORMATION: Sox9 Reverse Primer

<400> SEQUENCE: 10
gtggtccttc ttgtgctgc                                                    19

<210> SEQ ID NO 11
<211> LENGTH: 20
<212> TYPE: DNA
<213> ORGANISM: Artificial Sequence
<220> FEATURE:
<223> OTHER INFORMATION: Villin Forward Primer

<400> SEQUENCE: 11
ccaaaggcct gagtgaaatc                                                   20

<210> SEQ ID NO 12
<211> LENGTH: 20
<212> TYPE: DNA
<213> ORGANISM: Artificial Sequence
<220> FEATURE:
<223> OTHER INFORMATION: Villin Reverse Primer

<400> SEQUENCE: 12
cctggagcag ctagtgaaca                                                   20

<210> SEQ ID NO 13
<211> LENGTH: 20
<212> TYPE: DNA
<213> ORGANISM: Artificial Sequence
<220> FEATURE:
<223> OTHER INFORMATION: Lysozyme Forward Primer

<400> SEQUENCE: 13
acaagctaca gcatcagcga                                                   20

<210> SEQ ID NO 14
<211> LENGTH: 20
<212> TYPE: DNA
<213> ORGANISM: Artificial Sequence
<220> FEATURE:
<223> OTHER INFORMATION: Lysozyme Reverse Primer

<400> SEQUENCE: 14
gtaatgatgg caaaacccca                                                   20

<210> SEQ ID NO 15
<211> LENGTH: 20
<212> TYPE: DNA
<213> ORGANISM: Artificial Sequence
<220> FEATURE:
<223> OTHER INFORMATION: HoxA13 Forward Primer

<400> SEQUENCE: 15
gcaccttggt ataaggcacg                                                   20

<210> SEQ ID NO 16
<211> LENGTH: 20
<212> TYPE: DNA
<213> ORGANISM: Artificial Sequence
```

```
<220> FEATURE:
<223> OTHER INFORMATION: HoxA13 Reverse Primer

<400> SEQUENCE: 16
cctctggaag tccactctgc                                              20
```